(12) United States Patent
Nakamura et al.

(10) Patent No.: US 7,972,772 B2
(45) Date of Patent: Jul. 5, 2011

(54) KIF11 AND METHOD FOR DIAGNOSING NON-SMALL CELL LUNG CANCER

(75) Inventors: Yusuke Nakamura, Tokyo (JP); Yataro Daigo, Tokyo (JP); Shuichi Nakatsuru, Kanagawa (JP)

(73) Assignee: Oncotherapy Science, Inc., Kanagawa (JP)

( * ) Notice: Subject to any disclaimer, the term of this patent is extended or adjusted under 35 U.S.C. 154(b) by 0 days.

(21) Appl. No.: 12/700,669

(22) Filed: Feb. 4, 2010

(65) Prior Publication Data
US 2010/0173317 A1 Jul. 8, 2010

Related U.S. Application Data

(62) Division of application No. 10/593,842, filed as application No. PCT/JP2005/005613 on Mar. 18, 2005, now Pat. No. 7,700,573.

(60) Provisional application No. 60/555,789, filed on Mar. 23, 2004.

(51) Int. Cl.
*C12Q 1/00* (2006.01)
*C12Q 1/68* (2006.01)
*A61K 48/00* (2006.01)
*G01N 33/53* (2006.01)

(52) U.S. Cl. .................. 435/4; 435/6; 435/7.1; 514/44 R

(58) Field of Classification Search .................. None
See application file for complete search history.

(56) References Cited

U.S. PATENT DOCUMENTS

| | | | |
|---|---|---|---|
| 6,331,396 B1 | 12/2001 | Silverman et al. | |
| 6,414,121 B1 | 7/2002 | Wood et al. | |
| 6,472,521 B1 | 10/2002 | Uhlmann et al. | |
| 6,506,559 B1 | 1/2003 | Fire et al. | |
| 6,544,766 B1 | 4/2003 | Beraud et al. | |
| 6,706,867 B1 | 3/2004 | Lorenz | |
| 7,358,353 B2 | 4/2008 | Jakobovits et al. | |
| 2002/0165240 A1* | 11/2002 | Kimball et al. | 514/258.1 |
| 2005/0245475 A1 | 11/2005 | Khvorova et al. | |
| 2006/0014686 A1 | 1/2006 | Wonsey et al. | |
| 2007/0031844 A1 | 2/2007 | Khvorova et al. | |
| 2008/0234941 A1 | 9/2008 | Jackson et al. | |

FOREIGN PATENT DOCUMENTS

| | | |
|---|---|---|
| WO | WO 01/31335 A2 | 5/2001 |
| WO | WO 01/94629 A2 | 12/2001 |
| WO | WO 03/015613 A2 | 2/2003 |
| WO | WO 03/030832 A2 | 4/2003 |
| WO | WO 03/099224 A2 | 12/2003 |

OTHER PUBLICATIONS

Tockman et al. "Consideration in Bringing a Cancer Biomarker to Clinical Application", Cancer Research (Suppl.), May 1, 1992, vol. 52, pp. 2711s-2718s.*
Song, E., et al.; "RNA interference targeting Fas protects mice from fulminant hepatitis," *Nat. Med.*; Mar. 2003, Epub Feb. 10, 2003; pp. 347-351; vol. 9(3).
Blangy, Anne, et al.; "Phosphorylation by p34$^{cdc2}$ Regulates Spindle Association of Human Eg5, a Kinesin-Related Motor Essential for Bipolar Spindle Formation in Vivo;" *Cell*; Dec. 29, 2005; pp. 1159-1169; 83:7.
Hamada, Kenji, et al.; "Increased Expression of the Genes for Mitotic Spindle Assembly and Chromosome Segregation in Both Lung and Pancreatic Carcinomas;" *Cancer Genomics & Proteomics*; May 2004; pp. 231-240; 1:3.
Houliston, Evelyn, et al.; "The Kinesin-Related Protein Eg5 Associates with both Interphase and Spindle Microtubules during *Xenopus* Early Development;" *Developmental Biology*; Jul. 1994; pp. 147-159; 164:1.
Kaiser, Astrid, et al.; "All-*trans*-Retinoic Acid-mediated Growth Inhibition Involves Inhibition of Human Kinesin-related Protein HsEg5;" *The Journal of Biological Chemistry*; Jul. 2, 1999; pp. 18925-18931; 274:27.
Sharp, David J., et al.; "The Bipolar Kinesin, KLP61F, Cross-links Microtubules within Interpolar Microtubule Bundles of *Drosophila* Embryonic Mitotic Spindles;" *The Journal of Cell Biology*; Jan. 11, 1999; pp. 125-135; 144:1.
Suzuki, Chie, et al.; "Identification of COX17 as a Therapeutic Target for Non-Small Cell Lung Cancer;" *Cancer Research*; Nov. 1, 2003; pp. 7038-7041; 63:21.
Tuschl, *The siRNA user guide*. 2001.
Weil, D, et al.; "Targeting the Kinesin Eg5 to Monitor siRNA Transfection in Mammalian Cells;" *Biotechniques*; Dec. 2003; pp. 1244-1248; 33:6.
Yarrow, J. C., et al.; "Phenotypic Screening of Small Molecule Libraries by High Throughput Cell Imaging;" *Combinatorial Chemistry & High Throughput Screening*; Jun. 2003; pp. 279-286; 6:4.
Fukukawa, Chiyuki et al.; "Identification and characterization of a candidate gene encoding a secretory protein as a novel target for diagnosis and treatment of lung cancer"; 2003, *Dai 62 Kai Nihon Gan Gakkai Sokai*, pp. 247, abstract.
Kikuchi, Takefumi et al.; Expression profiles of non-small cell lung cancers on cDNA microarrays: Identification of genes for prediction of lymph-node metastasis and sensitivity to anti-cancer drugs; 2003, *Oncogene*, vol. 22, pp. 2192-2205.
U.S. Appl. No. 12/903,961, filed Oct. 13, 2010, 46 pgs.
U.S. Appl. No. 12/673,432, which is a U.S. Nat'l Phase of PCT/JP2008/064437, filed Aug. 12, 2008, 83 pgs.

* cited by examiner

*Primary Examiner* — Suzanne M. Noakes
(74) *Attorney, Agent, or Firm* — Kilpatrick Townsend & Stockton LLP

(57) ABSTRACT

Disclosed are methods for detecting non-small cell lung cancer (NSCLC) using differentially expressed genes KIF11, GHSR1b, NTSR1, and FOXM1. Also disclosed are methods of identifying compounds for treating and preventing NSCLC, based on the interaction between KOC1 and KIF11, or NMU and GHSR1b or NTSR1.

7 Claims, 26 Drawing Sheets a *Clinical sample*
b *Lung-cancer cell line*

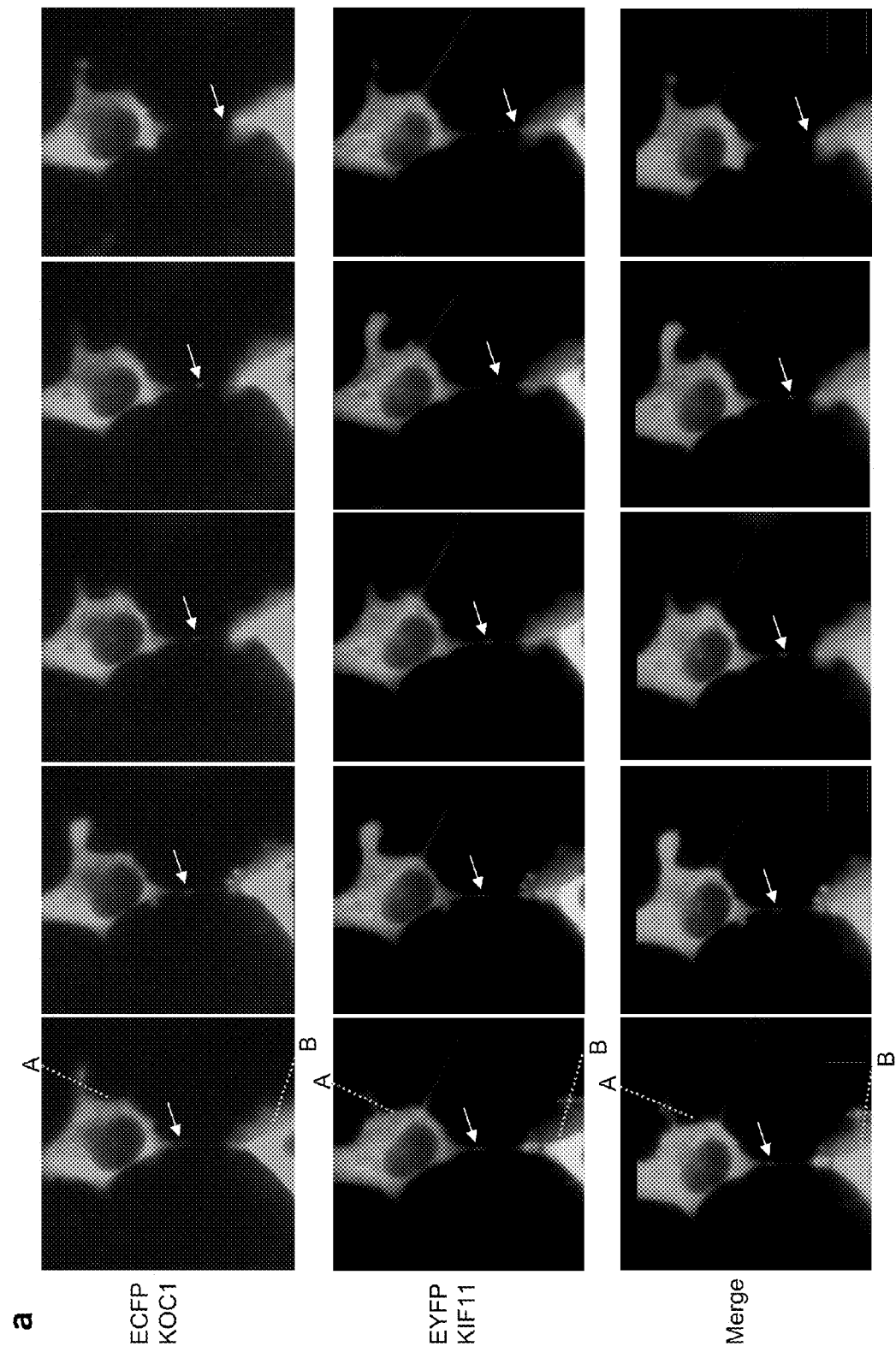

a

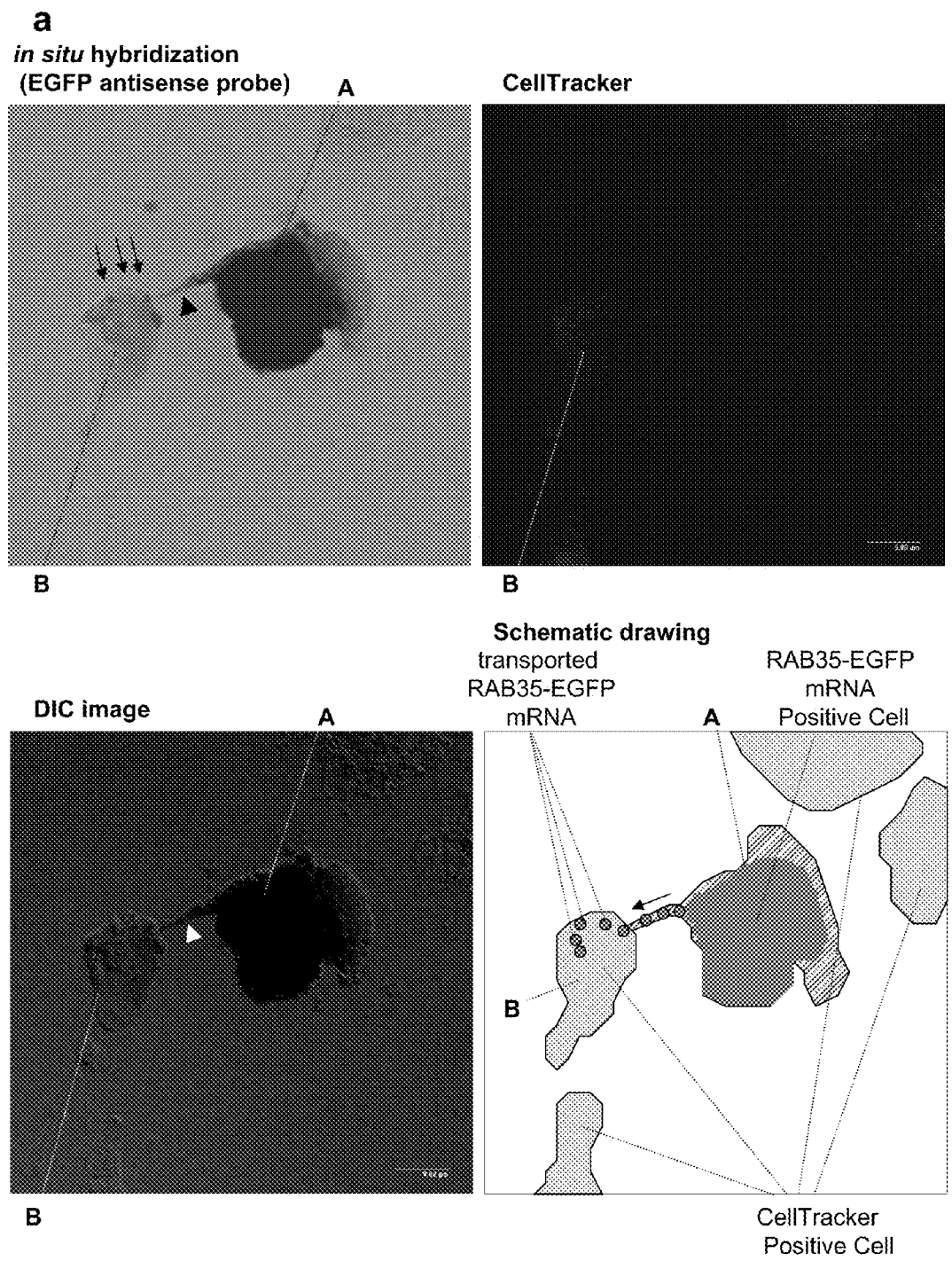

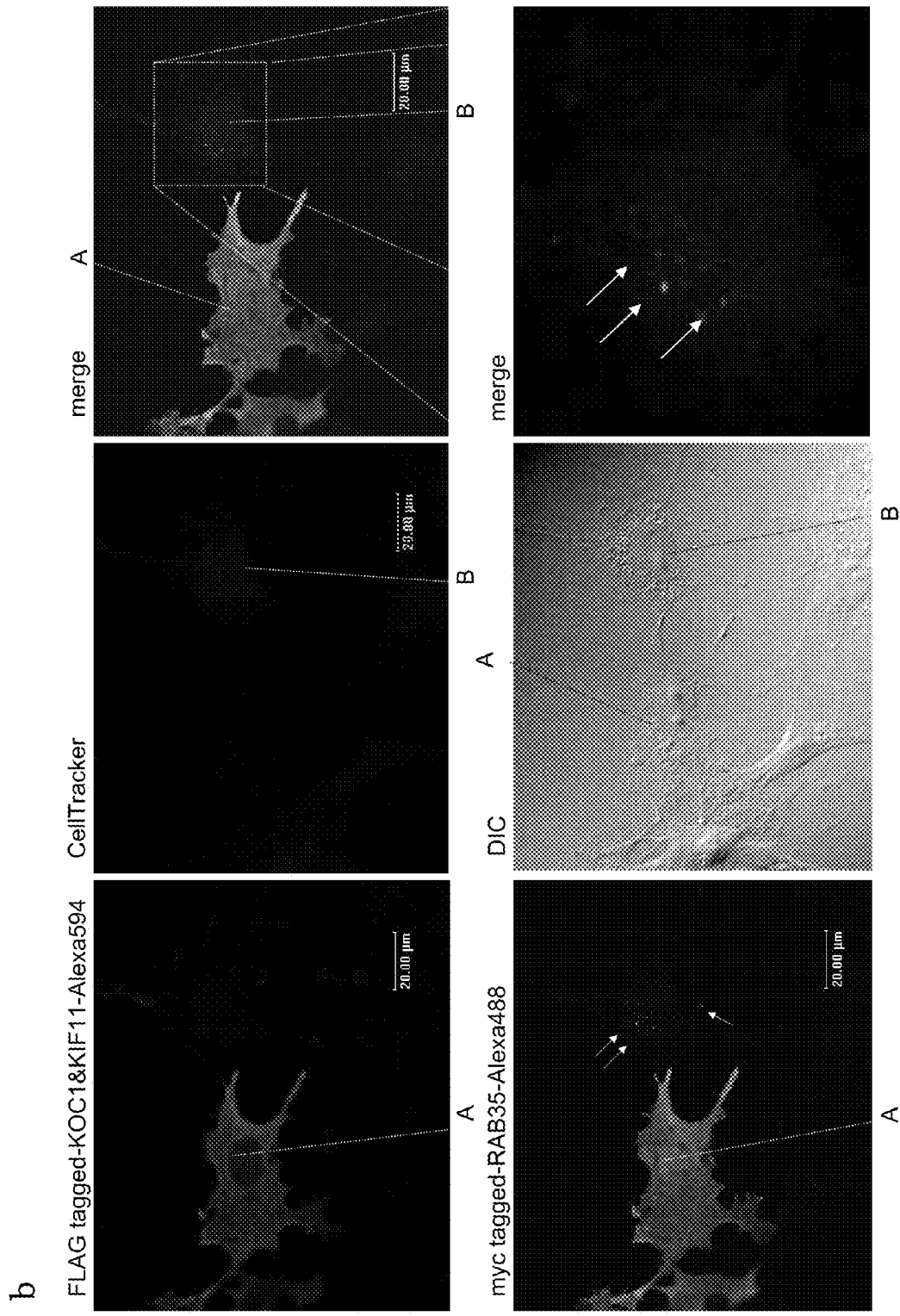

a b (-80°C, 7 days)

c d

*Three control assays used for this study:
1. COS-7 cells (no receptor) only
2. No receptor & NMU-25
3. GHSR1b(+)-COS-7 cells only

**Three control assays used for this study:
1. COS-7 cells (no receptor) only
2. No receptor & NMU-25
3. NTSR1(+)-COS-7 cells only e f a b

*MTT assay* a b c

KIF11 AND METHOD FOR DIAGNOSING NON-SMALL CELL LUNG CANCER

CROSS REFERENCE TO RELATED APPLICATIONS

The present application is a division of U.S. patent application Ser. No. 10/593,842, filed Jul. 10, 2007, now U.S. Pat. No. 7,700,573, which is a U.S. National Phase of International Application No. PCT/JP2005/005613, filed Mar. 18, 2005, which claims the benefit of U.S. Provisional Application Ser. No. 60/555,789 filed Mar. 23, 2004, all of which are incorporated herein by reference.

FIELD OF THE INVENTION

The present invention relates to the field of biological science, more specifically to the field of cancer therapy and diagnosis. In particular, the invention relates to methods of diagnosing non-small cell lung cancers using genes, KIF11, GHSR1b, NTSR1, and FOXM1, that show elevated expression in such cancerous cells.

BACKGROUND OF THE INVENTION

Lung cancer is one of the most commonly fatal human tumors. Many genetic alterations associated with the development and progression of lung cancer have been reported. Although genetic changes can aid prognostic efforts and predictions of metastatic risk or response to certain treatments, information about a single or a limited number of molecular markers generally fails to provide satisfactory results for clinical diagnosis of non-small cell lung cancer (NSCLC) (Mitsudomi et al., *Clin Cancer Res* 6: 4055-63 (2000); Niklinski et al., *Lung Cancer.* 34 Suppl 2: S53-8 (2001); Watine, *BMJ* 320: 379-80 (2000)). NSCLC is by far the most common form, accounting for nearly 80% of lung tumors (Society, A. C. *Cancer Facts and Figures* 2001 (2001)). The overall 10-year survival rate remains as low as 10% despite recent advances in multi-modality therapy, because the majority of NSCLCs are not diagnosed until advanced stages (Fry, W. A. et al., *Cancer* 86: 1867-76 (1999)). Although chemotherapy regimens based on platinum are considered the reference standards for treatment of NSCLC, those drugs are able to extend survival of patients with advanced NSCLC only about six weeks (Non-small Cell Lung Cancer Collaborative Group, *BMJ.* 311: 899-909 (1995)). Numerous targeted therapies are being investigated for this disease, including tyrosine kinase inhibitors, but so far promising results have been achieved in only a limited number of patients and some recipients suffer severe adverse reactions (Kris M. N. R., Herbst R. S. *Proc. Am. Soc. Clin. Oncol.* 21: 292a (A1166) (2002)).

Many genetic alterations associated with development and progression of lung cancer have been reported, but the precise molecular mechanisms remain unclear (Sozzi, G. *Eur. J Cancer* 37: 63-73 (2001)). Over the last decade newly developed cytotoxic agents including paclitaxel, docetaxel, gemcitabine, and vinorelbine have emerged to offer multiple therapeutic choices for patients with advanced NSCLC; however, each of the new regimens can provide only modest survival benefits compared with cisplatin-based therapies (Schiller, J. H. et al., *N. Engl. J. Med.* 346: 92-98 (2002); Kelly, K. et al., *J. Clin. Oncol.* 19: 3210-3218 (2001)). Hence, new therapeutic strategies, such as development of molecular-targeted agents, are eagerly awaited by clinicians.

Systematic analysis of expression levels of thousands of genes on cDNA microarrays is an effective approach to identifying unknown molecules involved in pathways of carcinogenesis (Kikuchi, T. et al., *Oncogene* 22: 2192-2205 (2003); Kakiuchi, S. et al., *Mol. Cancer. Res.* 1: 485-499 (2003); Zembutsu, H. et al., *Int. J. Oncol.* 23: 29-39 (2003); Suzuki, C. et al., *Cancer Res.* 63: 7038-7041 (2003)) and can reveal candidate targets for development of novel anti-cancer drugs and tumor markers. To isolate novel molecular targets for diagnosis, treatment and prevention of NSCLC, pure populations of tumor cells were prepared from 37 cancer tissues by laser-capture microdissection and genome-wide expression profiles of NSCLC cells were analyzed on a cDNA microarray containing 23,040 genes (Kikuchi, T. et al., *Oncogene* 22: 2192-2205 (2003)). In the course of those experiments, KOC1 (GenBank Accession No. NM_006547) and neuromedin U (NMU; GenBank Accession No. NM_006681) were identified as genes that were frequently over-expressed in lung tumors and indispensable for growth of NSCLC cells.

Cell-to-cell communication is a prerequisite for development and maintenance of multicellular organisms. Several intercellular information-exchange systems such as chemical synapses, gap junctions, and plasmadesmata in plant cells have long been observed, but a new transporting system involving a highly sensitive nanotubular structure, tunneling nanotubes (TNTs) between the cells, was only recently reported in mammalian cells (Rustom, A. et al., *Science* 303, 1007-1010 (2004). Such a structure would facilitate the selective transfer of membrane vesicles and organelles; therefore TNTs in mammalian somatic cells might contribute to a cell-to-cell transporting system(s) by carrying transcription factors or ribonucleoparticles (RNPs), as in plants (Nakajima, K. et al., *Nature* 413, 307-311 (2001); Lucas, W. J. et al., *Nat. Rev. Mol. Cell. Biol.* 2, 849-857 (2001)). Some investigators have documented interactions between some RNA-binding proteins and motor proteins like kinesin and dynein within mammalian somatic cells, as well as intercellular mRNA transport in mammalian germ cells (Brendza, R. P. et al., *Science* 289, 2120-2122 (2000); Chemathukuzhi, V. et al., *Proc. Natl. Acad. Sci. USA* 100, 15566-15571 (2003); Villace, P. et al., *Nucleic Acids Res.* 32, 2411-2420 (2004); Morales, C. R. et al. *Dev. Biol.* 246, 480-494 (2002).). However, no report has emerged describing an intercellular mRNA transporting system in mammalian somatic cells involving a complex of RNA-binding proteins and motor proteins.

The phenomenon of mRNA localization has been reported in oocytes and developing embryos of *Drosophila* and *Xenopus* and in somatic cells such as fibroblasts and neurons (King, M. L. et al., *Bioessays* 21: 546-557 (1999); Mowry, K. L., Cote, C. A. *FASEB J.* 13: 435-445 (1999); Lasko, P. J. *Cell Biol.* 150: F51-56 (2000); Steward, O. *Neuron* 18: 9-12 (1997)). Beta actin (ACTB) mRNA is localized at the leading lamellae of chicken embryo fibroblasts (CEFs) (Lawrence, J. B., Singer, R. H. *Cell* 45: 407-415 (1986)) and at the growth cone of developing neurons (Bassell, G. J. et al., *J. Neurosci.* 18: 251-265 (1998)). The localization of ACTB mRNA is dependent on the zipcode, a cis-acting element located in the 3' UTR of the mRNA (Kislauskis, E. H. et al., *J. Cell Biol.* 123:165-172 (1993)). The trans-acting factor, zipcode binding protein 1 (ZBP1), was affinity purified with the zipcode of ACTB mRNA (Ross, A. F. et al., *Mol. Cell. Biol.* 17, 2158-2165 (1997)). After the identification of ZBP1, additional homologues were identified in a wide range of organisms including *Xenopus, Drosophila*, human, and mouse (Mueller-Pillasch, F. et al., *Oncogene* 14: 2729-2733 (1997); Deshler, J. O. et al., *Science* 276: 1128-1131 (1997); Doyle, G. A. et al., *Nucleic Acids Res.* 26: 5036-5044 (1998)). ZBP1 family members are expressed in germ embryonic fibroblasts and in several types of cancer (Mueller-Pillasch, F. et al., *Oncogene* 14: 2729-2733 (1997); Mueller, F. et al., *Br. J. Cancer* 88; 699-701 (2003)). ZBP1-like proteins contain two RNA-recognition motifs (RRMs) at the NH2-terminal part of the protein and four hnRNP K homology (KH) domains at the COOH-terminal end.

KOC1 (alias IGF-II mRNA-binding protein 3: IMP-3) is one of the IMPs (IMP-1, IMP-2, and IMP-3), which belong to the ZBP1 family members and exhibit multiple attachments to IGF-II leader 3 mRNA and the reciprocally imprinted H19 RNA (Mueller-Pillasch, F. et al., *Oncogene* 14: 2729-2733 (1997)). Although KOC1 was initially reported to be over-expressed in pancreatic cancer (Mueller-Pillasch, F. et al., *Oncogene* 14: 2729-2733 (1997); Mueller, F. et al., *Br. J. Cancer* 88: 699-701 (2003)), its precise function in cancer cells or even in normal mammalian somatic cells remains unclear.

KOC1 is orthologous to the *Xenopus* Vg1 RNA-binding protein (Vg1RBP/Vera), which mediates the localization of Vg1 mRNA to the vegetal pole of the oocyte during oocyte maturation, and IMP-1 is orthologous to the ZBP1. IMP is mainly located at the cytoplasm and its cellular distribution ranges from a distinct concentration in perinuclear regions and lamellipodia to a completely delocalized pattern. H19 RNA co-localized with IMP, and removal of the high-affinity attachment site led to delocalization of the truncated RNA (Runge, S. et al., *J. Biol. Chem.* 275: 29562-29569 (2000)), suggesting that IMPs are involved in cytoplasmic trafficking of RNA. IMP-1 was able to associate with microtubules (Nielsen, F. C. et al., *J. Cell Sci.* 115: 2087-2097 (2002); Havin, L. et al., *Genes Dev.* 12: 1593-1598 (1998)), and is likely to involve a motor protein such as kinesin, myosin, and dyenin. On the other hand, Oskar mRNA localization to the posterior pole requires Kinesin I (Palacios, I. M., St. Johnston D. *Development* 129: 5473-5485 (2002); Brendza, R. P. et al., *Science* 289: 2120-2102 (2000)).

KIF11 (alias EG5) is a member of kinesin family, and plays a role in establishing and/or determining the stability of specific microtuble arrays that form during cell division. This role may encompass the ability of KIF11 to influence the distribution of other protein components associated with cell division (Whitehead, C. M., Rattner, J. B. *J. Cell Sci.* 111: 2551-2561 (1998); Mayer, T. U. et al., *Science* 286: 971-974 (1999)).

NMU is a neuropeptide that was first isolated from porcine spinal cord. It has potent activity on smooth muscles (Minamino, N. et al., *Biochem. Biophys. Res. Commun.* 130: 1078-1085 (1985); Domin, J. et al., *Biochem. Biophys. Res. Commun.* 140: 1127-1134 (1986); Conlon, J. M. et al., *J. Neurochem.* 51: 988-991 (1988); Minamino, N. et al., *Biochem. Biophys. Res. Commun.* 156: 355-360 (1988); Domin, J. et al., *J. Biol. Chem.* 264: 20881-20885 (1989), O'Harte, F. et al., *Peptides* 12: 809-812 (1991); Kage, R. et al., *Regul. Pept.* 33: 191-198 (1991); Austin, C. et al., *J. Mol. Endocrinol.* 12: 257-263 (1994); Fujii, R. et al., *J. Biol. Chem.* 275: 21068-21074 (2000)), and in mammalian species NMU is distributed predominantly in the gastrointestinal tract and central nervous system (Howard, A. D. et al., *Nature* 406: 70-74 (2000); Funes, S. et al., *Peptides* 23: 1607-1615 (2002)). Peripheral activities of NMU include stimulation of smooth muscle, elevation of blood pressure, alternation of ion transport in the gut, and regulation of feeding (Minamino, N. et al., *Biochem. Biophys. Res. Commun.* 130: 1078-1085 (1985)); however, the role of NMU during carcinogenesis has not been addressed. Neuropeptides function peripherally as paracrine and autocrine factors to regulate diverse physiologic processes and act as neurotransmitters or neuromodulators in the nervous system. In general, receptors that mediate signaling by binding neuropeptides are members of the superfamily of G protein-coupled receptors (GPCRs) having seven transmembrane-spanning domains. Two known receptors for NMU, NMU1R and NMU2R, show a high degree of homology to other neuropeptide receptors such as GHSR and NTSR1, for which the corresponding known ligands are Ghrelin (GHRL) and neurotensin (NTS), respectively. NMU1R (FM3/GPR66) and NMU2R (FM4) have seven predicted alpha-helical transmembrane domains containing highly conserved motifs, as do other members of the rhodopsin GPCR family (Fujii, R. et al., *J. Biol. Chem.* 275: 21068-21074 (2000); Howard, A. D. et al., *Nature* 406: 70-74 (2000); Funes, S. et al., *Peptides* 23: 1607-1615 (2002)).

A C-terminal asparaginamide structure and the C-terminal hepatapeptide core of NMU protein are essential for its contractile activity in smooth-muscle cells (Westfall, T. D. et al., *J. Pharmacol. Exp. Ther* 301: 987-992 (2002); Austin, C. *J. Mol. Endocrinol.* 14: 157-169 (1995)). Recent studies have contributed evidence that NMU acts at the hypothalamic level to inhibit food intake; therefore this protein might be a physiological regulator of feeding and body weight (Howard, A. D. et al., *Nature* 406: 70-74 (2000); Maggi, C. A. et al., *Br J. Pharmacol.* 99: 186-188 (1990); Wren, A. M. et al., *Endocrinology* 143: 227-234 (2002); Ivanov, T. R. et al., *Endocrinology* 143: 3813-3821 (2002)). However, so far no reports have suggested involvement of NMU over-expression in carcinogenesis.

Studies designed to reveal mechanisms of carcinogenesis have already facilitated identification of molecular targets for anti-tumor agents. For example, inhibitors of farnesyltransferase (FTIs) which were originally developed to inhibit the growth-signaling pathway related to Ras, whose activation depends on posttranslational farnesylation, has been effective in treating Ras-dependent tumors in animal models (He et al., *Cell* 99:335-45 (1999)). Clinical trials on human using a combination or anti-cancer drugs and anti-HER2 monoclonal antibody, trastuzumab, have been conducted to antagonize the proto-oncogene receptor HER2/neu; and have been achieving improved clinical response and overall survival of breast-cancer patients (Lin et al., *Cancer Res.* 61:6345-9 (2001)). A tyrosine kinase inhibitor, STI-571, which selectively inactivates bcr-abl fusion proteins, has been developed to treat chronic myelogenous leukemias wherein constitutive activation of bcr-abl tyrosine kinase plays a crucial role in the transformation of leukocytes. Agents of these kinds are designed to suppress oncogenic activity of specific gene products (Fujita et al., *Cancer Res.* 61:7722-6 (2001)). Therefore, gene products commonly up-regulated in cancerous cells may serve as potential targets for developing novel anti-cancer agents.

It has been demonstrated that CD8+ cytotoxic T lymphocytes (CTLs) recognize epitope peptides derived from tumor-associated antigens (TAAs) presented on MHC Class I molecule, and lyse tumor cells. Since the discovery of MAGE family as the first example of TAAs, many other TAAs have been discovered using immunological approaches (Boon, *Int. J. Cancer* 54: 177-80 (1993); Boon and van der Bruggen, *J. Exp. Med.* 183: 725-9 (1996); van der Bruggen et al., *Science* 254: 1643-7 (1991); Brichard et al., *J. Exp. Med.* 178: 489-95 (1993); Kawakami et al., *J. Exp. Med.* 180: 347-52 (1994)). Some of the discovered TAAs are now in the stage of clinical development as targets of immunotherapy. TAAs discovered so far include MAGE (van der Bruggen et al., *Science* 254: 1643-7 (1991)), gp100 (Kawakami et al., *J. Exp. Med.* 180: 347-52 (1994)), SART (Shichijo et al., *J. Exp. Med.* 187:

277-88 (1998)), and NY-ESO-1 (Chen et al., *Proc. Natl. Acad. Sci. USA* 94: 1914-8 (1997)). On the other hand, gene products which had been demonstrated to be specifically over-expressed in tumor cells, have been shown to be recognized as targets inducing cellular immune responses. Such gene products include p53 (Umano et al., *Brit. J. Cancer* 84: 1052-7 (2001)), HER2/neu (Tanaka et al., *Brit. J. Cancer* 84: 94-9 (2001)), CEA (Nukaya et al., *Int. J. Cancer* 80: 92-7 (1999)), and so on.

In spite of significant progress in basic and clinical research concerning TAAs (Rosenbeg et al., *Nature Med.* 4: 321-7 (1998); Mukherji et al., *Proc. Natl. Acad. Sci. USA* 92: 8078-82 (1995); Hu et al., *Cancer Res.* 56: 2479-83 (1996)), only limited number of candidate TAAs for the treatment of cancer are available. TAAs abundantly expressed in cancer cells, and at the same time which expression is restricted to cancer cells would be promising candidates as immunotherapeutic targets. Further, identification of new TAAs inducing potent and specific antitumor immune responses is expected to encourage clinical use of peptide vaccination strategy in various types of cancer (Boon and can der Bruggen, *J. Exp. Med.* 183: 725-9 (1996); van der Bruggen et al., *Science* 254: 1643-7 (1991); Brichard et al., *J. Exp. Med.* 178: 489-95 (1993); Kawakami et al., *J. Exp. Med.* 180: 347-52 (1994); Shichijo et al., *J. Exp. Med.* 187: 277-88 (1998); Chen et al., *Proc. Natl. Acad. Sci. USA* 94: 1914-8 (1997); Harris, J. Natl. Cancer Inst. 88: 1442-5 (1996); Butterfield et al., *Cancer Res.* 59: 3134-42 (1999); Vissers et al., *Cancer Res.* 59: 5554-9 (1999); van der Burg et al., *J. Immunol* 156: 3308-14 (1996); Tanaka et al., *Cancer Res.* 57: 4465-8 (1997); Fujie et al., *Int. J. Cancer* 80: 169-72 (1999); Kikuchi et al., *Int. J. Cancer* 81: 459-66 (1999); Oiso et al., *Int. J. Cancer* 81: 387-94 (1999)).

It has been repeatedly reported that peptide-stimulated peripheral blood mononuclear cells (PBMCs) from certain healthy donors produce significant levels of IFN-γ in response to the peptide, but rarely exert cytotoxicity against tumor cells in an HLA-A24 or -A0201 restricted manner in $^{51}$Cr-release assays (Kawano et al., *Cancer Res.* 60: 3550-8 (2000); Nishizaka et al., *Cancer Res.* 60: 4830-7 (2000); Tamura et al., *Jpn. J. Cancer Res.* 92: 762-7 (2001)). However, both of HLA-A24 and HLA-A0201 are one of the popular HLA alleles in Japanese, as well as Caucasian (Date et al., *Tissue Antigens* 47: 93-101 (1996); Kondo et al., *J. Immunol.* 155: 4307-12 (1995); Kubo et al., *J. Immunol.* 152: 3913-24 (1994); Imanishi et al., *Proceeding of the eleventh International Histocompatibility Workshop and Conference Oxford University Press, Oxford*, 1065 (1992); Williams et al., *Tissue Antigen* 49: 129 (1997)). Thus, antigenic peptides of cancers presented by these HLAs may be especially useful for the treatment of cancers among Japanese and Caucasian. Further, it is known that the induction of low-affinity CTL in vitro usually results from the use of peptide at a high concentration, generating a high level of specific peptide/MHC complexes on antigen presenting cells (APCs), which will effectively activate these CTL (Alexander-Miller et al., *Proc. Natl. Acad. Sci. USA* 93: 4102-7 (1996)).

Although advances have been made in the development of molecular-targeting drugs for cancer therapy, the ranges of tumor types that respond as well as the effectiveness of the treatments are still very limited. Hence, it is urgent to develop new anti-cancer agents that target molecules highly specific to malignant cells and are likely to cause minimal or no adverse reactions. To achieve the goal molecules whose physiological mechanisms are well defined need to be identified. A powerful strategy toward these ends would combine screening of up-regulated genes in cancer cells on the basis of genetic information obtained on cDNA microarrays with high-throughput screening of their effect on cell growth, by inducing loss-of-function phenotypes with RNAi systems (Kikuchi, T. et al., *Oncogene* 22: 2192-2205 (2003)).

SUMMARY OF THE INVENTION

The present invention features a method of diagnosing or determining a predisposition to non-small cell lung cancer (NSCLC) in a subject by determining an expression level of a non-small cell lung cancer-associated gene that is selected from the group of KIF11, GHSR1b, NTSR1, and FOXM1 in a patient derived biological sample. An increase of the expression level of any of the genes compared to a normal control level of the genes indicates that the subject suffers from or is at risk of developing NSCLC.

The invention also provides methods of providing a prognosis of a patient diagnosed with NSCLC. In particular, the methods involve detecting expression of KOC1, KIF11, or KOC1 in combination with expression of KIF11.

A "normal control level" indicates an expression level of any of the genes detected in a normal, healthy individual or in a population of individuals known not to be suffering from NSCLC. A control level is a single expression pattern derived from a single reference population or from a plurality of expression patterns. In contrast to a "normal control level", the "control level" is an expression level of the gene detected in an individual or a population of individuals whose background of the disease state is known (i.e., cancerous or non-cancerous). Thus, the control level may be determined base on the expression level of the gene in a normal, healthy individual, in a population of individuals known not to be suffering from NSCLC, a patient of NSCLC or a population of the patients. The control level corresponding to the expression level of the gene in a patient of non-small cell lung cancer or a population of the patients is referred to as "NSCLC control level". Furthermore, the control level can be a database of expression patterns from previously tested cells.

An increase in the expression level of any one of the genes of KIF11, GHSR1b, NTSR1, and FOXM1 detected in a test biological sample compared to a normal control level indicates that the subject (from which the sample was obtained) suffers from NSCLC. Alternatively, the expression level of any one or all of the genes in a biological sample may be compared to an NSCLC control level of the same gene(s).

Gene expression is increased or decreased 10%, 25%, 50% or more compared to the control level. Alternatively, gene expression is increased or decreased 1, 2, 5 or more fold compared to the control level. Expression is determined by detecting hybridization, e.g., on a chip or an array, of an NSCLC gene probe to a gene transcript of a patient-derived biological sample. The patient-derived biological sample may be any sample derived from a subject, e.g., a patient known to or suspected of having NSCLC. For example, the biological sample may be tissue containing sputum, blood, serum, plasma or lung cell.

The invention also provides a non-small cell lung cancer reference expression profile comprising a pattern of gene expression levels of two or more genes selected from the group of KIF11, GHSR1b, NTSR1, and FOXM1.

The invention also provides a kit comprising two or more detection reagents which detects the expression of one or more of genes selected from the group of KIF11, GHSR1b, NTSR1, and FOXM1 (e.g., via detecting mRNA and polypeptide). Also provided is an array of polynucleotides that binds to one or more of the genes selected from the group of KIF1, GHSR1b, NTSR1, and FOXM1. The kits of the invention may also comprise reagents used to detect the expression of KIF11 and KOC1 to be used for the prognosis of NSCLC. The invention also provides kits for the detection of compounds that regulate RNA transporting activity. The kits may comprise a cell expressing a KIF11 polypeptide, or functional equivalent, a KOC1 polypeptide, or functional equivalent, and RNA to be transported, and DCTN1. The kits of the invention may also be used to screen for compounds for treating or preventing NSCLC. The kits may comprise a KOC1 polypeptide, or functional equivalent, and an RNA that is bound by the KOC1 polypeptide or functional equivalent.

The invention further provides methods of identifying compounds that inhibit the expression level of an NSCLC-associated gene (KIF11, GHSR1b, NTSR1 or FOXM1) by contacting a test cell expressing an NSCLC-associated gene with a test compound and determining the expression level of the NSCLC-associated gene. The test cell may be an NSCLC cell. A decrease of the expression level compared to a normal control level of the gene indicates that the test compound is an inhibitor of the expression or function of the NSCLC-associated gene. Therefore, if a compound suppresses the expression level of KIF11, GHSR1b, NTSR1 or FOXM1 compared to a control level, the compound is expected to reduce a symptom of NSCLC.

Alternatively, the present invention provides a method of screening for a compound for treating or preventing NSCLC. The method includes contacting a polypeptide selected from the group of KIF11, GHSR1b, NTSR1, and FOXM1 with a test compound, and selecting the test compound that binds to or suppresses the biological activity of the polypeptide. The invention further provides a method of screening for a compound for treating or preventing NSCLC, which includes the steps of contacting a test compound with a cell that expresses KIF11, GHSR1b, NTSR1 or FOXM1 protein or introduced with a vector comprising the transcriptional regulatory region of KIF11, GHSR1b, NTSR1 or FOXM1 gene upstream of a reporter gene, and then selecting the test compound that reduces the expression level of the KIF11, GHSR1b, NTSR1 or FOXM1 protein or protein encoded by the reporter gene. According to these screening methods, the test compound that suppresses the biological activity or the expression level compared to a control level is expected to reduce a symptom of NSCLC. Furthermore, the present invention provides a method of screening for a compound for treating or preventing NSCLC wherein the binding between KIF11 and KOC1, or GHSR1b or NTSR1 and NMU is detected. Compounds that inhibit the binding between KIF11 and KOC1, or GHSR1b or NTSR1 and NMU are expected to reduce a symptom of NSCLC.

We detected a novel intra-cellular and inter-cellular RNA-transporting system in lung carcinomas, involving transactivation of KOC1 and KIF11. A complex of these two molecules in lung tumors was able to bind mRNAs encoding proteins known to function in intercellular adhesion, cancer-cell progression, and oncogenesis, and transport them to neighboring cells through ultrafine intercellular structures. In particular, evidence provided here shows that KOC1 binds to KIF11 at the RRM domain in the N-terminal region of KOC1. In addition, evidence provided here shows inhibition of their binding by dominant-negative KOC1 mutants effectively suppressed growth of NSCLC cells in vitro. For example, KOC1 fragments (or nucleic acids encoding them) comprising the RRM domains of KOC1 can be used as dominant negative fragments to suppress cell proliferation and thus treat cancer. Alternatively, the KOC1 fragment may comprise the ribonucleoprotein K-homologous (KH) domain.

The invention also provides methods of identifying polypeptides and other compounds that modulate RNA transport activity. For example, a polypeptide can be tested for RNA transporting activity by contacting the polypeptide with a KIF11 polypeptide or a functional equivalent thereof with an RNA that can be transported by KIF11 under conditions suitable for transportation of RNA. Alternatively, agents that modulate RNA transporting activity can be tested by contacting a test agent with a KIF11 polypeptide or a functional equivalent thereof with an RNA that can be transported by KIF11 under conditions suitable for transportation of RNA. Test agents useful for treating NSCLC by testing the agents for the ability to inhibit binding between a KOC1 polypeptide, or a functional equivalent, and an RNA that is bound by KOC1 or the complex of KOC1 and KIF11.

Immunohistochemical analysis of lung-cancer tissue microarrays demonstrated that transactivation of KOC1 and KIF11 was significantly associated with poor prognosis of lung-cancer patients.

Methods for treating or preventing NSCLC and compositions to be used for such methods are also provided. Therapeutic methods include a method of treating or preventing NSCLC in a subject by administering to the subject a composition of an antisense, short interfering RNA (siRNA) or a ribozyme that reduce the expression of KIF11, GHSR1b, NTSR1 or FOXM1 gene, or a composition comprising an antibody or fragment thereof that binds and suppresses the function of a polypeptide encoded by the gene. The compositions of the invention may also comprise a dominant negative KOC1 mutant (or nucleic acids encoding it) comprising a KOC1 fragment that contains one or more RRM domains and/or KH domains of KOC1.

The invention also includes vaccines and vaccination methods. For example, a method of treating or preventing NSCLC in a subject is carried out by administering to the subject a vaccine containing a polypeptide encoded by KIF11, GHSR1b, NTSR1 or FOXM1 gene, or an immunologically active fragment of the polypeptide. An immunologically active fragment is a polypeptide that is shorter in length than the full-length naturally-occurring protein and which induces an immune response upon introduction into the body. For example, an immunologically active fragment includes a polypeptide of at least 8 residues in length that stimulates an immune cell such as a T cell or a B cell in vivo. Immune cell stimulation can be measured by detecting cell proliferation, elaboration of cytokines (e.g., IL-2) or production of antibody.

Other therapeutic methods include those wherein a compound selected by the screening method of the present invention is administered.

Also included in the invention are double-stranded molecules that comprise a sense strand and an antisense strand. The sense strand comprises a ribonucleotide sequence corresponding to a target sequence comprised within the mRNA of a KIF11, GHSR1b, NTSR1 or FOXM1 gene, and the antisense strand is a complementary sequence to the sense strand. Such double-stranded molecules of the present invention can be used as siRNAs against KIF11, GHSR1b, NTSR1 or FOXM1 gene. Furthermore, the present invention relates to vectors encoding the double-stranded molecules of the present invention.

The present application also provides a composition for treating and/or preventing NSCLC using any of the antisense polynucleotides or siRNAs against KIF11, GHSR1b, NTSR1 or FOXM1 gene, or an antibody that binds to a polypeptide encoded by KIF11, GHSR1b, NTSR1 or FOXM1 gene. Other compositions include those that contain a compound selected by the screening method of the present invention as an active ingredient.

It is to be understood that both the foregoing summary of the invention and the following detailed description are of a preferred embodiment, and not restrictive of the invention or other alternate embodiments of the invention.

BRIEF DESCRIPTION OF THE DRAWINGS

FIG. 8 shows the relationship between NMU and GHSR1b/NTSR1.

from the regulatory subunits (R) is resulting in the activation of downstream FOXM1 gene and/or related target genes.

DETAILED DESCRIPTION OF THE INVENTION

The words "a", "an" and "the" as used herein mean "at least one" unless otherwise specifically indicated. The terms "protein" and "polypeptide" are used interchangeably. Furthermore, the terms "gene", "polynucleotide", and "nucleic acids" are used interchangeably unless otherwise specifically indicated.

To investigate the mechanisms of lung carcinogenesis and identify genes that might be useful as diagnostic markers or targets for development of new molecular therapies, genes specifically up-regulated in non-small cell lung cancers (NSCLC) were searched by means of cDNA microarray. Through the analysis, a couple of candidate therapeutic target genes were identified. Two genes, KH domain containing protein over-expressed in cancer (KOC1) and neuromedin U (NMU) were abundantly expressed in clinical NSCLC samples as well as NSCLC cell lines examined. However, their expression was hardly detectable in corresponding non-cancerous lung tissue. The growth of NSCLC cells that over-expressed endogenous NMU was significantly inhibited by anti-NMU antibody. Furthermore, the treatment of NSCLC cells with siRNA against KOC1 and/or NMU suppressed the expression of the gene and resulted in growth inhibition of the NSCLC cells. Furthermore, KOC1 was identified to bind to kinesin family member 11 (KIF11) of the cancer cells, whereas NMU bound to the neuropeptide G protein-coupled receptors (GPCRs), growth hormone secretagogue receptor 1b (GHSR1b) and neurotensin receptor 1 (NTSR1). NMU ligand-receptor system was identified to activate Homo sapiens forkhead box M1 (FOXM1). Interestingly, GHSR1b, NTSR1, FOXM1, and KIF11 were all specifically over-expressed in NSCLC cells.

Figure 12:
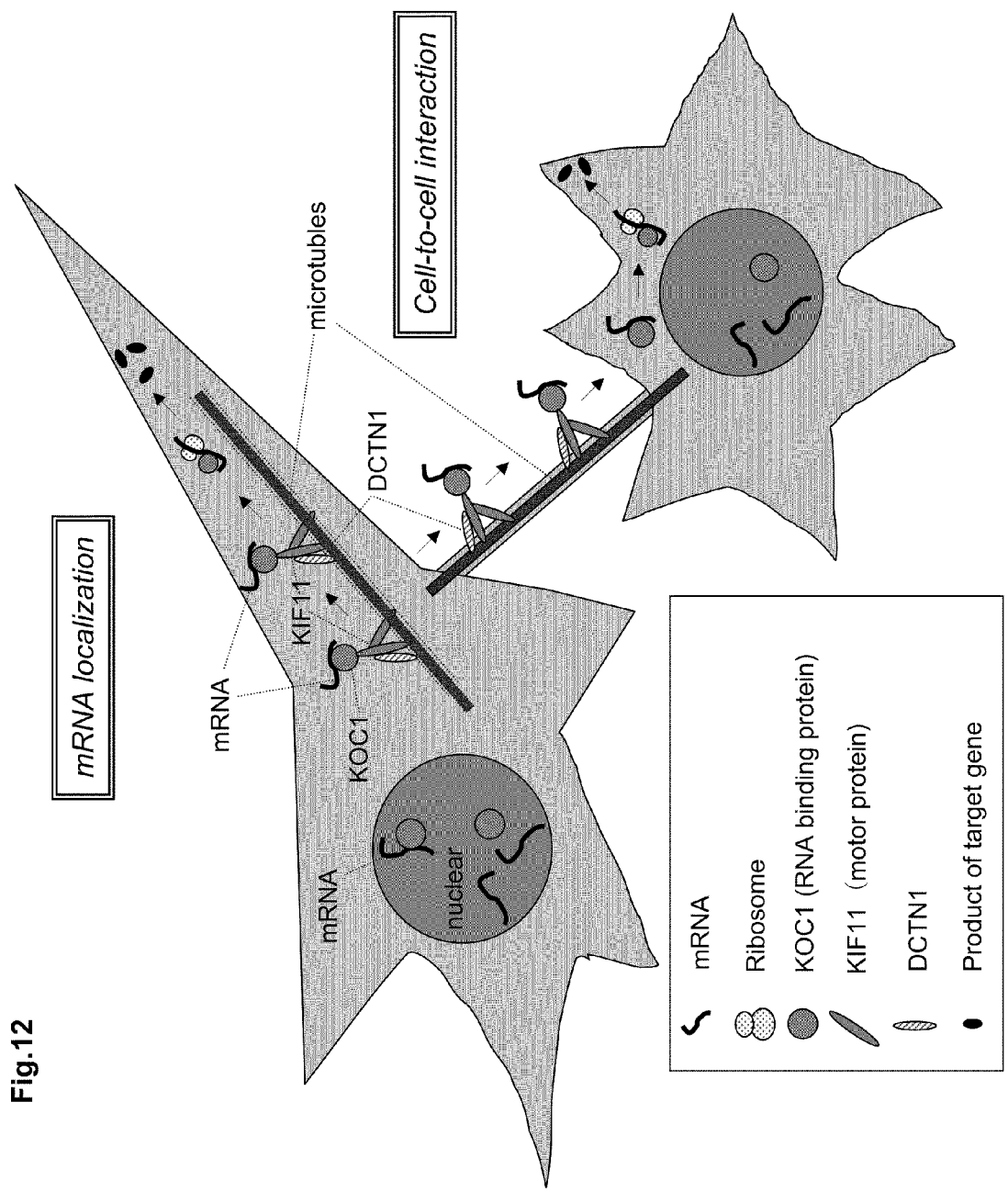
FIG. 12 is schematic model for the mechanism of intracellular and cell-to-cell mRNA transport by KOC1-KIF11-DCTN1 complexes on microtubules. The KOC1 ribonucleoprotein complex, including KIF11 motor-protein and DCTN1, transports KOC1-associated mRNAs through the structure of microtubules within or between mammalian somatic cells. This model implies that proliferating cancer-cells may communicate actively by engaging this molecular complex in a system that transports mRNAs critical for cancer growth or progression from one cell to another

RNA binding protein KOC1 and microtubles motor protein KIF11 is required for the localization of some kinds of mRNA needed in embryogenesis and carcinogenesis (FIG. 12). As previously reported by the present inventors, treatment of NSCLC cells with specific siRNA to reduce expression of KOC1 resulted in growth suppression. In this study, KIF11 was demonstrated to associate with KOC1 in NSCLC cells and to be the target for the growth-promoting effect of KOC1 in lung tumors. The present inventors revealed that KOC1 not only co-localized with KIF11 in human normal tissues, NSCLCs, and cell lines, but also directly interacted with KIF11 in NSCLC cells in vitro, and that the treatment of NSCLC cells with siRNAs for KIF11 reduced its expression and led to growth suppression. The results show that KOC1-KIF11 signaling affects growth of NSCLC cells. As shown below, dominant negative fragments of KOC1 (e.g., those containing the RRM domains) can be used to inhibit proliferation of cancer cells. By expression analysis, increased expression of KOC1 and KIF11 was detected in the majority of NSCLC samples, but not in normal lung tissues. Since most of the clinical NSCLC samples used for the present analysis were at an early and operable stage, KOC1 and KIF11 can be conveniently used as a biomarker for diagnosing early-stage lung cancer, in combination with fiberscopic transbronchial biopsy (TBB) or sputum cytology.

Therefore, KOC1 and KIF11 are essential for an oncogenic pathway in NSCLCs. The data reported here provide evidence for designing new anti-cancer drugs, specific for lung cancer, which target the KOC1-KIF11 pathway. They also show that siRNAs can be used to treat chemotherapy-resistant, advanced lung cancers.

A significant increase in the sub-G1 fraction of NSCLC cells transfected with siRNA-NMU suggested that blocking the autocrine NMU-signaling pathway could induce apoptosis. The present inventors also found other evidence supporting the significance of this pathway in carcinogenesis; e.g., addition of NMU into the medium promoted the growth of COS-7 cells in a dose-dependent manner, and addition of anti-NMU antibody into the culture medium inhibited this NMU-enhanced cell growth, possibly by neutralizing NMU activity. Moreover, the growth of NSCLC cells that endogenously over-expressed NMU was significantly inhibited by anti-NMU antibody. The expression of NMU also resulted in significant promotion of COS-7 cell invasion in in vitro assays. These results show that NMU is an important growth factor for NSCLC and is associated with cancer cell invasion, functioning in an autocrine manner, and that screening molecules targeting the NMU-receptor growth-promoting pathway is a useful therapeutic approach for treating NSCLCs. By immunohistochemical analysis, increased expression of NMU protein was detected in the majority of NSCLC (SCC, ADC, LCC, and BAC) and SCLC samples, but not in normal lung tissues. Since NMU is a secreted protein and most of the clinical NSCLC samples used for the present analysis were at an early and operable stage, NMU can be conveniently used as a biomarker for diagnosis of early-stage lung cancer, in combination with fiberscopic transbronchial biopsy (TBB), sputum cytology, or blood tests.

Figure 14:
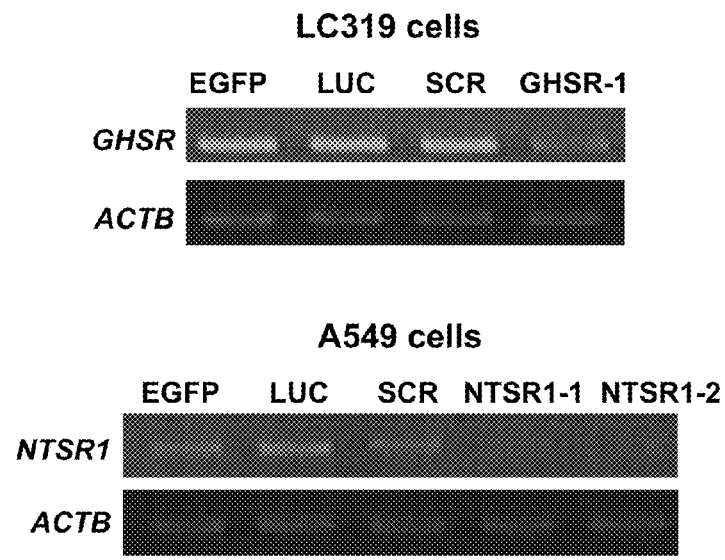
FIG. 14 shows the effect of siRNAs on cells.
(a) depicts the inhibition on the growth of NSCLC cells by siRNAs against GHSR1b and NTSR1. Expression of GHSR or NTSR1 in response to specific siRNAs (si-GHSR or si-NTSR1) or control siRNAs (EGFP, LUC, SCR) in A549 and LC319 cells were analyzed by semiquantitative RT-PCR.
(b) depicts the result of triplicate MTT assays evaluating viability of A549 or LC319 cells in response to si-GHSR, NTSR1, EGFP, LUC, or SCR.
Figure 14:
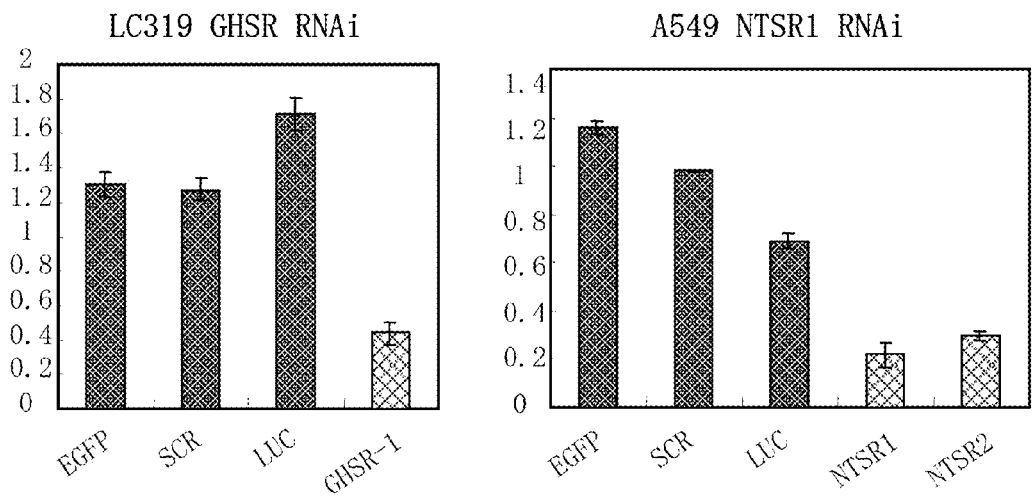

Two receptors, NMU1R (FM3/GPR66) and NMU2R (FM4) are known to interact with NMU. The results presented here, however, indicated that these two known receptors were not the targets for the autocrine NMU-signaling pathway in NSCLCs; instead, GHSR1b and NTSR1 proved to be the targets for the growth-promoting effect of NMU in lung tumors. The present inventors revealed that NMU-25 bound to these receptors on the cell surface, and that treatment of NSCLC cells with siRNAs for GHSR1b or NTSR1 reduced expression of the receptors and led to apoptosis. The results show that NMU affects growth of NSCLC cells by acting through GHSR1b and/or NTSR1 (FIG. 14). GHSR is a known receptor of Ghrelin (GHRL), a recently identified 28-amino-acid peptide capable of stimulating release of pituitary growth hormone and appetite in humans (Lambert, P. D. et al., Proc. Natl. Acad. Sci. 98: 4652-4657 (2001); Petersenn, S. et al., Endocrinology 142: 2649-2659 (2001); Kim K. et al., Clin. Endocrinol. 54: 705-860 (2001); Kojima, M. et al., Nature 402: 656-660 (1999)). Of the two transcripts known to be receptors for GHRL, GHSR1a and GHSR1b, over-expression of only GHSR1b was detected in NSCLC tissues and cell lines. Since GHRL was not expressed in the NSCLCs examined, GHSR1b was suspected to have a growth-promoting function in lung tumors through binding to NMU, but not to GHRL.

NTSR1 is one of three receptors of neurotensin (NTS), a brain and gastrointestinal peptide that fulfills many central and peripheral functions (Heasley, L. E. Oncogene 20: 1563-1569 (2001)). NTS modulates transmission of dopamine and secretion of pituitary hormones, and exerts hypothermic and analgesic effects in the brain while it functions as a peripheral hormone in the digestive tract and cardiovascular system. Others have reported that NTS is produced and secreted in several human cancers, including small-cell lung cancers (SCLC) (Heasley, L. E. Oncogene 20:1563-1569 (2001)). The expression of NTS was detected in four of the 15 NSCLC cell lines that were examined in the present invention (FIG. 13a), but the expression pattern of NTS was not necessarily concordant with that of NMU or NTSR1. Therefore NTS may, along with NMU, contribute to the growth of NSCLC through NTSR1 or other receptor(s) in a small subset of NSCLCs. In the present experiments the majority of the cancer cell lines and clinical NSCLCs that expressed NMU also expressed GHSR1b and/or NTSR1, indicating that these ligand-receptor interactions were involved in a pathway that is central to the growth-promoting activity of NMU in NSCLCs.

NMU signaling pathway affects the growth promotion of lung-cancer cells by transactivating a set of downstream genes including FOXM1. FOXM1 was known to be overexpressed in several types of human cancers (Teh, M. T. et al., *Cancer Res.* 62, 4773-4780; van den Boom, J. et al., (2003). *Am. J. Pathol.* 163, 1033-1043; Kalinichenko, V. V. et al., (2004). *Genes. Dev.* 18, 830-850). The "forkhead" gene family, originally identified in *Drosophila*, comprises transcription factors with a conserved 100-amino acid DNA-binding motif, and has been shown to play important roles in regulating the expression of genes involved in cell growth, proliferation, differentiation, longevity, and transformation. Cotransfection assays in the human hepatoma HepG2 cell line demonstrated that FOXM1 protein stimulated expression of both the cyclin B1 (CCNB1) and cyclin D1 (CCND1) (Wang, X. et al., (2002). *Proc. Nat. Acad. Sci.* 99, 16881-16886.), suggesting that these cyclin genes are direct FOXM1 transcription targets and that FOXM1 controls the transcription network of genes that are essential for cell division and exit from mitosis. It should be noted that we observed activation of CCNB1 in the majority of a series of NSCLC and its good concordance of the expression to FOXM1 (data not shown). The promotion of cell growth in NSCLC cells by NMU might reflect transactivation of FOXM1, which would affect the function of those molecular pathways in consequence. Therefore, NMU, two newly revealed receptors for this molecule, GHSR1b and NTSR1, and their downstream gene FOXM1 are involved in an autocrine growth-promoting pathway in NSCLCs. The data reported here provide the basis for designing new anti-cancer drugs, specific for lung cancer, that target the NMU-GHSR1b/NTSR1-FOXM1 pathway. They also show that siRNAs that interfere with this pathway can be used to treat chemotherapy-resistant, advanced lung cancers.

These data show that KOC1-KIF11 signaling pathway is frequently up-regulated in lung carcinogenesis, and that NMU an important autocrine growth factor for NSCLC, acting through GHSR1b and NTSR1 receptor molecules. Thus, selective suppression of components of these complexes can suppress the development and/or progression of lung carcinogenesis and targeting these pathways are conveniently used in therapeutic and diagnostic strategies for the treatment of lung-cancer patients.

Diagnosing Non-Small Cell Lung Cancer (NSCLC)

By measuring the expression level of KIF11, GHSR1b, NTSR1 or FOXM1 gene in a biological derived from a subject, the occurrence of NSCLC or a predisposition to develop NSCLC in the subject can be determined. The invention involves determining (e.g., measuring) the expression level of at least one, and up to all of KIF11, GHSR1b, NTSR1, and FOXM1 gene in the biological sample.

According to the present invention, a gene transcript of NSCLC-associated gene, KIF11, GHSR1b, NTSR1 or FOXM1, is detected for determining the expression level of the gene. The expression level of a gene can be detected by detecting the expression products of the gene, including both transcriptional and translational products, such as mRNA and proteins. Based on the sequence information provided by the GenBank™ database entries for the known sequences, KIF11 (NM_004523), GHSR1b (NM_004122), NTSR1 (NM_002531), and FOXM1 (No. NM_202003) genes can be detected and measured using techniques well known to one of ordinary skill in the art. The nucleotide sequences of the KIF11, GHSR1b, NTSR1, and FOXM1 genes are described as SEQ ID NOs: 1, 3, 5, and 106, respectively, and the amino acid sequences of the proteins encoded by the genes are described as SEQ ID NOs: 2, 4, 6, and 107.

For example, sequences within the sequence database entries corresponding to KIF11, GHSR1b, NTSR1 or FOXM1 gene can be used to construct probes for detecting their mRNAs by, e.g., Northern blot hybridization analysis. The hybridization of the probe to a gene transcript in a subject biological sample can be also carried out on a DNA array. The use of an array is preferred for detecting the expression level of a plurality of the NSC genes (KIF11, GHSR1b, NTSR1, and FOXM1). As another example, the sequences can be used to construct primers for specifically amplifying KIF11, GHSR1b, NTSR1 or FOXM1 gene in, e.g., amplification-based detection methods such as reverse-transcription based polymerase chain reaction (RT-PCR). Furthermore, the expression level of KIF11, GHSR1b, NTSR1 or FOXM1 gene can be analyzed based on the quantity of the expressed proteins encoded by the gene. A method for determining the quantity of the expressed protein includes immunoassay methods. Alternatively, the expression level of KIF11, GHSR1b, NTSR1 or FOXM1 gene can also be determined based on the biological activity of the expressed protein encoded by the gene. For example, a protein encoded by KIF11 gene is known to bind to KOC1, and thus the expression level of the gene can be detected by measuring the binding ability to KOC1 due to the expressed protein. Furthermore, KIF11 protein is known to have a cell proliferating activity. Therefore, the expression level of KIF11 gene can be determined using such cell proliferating activity as an index. On the other hand GHSR1b and NTSR1 proteins are known to bind to NMU, and also have a cell proliferating activity. Thus, similarly to KIF1, the expression levels of GHSR1b and NTSR1 genes can be detected by measuring their binding ability to NMU or cell proliferating activity due to the expressed protein.

Any biological materials may be used as the biological sample for determining the expression level so long as any of the KIF11, GHSR1b, NTSR1, and FOXM1 genes can be detected in the sample and includes test cell populations (i.e., subject derived tissue sample). Preferably, the biological sample comprises a lung cell (a cell obtained from the lung). Gene expression may also be measured in blood, serum or other bodily fluids such as sputum. Furthermore, the test sample may be cells purified from a tissue.

The subject diagnosed for NSCLC according to the method is preferably a mammal and includes human, non-human primate, mouse, rat, dog, cat, horse and cow.

The expression level of one or more of KIF11, GHSR1b, NTSR1 or FOXM1 gene in the biological sample is compared to the expression level(s) of the same genes in a reference sample. The reference sample includes one or more cells with known parameters, i.e., cancerous or non-cancerous. The reference sample should be derived from a tissue type similar to that of the test sample. Alternatively, the control expression level may be determined based on a database of molecular information derived from cells for which the assayed parameter or condition is known.

Whether or not a pattern of the gene expression levels in a biological sample indicates the presence of NSCLC depends upon the composition of the reference cell population. For example, when the reference cell population is composed of non-cancerous cells, a similar gene expression level in the test biological sample to that of the reference indicates that the test biological sample is non-cancerous. On the other hand, when the reference cell population is composed of cancerous cells, a similar gene expression profile in the biological sample to that of the reference indicates that the test biological sample includes cancerous cells.

The test biological sample may be compared to multiple reference samples. Each of the multiple reference samples may differ in the known parameter. Thus, a test sample may be compared to a reference sample known to contain, e.g., NSCLC cells, and at the same time to a second reference sample known to contain, e.g., non-NSCLC cells (normal cells).

According to the invention, the expression of one or more of the NSCLC-associated genes, KIF11, GHSR1b, NTSR1, and FOXM1, is determined in the biological sample and compared to the normal control level of the same gene. The phrase "normal control level" refers to an expression profile of KIF11, GHSR1b, NTSR1 or FOXM1 gene typically found in a biological sample derived from a population not suffering from NSCLC. The expression level of KIF11, GHSR1b, NTSR1 or FOXM1 gene in the biological samples from a control and test subjects may be determined at the same time or the normal control level may be determined by a statistical method based on the results obtained by analyzing the expression level of the gene in samples previously collected from a control group. An increase of the expression level of KIF11, GHSR1b, NTSR1 or FOXM1 gene in the biological sample derived from a patient derived tissue sample indicates that the subject is suffering from or is at risk of developing NSCLC.

An expression level of KIF11, GHSR1b, NTSR1 or FOXM1 gene in a test biological sample can be considered altered when the expression level differs from that of the reference by more than 1.0, 1.5, 2.0, 5.0, 10.0 or more fold. Alternatively, an expression level of KIF11, GHSR1b, NTSR1 or FOXM1 gene in a test biological sample can be considered altered, when the expression level is increased or decreased to that of the reference at least 50%, 60%, 80%, 90% or more.

The difference in gene expression between the test sample and a reference sample may be normalized to a control, e.g., housekeeping gene. For example, a control polynucleotide includes those whose expression levels are known not to differ between the cancerous and non-cancerous cells. The expression levels of the control polynucleotide in the test and reference samples can be used to normalize the expression levels detected for KIF11, GHSR1b, NTSR1 or FOXM1 gene. The control genes to be used in the present invention include β-actin, glyceraldehyde 3-phosphate dehydrogenase and ribosomal protein P1.

The differentially expressed KIF11, GHSR1b, NTSR1 or FOXM1 gene identified herein also allow for monitoring the course of treatment of NSCLC. In this method, a test biological sample is provided from a subject undergoing treatment for NSCLC. If desired, multiple test biological samples are obtained from the subject at various time points before, during or after the treatment. The expression of one or more of KIF11, GHSR1b, NTSR1 or FOXM1 gene in the sample is then determined and compared to a reference sample with a known state of NSCLC that has not been exposed to the treatment.

If the reference sample contains no NSCLC cells, a similarity in the expression level of KIF11, GHSR1b, NTSR1 or FOXM1 gene in the test biological sample and the reference sample indicates the efficaciousness of the treatment. However, a difference in the expression level of KIF11, GHSR1b, NTSR1 or FOXM1 gene in the test and the reference samples indicates a less favorable clinical outcome or prognosis. In particular, increased expression of KOC1, KIF11, or KOC1 in combination with increased expression of KIF11 is significantly associated with poor prognosis.

The term "efficacious" refers that the treatment leads to a reduction in the expression of a pathologically up-regulated gene (including the present indicator genes, KIF11, GHSR1b, NTSR1, and FOXM1), or a decrease in size, prevalence or metastatic potential of NSCLC in a subject. When a treatment is applied prophylactically, "efficacious" means that the treatment retards or prevents occurrence of NSCLC or alleviates a clinical symptom of NSCLC. The assessment of NSCLC can be made using standard clinical protocols. Furthermore, the efficaciousness of a treatment is determined in association with any known method for diagnosing or treating NSCLC. For example, NSCLC is diagnosed histopathologically or by identifying symptomatic anomalies such as chronic cough, hoarseness, coughing up blood, weight loss, loss of appetite, shortness of breath, wheezing, repeated bouts of bronchitis or pneumonia and chest pain.

Moreover, the present method for diagnosing NSCLC may also be applied for assessing the prognosis of a patient with the cancer by comparing the expression level of KIF1, KOC1, GHSR1b, NTSR1, FOXM1 gene, or a combination thereof (e.g., KOC1 and KIF11) in the patient-derived biological sample. Alternatively, the expression level of the gene(s) in the biological sample may be measured over a spectrum of disease stages to assess the prognosis of the patient.

An increase in the expression level of KIF11, KOC1, GHSR1b, NTSR1 or FOXM1 gene compared to a normal control level indicates less favorable prognosis. A similarity in the expression level of KIF11, KOC1, GHSR1b, NTSR1 or FOXM1 gene compared to a normal control level indicates a more favorable prognosis of the patient. Preferably, the prognosis of a subject can be assessed by comparing the expression profile of KIF11, KOC1, GHSR1b, NTSR1 or FOXM1 gene. In some embodiments, expression levels of KIF11 and KOC1 are determined.

Expression Profile

The invention also provides an NSCLC reference expression profile comprising a pattern of gene expression levels of two or more of KIF11, KOC1, GHSR1b, NTSR1 and FOXM1 genes. The expression profile serves as a control for the diagnosis of NSCLC or predisposition for developing the disease, monitoring the course of treatment and assessing prognosis of a subject with the disease.

Kits of the Invention

The invention also provides a kit comprising two or more detection reagents, e.g., a nucleic acid that specifically binds to or identifies one or more of KIF11, KOC1, GHSR1b, NTSR1 and FOXM1 genes. Such nucleic acids specifically binding to or identifying one or more of KIF11, KOC1, GHSR1b, NTSR1 and FOXM1 genes are exemplified by oligonucleotide sequences that are complementary to a portion of KIF11, KOC1, GHSR1b, NTSR1 or FOXM1 polynucleotides or antibodies which bind to polypeptides encoded by the KIF11, KOC1, GHSR1b, NTSR1 or FOXM1 gene. The reagents are packaged together in the form of a kit. The reagents, such as a nucleic acid or antibody (either bound to a solid matrix or packaged separately with reagents for binding them to the matrix), a control reagent (positive and/or negative) and/or a means of detection of the nucleic acid or antibody are preferably packaged in separate containers. Instructions (e.g., written, tape, VCR, CD-ROM, etc.) for carrying out the assay may be included in the kit. The assay format of the kit may be Northern hybridization or sandwich ELISA known in the art.

For example, a detection reagent is immobilized on a solid matrix such as a porous strip to form at least one detection site. The measurement or detection region of the porous strip may include a plurality of detection sites, each detection site containing a detection reagent. A test strip may also contain sites for negative and/or positive controls. Alternatively, control site(s) is located on a separate strip from the test strip. Optionally, the different detection sites may contain different amounts of immobilized reagents, i.e., a higher amount in the first detection site and lesser amounts in subsequent sites. Upon the addition of a test biological sample, the number of sites displaying a detectable signal provides a quantitative indication of the amount of KIF11, GHSR1b, NTSR1 or FOXM1 gene, or polypeptides encoded by the gene present in the sample. The detection sites may be configured in any suitably detectable shape and are typically in the shape of a bar or dot spanning the width of a teststrip.

Alternatively, the kit contains a nucleic acid substrate array comprising two or more of the KIF11, GHSR1b, NTSR1, and FOXM1 gene sequences. The expression of 2 or 3 of the genes represented by KIF11, GHSR1b, NTSR1, and FOXM1 genes are identified by virtue of the level of binding to an array test strip or chip. The substrate array can be on, e.g., a solid substrate, e.g., a "chip" as described in U.S. Pat. No. 5,744,305.

In some embodiments, the kits can be used for predicting an NSCLC prognosis. The kits in these embodiments, can comprise a reagent for detecting mRNA encoding the amino acid sequence of KIF11 or KOC1, a reagent for detecting the proteins or reagents for detecting the biological activity of the KIF11 or KOC1 protein.

The invention also provides kits for the detection of a compound that regulates RNA transporting activity. The kits may comprise a cell expressing a KIF11 polypeptide, or functional equivalent, a KOC1 polypeptide, or functional equivalent, and RNA to be transported, and DCTN1.

The kits of the invention may also be used to screen for compounds for treating or preventing NSCLC. The kits may comprise a KOC1 polypeptide, or functional equivalent, and an RNA that is bound by the KOC1 polypeptide or functional equivalent. In the present invention, any RNA transportable with RNA transporter activity of KOC1-KIF11 complex can be used as the RNA to be transported. Prefer RNA can be selected from transcripts of genes shown in table 2, or fragment thereof. An RNA to be transported may also be labeled for detecting RNA transporter activity. Furthermore, in the present invention, KOC1 and KIF11 polypeptide or functional equivalent thereof is expressed as fusion protein with signal generating protein for observation by microscopy or cell imaging systems. For example, ECFP, EYFP, and EGFP may be used for signal generating protein.

Array and Pluralities

The invention also includes a nucleic acid substrate array comprising one or more of the KIF11, GHSR1b, NTSR1, and FOXM1 genes. The nucleic acids on the array specifically correspond to one or more polynucleotide sequences represented by KIF11, GHSR1b, NTSR1, and FOXM1 genes. The expression level of 2, 3 or 4 of the KIF11, GHSR1b, NTSR1, and FOXM1 genes is identified by detecting the binding of nucleic acid to the array.

The invention also includes an isolated plurality (i.e., a mixture of two or more nucleic acids) of nucleic acids. The nucleic acids are in a liquid phase or a solid phase, e.g., immobilized on a solid support such as a nitrocellulose membrane. The plurality includes one or more of the polynucleotides represented by KIF11, GHSR1b, NTSR1, and FOXM1 genes. According to a further embodiment of the present invention, the plurality includes 2, 3, or 4 of the polynucleotides represented by KIF11, GHSR1b, NTSR1, and FOXM1 genes.

Chips

The DNA chip is a device that is convenient to compare the expression levels of a number of genes at the same time. DNA chip-based expression profiling can be carried out, for example, by the method as disclosed in "Microarray Biochip Technology" (Mark Schena, Eaton Publishing, 2000), etc.

A DNA chip comprises immobilized high-density probes to detect a number of genes. Thus, the expression levels of many genes can be estimated at the same time by a single-round analysis. Namely, the expression profile of a specimen can be determined with a DNA chip. The DNA chip-based method of the present invention comprises the following steps of:

(1) synthesizing aRNAs or cDNAs corresponding to the marker genes;
(2) hybridizing the aRNAs or cDNAs with probes for marker genes; and
(3) detecting the aRNA or cDNA hybridizing with the probes and quantifying the amount of mRNA thereof.

The term "aRNA" refers to RNA transcribed from a template cDNA with RNA polymerase. An aRNA transcription kit for DNA chip-based expression profiling is commercially available. With such a kit, aRNA can be synthesized from T7 promoter-attached cDNA as a template using T7 RNA polymerase. On the other hand, by PCR using random primer, cDNA can be amplified using as a template a cDNA synthesized from mRNA.

Alternatively, the DNA chip comprises probes, which have been spotted thereon, to detect the marker genes of the present invention (KIF11, GHSR1b, NTSR1 or FOXM1 gene). There is no limitation on the number of marker genes spotted on the DNA chip, and 1, 2, 3 or all of the genes, KIF11, GHSR1b, NTSR1, and FOXM1, may be used. Any other genes as well as the marker genes can be spotted on the DNA chip. For example, a probe for a gene whose expression level is hardly altered may be spotted on the DNA chip. Such a gene can be used to normalize assay results when the assay results are intended to be compared between multiple chips or between different assays.

A probe is designed for each marker gene selected, and spotted on a DNA chip. Such a probe may be, for example, an oligonucleotide comprising 5-50 nucleotide residues. A method for synthesizing such oligonucleotides on a DNA chip is known to those skilled in the art. Longer DNAs can be synthesized by PCR or chemically. A method for spotting long DNA, which is synthesized by PCR or the like, onto a glass slide is also known to those skilled in the art. A DNA chip that is obtained by the method as described above can be used for diagnosing NSCLC according to the present invention.

The prepared DNA chip is contacted with aRNA, followed by the detection of hybridization between the probe and aRNA. The aRNA can be previously labeled with a fluorescent dye. A fluorescent dye such as Cy3 (red) and Cy5 (green) can be used to label an aRNA. aRNAs from a subject and a control are labeled with different fluorescent dyes, respectively. The difference in the expression level between the two can be estimated based on a difference in the signal intensity. The signal of fluorescent dye on the DNA chip can be detected by a scanner and analyzed using a special program. For example, the Suite from Affymetrix is a software package for DNA chip analysis.

Identifying Compounds that Inhibit NSCLC-Associated Gene Expression

A compound that inhibits the expression or activity of a target NSCLC-associated gene (KIF11, GHSR1b, NTSR1 or FOXM1 gene) is identified by contacting a test cell expressing the NSCLC-associated gene with a test compound and determining the expression level or activity of the NSCLC-associated gene. A decrease in expression compared to the normal control level indicates that the compound is an inhibitor of the NSCLC-associated gene. Such compounds identified according to the method are useful for inhibiting NSCLC.

The test cell may be a population of cells and includes any cells as long as the cell expresses the target NSCLC-associated gene(s). For example, the test cell may be an immortalized cell line derived from an NSCLC cell. Alternatively, the test cell may be a cell transfected with any of the KIF11, GHSR1b, NTSR1, and FOXM1 genes, or which has been transfected with the regulatory sequence (e.g., promoter) of any of the genes that is operably linked to a reporter gene.

Screening Compounds

Using KIF11, GHSR1b, NTSR1 or FOXM1 gene, proteins encoded by the gene or transcriptional regulatory region of the gene, compounds can be screened that alter the expression of the gene or biological activity of a polypeptide encoded by the gene. Such compounds are expected to serve as pharmaceuticals for treating or preventing NSCLC.

Therefore, the present invention provides a method of screening for a compound for treating or preventing NSCLC using the polypeptide of the present invention. An embodiment of this screening method comprises the steps of: (a) contacting a test compound with a polypeptide encoded by KIF11, GHSR1b, NTSR1 or FOXM1 gene; (b) detecting the binding activity between the polypeptide of the present invention and the test compound; and (c) selecting the compound that binds to the polypeptide.

As explained in more detail below, KOC1 and KIF11 form a complex that has RNA transporting activity. Thus, the present invention also provides methods of identifying polypeptides and other compounds that modulate RNA transport activity. For example, a polypeptide can be tested for RNA transporting activity by contacting a KIF11 polypeptide (SEQ ID NO: 2) or a functional equivalent thereof with an RNA that can be transported by KIF11 under conditions suitable for transportation of RNA. The level of RNA transported can be measured using well known techniques, such as by RNA immunoprecipitation, as described in detail below.

A functional equivalent of a KIF11 polypeptide is a polypeptide that has a biological activity equivalent to a polypeptide consisting of the amino acid sequence of SEQ ID NO: 2 and, for example, comprising the amino acid sequence of SEQ ID NO: 2 (KIF11), wherein one or more amino acids (usually less than five) are substituted, deleted, or inserted. Alternatively, the polypeptide may be one that comprises an amino acid sequence having at least about 80% homology (also referred to as sequence identity) to SEQ ID NO: 2. In other embodiments, the polypeptide can be encoded by a polynucleotide that hybridizes under stringent conditions (as defined below) to a polynucleotide consisting of the nucleotide sequence of SEQ ID NO: 1.

In some embodiments, the KIF11 polypeptide or functional equivalent is contacted with a KOC1 polypeptide or functional equivalent thereof. A functional equivalent of a KOC1 polypeptide is a polypeptide that has a biological activity equivalent to a polypeptide consisting of the amino acid sequence of SEQ ID NO: 105 and, for example, comprising the amino acid sequence of SEQ ID NO: 105, wherein one or more amino acids (usually less than five) are substituted, deleted, or inserted. Alternatively, the polypeptide may be one that comprises an amino acid sequence having at least about 80% homology (also referred to as sequence identity) to SEQ ID NO: 105. In other embodiments, the polypeptide can be encoded by a polynucleotide that hybridizes under stringent conditions (as defined below) to a polynucleotide consisting of the nucleotide sequence of SEQ ID NO: 104. In some embodiments, a functional equivalent comprises at least one RRM or KH domain.

The invention also provides methods of identifying agents that modulate RNA transporting activity. In these methods, an agent suspected of modulating RNA transporting activity with a KIF11 polypeptide or functional equivalent. The level of transported RNA is detected and compared to the level in a control in the absence of the agent.

The polypeptide to be used for the screening may be a recombinant polypeptide or a protein derived from the nature or a partial peptide thereof. The polypeptide to be contacted with a test compound can be, for example, a purified polypeptide, a soluble protein, a form bound to a carrier or a fusion protein fused with other polypeptides.

As a method of screening for proteins that bind to KIF11, GHSR1b, NTSR1 or FOXM1 polypeptide, many methods well known by a person skilled in the art can be used. Such a screening can be conducted by, for example, immunoprecipitation method using methods well known in the art. The proteins of the invention can be recombinantly produced using standard procedures. For example, a gene encoding any of the KIF11, GHSR1b, NTSR1, and FOXM1 polypeptides is expressed in animal cells by inserting the gene into an expression vector for foreign genes, such as pSV2neo, pcDNA I, pcDNA3.1, pCAGGS and pCD8. The promoter to be used for the expression may be any promoter that can be used commonly and include, for example, the SV40 early promoter (Rigby in Williamson (ed.), *Genetic Engineering*, vol. 3. Academic Press, London, 83-141 (1982)), the EF-α promoter (Kim et al., *Gene* 91: 217-23 (1990)), the CAG promoter (Niwa et al., *Gene* 108: 193-200 (1991)), the RSV LTR promoter (Cullen, *Methods in Enzymology* 152: 684-704 (1987)) the SRα promoter (Takebe et al., *Mol Cell Biol* 8: 466 (1988)), the CMV immediate early promoter (Seed and Aruffo, *Proc. Natl Acad Sci USA* 84: 3365-9 (1987)), the SV40 late promoter (Gheysen and Fiers, *J Mol Appl Genet* 1: 385-94 (1982)), the Adenovirus late promoter (Kaufman et al., *Mol Cell Biol* 9: 946 (1989)), the HSV TK promoter and so on. The introduction of the gene into animal cells to express a foreign gene can be performed according to any methods, for example, the electroporation method (Chu et al., *Nucleic Acids Res* 15: 1311-26 (1987)), the calcium phosphate method (Chen and Okayama, *Mol Cell Biol* 7: 2745-52 (1987)), the DEAE dextran method (Lopata et al., *Nucleic Acids Res* 12: 5707-17 (1984); Sussman and Milman, *Mol Cell Biol* 4: 1642-3 (1985)), the Lipofectin method (Derijard, *B Cell* 7: 1025-37 (1994); Lamb et al., *Nature Genetics* 5: 22-30 (1993): Rabindran et al., *Science* 259: 230-4 (1993)), and so on. The NSC polypeptide can also be expressed as a fusion protein comprising a recognition site (epitope) of a monoclonal antibody by introducing the epitope of the monoclonal antibody, whose specificity has been revealed, to the N- or C-terminus of the polypeptide. A commercially available epitope-antibody system can be used (*Experimental Medicine* 13: 85-90 (1995)). Vectors which can express a fusion protein with, for example, β-galactosidase, maltose binding protein, glutathione S-transferase, green florescence protein (GFP), and so on, by the use of its multiple cloning sites are commercially available.

A fusion protein prepared by introducing only small epitopes consisting of several to a dozen amino acids so as not to change the property of the original polypeptide by the fusion is also reported. Epitopes, such as polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage) and such, and monoclonal antibodies recognizing them can be used as the epitope-antibody system for screening proteins binding to the KIF11, GHSR1b, NTSR1 or FOXM1 polypeptide (*Experimental Medicine* 13: 85-90 (1995)).

In immunoprecipitation, an immune complex is formed by adding these antibodies to cell lysate prepared using an appropriate detergent. The immune complex consists of the KIF11, GHSR1b, NTSR1 or FOXM1 polypeptide, a polypeptide comprising the binding ability with the polypeptide, and an antibody. Immunoprecipitation can be also conducted using antibodies against the KIF11, GHSR1b, NTSR1 or FOXM1 polypeptide, in addition to the use of antibodies against the above epitopes, which antibodies can be prepared according to conventional methods and may be in any form, such as monoclonal or polyclonal antibodies, and includes antiserum obtained by immunizing an animal such as a rabbit with the polypeptide, all classes of polyclonal and monoclonal antibodies, as well as recombinant antibodies (e.g., humanized antibodies).

Specifically, antibodies against KIF11, GHSR1b, NTSR1 or FOXM1 polypeptide can be prepared using techniques well known in the art. For example, KIF11, GHSR1b, NTSR1 or FOXM1 polypeptide used as an antigen to obtain an antibody may be derived from any animal species, but preferably is derived from a mammal such as a human, mouse, or rat, more preferably from a human. The polypeptide used as the antigen can be recombinantly produced or isolated from natural sources. According to the present invention, the polypeptide to be used as an immunization antigen may be a complete protein or a partial peptide of the KIF11, GHSR1b, NTSR1 or FOXM1 polypeptide. A partial peptide may comprise, for example, the amino (N)-terminal or carboxy (C)-terminal fragment of the KIF11, GHSR1b, NTSR1 or FOXM1 polypeptide.

Any mammalian animal may be immunized with the antigen, but preferably the compatibility with parental cells used for cell fusion is taken into account. In general, animals of Rodentia, Lagomorpha or Primates are used. Animals of Rodentia include, for example, mouse, rat and hamster. Animals of Lagomorpha include, for example, rabbit. Animals of Primates include, for example, a monkey of Catarrhini (old world monkey) such as *Macaca fascicularis*, rhesus monkey, sacred baboon and chimpanzees.

Methods for immunizing animals with antigens are known in the art. Intraperitoneal injection or subcutaneous injection of antigens is a standard method for immunization of mammals. More specifically, antigens may be diluted and suspended in an appropriate amount of phosphate buffered saline (PBS), physiological saline, etc. If desired, the antigen suspension may be mixed with an appropriate amount of a standard adjuvant, such as Freund's complete adjuvant, made into emulsion, and then administered to mammalian animals. Preferably, it is followed by several administrations of the antigen mixed with an appropriately amount of Freund's incomplete adjuvant every 4 to 21 days. An appropriate carrier may also be used for immunization. After immunization as above, the serum is examined by a standard method for an increase in the amount of desired antibodies.

Polyclonal antibodies against KIF11, GHSR1b, NTSR1 or FOXM1 polypeptide may be prepared by collecting blood from the immunized mammal examined for the increase of desired antibodies in the serum, and by separating serum from the blood by any conventional method. Polyclonal antibodies include serum containing the polyclonal antibodies, as well as the fraction containing the polyclonal antibodies may be isolated from the serum. Immunoglobulin G or M can be prepared from a fraction which recognizes only the KIF11, GHSR1b, NTSR1 or FOXM1 polypeptide using, for example, an affinity column coupled with the polypeptide, and further purifying this fraction using protein A or protein G column.

To prepare monoclonal antibodies, immune cells are collected from the mammal immunized with the antigen and checked for the increased level of desired antibodies in the serum as described above, and are subjected to cell fusion. The immune cells used for cell fusion are preferably obtained from spleen. Other preferred parental cells to be fused with the above immunocyte include, for example, myeloma cells of mammalians, and more preferably myeloma cells having an acquired property for the selection of fused cells by drugs.

The above immunocyte and myeloma cells can be fused according to known methods, for example, the method of Milstein et al., (Galfre and Milstein, *Methods Enzymol* 73: 3-46 (1981)).

Resulting hybridomas obtained by the cell fusion may be selected by cultivating them in a standard selection medium, such as HAT medium (hypoxanthine, aminopterin, and thymidine containing medium). The cell culture is typically continued in the HAT medium for several days to several weeks, the time being sufficient to allow all the other cells, with the exception of the desired hybridoma (non-fused cells), to die. Then, the standard limiting dilution is performed to screen and clone a hybridoma cell producing the desired antibody.

In addition to the above method, in which a non-human animal is immunized with an antigen for preparing hybridoma, human lymphocytes such as those infected by EB virus may be immunized with KIF11, GHSR1b, NTSR1 or FOXM1 polypeptide, cells expressing the polypeptide, or their lysates in vitro. Then, the immunized lymphocytes are fused with human-derived myeloma cells that are capable of indefinitely dividing, such as U266, to yield a hybridoma producing a desired human antibody that is able to bind to the KIF11, GHSR1b, NTSR1 or FOXM1 polypeptide can be obtained (Unexamined Published Japanese Patent Application No. (JP-A) Sho 63-17688).

The obtained hybridomas are subsequently transplanted into the abdominal cavity of a mouse and the ascites are extracted. The obtained monoclonal antibodies can be purified by, for example, ammonium sulfate precipitation, a protein A or protein G column, DEAE ion exchange chromatography, or an affinity column to which any of the target proteins of the present invention (KIF11, GHSR1b, NTSR1, and FOXM1 polypeptide) is coupled. The antibody can be used not only in the present screening method, but also for purification and detection of KIF11, GHSR1b, NTSR1 or FOXM1 polypeptide, and serve also as candidates for agonists and antagonists of the polypeptide. In addition, this antibody can be applied to the antibody treatment for diseases related to the KIF11, GHSR1b, NTSR1 or FOXM1 polypeptide including NSCLC as described infra.

Monoclonal antibodies thus obtained can be also recombinantly prepared using genetic engineering techniques (see, for example, Borrebaeck and Larrick, Therapeutic Monoclonal Antibodies, published in the United Kingdom by MacMilan Publishers LTD (1990)). For example, a DNA encoding an antibody may be cloned from an immune cell, such as a hybridoma or an immunized lymphocyte producing the antibody, inserted into an appropriate vector, and introduced into host cells to prepare a recombinant antibody. Such recombinant antibody can also be used for the present screening.

Furthermore, an antibody used in the screening and so on may be a fragment of an antibody or modified antibody, so long as it binds to one or more of KIF11, GHSR1b, NTSR1, and FOXM1 polypeptides. For instance, the antibody fragment may be Fab, F(ab')$_2$, Fv, or single chain Fv (scFv), in which Fv fragments from H and L chains are ligated by an appropriate linker (Huston et al., *Proc Natl Acad Sci USA* 85: 5879-83 (1988)). More specifically, an antibody fragment may be generated by treating an antibody with an enzyme, such as papain or pepsin. Alternatively, a gene encoding the antibody fragment may be constructed, inserted into an expression vector, and expressed in an appropriate host cell (see, for example, Co et al., *J Immunol* 152: 2968-76 (1994); Better and Horwitz, *Methods Enzymol* 178: 476-96 (1989); Pluckthun and Skerra, *Methods Enzymol* 178: 497-515 (1989); Lamoyi, *Methods Enzymol* 121: 652-63 (1986); Rousseaux et al., *Methods Enzymol* 121: 663-9 (1986); Bird and Walker, *Trends Biotechnol* 9: 132-7 (1991)).

An antibody may be modified by conjugation with a variety of molecules, such as polyethylene glycol (PEG). Modified antibodies can be obtained through chemically modification of an antibody. These modification methods are conventional in the field.

Alternatively, an antibody may be obtained as a chimeric antibody, between a variable region derived from nonhuman antibody and the constant region derived from human antibody, or as a humanized antibody, comprising the complementarity determining region (CDR) derived from nonhuman antibody, the frame work region (FR) derived from human antibody, and the constant region. Such antibodies can be prepared using known technology.

Humanization can be performed by substituting rodent CDRs or CDR sequences for the corresponding sequences of a human antibody (see e.g., Verhoeyen et al., *Science* 239: 1534-1536 (1988)). Accordingly, such humanized antibodies are chimeric antibodies, wherein substantially less than an intact human variable domain has been substituted by the corresponding sequence from a non-human species.

Fully human antibodies comprising human variable regions in addition to human framework and constant regions can also be used. Such antibodies can be produced using various techniques known in the art. For example in vitro methods involve use of recombinant libraries of human antibody fragments displayed on bacteriophage (e.g., Hoogenboom & Winter, *J. Mol. Biol.* 227:381 (1991), Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584, 5,545,807; 5,545,806; 5,569,825; 5,625,126; 5,633,425; 5,661,016.

Antibodies obtained as above may be purified to homogeneity. For example, the separation and purification of the antibody can be performed according to separation and purification methods used for general proteins. For example, the antibody may be separated and isolated by the appropriately selected and combined use of column chromatographies, such as affinity chromatography, filter, ultrafiltration, salting-out, dialysis, SDS polyacrylamide gel electrophoresis, isoelectric focusing, and others (Antibodies: A Laboratory Manual. Ed Harlow and David Lane, Cold Spring Harbor Laboratory (1988)), but are not limited thereto. A protein A column and protein G column can be used as the affinity column. Exemplary protein A columns to be used include, for example, Hyper D, POROS, and Sepharose F. F. (Pharmacia).

Exemplary chromatography, with the exception of affinity includes, for example, ion-exchange chromatography, hydrophobic chromatography, gel filtration, reverse-phase chromatography, adsorption chromatography, and the like (Strategies for Protein Purification and Characterization: A Laboratory Course Manual. Ed Daniel R. Marshak et al., Cold Spring Harbor Laboratory Press (1996)). The chromatographic procedures can be carried out by liquid-phase chromatography, such as HPLC and FPLC.

An immune complex can be precipitated, for example with Protein A sepharose or Protein G sepharose when the antibody is a mouse IgG antibody. If the KIF11, GHSR1b, NTSR1 or FOXM1 polypeptide is prepared as a fusion protein with an epitope, such as GST, an immune complex can be formed in the same manner as in the use of the antibody against the KIF11, GHSR1b, NTSR1 or FOXM1 polypeptide, using a substance specifically binding to these epitopes, such as glutathione-Sepharose 4B.

Immunoprecipitation can be performed by following or according to, for example, the methods in the literature (Harlow and Lane, Antibodies, 511-52, Cold Spring Harbor Laboratory publications, New York (1988)).

SDS-PAGE is commonly used for analysis of immunoprecipitated proteins and the bound protein can be analyzed by the molecular weight of the protein using gels with an appropriate concentration. Since the protein bound to the KIF11, GHSR1b, NTSR1 or FOXM1 polypeptide is difficult to detect by a common staining method, such as Coomassie staining or silver staining, the detection sensitivity for the protein can be improved by culturing cells in culture medium containing radioactive isotope, $^{35}$S-methionine or $^{35}$S-cystein, labeling proteins in the cells, and detecting the proteins. The target protein can be purified directly from the SDS-polyacrylamide gel and its sequence can be determined, when the molecular weight of the protein has been revealed.

As a method for screening proteins binding to any of KIF11, GHSR1b, NTSR1, and FOXM1 polypeptides using the polypeptide, for example, West-Western blotting analysis (Skolnik et al., *Cell* 65: 83-90 (1991)) can be used. Specifically, a protein binding to KIF11, GHSR1b, NTSR1 or FOXM1 polypeptide can be obtained by preparing a cDNA library from cells, tissues, organs (for example, tissues such as lung cells) or cultured cells (particularly those derived from NSCLC cells) expected to express a protein binding to the KIF11, GHSR1b, NTSR1 or FOXM1 polypeptide using a phage vector (e.g., ZAP), expressing the protein on LB-agarose, fixing the protein expressed on a filter, reacting the purified and labeled KIF11, GHSR1b, NTSR1 or FOXM1 polypeptide with the above filter, and detecting the plaques expressing proteins bound to the KIF11, GHSR1b, NTSR1 or FOXM1 polypeptide according to the label. The KIF11, GHSR1b, NTSR1 or FOXM1 polypeptide may be labeled by utilizing the binding between biotin and avidin, or by utilizing an antibody that specifically binds to the KIF11, GHSR1b, NTSR1 or FOXM1 polypeptide, or a peptide or polypeptide (for example, GST) that is fused to the KIF11, GHSR1b, NTSR1 or FOXM1 polypeptide. Methods using radioisotope or fluorescence and such may be also used.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech);

"HybriZAP Two-Hybrid Vector System" (Stratagene); the references "Dalton and Treisman, *Cell* 68: 597-612 (1992)", "Fields and Stemglanz, *Trends Genet* 10: 286-92 (1994)").

In the two-hybrid system, KIF11, GHSR1b, NTSR1 or FOXM1 polypeptide is fused to the SRF-binding region or GAL4-binding region and expressed in yeast cells. A cDNA library is prepared from cells expected to express a protein binding to the KIF11, GHSR1b, NTSR1 or FOXM1 polypeptide, such that the library, when expressed, is fused to the VP16 or GAL4 transcriptional activation region. The cDNA library is then introduced into the above yeast cells and the cDNA derived from the library is isolated from the positive clones detected (when a protein binding to the polypeptide of the invention is expressed in yeast cells, the binding of the two activates a reporter gene, making positive clones detectable). A protein encoded by the cDNA can be prepared by introducing the cDNA isolated above to *E. coli* and expressing the protein.

As a reporter gene, for example, Ade2 gene, lacZ gene, CAT gene, luciferase gene and such can be used in addition to the HIS3 gene.

A compound binding to KIF11, GHSR1b, NTSR1 or FOXM1 polypeptide can also be screened using affinity chromatography. For example, KIF11, GHSR1b, NTSR1 or FOXM1 polypeptide may be immobilized on a carrier of an affinity column, and a test compound, containing a protein capable of binding to KIF11, GHSR1b, NTSR1 or FOXM1 polypeptide, is applied to the column. A test compound herein may be, for example, cell extracts, cell lysates, etc. After loading the test compound, the column is washed, and compounds bound to KIF11, GHSR1b, NTSR1 or FOXM1 polypeptide can be prepared.

When the test compound is a protein, the amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon may be used as a mean for detecting or quantifying the bound compound in the present invention. When such a biosensor is used, the interaction between KIF11, GHSR1b, NTSR1 or FOXM1 polypeptide and a test compound can be observed real-time as a surface plasmon resonance signal, using only a minute amount of polypeptide and without labeling (for example, BIAcore, Pharmacia). Therefore, it is possible to evaluate the binding between KIF11, GHSR1b, NTSR1 or FOXM1 polypeptide and a test compound using a biosensor such as BIAcore.

The methods of screening for molecules that bind when an immobilized KIF11, GHSR1b, NTSR1 or FOXM1 polypeptide is exposed to synthetic chemical compounds, or natural substance banks or a random phage peptide display library, and the methods of screening using high-throughput based on combinatorial chemistry techniques (Wrighton et al., *Science* 273: 458-64 (1996); Verdine, *Nature* 384: 11-13 (1996); Hogan, *Nature* 384: 17-9 (1996)) to isolate not only proteins but chemical compounds that bind to KIF11, GHSR1b, NTSR1 or FOXM1 protein (including agonist and antagonist) are well known to one skilled in the art.

Alternatively, the present invention provides a method of screening for a compound for treating or preventing NSCLC using KIF11, GHSR1b, NTSR1 or FOXM1 polypeptide comprising the steps as follows:
 (a) contacting a test compound with KIF11, GHSR1b, NTSR1 or FOXM1 polypeptide;
 (b) detecting the biological activity of the KIF11, GHSR1b, NTSR1 or FOXM1 polypeptide of step (a); and
 (c) selecting a compound that suppresses the biological activity of the KIF11, GHSR1b, NTSR1 or FOXM1 polypeptide in comparison with the biological activity detected in the absence of the test compound.

Since proteins encoded by any of the genes of KIF11, GHSR1b, NTSR1, and FOXM1 have the activity of promoting cell proliferation of NSCLC cells, a compound which inhibits this activity of one of these proteins can be screened using this activity as an index.

Any polypeptides can be used for screening so long as they comprise the biological activity of KIF1, GHSR1b, NTSR1 or FOXM1 proteins. Such biological activity includes cell-proliferating activity and binding ability to other proteins of the proteins encoded by KIF11, GHSR1b, NTSR1 or FOXM1 gene. For example, a human protein encoded by KIF11, GHSR1b, NTSR1 or FOXM1 gene can be used and polypeptides functionally equivalent to these proteins can also be used. Such polypeptides may be expressed endogenously or exogenously by cells.

The compound isolated by this screening is a candidate for antagonists of the KIF11, GHSR1b, NTSR1 or FOXM1 polypeptide. The term "antagonist" refers to molecules that inhibit the function of KIF11, GHSR1b, NTSR1 or FOXM1 polypeptide by binding thereto. Moreover, a compound isolated by this screening is a candidate for compounds which inhibit the in vivo interaction of KIF11, GHSR1b, NTSR1 or FOXM1 polypeptide with molecules (including DNAs and proteins).

When the biological activity to be detected in the present method is cell proliferation, it can be detected, for example, by preparing cells which express KIF11, GHSR1b, NTSR1 or FOXM1 polypeptide, culturing the cells in the presence of a test compound, and determining the speed of cell proliferation, measuring the cell cycle and such, as well as by measuring the colony forming activity.

As discussed in detail above, by controlling the expression levels of KIF11, GHSR1b, NTSR1 or FOXM1 gene, one can control the onset and progression of NSCLC. Thus, compounds that may be used in the treatment or prevention of NSCLC, can be identified through screenings that use the expression levels of one or more of KIF11, GHSR1b, NTSR1, and FOXM1 genes as indices. In the context of the present invention, such screening may comprise, for example, the following steps:
 (a) contacting a test compound with a cell expressing one or more of KIF11, GHSR1b, NTSR1, and FOXM1 genes; and
 (b) selecting a compound that reduces the expression level of one or more of the genes in comparison with the expression level detected in the absence of the test compound.

Cells expressing at least one of KIF11, GHSR1b, NTSR1, and FOXM1 genes include, for example, cell lines established from NSCLC cells; such cells can be used for the above screening of the present invention (e.g., A549, NCI-H226, NCI-H522, LC319). The expression level can be estimated by methods well known to one skilled in the art. In the method of screening, a compound that reduces the expression level of at least one of the genes can be selected as candidate agents to be used for the treatment or prevention of NSCLC.

Alternatively, the screening method of the present invention may comprise the following steps:
 (a) contacting a test compound with a cell into which a vector comprising the transcriptional regulatory region of one or more of the marker genes and a reporter gene that is expressed under the control of the transcriptional regulatory region has been introduced, wherein the marker genes are selected from the group of KIF11, GHSR1b, NTSR1, and FOXM1;

(b) measuring the activity of said reporter gene; and (c) selecting a compound that reduces the expression level of said reporter gene as compared to a control.

Suitable reporter genes and host cells are well known in the art. The reporter construct required for the screening can be prepared using the transcriptional regulatory region of a marker gene. When the transcriptional regulatory region of a marker gene has been known to those skilled in the art, a reporter construct can be prepared using the previous sequence information. When the transcriptional regulatory region of a marker gene remains unidentified, a nucleotide segment containing the transcriptional regulatory region can be isolated from a genome library based on the nucleotide sequence information of the marker gene (e.g., based the 5' upstream sequence information).

In a further embodiment of the method of screening for a compound for treating or preventing NSCLC of the present invention, the method utilizes the binding ability of KIF11 to KOC1, or GHSR1b or NTSR1 to NMU.

As described above, the present inventors revealed that KOC1 not only co-localized with KIF11 in human normal tissues, NSCLCs, and cell lines, but also directly interacted with KIF11 in NSCLC cells in vitro, and that the treatment of NSCLC cells with siRNAs for KIF11 reduced its expression and led to growth suppression. The results suggest that KOC1-KIF11 signaling affects growth of NSCLC cells. Thus, it is expected that the inhibition of the binding between KOC1 and KIF11 leads to the suppression of cell proliferation, and compounds inhibiting the binding serve as pharmaceuticals for treating or preventing NSCLCs. This screening method includes the steps of: (a) contacting a KIF11 polypeptide or functional equivalent thereof with KOC1, or a functional equivalent thereof, in the presence of a test compound; (b) detecting the binding between the polypeptide and KOC1; and (c) selecting the test compound that inhibits the binding between the polypeptide and KOC1.

Furthermore, as described above, the present inventors revealed GHSR1b and NTSR1 as the likely targets for the growth-promoting effect of NMU in lung tumors. The present inventors revealed that NMU-25 bound to these receptors on the cell surface, and that treatment of NSCLC cells with siRNAs for GHSR1 or NTSR1 reduced expression of the receptors and led to apoptosis. The results suggest that NMU affects growth of NSCLC cells by acting through GHSR1b and/or NTSR1 (FIG. 14). Thus, it is expected that the inhibition of binding between GHSR1b or NTSR1 and NMU leads to the suppression of cell proliferation, and compounds inhibiting the binding serve as pharmaceuticals for treating or preventing NSCLCs. This screening method includes the steps of: (a) contacting a GHSR1b or NTSR1 polypeptide or functional equivalent thereof with NMU in the presence of a test compound; (b) detecting binding between the polypeptide and NMU; and (c) selecting the test compound that inhibits binding between the polypeptide and NMU.

KOC1 and KIF11 polypeptides, or GHSR1b or NTSR1 and NMU polypeptides to be used for the screening may be a recombinant polypeptide or a protein derived from the nature, or may also be a partial peptide thereof so long as it retains the binding ability to each other. Such partial peptides retaining the binding ability are herein referred to as "functional equivalents". The KOC1 and KIF11 polypeptides, or GHSR1b or NTSR1 and NMU polypeptides to be used in the screening can be, for example, a purified polypeptide, a soluble protein, a form bound to a carrier or a fusion protein fused with other polypeptides.

As a method of screening for compounds that inhibit binding between KOC1 and KIF11, or GHSR1b or NTSR1 and NMU, many methods well known by one skilled in the art can be used. Such a screening can be carried out as an in vitro assay system, for example, in a cellular system. More specifically, first, either KOC1 or KIF11, or GHSR1b or NTSR1, or NMU is bound to a support, and the other protein is added together with a test compound thereto. Next, the mixture is incubated, washed and the other protein bound to the support is detected and/or measured.

Examples of supports that may be used for binding proteins include insoluble polysaccharides, such as agarose, cellulose and dextran; and synthetic resins, such as polyacrylamide, polystyrene and silicon; preferably commercial available beads and plates (e.g., multi-well plates, biosensor chip, etc.) prepared from the above materials may be used. When using beads, they may be filled into a column. Alternatively, the use of magnetic beads of also known in the art, and enables to readily isolate proteins bound on the beads via magnetism.

The binding of a protein to a support may be conducted according to routine methods, such as chemical bonding and physical adsorption. Alternatively, a protein may be bound to a support via antibodies specifically recognizing the protein. Moreover, binding of a protein to a support can be also conducted by means of avidin and biotin.

The binding between proteins is carried out in buffer, for example, but are not limited to, phosphate buffer and Tris buffer, as long as the buffer does not inhibit binding between the proteins.

In the present invention, a biosensor using the surface plasmon resonance phenomenon may be used as a mean for detecting or quantifying the bound protein. When such a biosensor is used, the interaction between the proteins can be observed real-time as a surface plasmon resonance signal, using only a minute amount of polypeptide and without labeling (for example, BIAcore, Pharmacia). Therefore, it is possible to evaluate binding between the KOC1 and KIF11, or GHSR1b or NTSR1 and NMU using a biosensor such as BIAcore.

Alternatively, either KOC1 or KIF11, or GHSR1b or NTSR1, or NMU may be labeled, and the label of the bound protein may be used to detect or measure the bound protein. Specifically, after pre-labeling one of the proteins, the labeled protein is contacted with the other protein in the presence of a test compound, and then bound proteins are detected or measured according to the label after washing.

Labeling substances such as radioisotope (e.g., $^3$H, $^{14}$C, $^{32}$P, $^{33}$P, $^{35}$S, $^{125}$I, $^{131}$I), enzymes (e.g., alkaline phosphatase, horseradish peroxidase, β-galactosidase, β-glucosidase), fluorescent substances (e.g., fluorescein isothiosyanete (FITC), rhodamine) and biotin/avidin, may be used for the labeling of a protein in the present method. When the protein is labeled with radioisotope, the detection or measurement can be carried out by liquid scintillation. Alternatively, proteins labeled with enzymes can be detected or measured by adding a substrate of the enzyme to detect the enzymatic change of the substrate, such as generation of color, with absorptiometer. Further, in case where a fluorescent substance is used as the label, the bound protein may be detected or measured using fluorophotometer.

Furthermore, binding of KOC1 and KIF11, or GHSR1b or NTSR1 and NMU can be also detected or measured using antibodies to the KOC1 and KIF11, or GHSR1b or NTSR1 and NMU. For example, after contacting the KOC1 polypeptide immobilized on a support with a test compound and KIF11, the mixture is incubated and washed, and detection or measurement can be conducted using an antibody against KIF11. Alternatively, KIF11 may be immobilized on a support, and an antibody against KOC1 may be used as the antibody. When the combination of GHSR1b or NTSR1 and NMU is used, GHSR1b or NTSR1 polypeptide may be immobilized on a support with a test compound and NMU, the mixture is incubated and washed, and detection or measurement can be conducted using an antibody against NMU. Alternatively, NMU may be immobilized on a support, and an antibody against GHSR1b or NTSR1 may be used as the antibody.

In case of using an antibody in the present screening, the antibody is preferably labeled with one of the labeling substances mentioned above, and detected or measured based on the labeling substance. Alternatively, the antibody against KOC1 or KIF11, or GHSR1b or NTSR1, or NMU may be used as a primary antibody to be detected with a secondary antibody that is labeled with a labeling substance. Furthermore, the antibody bound to the protein in the screening of the present invention may be detected or measured using protein G or protein A column.

Alternatively, in another embodiment of the screening method of the present invention, a two-hybrid system utilizing cells may be used ("MATCHMAKER Two-Hybrid system", "Mammalian MATCHMAKER Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Stemglanz, Trends Genet 10: 286-92 (1994)").

In the two-hybrid system, for example, KOC1 polypeptide is fused to the SRF-binding region or GAL4-binding region and expressed in yeast cells. KIF11 polypeptide that binds to KOC1 polypeptide is fused to the VP16 or GAL4 transcriptional activation region and also expressed in the yeast cells in the existence of a test compound. Alternatively, KIF11 polypeptide may be fused to the SRF-binding region or GAL4-binding region, and KOC1 polypeptide to the VP16 or GAL4 transcriptional activation region. When the combination of GHSR1b or NTSR1 and NMU is used in the two-hybrid system, for example, GHSR1b or NTSR1 polypeptide is fused to the SRF-binding region or GAL4-binding region and expressed in yeast cells. NMU polypeptide that binds to GHSR1b or NTSR1 polypeptide is fused to the VP16 or GAL4 transcriptional activation region and also expressed in the yeast cells in the existence of a test compound. Alternatively, NMU polypeptide may be fused to the SRF-binding region or GAL4-binding region, and GHSR1b or NTSR1 polypeptide to the VP16 or GAL4 transcriptional activation region. When the test compound does not inhibit the binding between KOC1 and KIF11, or GHSR1b or NTSR1 and NMU, the binding of the two activates a reporter gene, making positive clones detectable.

As a reporter gene, for example, Ade2 gene, lacZ gene, CAT gene, luciferase gene and such can be used besides HIS3 gene.

Moreover, when the combination of GHSR1b or NTSR1 and NMU is used in the screening method, since GHSR1b and NTSR1 are polypeptides naturally expressed on the cell surface, in a preferable embodiment of the present screening method, the polypeptides are expressed on the surface of a living cell. When the polypeptides are expressed on the surface of a living cell, the binding between the polypeptide and NMU can be detected by methods detecting the autocrine and paracrine signaling leading to stimulation of tumor cell growth (Heasley, *Oncogene* 20: 1563-1569 (2001)). For example, the binding between GHSR1 or NTSR1 polypeptide and NMU can be detected by:

(1) detecting the concentration of calcium or cAMP in the cell (e.g. FLIPR assay, *Biochem. Biophys. Res. Commun.* 276: 435-438, 2000; *Nature* 406: 70-74, 2000; *J. Biol. Chem.* 275:21068-21074, 2000);
(2) detecting the activation of the polypeptide;
(3) detecting the interaction between the polypeptide and G-protein (e.g. FLIPR assay, *Biochem. Biophys. Res. Commun.* 276: 435-438, 2000; *Nature* 406: 70-74, 2000; *J. Biol. Chem.* 275:21068-21074, 2000, or binding assay with $^{125}$I labeled peptide);
(4) detecting the activation of phospholipase C or its down stream pathway (*Oncogene* 20:1563-1569, 2001);
(5) detecting the activation of kinases of the protein kinase cascade, such as Raf, MEK, ERKs, and protein kinase D (PKD) (*Oncogene* 20:1563-1569, 2001);
(6) detecting the activation of a member of Src/Tec/Bmx-family of tyrosine kinases (*Oncogene* 20:1563-1569, 2001);
(7) detecting the activation of a member of the Ras and Rho family, regulation of a member of the JNK members of MAP families, or the reorganization of the actin cytoskeleton (*Oncogene* 20:1563-1569, 2001);
(8) detecting the activation of any signal complex mediated by the polypeptide activation;
(9) detecting the change in subcellular localization of the polypeptide including the ligand-induced internalization/endocytosis of the polypeptide (*J. Cell Sci.*, 113: 2963-2975, 2000; *J. Histochem. Cytochem.* 48:1553-1563, 2000; *Endocrinology* Oct. 23, 2003. as doi: 10. 1210/en. 2003-0974);
(10) detecting the activation of any transcription factor downstream of the polypeptides or the activation of their downstream gene; and
(11) detecting cell proliferation, transformation, or any other oncogenic phenotype of the cell.

Any test compound, for example, cell extracts, cell culture supernatant, products of fermenting microorganism, extracts from marine organism, plant extracts, purified or crude proteins, peptides, non-peptide compounds, synthetic micromolecular compounds and natural compounds can be used in the screening methods of the present invention. The test compound of the present invention can be also obtained using any of the numerous approaches in combinatorial library methods known in the art, including (1) biological libraries, (2) spatially addressable parallel solid phase or solution phase libraries, (3) synthetic library methods requiring deconvolution, (4) the "one-bead one-compound" library method and (5) synthetic library methods using affinity chromatography selection. The biological library methods using affinity chromatography selection is limited to peptide libraries, while the other four approaches are applicable to peptide, non-peptide oligomer or small molecule libraries of compounds (Lam, *Anticancer Drug Des.* 12: 145 (1997)). Examples of methods for the synthesis of molecular libraries can be found in the art (DeWitt et al., *Proc. Natl. Acad. Sci. USA* 90: 6909 (1993); Erb et al., *Proc. Natl. Acad. Sci. USA* 91: 11422 (1994); Zuckermann et al., *J. Med. Chem.* 37: 2678 (1994); Cho et al., *Science* 261: 1303 (1993); Carell et al., *Angew. Chem. Int. Ed. Engl.* 33: 2059 (1994); Carell et al., *Angew. Chem. Int. Ed Engl.* 33: 2061 (1994); Gallop et al., *J. Med. Chem.* 37:1233 (1994)). Libraries of compounds may be presented in solution (see Houghten, *Bio/Techniques* 13: 412 (1992)) or on beads (Lam, *Nature* 354: 82 (1991)), chips (Fodor, *Nature* 364: 555 (1993)), bacteria (U.S. Pat. No. 5,223,409), spores (U.S. Pat. Nos. 5,571,698; 5,403,484, and 5,223,409), plasmids (Cull et al., *Proc. Natl. Acad. Sci. USA* 89: 1865 (1992)) or phage (Scott and Smith, *Science* 249: 386 (1990); Delvin, *Science* 249: 404 (1990); Cwirla et al., *Proc. Natl. Acad. Sci. USA* 87: 6378 (1990); Felici, *J. Mol. Biol.* 222: 301 (1991); US Pat. Application 2002103360). The test compound exposed to a cell or protein according to the screening methods of the present invention may be a single compound or a combination of compounds. When a combination of compounds are used in the screening methods of the invention, the compounds may be contacted sequentially or simultaneously.

A compound isolated by the screening methods of the present invention is a candidate for drugs which inhibit the activity of KIF11, GHSR1b, NTSR1 or FOXM1 polypeptide, for treating or preventing diseases attributed to, for example, cell proliferative diseases, such as NSCLC. A compound in which a part of the structure of the compound obtained by the present screening methods of the present invention is converted by addition, deletion and/or replacement, is included in the compounds obtained by the screening methods of the present invention. A compound effective in suppressing the expression of over-expressed genes, i.e., KIF11, GHSR1b, NTSR1 or FOXM1 gene, is deemed to have a clinical benefit and can be further tested for its ability to prevent cancer cell growth in animal models or test subjects.

Selecting a Therapeutic Agent for Treating and/or Preventing NSCLC that is Appropriate for a Particular Individual Differences in the genetic makeup of individuals can result in differences in their relative abilities to metabolize various drugs. A compound that is metabolized in a subject to act as an anti-NSCLC agent can manifest itself by inducing a change in gene expression pattern in the subject's cells from that characteristic of a cancerous state to a gene expression pattern characteristic of a non-cancerous state. Accordingly, the differentially expressed KIF11, GHSR1b, NTSR1, and FOXM1 genes disclosed herein allow for selection of a putative therapeutic or prophylactic inhibitor of NSCLC specifically adequate for a subject by testing candidate compounds in a test cell (or test cell population) derived from the selected subject.

To identify an anti-NSCLC agent, that is appropriate for a specific subject, a test cell or test cell population derived from the subject is exposed to a therapeutic agent and the expression of one or more of the KIF11, GHSR1b, NTSR1, and FOXM1 genes is determined.

The test cell is or the test cell population contains an NSCLC cell expressing an NSCLC-associated gene. Preferably, the test cell is or the test cell population contains a lung cell. For example, the test cell or test cell population is incubated in the presence of a candidate agent and the pattern of gene expression of the test cell or cell population is measured and compared to one or more reference profiles, e.g., an NSCLC reference expression profile or an non-NSCLC reference expression profile.

A decrease in the expression of one or more of KIF11, GHSR1b, NTSR1, and FOXM1 in a test cell or test cell population relative to a reference cell population containing NSCLC is indicative that the agent is therapeutic.

The test agent can be any compound or composition. For example, the test agent is an immunomodulatory agent.

Methods for Treating or Preventing NSCLC

The present invention provides a method for treating, alleviating or preventing NSCLC in a subject. Therapeutic compounds are administered prophylactically or therapeutically to subjects suffering from or at risk of (or susceptible to) developing NSCLC. Such subjects are identified using standard clinical methods or by detecting an aberrant level of expression or activity of KIF11, GHSR1b, NTSR1 or FOXM1 gene or polypeptide. Prophylactic administration occurs prior to the manifestation of overt clinical symptoms of disease, such that a disease or disorder is prevented or alternatively delayed in its progression.

The method includes decreasing the expression or function, or both, of one or more gene products of genes whose expression is aberrantly increased ("over-expressed gene"; KIF11, GHSR1b, NTSR1 or FOXM1 gene) in an NSCLC cell relative to normal cells of the same tissue type from which the NSCLC cells are derived. The expression may be inhibited by any method known in the art. For example, a subject may be treated with an effective amount of a compound that decreases the amount of one or more of the KIF11, GHSR1b, NTSR1 or FOXM1 gene in the subject. Administration of the compound can be systemic or local. Such therapeutic compounds include compounds that decrease the expression level of such gene that endogenously exists in the NSCLC cells (i.e., compounds that down-regulate the expression of the over-expressed gene(s), KIF11, GHSR1b and/or NTSR1 genes). The administration of such therapeutic compounds counter the effects of aberrantly-over expressed gene(s) in the subjects NSCLC cells and are expected to improve the clinical condition of the subject. Such compounds can be obtained by the screening method of the present invention described above.

The compounds that modulate the activity of a protein encoded by KIF11, GHSR1b, NTSR1 or FOXM1 gene that can be used for treating or preventing NSCLC of the present invention include besides proteins, naturally-occurring cognate ligand of these proteins, peptides, peptidomimetics and other small molecules.

Alternatively, the expression of these over-expressed gene(s) (KIF11, GHSR1b, NTSR1 and/or FOXM1) can be inhibited by administering to the subject a nucleic acid that inhibits or antagonizes the expression of the over-expressed gene(s). Antisense oligonucleotides, siRNAs or ribozymes which disrupt the expression of the over-expressed gene(s) can be used for inhibiting the expression of the over-expressed gene(s).

As noted above, antisense-oligonucleotides corresponding to any of the nucleotide sequence of KIF11, GHSR1b, NTSR1 or FOXM1 gene can be used to reduce the expression level of the gene. Antisense-oligonucleotides corresponding to KIF11, GHSR1b, NTSR1, and FOXM1 genes that are up-regulated in NSCLC are useful for the treatment or prevention of NSCLC. Specifically, the antisense-oligonucleotides against the genes may act by binding to any of the corresponding polypeptides encoded by these genes, or mRNAs corresponding thereto, thereby inhibiting the transcription or translation of the genes, promoting the degradation of the mRNAs, and/or inhibiting the expression of proteins encoded by the KIF11, GHSR1b, NTSR1, and FOXM1 nucleotides, and finally inhibiting the function of the proteins. The term "antisense-oligonucleotides" as used herein encompasses both nucleotides that are entirely complementary to the target sequence and those having a mismatch of one or more nucleotides, so long as the antisense-oligonucleotides can specifically hybridize to the target sequence. For example, the antisense-oligonucleotides of the present invention include polynucleotides that have a homology (also referred to as sequence identity) of at least 70% or higher, preferably at 80% or higher, more preferably 90% or higher, even more preferably 95% or higher over a span of at least 15 continuous nucleotides up to the full length sequence of any of the nucleotide sequences of KIF11, GHSR1b, NTSR1 or FOXM1 gene. Algorithms known in the art can be used to determine the homology. Furthermore, derivatives or modified products of the antisense-oligonucleotides can also be used as antisense-oligonucleotides in the present invention. Examples of such modified products include lower alkyl phosphonate modifications such as methyl-phosphonate-type or ethyl-phosphonate-type, phosphorothioate modifications and phosphoroamidate modifications.

siRNA molecules of the invention can also be defined by their ability to hybridize specifically to mRNA or cDNA from the genes disclosed here. For the purposes of this invention the terms "hybridize" or "hybridize specifically" are used to refer the ability of two nucleic acid molecules to hybridize under "stringent hybridization conditions." The phrase "stringent hybridization conditions" refers to conditions under which a nucleic acid molecule will hybridize to its target sequence, typically in a complex mixture of nucleic acids, but not detectably to other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 50° C. The antisense-oligonucleotides and derivatives thereof act on cells producing the proteins encoded by KIF11, GHSR1b, NTSR1 or FOXM1 gene by binding to the DNA or mRNA encoding the protein, inhibiting transcription or translation thereof, promoting the degradation of the mRNAs and inhibiting the expression of the protein, thereby resulting in the inhibition of the protein function.

An antisense-oligonucleotides and derivatives thereof can be made into an external preparation, such as a liniment or a poultice, by mixing with a suitable base material which is inactive against the derivative.

The antisense-oligonucleotides of the invention inhibit the expression of at least one protein encoded by any one of KIF11, GHSR1b, NTSR1, and FOXM1 genes, and thus are useful for suppressing the biological activity of the protein.

The polynucleotides that inhibit one or more gene products of over-expressed genes also include small interfering RNAs (siRNA) comprising a combination of a sense strand nucleic acid and an antisense strand nucleic acid of the nucleotide sequence encoding an over-expressed protein encoded by KIF11, GHSR1b, NTSR1 or FOXM1 gene. The term "siRNA" refers to a double stranded RNA molecule which prevents translation of a target mRNA. Standard techniques of introducing siRNA into the cell can be used in the treatment or prevention of the present invention, including those in which DNA is a template from which RNA is transcribed. The siRNA is constructed such that a single transcript has both the sense and complementary antisense sequences from the target gene, e.g., a hairpin.

The method is used to suppress gene expression of a cell with up-regulated expression of KIF11, GHSR1b, NTSR1 or FOXM1 gene. Binding of the siRNA to KIF11, GHSR1b, NTSR1 or FOXM1 gene transcript in the target cell results in a reduction of KIF11, GHSR1b, NTSR1 or FOXM1 protein production by the cell. The length of the oligonucleotide is at least about 10 nucleotides and may be as long as the naturally occurring transcript. Preferably, the oligonucleotide is about 19 to about 25 nucleotides in length. Most preferably, the oligonucleotide is less than about 75, about 50 or about 25 nucleotides in length. Preferable siRNA of the present invention include the polynucleotides having the nucleotide sequence of SEQ ID NO: 32, 33, 34, 35, 36, 37, or 108 as the target sequence, which all proved to be effective for suppressing cell viability of NSCLC cell lines. Specifically, a preferable siRNA used in the present invention has the general formula:

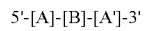

5'-[A]-[B]-[A']-3' wherein [A] is a ribonucleotide sequence corresponding to a target sequence of KIF11, GHSR1b, NTSR1 or FOXM1; [B] is a ribonucleotide sequence consisting of about 3 to about 23 nucleotides; and [A'] is a ribonucleotide sequence complementary to [A]. Herein, the phrase a "target sequence of KIF11, GHSR1b, NTSR1 or FOXM1 gene" refers to a sequence that, when introduced into NSCLC cell lines, is effective for suppressing cell viability. Preferred target sequence of KIF11, GHSR1b, NTSR1 or FOXM1 gene includes nucleotide sequences comprising: SEQ ID NOs: 32, 33, 34, 35, 36, 37, and 108. The complementary sequence [A'] and [A] hybridize to each other to form a double strand, and the whole siRNA molecule with the general formula 5'-[A]-[B]-[A']-3' forms a hairpin loop structure. As used herein, the term "complementary" refers to a Watson-Crick or Hoogsteen base pairing between nucleotide units of a polynucleotide, and hybridization or binding of nucleotide units indicates physical or chemical interaction between the units under appropriate conditions to form a stable duplex (double-stranded configuration) containing few or no mismatches. In a preferred embodiment, such duplexes contain no more than 1 mismatch for every 10 base pairs. Particularly preferred duplexes are fully complementary and contain no mismatch. The siRNA against the mRNA of KIF11, GHSR1b, NTSR1 or FOXM1 gene to be used in the present invention contains a target sequence shorter than the whole mRNA of KIF11, GHSR1b, NTSR1 or FOXM1 gene, and has a sequence of 500, 200, or 75 nucleotides as the whole length. Also included in the invention is a vector containing one or more of the nucleic acids described herein, and a cell containing the vectors. The isolated nucleic acids of the present invention are useful for siRNA against KIF11, GHSR1b, NTSR1 or FOXM1 or DNA encoding the siRNA. When the nucleic acids are used for siRNA or coding DNA thereof, the sense strand is preferably longer than about 19 nucleotides, and more preferably longer than about 21 nucleotides.

Furthermore, the nucleotide sequence of siRNAs may be designed using a siRNA design computer program available from the Ambion website (http://www.ambion.com/techlib/misc/siRNA_finder.html). The nucleotide sequences for the siRNA are selected by the computer program based on the following protocol:

Selection of siRNA Target Sites:
1. Beginning with the AUG start codon of the transcript, scan downstream for AA dinucleotide sequences. Record the occurrence of each AA and the 3' adjacent 19 nucleotides as potential siRNA target sites. Tuschl, et al. *Genes Dev* 13(24): 3191-7 (1999), not recommend against designing siRNA against the 5' and 3' untranslated regions (UTRs) and regions near the start codon (within 75 bases) as these may be richer in regulatory protein binding sites, and thus the complex of endonuclease and siRNAs that were designed against these regions may interfere with the binding of UTR-binding proteins and/or translation initiation complexes.
2. Compare the potential target sites to the human genome database and eliminate from consideration any target sequences with significant homology to other coding sequences. The homology search can be performed using BLAST, which can be found on the NCBI server at: www.ncbi.nlm.nih.gov/BLAST/
3. Select qualifying target sequences for synthesis. On the website of Ambion, several preferable target sequences can be selected along the length of the gene for evaluation.

The siRNAs inhibit the expression of over-expressed KIF11, GHSR1b, NTSR1 or FOXM1 protein and is thereby useful for suppressing the biological activity of the protein. Therefore, a composition comprising the siRNA is useful in treating or preventing non-small cell lung cancer.

The nucleic acids that inhibit one or more gene products of over-expressed genes KIF11, GHSR1b, NTSR1, and FOXM1 also include ribozymes against the gene(s).

The ribozymes inhibit the expression of over-expressed KIF11, GHSR1b, NTSR1 or FOXM1 protein and is thereby useful for suppressing the biological activity of the protein. Therefore, a composition comprising the ribozyme is useful in treating or preventing NSCLC.

Generally, ribozymes are classified into large ribozymes and small ribozymes. A large ribozyme is known as an enzyme that cleaves the phosphate ester bond of nucleic acids. After the reaction with the large ribozyme, the reacted site consists of a 5'-phosphate and 3'-hydroxyl group. The large ribozyme is further classified into (1) group I intron RNA catalyzing transesterification at the 5'-splice site by guanosine; (2) group II intron RNA catalyzing self-splicing through a two step reaction via lariat structure; and (3) RNA component of the ribonuclease P that cleaves the tRNA precursor at the 5' site through hydrolysis. On the other hand, small ribozymes have a smaller size (about 40 bp) compared to the large ribozymes and cleave RNAs to generate a 5'-hydroxyl group and a 2'-3' cyclic phosphate. Hammerhead type ribozymes (Koizumi et al., *FEBS Lett.* 228: 225 (1988)) and hairpin type ribozymes (Buzayan, *Nature* 323: 349 (1986); Kikuchi and Sasaki, *Nucleic Acids Res.* 19: 6751 (1992)) are included in the small ribozymes. Methods for designing and constructing ribozymes are known in the art (see Koizumi et al., *FEBS Lett.* 228: 225 (1988); Koizumi et al., *Nucleic Acids Res.* 17: 7059 (1989); Kikuchi and Sasaki, *Nucleic Acids Res.* 19: 6751 (1992)) and ribozymes inhibiting the expression of an over-expressed NSC protein can be constructed based on the sequence information of the nucleotide sequence encoding KIF11, GHSR1b, NTSR1 or FOXM1 protein according to conventional methods for producing ribozymes.

The ribozymes inhibit the expression of over-expressed KIF11, GHSR1b, NTSR1 or FOXM1 protein and is thereby useful for suppressing the biological activity of the protein. Therefore, a composition comprising the ribozyme is useful in treating or preventing NSCLC.

Alternatively, the function of one or more gene products of the over-expressed genes is inhibited by administering a compound that binds to or otherwise inhibits the function of the gene products. For example, the compound is an antibody which binds to the over-expressed gene product or gene products.

The present invention refers to the use of antibodies, particularly antibodies against a protein encoded by any of the up-regulated genes KIF11, GHSR1b, NTSR1 or FOXM1, or a fragment of the antibody. As used herein, the term "antibody" refers to an immunoglobulin molecule having a specific structure that interacts (binds) specifically with a molecule comprising the antigen used for synthesizing the antibody (i.e., the up-regulated gene product) or with an antigen closely related to it. An antibody that binds to the over-expressed KIF11, GHSR1b, NTSR1 or FOXM1 nucleotide may be in any form, such as monoclonal or polyclonal antibodies, and includes antiserum obtained by immunizing an animal such as a rabbit with the polypeptide, all classes of polyclonal and monoclonal antibodies, human antibodies and humanized antibodies produced by genetic recombination. Furthermore, the antibody used in the method of treating or preventing NSCLC of the present invention may be a fragment of an antibody or a modified antibody, so long as it binds to one or more of the proteins encoded by the marker genes (KIF11, GHSR1b, NTSR1 or FOXM1 gene). The antibodies and antibody fragments used in the present method of treating or preventing NSCLC may be modified, and include chemically modified and chimeric antibodies. Such antibodies and antibody fragments can be obtained according to the above-mentioned methods, supra.

When the obtained antibody is to be administered to the human body (antibody treatment), a human antibody or a humanized antibody is preferable for reducing immunogenicity.

For example, transgenic animals having a repertory of human antibody genes may be immunized with an antigen such as KIF11, GHSR1b, NTSR1 or FOXM1 polypeptide, cells expressing the polypeptide, or their lysates. Antibody producing cells are then collected from the animals and fused with myeloma cells to obtain hybridoma, from which human antibodies against the polypeptide can be prepared (see WO92-03918, WO93-2227, WO94-02602, WO94-25585, WO96-33735, and WO96-34096).

Alternatively, an immune cell, such as an immunized lymphocyte, producing antibodies may be immortalized by an oncogene and used for preparing monoclonal antibodies.

The present invention provides a method for treating or preventing NSCLC, using an antibody against an over-expressed KIF11, GHSR1b, NTSR1 or FOXM1 polypeptide. According to the method, a pharmaceutically effective amount of an antibody against KIF11, GHSR1b, NTSR1 or FOXM1 polypeptide is administered. An antibody against an over-expressed KIF11, GHSR1b, NTSR1 or FOXM1 polypeptide is administered at a dosage sufficient to reduce the activity of KIF11, GHSR1b, NTSR1 or FOXM1 protein. Alternatively, an antibody binding to a cell surface marker specific for tumor cells can be used as a tool for drug delivery. Thus, for example, an antibody against an over-expressed KIF11, GHSR1b, NTSR1 or FOXM1 polypeptide conjugated with a cytotoxic agent may be administered at a dosage sufficient to injure tumor cells.

In addition, dominant negative mutants of the proteins disclosed here can be used to treat or prevent NSCLC. For example, fragments of KOC1 that specifically bind KIF11 can be used. As used here "dominant negative fragment of KOC1" is a mutated form of KOC1 that is capable of complexing with either of KIF11 and RNA to be transported such that the RNA transporter activity of the complex is diminished. Thus, a dominant negative fragment is one that is not functionally equivalent to the full length KOC1 polypeptide. Preferred dominant negative fragments are those that comprise at least one RRM domain of KOC1. Alternatively, in another embodiment, the dominant negative fragments have two RRM domains and zero to three of KH domains. For example KOC1DEL2 (2×RRM+2×KH) and KOC1DEL3 (2×RRM without KH) are preferable fragment for dominant negative effect. The amino acid sequences of KOC1DEL2 and KOC1DEL3 consist of positions 1 to 406 and 1-197 of SEQ ID NO:105, respectively. The fragments are typically less than about 300 amino acids, typically less than about 200 amino acids.

The present invention also relates to a method of treating or preventing NSCLC in a subject comprising administering to said subject a vaccine comprising a polypeptide encoded by a nucleic acid selected from the group consisting of KIF11, GHSR1b, NTSR1, and FOXM1 genes or an immunologically active fragment of said polypeptide, or a polynucleotide encoding the polypeptide or the fragment thereof. Administration of the polypeptide induces an anti-tumor immunity in a subject. Thus, the present invention further provides a method for inducing anti tumor immunity. The polypeptide or the immunologically active fragments thereof are useful as vaccines against NSCLC. In some cases the proteins or fragments thereof may be administered in a form bound to the T cell receptor (TCR) or presented on an antigen presenting cell (APC), such as macrophage, dendritic cell (DC) or B-cells. Due to the strong antigen presenting ability of DC, the use of DC is most preferable among the APCs.

In the present invention, the phrase "vaccine against NSCLC" refers to a substance that has the function to induce anti-tumor immunity or immunity to suppress NSCLC upon inoculation into animals. In general, anti-tumor immunity includes immune responses such as follows:
  induction of cytotoxic lymphocytes against tumors,
  induction of antibodies that recognize tumors, and
  induction of anti-tumor cytokine production.

Therefore, when a certain protein induces any one of these immune responses upon inoculation into an animal, the protein is decided to have anti-tumor immunity inducing effect. The induction of the anti-tumor immunity by a protein can be detected by observing in vivo or in vitro the response of the immune system in the host against the protein.

For example, a method for detecting the induction of cytotoxic T lymphocytes is well known. A foreign substance that enters the living body is presented to T cells and B cells by the action of antigen presenting cells (APCs). T cells that respond to the antigen presented by APC in antigen specific manner differentiate into cytotoxic T cells (or cytotoxic T lymphocytes; CTLs) due to stimulation by the antigen, and then proliferate (this is referred to as activation of T cells). Therefore, CTL induction by a certain peptide can be evaluated by presenting the peptide to T cell by APC, and detecting the induction of CTL. Furthermore, APC has the effect of activating CD4+ T cells, CD8+ T cells, macrophages, eosinophils and NK cells. Since CD4+ T cells are also important in anti-tumor immunity, the anti-tumor immunity inducing action of the peptide can be evaluated using the activation effect of these cells as indicators.

A method for evaluating the inducing action of CTL using dendritic cells (DCs) as APC is well known in the art. DC is a representative APC having the strongest CTL inducing action among APCs. In this method, the test polypeptide is initially contacted with DC and then this DC is contacted with T cells. Detection of T cells having cytotoxic effects against the cells of interest after the contact with DC shows that the test polypeptide has an activity of inducing the cytotoxic T cells. Activity of CTL against tumors can be detected, for example, using the lysis of $^{51}$Cr-labeled tumor cells as the indicator. Alternatively, the method of evaluating the degree of tumor cell damage using $^{3}$H-thymidine uptake activity or LDH (lactose dehydrogenase)-release as the indicator is also well known.

Apart from DC, peripheral blood mononuclear cells (PBMCs) may also be used as the APC. The induction of CTL is reported to be enhanced by culturing PBMC in the presence of GM-CSF and IL-4. Similarly, CTL is shown to be induced by culturing PBMC in the presence of keyhole limpet hemocyanin (KLH) and IL-7.

The test polypeptides confirmed to possess CTL inducing activity by these methods are polypeptides having DC activation effect and subsequent CTL inducing activity. Therefore, polypeptides that induce CTL against tumor cells are useful as vaccines against NSCLC. Furthermore, APC that acquired the ability to induce CTL against NSCLC by contacting with the polypeptides are useful as vaccines against NSCLC. Furthermore, CTL that acquired cytotoxicity due to presentation of the polypeptide antigens by APC can be also used as vaccines against NSCLC. Such therapeutic methods for NSCLC using anti-tumor immunity due to APC and CTL are referred to as cellular immunotherapy.

Generally, when using a polypeptide for cellular immunotherapy, efficiency of the CTL-induction is known to increase by combining a plurality of polypeptides having different structures and contacting them with DC. Therefore, when stimulating DC with protein fragments, it is advantageous to use a mixture of multiple types of fragments.

Alternatively, the induction of anti-tumor immunity by a polypeptide can be confirmed by observing the induction of antibody production against tumors. For example, when antibodies against a polypeptide are induced in a laboratory animal immunized with the polypeptide, and when growth, proliferation or metastasis of tumor cells is suppressed by those antibodies, the polypeptide can be determined to have an ability to induce anti-tumor immunity.

Anti-tumor immunity is induced by administering the vaccine of this invention, and the induction of anti-tumor immunity enables treatment and prevention of NSCLC. Therapy against or prevention of the onset of NSCLC includes any of the steps, such as inhibition of the growth of NSCLC cells, involution of NSCLC cells and suppression of occurrence of NSCLC cells. Decrease in mortality of individuals having NSCLC, decrease of marker genes (in addition to KIF11, GHSR1 and/or NTSR1 genes) in the blood, alleviation of detectable symptoms accompanying NSCLC and such are also included in the therapy or prevention of NSCLC. Such therapeutic and preventive effects are preferably statistically significant. For example, in observation, at a significance level of 5% or less, wherein the therapeutic or preventive effect of a vaccine against NSCLC is compared to a control without vaccine administration. For example, Student's t-test, the Mann-Whitney U-test or ANOVA may be used for statistical analysis.

The above-mentioned protein having immunological activity, or a polynucleotide or vector encoding the protein may be combined with an adjuvant. An adjuvant refers to a compound that enhances the immune response against the protein when administered together (or successively) with the protein having immunological activity. Examples of adjuvants include cholera toxin, *salmonella* toxin, alum and such, but are not limited thereto. Furthermore, the vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally.

Vaccine administration may be performed by single administration or boosted by multiple administrations.

When using APC or CTL as the vaccine of this invention, NSCLC can be treated or prevented, for example, by the ex vivo method. More specifically, PBMCs of the subject receiving treatment or prevention are collected, the cells are contacted with the polypeptide ex vivo, and following the induction of APC or CTL, the cells may be administered to the subject. APC can be also induced by introducing a vector encoding the polypeptide into PBMCs ex vivo. APC or CTL induced in vitro can be cloned prior to administration. By cloning and growing cells having high activity of damaging target cells, cellular immunotherapy can be performed more effectively. Furthermore, APC and CTL isolated in this manner may be used for cellular immunotherapy not only against individuals from whom the cells are derived, but also against similar types of diseases in other individuals.

Moreover, the present invention provides a method for treating or preventing NSCLC in a subject, wherein a compound obtained according to any of the above-described screening methods is administered to the subject. Any compound that are obtained according to any of the screening methods of the present invention can be administered to the subject so long as it decreases the expression or function, or both, of one or more gene products of KIF11, GHSR1b, NTSR1, and FOXM1 genes.

siRNA and Vectors Encoding Them

Transfection of vectors expressing siRNA for KIF11, GHSR1b, NTSR1 or FOXM1 leads to growth inhibition of NSCLC cells. Thus, it is another aspect of the present invention to provide a double-stranded molecule comprising a sense-strand and antisense-strand which molecule functions as an siRNA for KIF11, GHSR1b, NTSR1 or FOXM1, and a vector encoding the double-stranded molecule.

The double-stranded molecule of the present invention comprises a sense strand and an antisense strand, wherein the sense strand comprises a ribonucleotide sequence corresponding to a KIF11, GHSR1b, NTSR1 or FOXM1 target sequence, and wherein the antisense strand comprises a ribonucleotide sequence which is complementary to said sense strand, wherein said sense strand and said antisense strand hybridize to each other to form said double-stranded molecule, and wherein said double-stranded molecule, when introduced into a cell expressing a KIF11, GHSR1b, NTSR1 or FOXM1 gene, inhibits expression of said gene.

The double-stranded molecule of the present invention may be a polynucleotide derived from its original environment (i.e., when it is a naturally occurring molecule, the natural environment), physically or chemically altered from its natural state, or chemically synthesized. According to the present invention, such double-stranded molecules include those composed of DNA, RNA, and derivatives thereof. A DNA is suitably composed of bases such as A, T, C and G, is replaced by U in an RNA.

As described above, the term "complementary" refers to a Watson-Crick or Hoogsteen base pairing between nucleotide units of a polynucleotide, and hybridization or binding of nucleotide units indicates physical or chemical interaction between the units under appropriate conditions to form a stable duplex (double-stranded configuration) containing few or no mismatches. In a preferred embodiment, such duplexes contain no more than 1 mismatch for every 10 base pairs. Particularly preferred duplexes are fully complementary and contain no mismatch.

The double-stranded molecule of the present invention contains a ribonucleotide sequence corresponding to a KIF11, GHSR1b, NTSR1 or FOXM1 target sequence shorter than the whole mRNA of KIF11, GHSR1b, NTSR1 or FOXM1 gene. Herein, the phrase a "target sequence of KIF11, GHSR1b, NTSR1 or FOXM1 gene" refers to a sequence that, when introduced into NSCLC cell lines, is effective for suppressing cell viability. Specifically, the target sequence comprises at least about 10, or suitably about 19 to about 25 contiguous nucleotides from the nucleotide sequences selected from the group of SEQ ID NOs: 1, 3, 5, and 106. That is, the sense strand of the present double-stranded molecule consists of at least about 10 nucleotides, suitably is longer than 19 nucleotides, and more preferably longer than 21 nucleotides. Preferred target sequences include the sequences of SEQ ID NOs: 32, 33, 34, 35, 36, 37, and 108. The present double-stranded molecule including the sense strand and the antisense strand is an oligonucleotide shorter than about 100, preferably 75, more preferably 50 and most preferably 25 nucleotides in length. A suitable double-stranded molecule of the present invention is an oligonucleotide of a length of about 19 to about 25 nucleotides. Furthermore, in order to enhance the inhibition activity of the siRNA, nucleotide "u" can be added to 3' end of the antisense strand of the target sequence. The number of "u"s to be added is at least 2, generally 2 to 10, preferably 2 to 5. The added "u"s form single strand at the 3' end of the antisense strand of the siRNA. In these embodiments, the siRNA molecules of the invention are typically modified as described above for antisense molecules. Other modifications are also possible, for example, cholesterol-conjugated siRNAs have shown improved pharmacological properties (Song et al. *Nature Med.* 9:347-351 (2003)).

Furthermore, the double-stranded molecule of the present invention may be a single ribonucleotide transcript comprising the sense strand and the antisense strand linked via a single-stranded ribonucleotide sequence. Namely, the present double-stranded molecule may have the general formula:

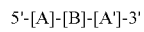

wherein [A] is a ribonucleotide sequence corresponding to a target sequence of KIF11, GHSR1b, NTSR1 or FOXM1;
[3] is a ribonucleotide sequence (loop sequence) consisting of 3 to 23 nucleotides; and
[A'] is a ribonucleotide sequence complementary to [A]. The complementary sequence [A'] and [A] hybridize to each other to form a double strand, and the whole siRNA molecule with the general formula 5'-[A]-[B]-[A']-3' forms a hairpin loop structure.

The region [A] hybridizes to [A'], and then a loop consisting of region [B] is formed. The loop sequence can be selected from those describe in http://www.ambion.com/techlib/tb/tb_506.html, or those described in Jacque, J.-M. et al., *Nature* 418: 435-438 (2002). Additional examples of the loop sequence that can be included in the present double-stranded molecules include:

CCC, CCACC or CCACACC: Jacque, J. M. et al., *Nature*, Vol. 418: 435-438 (2002);

UUCG: Lee, N. S. et al., *Nature Biotechnology* 20:500-505 (2002); Fruscoloni, P. et. al., *Proc. Natl. Acad. Sci. USA* 100(4): 1639-1644 (2003); and UUCAAGAGA: Dykxhoorn, D. M. et al., *Nature Reviews Molecular Cell Biology* 4: 457-467 (2002).

Preferable siRNAs having hairpin loop structure of the present invention are shown below. In the following structure, the loop sequence can be selected from the group consisting of: CCC, UUCG, CCACC, CCACACC, and UUCAAGAGA. Among these sequences, the most preferable loop sequence is UUCAAGAGA (corresponding to "ttcaagaga" in a DNA):

```
guuaguguac gaacuggag-[B]-cuccaguuc guacacuaac;
(for the target sequence of SEQ ID NO: 32)

gugucucugu uggagaucu-[B]-agaucucca acagagacac;
(for the target sequence of SEQ ID NO: 33)

gaaggcaguu gaccaacac-[B]-guguugguc aacugccuuc;
(for the target sequence of SEQ ID NO: 34)

ccucuaccug uccagcaug-[B]-caugcugga cagguagagg;
(for the target sequence of SEQ ID NO: 35)

guucaucagc gccaucugg-[B]-ccagauggc gcugaugaac;
(for the target sequence of SEQ ID NO: 36)

ggucgucaua caggucaac-[B]-guugaccug uaugacgacc;
(for the target sequence of SEQ ID NO: 37)
and gcagcagaaa cgaccgaau-[B]-auucggucg uuucugcugc.
(for the target sequence of SEQ ID NO: 108)
```

The present invention further provides a vector encoding the double-stranded molecule of the present invention. The vector encodes a transcript having a secondary structure and which comprises the sense strand and the antisense strand, and suitably comprises a single-stranded ribonucleotide sequence linking said sense strand and said antisense strand. The vector preferably comprises a regulatory sequence adjacent to the region encoding the present double-stranded molecule that directs the expression of the molecule in an adequate cell. For example, the double-stranded molecules of the present invention are intracellularly transcribed by cloning their coding sequence into a vector containing, e.g., a RNA pol III transcription unit from the small nuclear RNA (snRNA) U6 or the human H1 RNA promoter.

Alternatively, the present vectors are produced, for example, by cloning the target sequence into an expression vector so the objective sequence is operatively-linked to a regulatory sequence of the vector in a manner to allow expression thereof (transcription of the DNA molecule) (Lee, N. S. et al., *Nature Biotechnology* 20: 500-505 (2002)). For example, the transcription of an RNA molecule having an antisense sequence to the target sequence is driven by a first promoter (e.g., a promoter sequence linked to the 3'-end of the cloned DNA) and that having the sense strand to the target sequence by a second promoter (e.g., a promoter sequence linked to the 5'-end of the cloned DNA). The expressed sense and antisense strands hybridize to each other in vivo to generate a siRNA construct to silence a gene that comprises the target sequence. Furthermore, two constructs (vectors) may be utilized to respectively produce the sense and anti-sense strands of a siRNA construct.

For introducing the vectors into a cell, transfection-enhancing agent can be used. FuGENE (Rochediagnostices), Lipofectamine 2000 (Invitrogen), Oligofectamine (Invitrogen), and Nucleofector (Wako pure Chemical) are useful as the transfection-enhancing agent.

Pharmaceutical Compositions for Treating or Preventing NSCLC

The present invention provides compositions for treating or preventing NSCLC comprising a compound selected by the present method of screening for a compound that alters the expression or activity of an NSCLC-associated gene.

When administering a compound isolated by the screening method of the present invention as a pharmaceutical for humans and other mammals, such as mice, rats, guinea-pig, rabbits, cats, dogs, sheep, pigs, cattle, monkeys, baboons or chimpanzees for treating a cell proliferative disease (e.g., non-small cell lung cancer), the isolated compound can be directly administered or can be formulated into a dosage form using conventional pharmaceutical preparation methods. Such pharmaceutical formulations of the present compositions include those suitable for oral, rectal, nasal, topical (including buccal and sub-lingual), vaginal or parenteral (including intramuscular, sub-cutaneous and intravenous) administration, or for administration by inhalation or insufflation. The formulations are optionally packaged in discrete dosage units.

Pharmaceutical formulations suitable for oral administration include capsules, cachets or tablets, each containing a predetermined amount of the active ingredient. Formulations also include powders, granules, solutions, suspensions or emulsions. The active ingredient is optionally administered as a bolus electuary or paste. Tablets and capsules for oral administration may contain conventional excipients such as binding agents, fillers, lubricants, disintegrant or wetting agents. A tablet may be made by compression or molding, optionally with one or more formulational ingredients. Compressed tablets may be prepared by compressing in a suitable machine the active ingredients in a free-flowing form such as powder or granules, optionally mixed with a binder, lubricant, inert diluent, lubricating, surface active or dispersing agent. Molded tablets may be made via molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for reconstitution with water or other suitable vehicle prior to use. Such liquid preparations may contain conventional additives such as suspending agents, emulsifying agents, non-aqueous vehicles (which may include edible oils) or preservatives. The tablets may optionally be formulated so as to provide slow or controlled release of the active ingredient in vivo. A package of tablets may contain one tablet to be taken on each of the month. The formulation or dose of medicament in these preparations makes a suitable dosage within the indicated range acquirable.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations for rectal administration include suppositories with standard carriers such as cocoa butter or polyethylene glycol. Formulations for topical administration in the mouth, for example, buccally or sublingually, include lozenges, which contain the active ingredient in a flavored base such as sucrose and acacia or tragacanth, and pastilles comprising the active ingredient in a base such as gelatin, glycerin, sucrose or acacia. For intra-nasal administration of an active ingredient, a liquid spray or dispersible powder or in the form of drops may be used. Drops may be formulated with an aqueous or non-aqueous base also comprising one or more dispersing agents, solubilizing agents or suspending agents.

For administration by inhalation the compositions are conveniently delivered from an insufflator, nebulizer, pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compositions may take the form of a dry powder composition, for example, a powder mix of an active ingredient and a suitable powder base such as lactose or starch. The powder composition may be presented in unit dosage form in, for example, capsules, cartridges, gelatin or blister packs from which the powder may be administered with the aid of an inhalator or insufflator.

Other formulations include implantable devices and adhesive patches; which release a therapeutic agent.

When desired, the above-described formulations, adapted to give sustained release of the active ingredient, may be employed. The pharmaceutical compositions may also contain other active ingredients such as antimicrobial agents, immunosuppressants or preservatives.

It should be understood that in addition to the ingredients particularly mentioned above, the formulations of this invention may include other agents conventional in the art having regard to the type of formulation in question, for example, those suitable for oral administration may include flavoring agents.

Preferred unit dosage formulations are those containing an effective dose, as recited below, of the active ingredient or an appropriate fraction thereof.

For each of the aforementioned conditions, the compositions, e.g., polypeptides and organic compounds are administered orally or via injection at a dose of from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg.

The dose employed will depend upon a number of factors, including the age and sex of the subject, the precise disorder being treated, and its severity. Also the route of administration may vary depending upon the condition and its severity.

The present invention further provides a composition for treating or preventing NSCLC comprising active ingredient that inhibits the expression of any one of the gene selected from the group of KIF11, GHSR1b, NTSR1, and FOXM1 genes. Such active ingredient can be an antisense-oligonucleotide, siRNA or ribozyme against the gene, or derivatives, such as expression vector, of the antisense-oligonucleotide, siRNA or ribozyme. The active ingredient may be made into an external preparation, such as liniment or a poultice, by mixing with a suitable base material which is inactive against the derivatives.

Also, as needed, the active ingredient can be formulated into tablets, powders, granules, capsules, liposome capsules, injections, solutions, nose-drops and freeze-drying agents by adding excipients, isotonic agents, solubilizers, preservatives, pain-killers and such. These can be prepared according to conventional methods for preparing nucleic acid containing pharmaceuticals.

Preferably, the antisense-oligonucleotide derivative, siRNA derivative or ribozyme derivative is given to the patient by direct application to the ailing site or by injection into a blood vessel so that it will reach the site of ailment. A mounting medium can also be used in the composition to increase durability and membrane-permeability. Examples of mounting mediums include liposome, poly-L-lysine, lipid, cholesterol, lipofectin and derivatives thereof.

The dosage of such compositions can be adjusted suitably according to the patient's condition and used in desired amounts. For example, a dose range of 0.1 to 100 mg/kg, preferably 0.1 to 50 mg/kg can be administered.

Another embodiment of the present invention is a composition for treating or preventing NSCLC comprising an antibody against a polypeptide encoded by any one of the genes selected from the group of KIF11, GHSR1b, NTSR1, and FOXM1 genes or fragments of the antibody that bind to the polypeptide.

Although there are some differences according to the symptoms, the dose of an antibody or fragments thereof for treating or preventing NSCLC is about 0.1 mg to about 100 mg per day, preferably about 1.0 mg to about 50 mg per day and more preferably about 1.0 mg to about 20 mg per day, when administered orally to a normal adult (weight 60 kg).

When administering parenterally, in the form of an injection to a normal adult (weight 60 kg), although there are some differences according to the condition of the patient, symptoms of the disease and method of administration, it is convenient to intravenously inject a dose of about 0.01 mg to about 30 mg per day, preferably about 0.1 to about 20 mg per day and more preferably about 0.1 to about 10 mg per day. Also, in the case of other animals too, it is possible to administer an amount converted to 60 kg of body-weight.

The following examples are presented to illustrate the present invention and to assist one of ordinary skill in making and using the same. The examples are not intended in any way to otherwise limit the scope of the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. Any patents, patent applications and publications sited herein are incorporated by reference.

BEST MODE FOR CARRYING OUT THE INVENTION

Materials and Methods (1) Patients and Tissue Samples

Primary NSCLC samples, of which 22 were classified as adenocarcinomas (ADCs), 14 as squamous-cell carcinomas (SCCs), and one as adenosquamous carcinoma, had been obtained earlier with informed consent from 37 patients (Kikuchi, T. et al., *Oncogene* 22, 2192-2205 (2003)). Fifteen additional primary NSCLCs, including seven ADCs and eight SCCs, were obtained along with adjacent normal lung tissue samples from patients undergoing surgery at our institutes.

(2) Cell Lines

The 30 human NSCLC and four SCLC cell lines used in this study were as follows: adenocarcinomas (ADCs) A427, A549, NCI-H23, NCI-H522, LC174, LC176, LC319, PC3, PC9, PC14, PC14-PE6, NCI-H1373, NCI-H1435, NCI-H1793, SK-LU-1, NCI-H358, NCI-H1650 and SW1573; adenosquamous carcinomas (ASCs) NCI-H226, NCI-H596 and NCI-H647; squamous-cell carcinomas (SCCs) RERF- LC-AI, SW-900, SK-MES-1, EBC-1, LU61, NCI-H520, NCI-H1703, and NCI-H2170; large-cell carcinoma (LCC) LX1; and SCLCs DMS114, DMS273, SBC-3, and SBC-5. Human small airway epithelial cells, SAEC were grown in optimized medium (SAGM) purchased from Cambrex Bio Science Inc. A human bronchial epithelial cell line, BEAS2B cells were also served.

Thirty-four human NSCLC or SCLC cancer cell lines and two normal bronchial epithelium cell lines were grown in monolayers in appropriate medium supplemented with 5 or 10% fetal bovine serum (see Table 1).

TABLE 1

| | Cell line name | Medium | Provider |
|---|---|---|---|
| | | adenocarcinoma (ADC) | |
| | A427 | EMEM (10% FBS) | ATCC (HTB-53) |
| | A549 | RPMI-1640 (10% FBS) | ATCC (CCL-185) |
| | NCI-H23 | RPMI-1640 (10% FBS) | ATCC (CRL-5800) |
| | NCI-H522 | RPMI-1640 (10% FBS) | ATCC (CRL-5810) |
| | LC174 | RPMI-1640 (10% FBS) | Aichi Cancer Center |
| | LC176 | RPMI-1640 (10% FBS) | Aichi Cancer Center |
| | LC319 | RPMI-1640 (10% FBS) | Aichi Cancer Center |
| | PC-3 | DMEM (10% FBS) | Tokushima Univerity |
| | PC-9 | DMEM (10% FBS) | Tokushima Univerity |
| | PC14 | RPMI-1640 (10% FBS) | Tokushima Univerity |
| | PC14-PE6 | RPMI-1640 (10% FBS) | Tokushima Univerity |
| | NCI-H1373 | RPMI-1640 (10% FBS) | ATCC (CRL-5866) |
| | NCI-H1435 | F12 + DMEM (5% FBS) + EGF(+) | SNU Bank |
| | NCI-H1793 | F12 + DMEM (5% FBS) + Glu | SNU Bank |
| | SK-LU-1 | DMEM (10% FBS) | SNU Bank |
| BAC | NCI-H358 | RPMI-1640 (10% FBS) | SNU Bank |
| BAC | NCI-H1650 | RPMI-1640 (10% FBS) | ATCC (CRL-5883) |
| BAC | SW1573 | Leibovitz's L-15 (10% FBS) | ATCC (CRL-2170) |
| | | adenosquamous carcinoma (ASCs) | |
| | NCI-H226 | RPMI-1640 (10% FBS) | ATCC (CRL-5826) |
| | NCI-H647 | RPMI-1640 (10% FBS) | ATCC (CRL-5834) |
| | NCI-H596 | RPMI-1640 (10% FBS) | SNU Bank |
| | | squamous cell carcinoma (SCC) | |
| | RERF-LC-AI | DMEM (10% FBS) | Tokushima Univerity |
| | SW-900 | Leibovitz's L-15 (10% FBS) | SNU Bank |
| | SK-MES-1 | DMEM (10% FBS) | SNU Bank |
| | EBC-1 | DMEM (10% FBS) | Tokushima Univerity |
| | LU61 | DMEM (10% FBS) | Central Institute for Experimental Animals |
| | NCI-H520 | RPMI-1640 (10% FBS) | ATCC (HTB-182) |
| | NCI-H1703 | RPMI-1640 (10% FBS) | ATCC (CRL-5889) |
| | NCI-H2170 | RPMI-1640 (10% FBS) | ATCC8 (CRL-5928) |
| | | large-cell carcinoma (LCC) | |
| | LX1 | DMEM (10% FBS) | Central Institute for Experimental Animals |
| | | small-cell lung carcinoma (SCLCs) | |
| | DMS114 | RPMI-1640 (10% FBS) | ATCC (CRL-2066) |
| | DMS273 | RPMI-1640 (10% FBS) | Japanese foundation for cancer research |
| | SBC-3 | RPMI-1640 (10% FBS) | Tokushima Univerity |
| | SBC-5 | EMEM (10% FBS) | Tokushima Univerity |
| | | small airway epithelial cells | |
| | SAEC | SAGM | Cambrex Bio Science Inc. |
| | | human bronchial cell line | |
| | BEAS2B | RPMI-1640 (10% FBS) | ATCC (CRL-9609) |

(3) Semiquantitative RT-PCR Analysis

Total RNA was extracted from cultured cells and clinical tissues using Trizol reagent (Life Technologies, Inc.) according to the manufacturer's protocol. Extracted RNAs and normal human tissue poly(A) RNAs were treated with DNase I (Nippon Gene) and reverse-transcribed using oligo(dT) primer and SuperScript II reverse transcriptase (Invitrogen). Semiquantitative RT-PCR experiments were carried out with the following synthesized gene-specific primers or with beta-actin (ACTB)-specific primers as an internal control:

```
KOC1,
5'-TAAATGGCTTCAGGAGACTTCAG-3'    (SEQ.ID.NO. 7)
and
5'-GGTTTTAAATGCAGCTCCTATGTG-3';  (SEQ.ID.NO. 8)

KIF11,
5'-CTGAACAGTGGGTATCTTCCTTA-3'    (SEQ.ID.NO. 9)
and
5'-GATGGCTCTTGACTTAGAGGTTC-3';   (SEQ.ID.NO. 10)

NMU,
5'-TGAAGAGATTCAGAGTGGACGA-3'     (SEQ.ID.NO. 11)
and
5'-ACTGAGAACATTGACAACACAGG-3';   (SEQ.ID.NO. 12)

NMU1R,
5'-AAGAGGGACAGGGACAAGTAGT-3'     (SEQ ID.NO. 13)
and
5'-ATGCCACTGTTACTGCTTCAG-3';     (SEQ.ID.NO. 14)

NMU2R,
5'-GGCTCTTACAACTCATGTACCCA-3'    (SEQ.ID.NO. 15)
and
5'-TGATACAGAGACATGAAGTGAGCA-3';  (SEQ.ID.NO. 16)

GHSR1a,
5'-TGGTGTTTGCCTTCATCCT-3'        (SEQ.ID.NO. 17)
and
5'-GAATCCCAGAAGTCTGAACA-3';      (SEQ.ID.NO. 18)

GHSR1b,
5'-ACGGTCCTCTACAGTCTCA-3'        (SEQ.ID.NO. 19)
and
5'-CACAGGGAGAGGATAGGA-3';        (SEQ.ID.NO. 20)

NTSR1,
5'-AGTGGGCTCAGAGTCTAGCAAAT-3'    (SEQ.ID.NO. 21)
and
5'-TATTGAGAGATACACGGGGTTTG-3';   (SEQ.ID.NO. 22)

GHRL,
5'-TGAGCCCTGAACACCAGAGAG-3'      (SEQ.ID.NO. 23)
and
5'-AAAGCCAGATGAGCGCTTCTA-3';     (SEQ.ID.NO. 24)

NTS,
5'-TCTTCAGCATGATGTGTTGTGT-3'     (SEQ.ID.NO. 25)
and
5'-TGAGAGATTCATGAGGAAGTCTTG-3';  (SEQ.ID.NO. 26)

ACTB,
5'-GAGGTGATAGCATTGCTTTCG-3'      (SEQ.ID.NO. 27)
and
5'-CAAGTCAGTGTACAGGTAAGC-3'.     (SEQ.ID.NO. 28)
```

PCR reactions were optimized for the number of cycles to ensure product intensity within the logarithmic phase of amplification.

Quantitative Real-Time RT-PCR (QRT-PCR) Analysis and Northern-Blot Analyses

Expression levels of the KOC1 and KIF11 genes were measured by QRT-PCR using the ABI Prism 7700 sequence detection system (Applied Biosystems). Total RNA was extracted from cultured cells and clinical tissues using Trizol reagent (Life Technologies, Inc.) according to the manufacturer's protocol. Extracted RNAs and normal human tissue poly(A) RNAs were treated with DNase I (Nippon Gene) and were reverse-transcribed using oligo (dT) primer and SuperScript II reverse transcriptase (Ivitrogen). The TaqMan Pre-Developed Assay Human ACTB (Applied Biosystems; #4333762F) was used for ACTB gene as a quantitative control. A primer pair and a TaqMan probe for each gene were designed by using Primer Express software as follows:

```
KOC1,
                                        (SEQ.ID.NO. 98)
5'-ACGAACTCATTTGCTCACTCCTT-3'   (sense), (SEQ.ID.NO. 99)
5'-ACCCACACCCAACACAATTGT-3'     (antisense), (SEQ.ID.NO. 100)
5'-ACAGCAAAGCCC-3'              (TaqMan-MGB probe);

KIF11,
                                        (SEQ.ID.NO. 101)
5'-TTCACCCTGACAGAGTTCACAAA-3'   (sense)

(SEQ.ID.NO. 102)
5'-GGGTGGTCTCCCATAATAGCAA-3'    (antisense), (SEQ.ID.NO. 103)
5'-AGCCCACTTTAGAGTATAC-3'       (TaqMan-MGB probe).
``` each containing His-tagged epitope at the N-terminal, were prepared using pET28 vector (Novagen). Recombinant proteins were expressed in *Escherichia coli* BL21 codon-plus strain (Stratagene), purified using TALON resin (BD Biosciences Clontech) according to the supplier's protocol, and inoculated into rabbits. The immune sera were purified on affinity columns according to standard methodology. Affinity-purified anti-KOC1 and anti-KIF11 antibodies were used for western-blot analysis, immunoprecipitation, and immunostaining. We confirmed by western-blot analysis that anti-KOC1 antibody are specific to KOC1 and do not cross-react with other homologous proteins, IMP-1 and IMP-2 using lysates of NCI-H520 cells, which expressed neither of endogenous IMP-1, -2, and -3, but had been transfected with HA-tagged IMP-1, -2, and -3 expression vector.

Construction of KOC1 Deletion Mutants and Immunoprecipitation Assays for Identification of the KOC1-KIF11 Binding Region KOC1 and several of its domains (FIG. 3a) were cloned into appropriate sites of N-terminal FLAG-tagged and C-terminal HA-tagged pCAGGS vector. COS-7 cells transfected only with an KOC1 deletion mutant, were immunoprecipitated with anti-HA agarose (SIGMA). Endogenous KIF11 bands were detected with affinity-purified anti-KIF11 antibody by western blotting.

TABLE 3

Primer sequence for constraction of deletion mutant by RT-PCR

|  | F | SEQ ID NO. | R | SEQ ID NO. |
|---|---|---|---|---|
| full length | 5'-ATGAACAAACTGTATATCGG-3' | 69 | 5'-CTTCCGTCTTGACTGAGG-3' | 70 |
| KOC1 DEL1 | 5'-ATGAACAAACTGTATATCGG-3' | 71 | 5'-ATGAGCTTCAAGTTTCACC-3' | 72 |
| KOC1 DEL2 | 5'-ATGAACAAACTGTATATCGG-3' | 73 | 5'-CTCCGTTTCTGATTGCTC-3' | 74 |
| KOC1 DEL3 | 5'-ATGAACAAACTGTATATCGG-3' | 75 | 5'-AGGCAAATCACATGGTTTCTG-3' | 76 |
| KOC1 DEL4 | 5'-TTGCCTCTGCGCCTGCTG-3' | 77 | 5'-CTTCCGTCTTGACTGAGG-3' | 78 |
| KOC1 DEL5 | 5'-TTGCCTCTGCGCCTGCTG-3' | 79 | 5'-CTCCGTTTCTGATTGCTC-3' | 80 |

PCR for each gene and the ACTB gene was performed in a single tube in duplicate. Results were expressed as the average of these two independent tests.

(4) Northern-Blot Analysis

Human multiple-tissue blots (BD Biosciences Clontech) were hybridized with $^{32}$P-labeled PCR products of KOC1, KIF11 and GHSR1. cDNA probes of KOC1, KIF11 and GHSR1 were prepared by RT-PCR using primers similarly as above. Prehybridization, hybridization, and washing were performed according to the supplier's recommendations. The blots were autoradiographed with intensifying BAS screens (BIO-RAD) at room temperature (RT) for 30 to 168 hours.

Generation of Anti-KOC1 and -KIF11 Antibodies

Plasmids expressing KOC1 (full-length) and KIF11 (partial amino acid sequence corresponding to codons 361-1056), RNA-Immunoprecipitation and cDNA Microarray Screening for Identification of KOC1-Associated mRNAs We adopted the RNA immunoprecipitation protocol of Niranjanakumari et al. (Niranjanakumari, S. et al. *Methods* 26, 182-190 (2002)) to analyze RNA-protein interactions involving KOC1 in vivo. Immunoprecipitated RNAs were isolated from five lung-cancer cell lines (A549, LC319, PC14, RERF-LC-AI, and SK-MES-1). A 2.5-μg aliquot of T7-based amplified RNAs (aRNAs) from each immunoprecipitated RNA (IP-RNA) and from the total RNA (control) were reversely transcribed in the presence of Cy5-dCTP and Cy3-dCTP respectively as described previously (Kikuchi, T. et al. *Oncogene* 22, 2192-2205 (2003)), for hybridization to a cDNA microarray representing 32,256 genes (IP-microarray analysis). To confirm the binding to KOC1 of the mRNAs identified by IP-microarray analysis, we carried out RT-PCR experiments using gene-specific primers and RNAs from NSCLC cell extracts immunoprecipitated with anti-KOC1 antibody (IP-RT-PCR). To confirm the region of KOC1 required for binding to the KOC1-associated mRNAs, we also carried out northwestern blot analysis as below and IP-RT-PCR of KOC1-associated mRNAs from these immunoprecipitated extracts transfected with various KOC1 deletion mutants.

RAB35, was performed using DAVIS Lab's protocol (found on the World Wide Web at ed.ac.uk/~ilan). To generate fluorescent riboprobes for in vivo co-localization with KOC1, the plasmids were transcribed using the mCAP RNA capping kit (Stratagene) in the presence of Alexa Fluor 546-labeled UTP (Molecular Probes). We constructed plasmids expressing EGFP-fused KOC1 (EGFP-KOC1) protein were prepared using pEGFP-N1 vectors (BD Biosciences Clontech). For live-cell imaging of co-localized EGFP-KOC1 and Alexa

TABLE 4

Primer sequence for IP-RT-PCR

| | F | SEQ ID NO. | R | SEQ ID NO. |
|---|---|---|---|---|
| CCT2 | 5'-TTATCCTGAACAGCTCT TTGGTG-3' | 81 | 5'-AAGCGAAGGTCAGCTAAATA TCC-3' | 82 |
| SBP2 | 5'-CTTTCTGAGCACACTAC GGATCT-3' | 83 | 5'-AAGCCCTCTTACTTACAGGG AAA-3' | 84 |
| SLC25A3 | 5'-GGTTCCCCTGGATTTAG TGAA-3' | 85 | 5'-CAACAGTAAATCTGAAACTC TTGCC-3' | 86 |
| RAB35 | 5'-GACAAAGGTAGCAAGA GGATTTC-3' | 87 | 5'-CTGGTGTTAAACTCGGTTCT TC-3' | 88 |
| PSMB7 | 5'-CTAGTGAGTGAGGCTAT TGCAGC-3' | 89 | 5'-GTCTCTTCTAGCACCTCAAT CTCC-3' | 90 |
| GL | 5'-ATCTGACTTTCTGTCCA CTGCAT-3' | 91 | 5'-TAATTCAGCATAAGCCAAAG CC-3' | 92 |
| PKP4 | 5'-ACACAGTATGGACTGAA ATCGAC-3' | 93 | 5'-CACCTCAATCTGAACAAGGT TAG-3' | 94 |
| WINS1 | 5'-GGCCTCTCAAAGTCTGG TAGATT-3' | 95 | 5'-ATATTCCCACTTCAGAGACG ACA-3' | 96 |

Northwestern Blot Analysis

Immunoprecipitated extracts from cells transfected with the KOC1 deletion mutants (µM) were boiled in 2×SDS-sample buffer, electrophoresed through 10-20% gradient polyacrylamide gels (BIO-RAD) and transferred to a polyvinylidene difluoride membrane (Hybond-P). The membrane was then blocked for 1 hour at room temperature in blocking buffer (10 mM Tris-HCl (pH 7.8), 150 mM NaCl, 1 mg/ml yeast tRNA), and washed twice with 50 ml of 10 mM Tris-HCl (pH 7.8) for 5 min and incubated with DIG-labeled RNA probe in 5 ml of NWB buffer (10 mM Tris-HCl (pH 7.8), 1 mM EDTA, 50 mM NaCl, 0.02% Ficoll, 0.02% polyvinyl pyrrolidone, 0.02% BSA) for 2 hours at room temperature. The membrane was washed four times with NWB buffer and the RNA probe bound to the proteins was then detected using DIG nucleic acid detection kit (Roche) according to the supplier's protocol.

Living-Cell Imaging of KOC1 and KIF11 Proteins and KOC1-Associated RAB35 mRNA

Plasmids expressing ECFP-fused KOC1 (ECFP-KOC1) protein were prepared using pECFP-N1 vectors (BD Biosciences Clontech). Plasmids expressing EYFP-fused KIF11 (EYFP-KIF11) protein were also prepared, using pEYFP-N1 vectors (BD Biosciences Clontech). Time-lapse images of COS-7 cells transfected with plasmids expressing ECFP-KOC1 or EYFP-KIF11 proteins were captured for 5-15 hours by the Live Cell Imaging System (Power IX81, OLYMPUS) and a confocal microscope (TCS SP2-AOBS, Leica Microsystems; FV1000 FLUOVIEW, OLYMPUS).

In vitro transcription of linearized plasmids carrying the full-length cDNA sequence of an KOC1-associated gene, Fluor 546-labeled RAB35 mRNA, COS-7 cells that had been transfected initially with pEGFP-KOC1 were additionally transfected 36 hours later with Alexa Fluor 546-labeled RAB35 mRNA (3 µg per 3.5-cm culture dish) in the presence of RNase Inhibitor (TAKARA). The plasmid-DNA and RNA samples were transfected using Lipofectamine 2000 (Invitrogen) according to the manufacturer's protocols. The cells were washed twice with PBS, and fresh medium was added 90 min after transfection with the labeled mRNA. The cells were allowed to recover in the incubator (37° C., 5% $CO_2$) for 30 min before live-cell imaging for 3-6 hours with a confocal microscope (FV1000 FLUOVIEW, OLYMPUS). To investigate the specific transport of mRNAs by KOC1-RNP complex from one cell to another cell, we prepared two different COS-7-derived cells; the COS-7 cells transfected with pEGFP-KOC1 and Alexa Fluor 546-labeled RAB35 mRNA and the other, parental COS-7 cells simply labeled with Cell-Tracker (Molecular Probes) according to the supplier's protocols. These two cell populations were mixed and co-cultured for 12 hours before live-cell imaging with confocal microscope for 6 hours.

To investigate the translation of the mRNA transported by KOC1-RNP complex in the recipient cells, we prepared two types of COS-7-derived cell; one type was COS-7 cells co-transfected with pCAGGS-FLAG tagged-KOC1 and -KIF11. After 24 hours culture, plasmid containing EGFP-fused RAB35 full length mRNA were re-transfected into these cells. The other type was COS-7 cells simply labeled with CellTracker (blue). These two cell-types were mixed and co-cultured for 24 hours before live-cell imaging with video microscope for 12 hours. Synthesis of EGFP-tagged RAB35 mRNAs and corresponding proteins in the CellTracker-stained recipient cells (blue) as well as on the ultrafine structure between the two cells was examined by in situ hybridization and time-lapse video microscopy.

Fluorescent In Situ Hybridization

We carried out in situ hybridization with DIG-labeled probes complementary to RAB35 or EGFP mRNA at 60° C. for 16 hours. The DIG label was detected using NBT-BCIP, an alkaline phosphatase color substrate. Cells were washed, mounted and visualized on light microscope. Fixed cells were hybridized with a mixture of DIG-labeled complementary to RAB35 mRNA for 16 hours in 50% formamide/2×SSC at 42° C. Cells were washed, mounted and visualized on confocal microscope.

(5) RNA Interference Assay

To prepare plasmid vector expressing short interfering RNA (siRNA), we amplified the genomic fragment of H1RNA gene containing its promoter region by PCR using a set of primers, 5'-TGGTAGCCAAGTGCAGGTTATA-3' (SEQ ID No: 44), and 5'-CCAAAGGGTTTCTG-CAGTTTCA-3' (SEQ ID No: 45) and human placental DNA as a template. The product was purified and cloned into pCR2.0 plasmid vector using a TA cloning kit according to the supplier's protocol (Invitrogen). The BamHI and XhoI fragment containing H1RNA was into pcDNA3.1(+) between nucleotides 1257 and 56, and the fragment was amplified by PCR using

```
                                      (SEQ ID No: 46)
5'-TGCGGATCCAGAGCAGATTGTACTGAGAGT-3'
and (SEQ ID No: 47)
5'-CTCTATCTCGAGTGAGGCGGAAAGAACCA-3',
```

The ligated DNA became the template for PCR amplification with primers,

```
                                      (SEQ ID No: 48)
5'-TTTAAGCTTGAAGACCATTTTTGGAAAAAAAAAAAAAAAAAA
AAC-3'
and (SEQ ID No: 49)
5'-TTTAAGCTTGAAGACATGGGAAAGAGTGGTCTCA-3'.
```

The product was digested with HindIII, and subsequently self-ligated to produce psiH1BX3.0 vector plasmid having a nucleotide sequence shown in SEQ ID NO: 50.

The DNA flagment encoding siRNA was inserted into the GAP at nucleotide 489-492 as indicated (–) in the following plasmid sequence (SEQ ID NO: 50).

GACGGATCGGGAGATCTCCCGATCCCTATGGTGCACTCTCAGTACA

ATCTGCTCTGGATCCACTAGTAACGGCCGCCAGTGTGCTGGAATTCG

GCTTGGTAGCCAAGTGCAGGTTATAGGGAGCTGAAGGGAAGGGGGTC

ACAGTAGGTGGCATCGTTCCTTTCTGACTGCCCGCCCCCGCATGCC

GTCCCGCGATATTGAGCTCCGAACCTCTCGCCCTGCCGCCGCCGGTG

CTCCGTCGCCGCCGCGCCGCCATGGAATTCGAACGCTGACGTCATCA

ACCCGCTCCAAGGAATCGCGGGCCCAGTGTCACTAGGCGGGAACACC

CAGCGCGCGTGCGCCCTGGCAGGAAGATGGCTGTGAGGGACAGGGA

GTGGCGCCCTGCAATATTTGCATGTCGCTATGTGTTCTGGGAAATCA

CCATAAACGTGAAATGTCTTTGGATTTGGGAATCTTATAAGTTCTGT

ATGAGACCACTCTTTCCC----TTTTTGGGAAAAAAAAAAAAAAAAA

AAAAACGAAACCGGGCCGGGCGCGGTGGTTCACGCCTATAATCCCAG

CACTTTGGGAGGCCGAGGCGGGCGGATCACAAGGTCAGGAGGTCGAG

ACCATCCAGGCTAACACGGTGAAACCCCCCCCCATCTCTACTAAAAA

AAAAAAATACAAAAAATTAGCCATTAGCCGGGCGTGGTGGCGGGCGC

CTATAATCCCAGCTACTTGGGAGGCTGAAGCAGAATGGCGTGAACCC

GGGAGGCGGACGTTGCAGTGAGCCGAGATCGCGCCGACTGCATTCCA

GCCTGGGCGACAGAGCGAGTCTCAAAAAAAAAACCGAGTGGAATGTG

AAAAGCTCCGTGAAACTGCAGAAACCCAAGCCGAATTCTGCAGATAT

CCATCACACTGGCGGCCGCTCGAGTGAGGCGGAAAGAACCAGCTGGG

GCTCTAGGGGGTATCCCCACGCGCCCTGTAGCGGCGCATTAAGCGCG

GCGGGTGTGGTGGTTACGCGCAGCGTGACCGCTACACTTGCCAGCGC

CCTAGCGCCCGCTCCTTTCGCTTTCTTCCCTTCCTTTCTCGCCACGT

TCGCCGGCTTTCCCCGTCAAGCTTCTAAATCGGGGGCTCCCTTTAGG

GTTCCGATTTAGTGCTTTACGGCACCTCGACCCCAAAAAACTTGATT

AGGGTGATGGTTCACGTAGTGGGCCATCGCCCTGATAGACGGTTTTT

CGCCCTTTGACGTTGGAGTCCACGTTCTTTAATAGTGGACTCTTGTT

CCAAACTGGAACAAACTCAACCCTATCTCGGTCTATTCTTTTGATTT

ATAAGGGATTTTGCCGATTTCGGCCTATTGGTTAAAAAATGAGCTGA

TTTAACAAAAATTTAACGCGAATTAATTCTGTGGAATGTGTGTCAGT

TAGGGTGTGGAAAGTCCCCAGGCTCCCCAGCAGGCAGAAGTATGCAA

AGCATGCATCTCAATTAGTCAGCAACCAGGTGTGGAAAGTCCCCAGG

CTCCCCAGCAGGCAGAAGTATGCAAAGCATGCATCTCAATTAGTCAG

CAACCATAGTCCCGCCCCTAACTCCGCCCATCCCGCCCCTAACTCCG

CCCAGTTCCGCCCATTCTCCGCCCCATGGCTGACTAATTTTTTTTAT

TTATGCAGAGGCCGAGGCCGCCTCTGCCTCTGAGCTATTCCAGAAGT

AGTGAGGAGGCTTTTTTGGAGGCCTAGGCTTTTGCAAAAAGCTCCCG

GGAGCTTGTATATCCATTTTCGGATCTGATCAAGAGACAGGATGAGG

ATCGTTTCGCATGATTGAACAAGATGGATTGCACGCAGGTTCTCCGG

CCGCTTGGGTGGAGAGGCTATTCGGCTATGACTGGGCACAACAGACA

ATCGGCTGCTCTGATGCCGCCGTGTTCCGGCTGTCAGCGCAGGGGCG

CCCGGTTCTTTTTGTCAAGACCGACCTGTCCGGTGCCCTGAATGAAC

TGCAGGACGAGGCAGCGCGGCTATCGTGGCTGGCCACGACGGGCGTT

CCTTGCGCAGCTGTGCTCGACGTTGTCACTGAAGCGGGAAGGGACTG

GCTGCTATTGGGCGAAGTGCCGGGGCAGGATCTCCTGTCATCTCACC

TTGCTCCTGCCGAGAAAGTATCCATCATGGCTGATGCAATGCGGCGG

CTGCATACGATTGATCCGGCTACCTGCCCATTCGACCACCAAGCGAA

ACATCGCATCGAGCGAGCACGTACTCGGATGGAAGCCGGTCTTGTCG

-continued
```
ATCAGGATGATCTGGACGAAGAGCATCAGGGGCTCGCGCCAGCCGAA
CTGTTCGCCAGGCTCAAGGCGCGCATGCCCGACGGCGAGGATCTCGT
CGTGACCCATGGCGATGCCTGCTTGCCGAATATCATGGTGGAAAATG
GCCGCTTTTCTGGATTCATCGACTGTGGCCGGCTGGGTGTGGCGGAC
CGCTATCAGGACATAGCGTTGGCTACCCGTGATATTGCTGAAGAGCT
TGGCGGCGAATGGGCTGACCGCTTCCTCGTGCTTTACGGTATCGCCG
CTCCCGATTCGCAGCGCATCGCCTTCTATCGCCTTCTTGACGAGTTC
TTCTGAGCGGGACTCTGGGGTTCGAAATGACCGACCAAGCGACGCCC
AACCTGCCATCACGAGATTTCGATTCCACCGCCGCCTTCTATGAAAG
GTTGGGCTTCGGAATCGTTTTCCGGGACGCCGGCTGGATGATCCTCC
AGCGCGGGGATCTCATGCTGGAGTTCTTCGCCCACCCCAACTTGTTT
ATTGCAGCTTATAATGGTTACAAATAAAGCAATAGCATCACAAATTT
CACAAATAAAGCATTTTTTTCACTGCATTCTAGTTGTGGTTTGTCCA
AACTCATCAATGTATCTTATCATGTCTGTATACCGTCGACCTCTAGC
TAGAGCTTGGCGTAATCATGGTCATAGCTGTTTCCTGTGTGAAATTG
TTATCCGCTCACAATTCCACACAACATACGAGCCGGAAGCATAAAGT
GTAAAGCCTGGGGTGCCTAATGAGTGAGCTAACTCACATTAATTGCG
TTGCGCTCACTGCCCGCTTTCCAGTCGGGAAACCTGTCGTGCCAGCT
GCATTAATGAATCGGCCAACGCGCGGGGAGAGGCGGTTTGCGTATTG
GGCGCTCTTCCGCTTCCTCGCTCACTGACTCGCTGCGCTCGGTCGTT
CGGCTGCGGCGAGCGGTATCAGCTCACTCAAAGGCGGTAATACGGTT
ATCCACAGAATCAGGGGATAACGCAGGAAAGAACATGTGAGCAAAAG
GCCAGCAAAAGGCCAGGAACCGTAAAAAGGCCGCGTTGCTGGCGTTT
TTCCATAGGCTCCGCCCCCCTGACGAGCATCACAAAAATCGACGCTC
AAGTCAGAGGTGGCGAAACCCGACAGGACTATAAAGATACCAGGCGT
TTCCCCCTGGAAGCTCCCTCGTGCGCTCTCCTGTTCCGACCCTGCCG
CTTACCGGATACCTGTCCGCCTTTCTCCCTTCGGGAAGCGTGGCGCT
TTCTCATAGCTCACGCTGTAGGTATCTCAGTTCGGTGTAGGTCGTTC
GCTCCAAGCTGGGCTGTGTGCACGAACCCCCCGTTCAGCCCGACCGC
TGCGCCTTATCCGGTAACTATCGTCTTGAGTCCAACCCGGTAAGACA
CGACTTATCGCCACTGGCAGCAGCCACTGGTAACAGGATTAGCAGAG
CGAGGTATGTAGGCGGTGCTACAGAGTTCTTGAAGTGGTGGCCTAAC
TACGGCTACACTAGAAGAACAGTATTTGGTATCTGCGCTCTGCTGAA
GCCAGTTACCTTCGGAAAAAGAGTTGGTAGCTCTTGATCCGGCAAAC
AAACCACCGCTGGTAGCGGTTTTTTTGTTTGCAAGCAGCAGATTACG
CGCAGAAAAAAAGGATCTCAAGAAGATCCTTTGATCTTTTCTACGGG
GTCTGACGCTCAGTGGAACGAAAACTCACGTTAAGGGATTTTGGTCA
TGAGATTATCAAAAAGGATCTTCACCTAGATCCTTTTAAATTAAAAA
TGAAGTTTTAAATCAATCTAAAGTATATATGAGTAAACTTGGTCTGA
CAGTTACCAATGCTTAATCAGTGAGGCACCTATCTCAGCGATCTGTC
TATTTCGTTCATCCATAGTTGCCTGACTCCCGTCGTGTAGATAACTA
CGATACGGGAGGGCTTACCATCTGGCCCCAGTGCTGCAATGATACCG
CGAGACCCACGCTCACCGGCTCCAGATTTATCAGCAATAAACCAGCC
AGCCGGAAGGGCCGAGCGCAGAAGTGGTCCTGCAACTTTATCCGCCT
CCATCCAGTCTATTAATTGTTGCCGGGAAGCTAGAGTAAGTAGTTCG
CCAGTTAATAGTTTGCGCAACGTTGTTGCCATTGCTACAGGCATCGT
GTGGTCACGCTCGTCGTTTGGTATGGCTTCATTCAGCTCCGGTTCCC
AACGATCAAGGCGAGTTACATGATCCCCCATGTTGTGCAAAAAAGCG
GTTAGCTCCTTCGGTCCTCCGATCGTTGTCAGAAGTAAGTTGGCCGC
ATGGTTATCACTCATGGTTATGGCAGCACTGCATAATTCTCTTACTG
TCATGCCATCCGTAAGATGCTTTTCTGTGACTGGTGAGTACTCAACC
AAGTCATTCTGAGAATAGTGTATGCGGCGACCGAGTTGCTCTTGCCC
GGCGTCAATACGGGATAATACCGCGCCACATAGCAGAACTTTAAAAG
TGCTCATCATTGGAAAACGTTCTTCGGGGCGAAAACTCTCAAGGATC
TTACCGCTGTTGAGATCCAGTTCGATGTAACCCACTCGTGCACCCAA
CTGATCTTCAGCATCTTTTACTTTCACCAGCGTTTCTGGGTGAGCAA
AAACAGGAAGGCAAAATGCCGCAAAAAAGGGAATAAGGGCGACACGG
AAATGTTGAATACTCATACTCTTCCTTTTTCAATATTATTGAAGCAT
TTATCAGGGTTATTGTCTCATGAGCGGATACATATTTGAATGTATTT
AGAAAAATAAACAAATAGGGGTTCCGCGCACATTTCCCCGAAAAGTG
CCACCTGACGTC
```

Using 30 μl of Lipofectamine 2000 (Invitrogen), 10 μg of siRNA-expression vector were transfected into NSCLC cell lines, A549 and LC319, both endogenously over-expressing KOC1, KIF11, NMU, GHSR1b, NTSR1, RAB35, and FOXM1. More than 90% of the transfected cells expressed the synthetic siRNAs, and endogenous expression of target genes (KIF11, GHSR1b, NTSR1, RAB35, or FOXM1) in these cells was effectively suppressed. The transfected cells were cultured for five days in the presence of appropriate concentrations of geneticin (G418), and then, cell numbers and viability were measured by Giemsa staining and triplicate MTT assays. The target sequences of the synthetic oligonucleotides for RNAi were as follows: control 1 (EGFP: enhanced green fluorescent protein (EGFP) gene, a mutant of Aequorea victoria EGFP), 5'-GAAGCAGCACGACTTCTTC-3' (SEQ.ID.NO.29); control 2 (Luciferase: Photinus pyralis luciferase gene), 5'-CGTACGCGGAATACTTCGA-3' (SEQ.ID.NO.30); control 3 (Scramble: chloroplast Euglena gracilis gene coding for 5S and 16S rRNAs), 5'-GCGCGCTTTGTAGGATTCG-3' (SEQ. ID. NO.31);

```
siRNA-KIF11-1 (#1),
5'-GTTAGTGTACGAACTGGAG-3';      (SEQ.ID.NO. 32)

siRNA-KIF11-2 (#2),
5'-GTGTCTCTGTTGGAGATCT-3';      (SEQ.ID.NO. 33)

siRNA-KIF11-3 (#3),
5'-GAAGGCAGTTGACCAACAC-3';      (SEQ.ID.NO. 34)

siRNA-GHSR-1 (si-GHSR-1),
5'-CCTCTACCTGTCCAGCATG-3';      (SEQ.ID.NO. 35)
```

-continued

```
siRNA-NTSR1-1 (si-NTSR1-1),
5'-GTTCATCAGCGCCATCTGG-3';      (SEQ.ID.NO. 36)

siRNA-NTSR1-2 (si-NTSR1-2),
5'-GGTCGTCATACAGGTCAAC-3',      (SEQ.ID.NO. 37)

siRNA-RAB35 (si-RAB35),
5'-GAGATGTTCAACTGCATCA-3',      (SEQ.ID.NO. 114)

siRNA-FOXM1 (si-FOXM1),
5'-GCAGCAGAAACGACCGAAT-3'.      (SEQ.ID.NO. 108)
```

The oligonucleotides used for these siRNAs are shown below. Each constructs were prepared by cloning the following double-stranded oligonucleotide into the BbsI site in the psiH1BX3.0 vector. The corresponding nucleotide position relative to the KIF11, GHSR1b, NTSR1, RAB35 and FOXM1 nucleic acid sequence of SEQ ID NOs:1, 3, 5, 112, and 106 are listed for each oligonucleotide sequence. Each oligonucleotide is a combination of a sense nucleotide sequence and an antisense nucleotide sequence of the target sequence of KIF11, GHSR1b, NTSR1, RAB35 and FOXM1. The nucleotide sequences of the hairpin loop structure of each siRNAs are also shown bellow. (endonuclease recognition sites are eliminated from each hairpin loop structure sequence).

```
KIF11 si1 288-306 (for the target sequence of
gttagtgtac gaactggag/SEQ ID NO: 32)
(insert F) Tccc gttagtgtacgaactggag ttcaagaga
ctccagttcgtacactaac/SEQ ID NO: 51
(insert R) Aaaa gttagtgtacgaactggag tctcttgaa
ctccagttcgtacactaac/SEQ ID NO: 52
(hairpin) gttagtgtacgaactggag ttcaagaga
ctccagttcgtacactaac/SEQ ID NO: 53

KIF11 si2 612-630 (for the target sequence of
gtgtctctgt tggagatct/SEQ ID NO: 33)
(insert F) Tccc gtgtctctgt tggagatct ttcaagaga
agatctccaacagagacac/SEQ ID NO: 54
(insert R) Aaaa gtgtctctgt tggagatct tctcttgaa
agatctccaacagagacac/SEQ ID NO: 55
(hairpin) gtgtctctgt tggagatct ttcaagaga
agatctccaacagagacac/SEQ ID NO: 56

KIF11 si3 1700-1718 (for the target sequence of
gaaggcagtt gaccaacac/SEQ ID NO: 34)
(insert F) Tccc gaaggcagtt gaccaacac ttcaagaga
gtgttggtcaactgccttc/SEQ ID NO: 57
(insert R) Aaaa gaaggcagtt gaccaacac tctcttgaa
gtgttggtcaactgccttc/SEQ ID NO: 58
(hairpin) gaaggcagtt gaccaacac ttcaagaga
gtgttggtcaactgccttc/SEQ ID NO: 59

GHSR1b si1 237-255 (for the target sequence of
cctctacctg tccagcatg/SEQ ID NO: 35)
(insert F) Tccc cctctacctg tccagcatg ttcaagaga
catgctggacaggtagagg/SEQ ID NO: 60
(insert R) Aaaa cctctacctg tccagcatg tctcttgaa
catgctggacaggtagagg/SEQ ID NO: 61
(hairpin) cctctacctg tccagcatg ttcaagaga
catgctggacaggtagagg/SEQ ID NO: 62

NTSR1 si1 933-951 (for the target sequence of
gttcatcagc gccatctgg/SEQ ID NO: 36)
(insert F) Tccc gttcatcagc gccatctgg ttcaagaga
ccagatggcgctgatgaac/SEQ ID NO: 63
(insert R) Aaaa gttcatcagc gccatctgg tctcttgaa
ccagatggcgctgatgaac/SEQ ID NO: 64
(hairpin) gttcatcagc gccatctgg ttcaagaga
ccagatggcgctgatgaac/SEQ ID NO: 65

NTSR1 si2 1074-1092 (for the target sequence of
ggtcgtcata caggtcaac/SEQ ID NO: 37)
(insert F) Tccc ggtcgtcata caggtcaac ttcaagaga
gttgacctgtatgacgacc/SEQ ID NO: 66
(insert R) Aaaa ggtcgtcata caggtcaac tctcttgaa
gttgacctgtatgacgacc/SEQ ID NO: 67
(hairpin) ggtcgtcata caggtcaac ttcaagaga
gttgacctgtatgacgacc/SEQ ID NO: 68

RAB35 si 620-638 (for the target sequence of
gagatgttca actgcatca/SEQ ID NO: 114)
(insert F) Tccc gagatgttca actgcatca ttcaagaga
tgatgcagt tgaacatctc/SEQ ID NO: 115
(insert R) Aaaa gagatgttca actgcatca tctcttgaa
tgatgcagt tgaacatctc/SEQ ID NO: 116
(hairpin) gagatgttca actgcatca ttcaagaga
tgatgcagt tgaacatctc/SEQ ID NO: 117

FOXM1 si 1240-1258 (for the target sequence of
gcagcagaaacgaccgaat/SEQ ID NO: 108)
(insert F) Tccc gcagcagaaa cgaccgaat ttcaagaga
attcggtcg tttctgctgc/SEQ ID NO: 109
(insert R) Aaaa gcagcagaaa cgaccgaat tctcttgaa
attcggtcg tttctgctgc/SEQ ID NO: 110
(hairpin) gcagcagaaa cgaccgaat ttcaagaga
attcggtcg tttctgctgc/SEQ ID NO: 111.
```

To validate RNAi system of the present invention, individual control siRNAs (EGFP, Luciferase, and Scramble) were initially confirmed using semiquantitative RT-PCR to decrease the expression of the corresponding target genes that had been transiently transfected into COS-7 cells. Down-regulation of KIF11, GHSR1b, NTSR1, RAB35 and FOXM1 expression by their respective siRNAs (si-KIF11-1, si-KIF11-2, si-KIF11-3, si-GHSR-1, si-NTSR1-1, si-NTSR1-2, si-RAB35 and si-FOXM1), but not by controls, was confined with semiquantitative RT-PCR in the cell lines used for this assay.

Dominant-Negative Assays

We performed dominant-negative assays using the KOC1 deletion mutants to investigate the functional role of the KOC1-KIF11 complex in growth or survival of lung-cancer cells. The KOC1DEL3 and KOC1DEL2 construct (FIG. 3a; 10 μg), mock plasmid (10 μg), or plasmid mixtures of both constructs in the final dose of 10-μg DNA (KOC1DEL3 or KOC1DEL2 vs mock (μg), 7.5:2.5; 5:5; or 2.5:7.5, individually) were transfected into LC319 cells. The transfected cells were cultured for 7 days in the presence of G418 and their viability was measured by triplicate MTT assays.

(6) Co-Immunoprecipitation and MALDI-TOF Mass Spectrometry

Human lung cancer cell line LC319 cells were transfected with bilateral-tagged pCAGGS-n3FH (NH2-terminal FLAG; COOH-terminal HA)-KOC1 expression vector or empty vector (mock transfection). Cells were extracted in IP-buffer (0.5% NP-40, 50 mM Tris-HCl, 150 mM NaCl, and protease inhibitor) for 30 min on ice. Extracts were centrifuged at 14,000 rpm for 15 min, and supernatants were subjected to immunoprecipitation using anti-Flag M2 agarose (Sigma-Aldrich) and anti-HA beads (Sigma-Aldrich) for 1-2 hours. The beads were washed six times with IP-buffer, and protein was eluted by boiling the beads in Laemmli sample buffer after removing the final wash fraction. The eluted protein was resolved by SDS-PAGE and stained with silver staining. A 125 kDa-band was extracted by gel extraction, and used for mass spectrometric sequencing using MALDI-TOF mass spectrometry. This analysis identified KIF11 as the 125 kDa product.

To confirm the interaction between KOC1 and KIF11, A549 cells were transiently co-transfected with Flag-tagged KIF11 and myc-tagged KOC1 and the cells were immuno-precipitated with anti-Flag M2 agarose. Subsequently, the cells were immunoblotted with anti-myc antibody (9E10; Santa Cruz). Next, using the same combination of vectors and cells, the cells were immunoprecipitated with anti-myc agarose (SIGMA) and immunoblotted with anti-Flag M2 antibody (Sigma-Aldrich).

To further confirm this interaction, A549 cells were transiently co-transfected with Flag-tagged KIF11 and myc-tagged KOC1, and co-localization of FITC-labeled KIF11 and rhodamine-labeled KOC1 mainly in the cytoplasm was detected by immunocytochemical staining using FITC-labeled anti-FLAG antibody and rhodamine-labeled anti-myc antibody, as described below.

(7) Immunocytochemistry

A549 cells grown on coverslips were cultured for 24 hours after passage, and were co-transfected with Flag-tagged KIF11 and myc-tagged KOC1. After 24-hours incubation, the cells were fixed with acetone/methanol (1:1) for 5 min on ice, blocked in CAS BLOCK (ZYMED) for 7 min at RT, and then incubated with rabbit anti-Flag polyclonal antibody (SIGMA) for 1 hour at RT. The fixed cells were washed 3 times with PBS, reacted with anti-rabbit IgG-FITC for 1 hour at RT. Then the cells were blocked again, and incubated with anti-myc antibody (9E10; Santa Cruz) for 1 hour at RT. Finally anti-mouse IgG-rhodamin was applied to the cells for 1 hour at RT. The cells were viewed on a Leica TCS SP2-AOBS confocal microscope.

Immunohistochemistry and Tissue-Microarray Analysis

Tumor-tissue microarrays using formalin-fixed NSCLCs were constructed as published elsewhere (Kononen, J. et al., *Nat. Med.* 4, 844-847 (1998); Sauter, G. et al., *Nat. Rev. Drug Discov.* 2, 962-972 (2003)). KOC1 and KIF11 positively were assessed semi-quantitatively as absent or positive according to staining intensity, by three independent investigators with no prior knowledge of clinical follow-up data.

(8) Ligand-Receptor Binding Assay

To identify direct binding of NMU-25 to its candidate receptors, GHSR1a, GHSR1b and NTSR1, the following experiments were performed. The entire coding region of each receptor gene was amplified by RT-PCR using primers

```
GHSR1a
(5'-GGAATTCCATGTGGAACGCGACGCCCAGCGAA-3' (SEQ. ID.
NO. 38) and 5'-CGCGGATCCGCGTGTATTAATACTAGATTCTGTCC
AGGCC-3' (SEQ. ID. NO. 39)), GHSR1b
(5'-GGAATTCCATGTGGAACGCGACGCCCAGCGAA-3' (SEQ. ID.
NO. 40) and 5'-CGCGGATCCGCGGAGAGAAGGGAGAAGGCACAGG
GA-3' (SEQ. ID. NO. 41)),
and NTSR1
(5'-GGAATTCCATGCGCCTCAACAGCTCCGCGCCGGGAA-3' (SEQ.
ID. NO. 42) and 5'-CGCGGATCCGCGGTACAGCGTCTCGCGGGTG
GCATTGCT-3' (SEQ. ID. NO. 43)).
```

The products were digested with EcoR1 and BainH1 and cloned into appropriate sites of p3XFLAG-CMV10 vector (Sigma-Aldrich Co.). COS-7 cells were transfected with GHSR1b or NTSR1 expression plasmids using FuGENE6, as described above. Transfected COS-7 cells were cultured with 0.5 µM rhodamine-labeled NMU-25 peptide (NMU-25-rhodamine: Phoenix Pharmaceuticals. Inc.) for 12 hours, washed five times in PBS(−), and fixed in 4% paraformaldehyde solution for 60 min at room temperature. Then the cells were incubated with antibodies to FLAG-tagged GHSR1a, GHSR1b, or NTSR1 proteins (Sigma-Aldrich Co.), stained with a goat anti-mouse secondary antibody conjugated to FITC (Cappel) and viewed under laser-confocal microscope (TCS SP2 AOBS: Leica Microsystems). In addition, three different negative controls were prepared for this assay: 1) non-transfected COS-7 cells without addition of NMU-25-rhodamine; 2) non-transfected COS-7 cells treated with NMU-25-rhodamine; and 3) COS-7 cells transfected with GHSR1a, GHSR1, or NTSR1 without NMU-25-rhodamine. COS-7 cells transfected with a known NMU receptor (NMU1R) served as a positive control for the assay.

To confirm the binding of NMU-25 to the candidate receptors, flow-cytometric analysis was performed using the same series of COS-7 cells. Specifically, COS-7 cells were plated at a density of $1\times10^5$ cells/100-mm dish and transfected with either GHSR1b, NTSR1, or NMU1R expression vectors; 24 hours after transfection, cells were incubated with 0.5 µM NMU-25-rhodamine for 12 hours, washed, trypsinized, collected in PBS, and washed once more in PBS. The population of cells binding to rhodamine-labeled NMU-25 was determined by flow cytometry.

To further confirm binding of NMU-25 to the endogenous candidate receptors on the NSCLC cells, we performed receptor-ligand binding assay using the LC319 and PC-14 cells. Briefly, these cells trypsinized were seeded onto 96-well black-wall, clear-bottom microtiter plates 24 hours prior to the assay. The medium was removed and the cells were incubated with Cy5-NMU-25 with a 10-fold excess of unlabeled competitor. The plate was incubated in the dark for 24 hours at 37° C. and was scanned on the 8200 Cellular Detection System (Applied Biosystems). 8200 Analysis Software creates a digitized gray scale image, quantitates the amount of fluorescence bound on the surface of each cell, and enumerates the fluorescent cells.

Measurement of cAMP Levels

Trypsinized LC319 cells were seeded onto 96-well microtiter plate ($5.0\times10^4$ cells) and cultured in 10% FCS (+) RPMI-1640 medium for 24 hours, and then medium was changed to serum free RPMI-1640 medium/1 mM IBMX (isobutylmethylxanthine) for 20 min prior to assay. Cells were incubated with NMU-25 peptides for 20 min prior to measuring the cAMP level using the cAMP EIA System (Amersham Biosystems).

Intracellular $Ca^{2+}$ Mobilization Assay

Trypsinized LC319 cells were seeded onto poly-D-lysine coated 384-well black-wall, clear-bottom microtiter plate ($1.0\times10^4$ cells/ml) 24 hours prior to assay. Cells were loaded for 1 hour with 1 mM Fluo-4-AM fluorescent indicator dye in assay buffer (Hank's balanced salts solution, 20 mM HEPES, 2.5 mM probenecid), washed three times with assay buffer, and then returned to the incubator for 10 min before assay on a fluorometric imaging plate reader (FLIPR, Molecular Devices). Maximum change in fluorescence over base line was used to determine the response of the cells to the NMU-25 peptides stimulation.

Identification of Downstream Genes of NMU by cDNA Microarray

LC319 cells were transfected with either siRNA against NMU (si-NMU) or Luciferase (control siRNA). mRNAs were extracted 12, 24, and 36 hours after transfection, labelled with Cy5 or Cy3 dye and subjected to co-hybridization onto cDNA microarray slides containing 32,256 genes as described (Kakiuchi, S., et al., (2004). *Hum. Mol. Genet.* 13, 3029-3043., Ochi, K. et al., (2004). *Int. J. Oncol.* 24, 647-655.). After normalization of the data, genes with signals higher than the cut-off value were analyzed further. Genes whose intensity were significantly decreased in accordance with the time-dependent reduction of NMU expression were initially selected using SOM cluster analysis. Validation of candidate downstream genes of NMU was performed using semiquantitative RT-PCR experiments of the same mRNAs from LC319 cells used for microarray hybridization, with gene-specific primers listed below.

```
FLJ42024
                                       (SEQ.ID.NO. 118)
(5'-AAAAAGGGGATGCCTAGAACTC-3'
and
                                      (SEQ.ID.NO. 119))
5'-CTTTCAGCACGTCAAGGACAT-3', GCDH
                                       (SEQ.ID.NO. 120)
(5'-ACACCTACGAAGGTACACATGAC-3'
and
                                      (SEQ.ID.NO. 121))
(5'-GCTATTTCAGGGTAAATGGAGTC-3', CDK5RAP1
                                       (SEQ.ID.NO. 122)
(5'-CAGAGATGGAGGATGTCAATAAC-3'
and
                                      (SEQ.ID.NO. 123))
(5'-CATAGCAGCTTTAAAGAGACACG-3', LOC134145
                                       (SEQ.ID.NO. 124)
(5'-CCACCATAACAGTGGAGTGGG-3'

(SEQ.ID.NO. 125))
(5'-CAGTTACAGGTGTATGACTGGGAG-3',

NUP188
                                       (SEQ.ID.NO. 126)
(5'-CTGAATACAACTTCCTGTTTGCC-3'
and
                                      (SEQ.ID.NO. 127))
(5'-GACCACAGAATTACCAAAACTGC-3'.
```

Expression of the candidate genes was additionally detected by semiquantitative RT-PCR using mRNAs isolated at 72 and 96 hours from LC319 cells treated with 1 μM NMU-25 or BSA at the time point of 0 and 48 hours.

Results (1) Identification of KIF11 as a Protein Interacting with KOC1

LC319 cells transfected with pCAGGS-n3FH-KOC1 vector were extracted and immunoprecipitated with anti-Flag M2 monoclonal antibody, and subsequently immunoprecipitated with anti-HA monoclonal antibody. The protein complex including KOC1 was stained with silver staining on SDS-PAGE gel. A 125 kDa band that was absent in mock transfection was extracted and determined to be KIF11 (NM_004523; SEQ.ID.NO.1) by Mass spectrometric sequencing.

(2) Confirmation of Interaction Between KOC1 and KIF11

Figure 1:
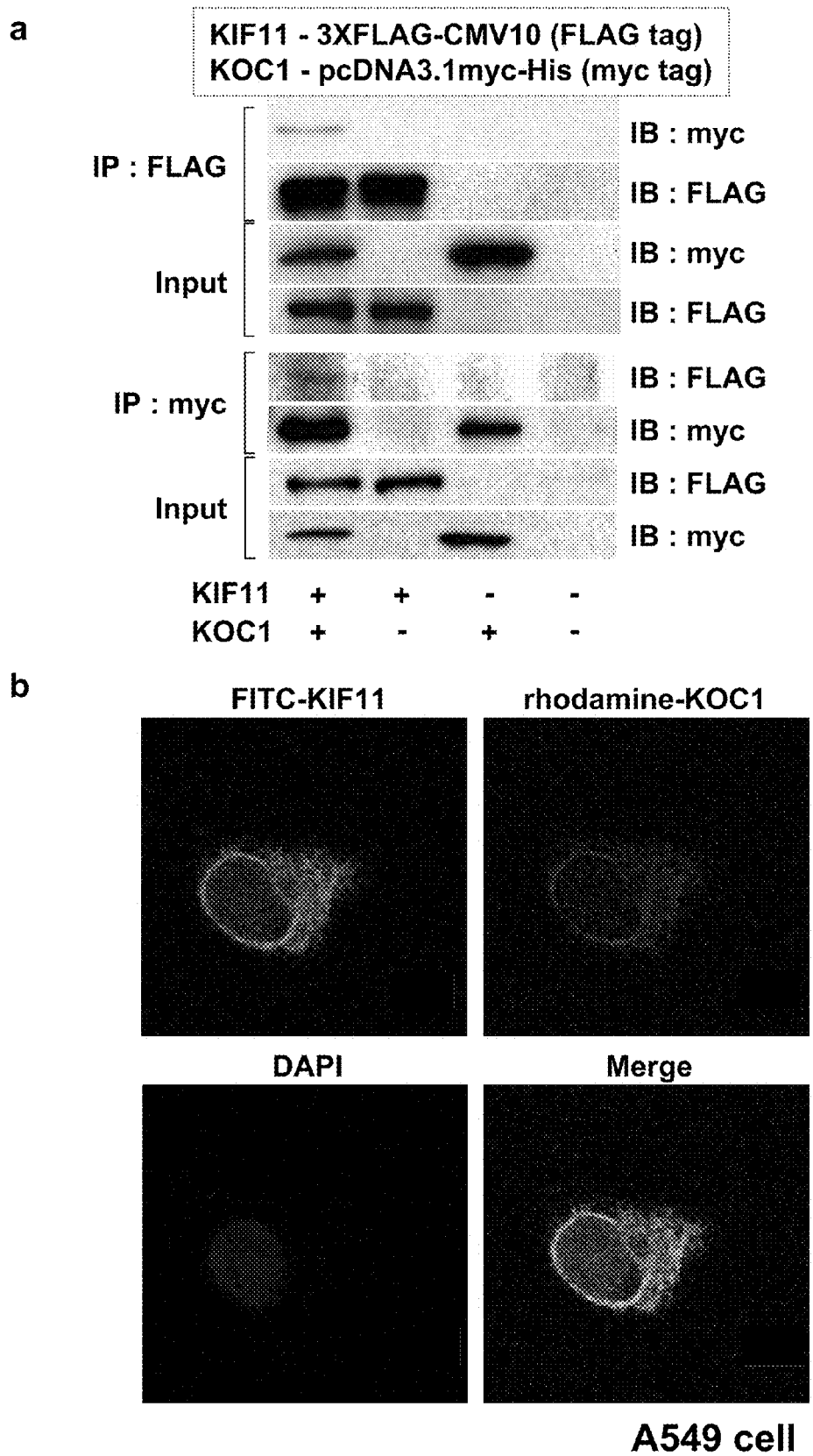
FIG. 1 shows photographs confirming the relationship between KOC1 and KIF11.
  (a) depicts the result of co-immunoprecipitation of KOC1 and KIF11 confirming the interaction between KOC1 and KIF11. A549 cells were transiently co-transfected with Flag-tagged KIF11 and myc-tagged KOC1, immunoprecipitated with anti-Flag M2 agarose, and subsequently immunoblotted with anti-myc antibody. In contrast, using the same combination of vectors and cells, the cells were immunoprecipitated with anti-myc agarose and immunoblotted with anti-Flag M2 antibody. A band corresponding to the immunoblotted protein was found only when both constructs were co-transfected.
  (b) depicts the result of immunocytochemical staining showing the co-localization of KOC1 and KIF11. COS-7 cells were transiently transfected with FLAG-tagged KIF11 and myc-tagged KOC1, and their co-localization was detected mainly in the cytoplasm using FITC-labeled anti-FLAG antibody and rhomamine-labeled anti-myc antibody.
  (c) depicts the result of reciprocal co-immunoprecipitation of endogenous KOC1 and KIF11 from extracts of lung-cancer cell lines A549 and LC319. (upper panel) Western-blot analysis of both cell extracts immunoprecipitated with anti-KOC1 antibodies, with KIF11 protein detected in the immunoprecipitate. (lowerpanel) Western-blot of extracts immunoprecipitated with anti-KIF11 antibodies, with KOC1 protein detected in the immunoprecipitate.
Figure 1:
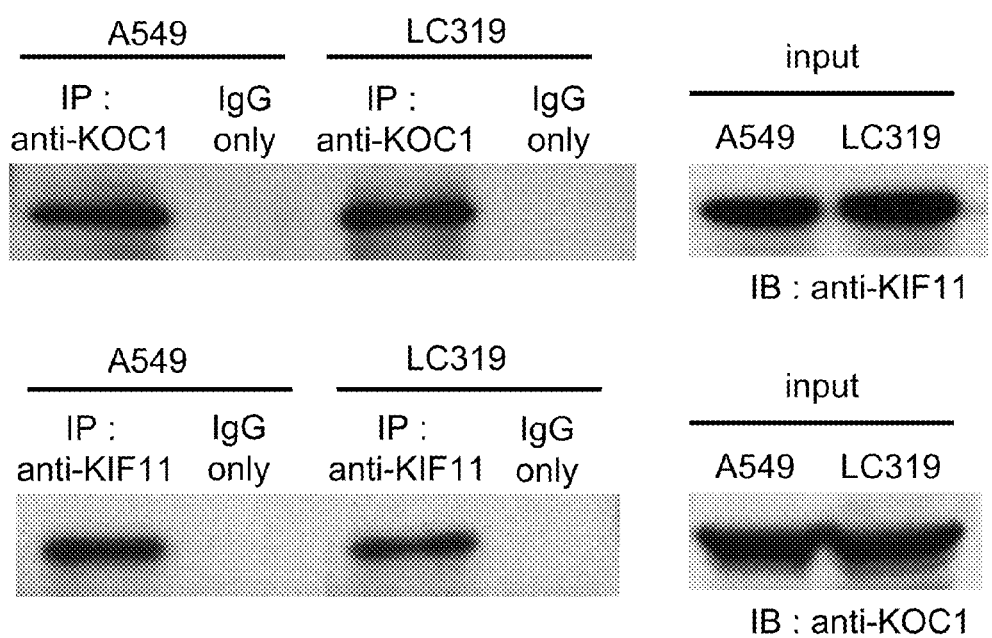

The A549 cells co-transfected with Flag-tagged KIF11 and myc-tagged KOC1, the cells transfected with either KIF11 or KOC1, and the non-transfected cells were immunoprecipitated with anti-Flag M2 agarose and subsequently immunoblotted with anti-myc antibody. In contrast, the same series of A549 cells were immunoprecipitated with anti-myc agarose and immunoblotted with anti-Flag M2 antibody. A single band was found only when both constructs were co-transfected (FIG. 1a). Immunocytochemistry showed that FLAG-tagged FITC-labeled KIF11 co-localized in cytoplasm of A549 with myc-tagged rhomamine-labeled KOC1 (FIG. 1b).

Next, we confirmed by western blot analysis that anti-KOC1 antibody are specific to KOC1 and do not cross-react with other homologous proteins, IMP-1 and IMP-2 using H520 cell lysate, which had been confirmed to be not expressed endogenous IMP-1, -2, and -3(KOC1), but had been transfected with HA-tagged IP-1, -2, and -3(KOC1) expression vector. Lysates of LC319 cells transfected with pCAGGS-FLAG-tagged-KOC1 vector or mock vector (control) were extracted and immunoprecipitated with anti-FLAG M2 monoclonal antibody. The protein complex including KOC1 was stained with SilverQuest (Invitrogen) on an SDS-PAGE gel. A 125-kDa band was detected specifically in immunoprecipitates from lysates of cells transfected with KOC1 expressing plasmids, but not in control lysates (mock plasmids). Subsequent MALDI-TOF mass spectrometric analysis identified this 125-kDa protein as KIF11, a member of the kinesin family. We confirmed direct interaction between endogenous KOC1 and KIF11 by immunoprecipitation experiments with extracts from A549 and LC319, using affinity-purified anti-KOC1 and anti-KIF11 polyclonal antibodies (FIG. 1c).

(3) KIF11 Expression in NSCLC

Validation of KIF11 expression was performed in primary NSCLCs (clinical samples) and lung cancer cell lines. Increased KIF11 expression was confirmed in 12 of 16 NSCLC cases (5 of 8 ADCs and in 7 of 8 SCCs. In addition, up-regulation of KIF11 were observed in 14 of the 15 NSCLC cell lines.

Figure 2:
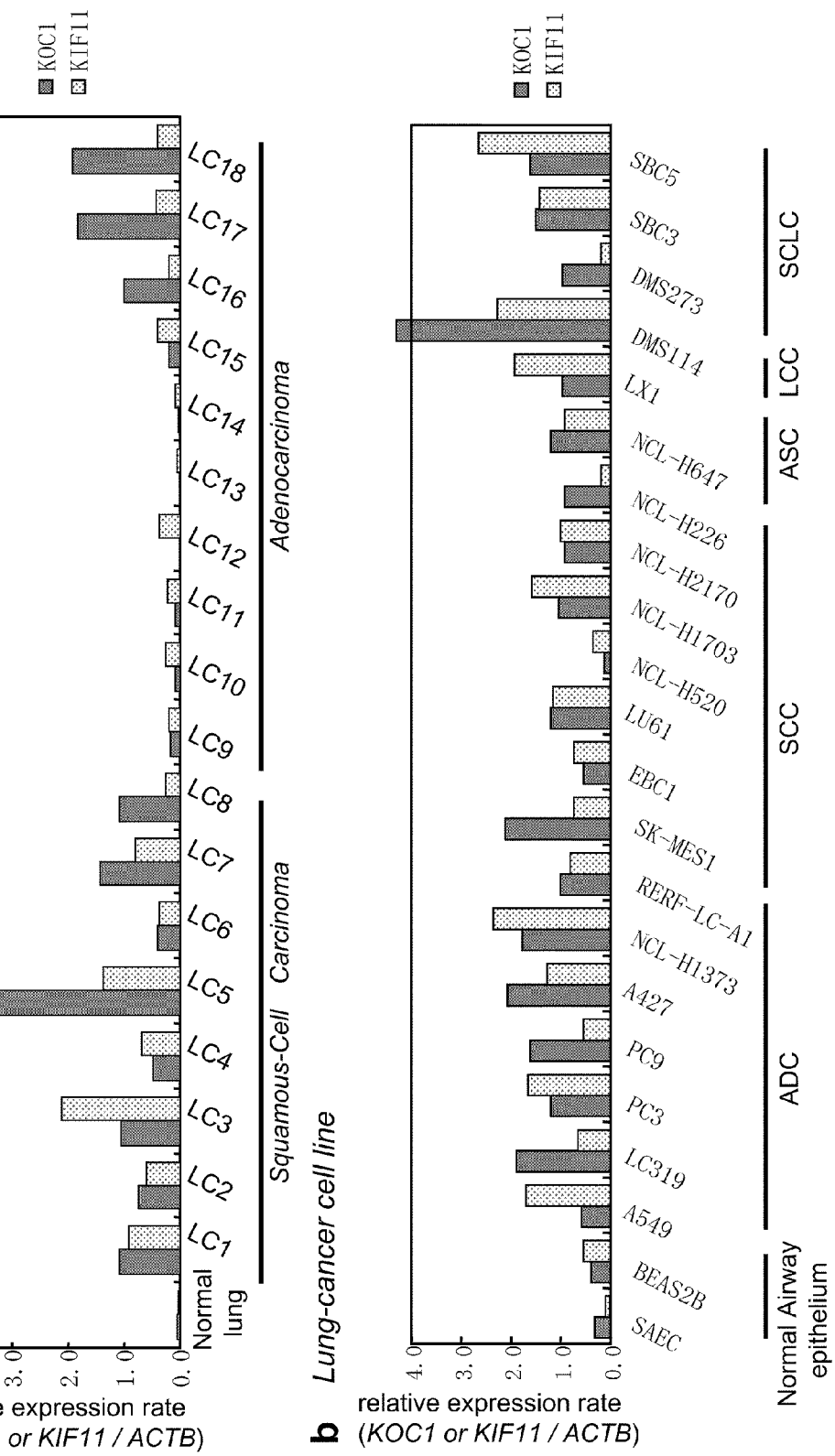
FIG. 2 shows photographs conforming co-activation of KOC1 and KIF11 in lung tumors and normal tissues.
  (a) depicts the result of QRT-PCR examining expression of KOC1 and KIF11 in clinical samples of NSCLC and corresponding normal lung tissues. Y-axis indicates the relative expression rate of the two genes (KOC1 or KIF11/ACTB).
  (b) depicts the result of QRT-PCR examining expression of KOC1 and KIF11 among 20 lung-cancer cell lines.
  (c) depicts the result of Northern-blot analysis detecting expression of KOC1 and KIF11 in normal human tissues.
Figure 2:
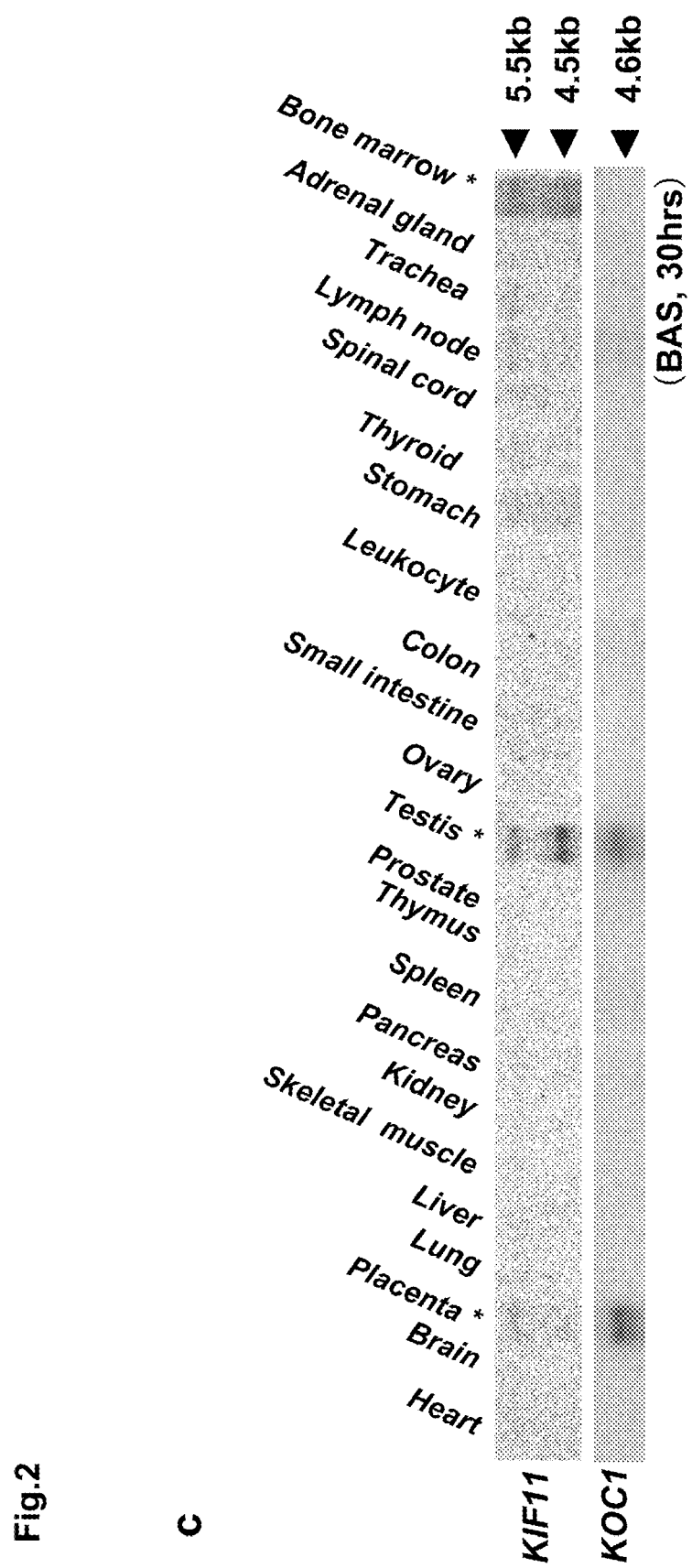

We subsequently re-examined primary NSCLC tissues and lung-cancer cell lines, and found increased KIF11 expression in 18 NSCLC clinical samples as well as in all of the 20 NSCLC or SCLC cell lines examined by quantitative RT-PCR (FIG. 2a,b). The mRNA levels of the KOC1 and KIF11 genes relative to ACTB genes were significantly correlated (r=0.702, P=0.0029 by the Spearman rank correlation). These two genes were coactivated in almost lung cancer cell lines (r=0.458, P=0.0359 by the Spearman rank correlation).

(4) KIF11 Expression in Normal Human Tissues

Northern blotting with KIF11 cDNA as a probe identified 4.5- and 5.5-kb transcripts as very weak bands, only seen in placenta, testis, and bone marrow, among the 23 normal human tissues examined. The reported cDNA sequence of KIF11 was considered to correspond to the larger transcript. To investigate the transcript corresponding to the smaller band, we reversely transcribed mRNAs isolated from tissues of the testis and NSCLC cell lines. We amplified the entire sequence of KIF11 cDNA by PCR using four primer sets, but found no alternatively-spliced transcript in these samples. Therefore, the smaller band may reflect cross-hybridization to the transcript of some related gene(s). The expression pattern of KIF11 in normal human tissues was significantly correlated with that of KOC1 (FIG. 2c).

Identification of the KIF11-Binding Region in KOC1

Figure 3:
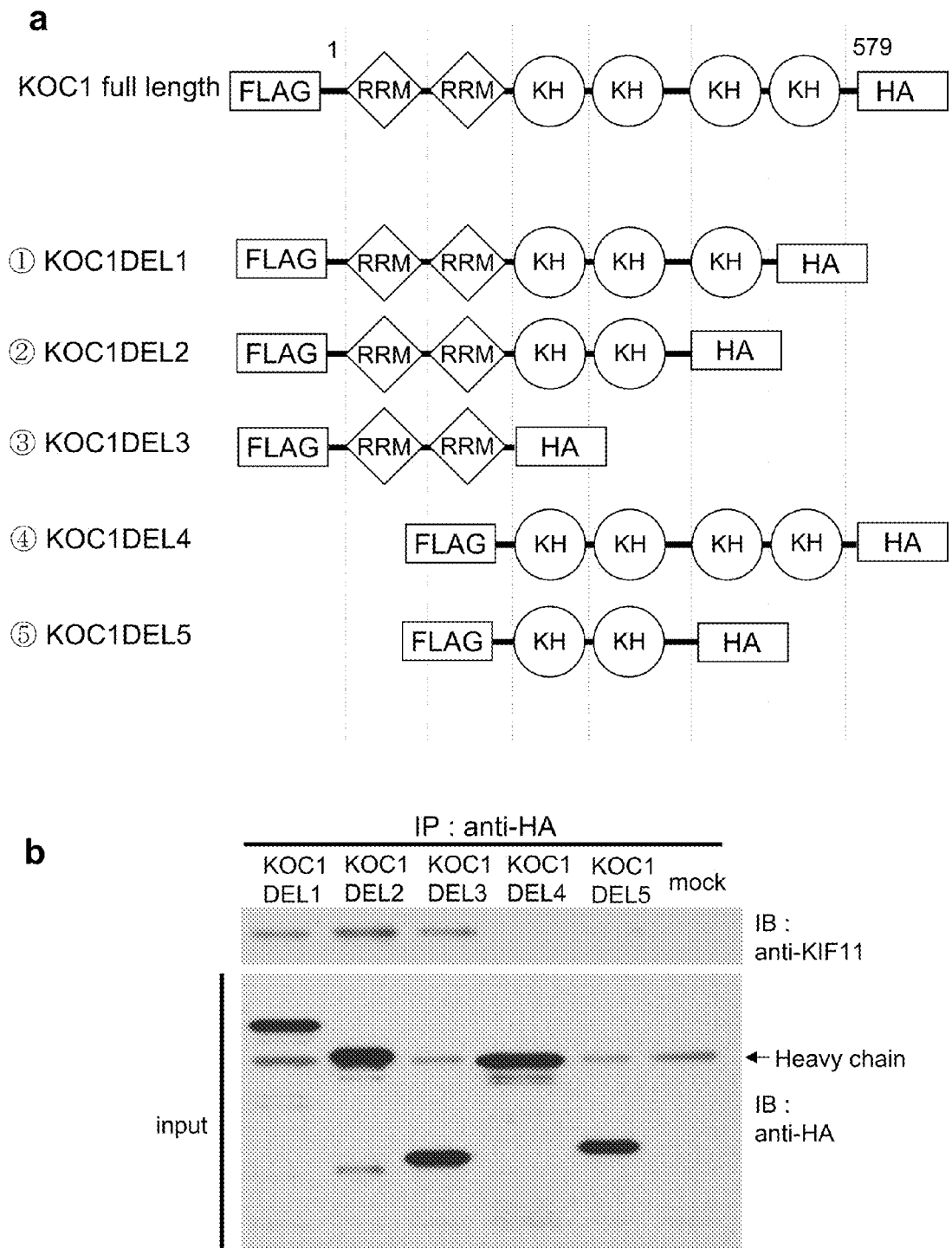
FIG. 3 shows photographs confirming the relationship between KOC1 and KIF11.
  (a) shows schematic drawing of five KOC1 deletion mutants lacking either or both of the terminal regions, with N- and C-terminals tagged with FLAG and HA respectively. KH, ribonucleoprotein K-homologous domain.
  (b) depicts the result of immunoprecipitation experiments for identification of the region of KOC1 that binds to KIF11. The KOC1DEL4 and KOC1DEL5 constructs, which lacked two RNA-recognition motifs, (RRM) did not retain any appreciable ability to interact with endogenous KIF11.

To determine the specific domain of KOC1 required for interaction with KIF11, we transfected into COS-7 cells one of five deletion-constructs of KOC1 with NH$_2$ (N)-terminal FLAG- or COOH (C)-terminal HA-tagged sequences (KOC1DEL1-5; FIG. 3a). Immunoprecipitation with monoclonal anti-HA indicated that the KOC1DEL4 and KOC1DEL5 constructs, which both lacked two RNA-recognition motifs (RRMs), were unable to interact with endogenous KIF11, while all KOC1 constructs possessing the two RRMs retained binding affinity for KIF11 (FIG. 3b).

Isolation of mRNAs Associated with the KOC1-KIF11 Complex Using RNA-Immunoprecipitation and cDNA Microarray KOC1 protein is known to exhibit multiple attachments to IGF2 leader-3 mRNA, possibly through its two functional RRMs and four K-homologous (KH) domains (Nielsen, J. et al., *Mol. Cell Biol.* 19, 1262-1270 (1999).). However, we did not detect expression of IGF2 mRNA in any of the lung-cancer cell lines or clinical NSCLC tissue samples we examined. Therefore, to elucidate the function of KOC1 in lung carcinogenesis, we searched for mRNA(s) that would interact with KOC1 and might thereby play important roles in growth and/or progression of lung cancer. First we immunoprecipitated mRNAs using anti-KOC1 antibody and five NSCLC cell lines (A549, LC319, PC14, RERF-LC-AI, and SK-MES-1). Then, Cy-5-labeled immunoprecipitated RNAs (IP-mRNA) and Cy-3-labeled total RNAs isolated from each matching cell line, were co-hybridized on human cDNA microarrays (IP-microarray). Among 32,256 genes screened, we identified a total of 55 that were enriched in IP-mRNA compared with total RNA in at least four of the five NSCLC cell lines tested (see Table 2), and confirmed enrichment of all those candidates by RT-PCR using the IP-mRNAs as templates (IP-RT-PCR). To examine the specificity of RNA-immunoprecipitation, we performed RT-PCR experiments with beta-actin (ACTB) mRNA using IP-mRNA as template; no ACTB was precipitated by anti-KOC1 antibody. As background controls of RNA-immunoprecipitation, we precipitated mRNAs using normal rabbit IgG and five NSCLC cell lines, and confirmed that none of eight KOC1 associated mRNAs tested (CCT2, SBP2, SLC25A3, RAB35, PSMB7, GL, PKP4, and WINS1) was precipitated by normal rabbit IgG. We also confirmed elevated expression of many of the candidate genes in NSCLC samples by RT-PCR (data not shown). To examine whether the KOC1-KIF11 complex formation requires the co-presence of these KOC1-associated mRNAs, we performed immunoprecipitation experiments using cell lysates which were treated or untreated in vitro with 30 units of RNase T1 (SIGMA), and found no difference in the interaction of the two proteins in the presence or absence of mRNAs, suggesting that the KOC1-KIF11 complex formation is unlikely to require these specific mRNAs.

By pursuing that strategy we have been able to show that KOC1 and KIF11 not only are co-over-expressed in the great majority of clinical NSCLC samples and cell lines, but also that a complex formed by the products of these genes is indispensable for growth and progression of NSCLC cells, by contributing to an intra- and inter-cellular mRNA-transporting system. Intracellular mRNA transport by RNA-binding proteins has been reported in oocytes and developing embryos of Drosophila and Xenopus, and in somatic cells such as fibroblasts and neurons (King, M. L. et al., Bioessays 21, 546-557 (1999); Mowry, K. L. & Cote, C. A. Faseb. J. 13, 435-445 (1999); Lasko, P., J. Cell Biol. 150, F51-56 (2000); Steward, O., Neuron 18, 9-12 (1997)) beta-actin mRNA is transported to the leading lamellae of chicken-embryo fibroblasts (CEFs) and to the growth cones of developing neurons (Lawrence, J. B. & Singer, R. H. Cell 45, 407-415 (1986); Bassell, G. J. et al., J. Neurosci. 18, 251-265 (1998)). The localization of ACTB mRNA depends on the "zipcode", a cis-acting element in the 3' UTR of the mRNA (Kislauskis, E. H. et al., J. Cell Biol. 123, 165-172 (1993)). The respective trans-acting factor, zipcode-binding protein 1 (ZBP1), was identified by affinity purification with the zipcode of ACTB mRNA; Ross, A. F. et al., Mol. Cell. Biol. 17, 2158-2165 (1997)) homologues of ZBP1 have since been identified in a wide range of organisms including Xenopus, Drosophila, mouse, and human (Mueller-Pillasch, F. et al., Oncogene 14, 2729-2733 (1997); Deshler, J. O. et al., Science 276, 1128-1131 (1997); Doyle, G. A. et al., Nucleic Acids Res. 26, 5036-5044 (1998)). ZBP1-like proteins contain two RRMs in the N-terminal region and four hnRNP KH (ribonucleoprotein K-homology) domains at the C-terminal end. KOC1, one of the IGF2 mRNA-binding proteins, is considered to be a member of the ZBP1 family; it exhibits multiple attachments to IGF2 leader-3 mRNA (Nielsen, J. et al., Mol. Cell. Biol. 19, 1262-1270 (1999)) and is over-expressed in several types of cancers (Mueller-Pillasch, F. et al., Oncogene 14, 2729-2733 (1997); Zhang, J. Y. et al., Clin. Immunol. 100, 149-156 (2001); Mueller, F. et al., Br. J. Cancer 88, 699-701 (2003); Wang, T. et al., Br. J. Cancer 88, 887-894 (2003)). However, since we failed to detect expression of IGF2 leader-3 mRNA in most of the NSCLC cell lines or clinical samples we examined, we suspected that KOC1 could mediate growth of lung-cancer cells through interaction with, and transport of, other mRNA(s). When we undertook RNA-immunoprecipitation experiments coupled with cDNA microarrays (IP-microarray), we identified dozens of candidate mRNAs that were likely to be associated with KOC1 in NSCLC cells (see Table 2). That list included genes encoding proteins with functions of cell-adhesion (PKP4, L1CAM1), cancer-cell progression and invasion (IGFBP2), and binding of small GTPs (RAB35), (Papagerakis, S. et al., Hum. Pathol. 34, 565-572 (2003); Fogel, M. et al., Cancer Lett. 189, 237-247 (2003); Wang, H. et al., Cancer Res. 63, 4315-4321 (2003); Zhao, H. et al., Biochem. Biophys. Res. Commun. 293, 1060-1065 (2002)) and many of them were expressed at high levels in clinical NSCLC samples (data not shown). Activation of a system that transports mRNAs whose products are associated with growth or movement of cells is very interesting, and further investigations along this line could lead to a better understanding of pulmonary carcinogenesis.

TABLE 2

| RANK[1] | GENE | ACCESSION | A549 | LC319 | PC14 | RERF | SKMES1 | SUM* |
|---|---|---|---|---|---|---|---|---|
| 1 | LOC283050 | AA843724 | 6.0 | 7.7 | 5.4 | 6.4 | 9.2 | 34.7 |
| 2 | KIAA0169 | R49113 | 6.2 | 8.9 | 4.9 | 5.7 | 6.8 | 32.5 |
| 3 | CCT2 | AF026166 | 4.1 | 8.0 | 5.4 | 5.7 | 9.1 | 32.3 |
| 4 | LOH11CR2A | NM_014622 | 9.1 | 5.6 | 5.8 | 3.9 | 4.5 | 28.8 |
| 5 | SNTB2 | AA625860 | 6.0 | 5.0 | 6.8 | 4.0 | 5.0 | 26.9 |
| 6 | CFLAR | U97074 | 5.3 | 5.7 | 3.8 | 4.3 | 5.9 | 25.0 |
| 7 | SBP2 | AF380995 | 5.0 | 6.1 | 3.9 | 2.9 | 6.1 | 24.0 |
| 8 | LOC56267 | AA420728 | 4.8 | 5.4 | 5.4 | 2.5 | 5.0 | 23.1 |
| 9 | SLC25A3 | NM_002635 | 3.5 | 5.8 | 2.9 | 4.1 | 5.3 | 21.7 |
| 10 | IFIT1 | M24594 | 4.4 | 4.2 | 3.8 | 3.6 | 5.2 | 21.2 |
| 11 | OSTalpha | H79642 | 2.3 | 5.9 | 5.6 | 3.8 | 2.8 | 20.4 |
| 12 | FILIP1 | XM_029179 | 10.3 | 2.3 | 2.1 | 2.7 | 2.5 | 19.9 |
| 13 | ZNF415 | AY283600 | 3.5 | 5.2 | 3.3 | 4.0 | 3.8 | 19.8 |
| 14 | RAB35 | BX344673; NM_006861 | 3.0 | 4.1 | 4.2 | 4.0 | 4.6 | 19.8 |
| 15 | APG-1 | AW966019 | 0.0 | 6.2 | 6.2 | 2.5 | 4.4 | 19.4 |
| 16 | INPP4B | AA759168 | 3.4 | 3.2 | 4.4 | 3.6 | 4.5 | 19.1 |
| 17 | na | AI160370 | 3.6 | 4.1 | 2.9 | 4.6 | 3.1 | 18.3 |

TABLE 2-continued

| RANK[1] | GENE | ACCESSION | A549 | LC319 | PC14 | RERF | SKMES1 | SUM* |
|---|---|---|---|---|---|---|---|---|
| 18 | N33 | NM_006765 | 4.5 | 0.0 | 4.0 | 4.7 | 5.0 | 18.1 |
| 19 | RPS3A | BX343424 | 1.6 | 4.5 | 3.2 | 3.1 | 4.3 | 16.8 |
| 20 | PSMB7 | BM837906 | 4.0 | 4.2 | 2.2 | 3.1 | 2.9 | 16.5 |
| 21 | GIT2 | NM_057169 | 3.4 | 4.2 | 2.3 | 2.9 | 3.4 | 16.1 |
| 22 | GL | AJ420489 | 4.4 | 3.2 | 3.2 | 2.3 | 2.9 | 16.0 |
| 23 | SOS2 | XM_043720 | 2.1 | 3.5 | 2.5 | 2.3 | 4.7 | 15.1 |
| 24 | L1CAM | M77640 | 3.4 | 2.9 | 2.5 | 2.6 | 3.6 | 14.9 |
| 25 | BRUNOL4 | BM671360 | 2.8 | 3.8 | 1.7 | 2.5 | 4.1 | 14.9 |
| 26 | RRAGA | U41654 | 2.9 | 4.3 | 2.4 | 2.4 | 2.8 | 14.8 |
| 27 | IGFBP2 | BC004312 | 3.9 | 3.7 | 2.0 | 2.5 | 2.6 | 14.8 |
| 28 | SRPK1 | BC038292 | 3.3 | 2.5 | 2.8 | 2.8 | 3.4 | 14.8 |
| 29 | FLJ12649 | R41135 | 1.2 | 2.8 | 2.6 | 3.4 | 4.5 | 14.4 |
| 30 | AGL | NM_000028 | 4.0 | 2.8 | 2.6 | 2.5 | 2.4 | 14.3 |
| 31 | FLJ23468 | BX355581 | 3.0 | 3.4 | 3.0 | 2.1 | 2.4 | 13.9 |
| 32 | MGC4730 | BM665147 | 2.6 | 2.8 | 2.6 | 2.3 | 3.1 | 13.4 |
| 33 | GAB2 | NM_012296 | 3.7 | 3.4 | 1.3 | 2.8 | 2.2 | 13.4 |
| 34 | USP15 | AF106069 | 2.0 | 3.0 | 2.4 | 2.6 | 3.2 | 13.1 |
| 35 | KIAA0657 | AB014557 | 0.0 | 4.7 | 2.2 | 3.0 | 3.1 | 13.1 |
| 36 | C6orf134 | AI146643 | 3.2 | 0.0 | 2.5 | 2.7 | 4.5 | 12.8 |
| 37 | MSCP | AK093931 | 2.5 | 3.0 | 4.2 | 3.0 | 0.0 | 12.7 |
| 38 | ACAA2 | D16294 | 2.1 | 2.0 | 3.0 | 2.6 | 3.1 | 12.7 |
| 39 | PKP4 | AI681111 | 3.2 | 2.5 | 2.9 | 1.7 | 2.3 | 12.6 |
| 40 | RGS5 | BX537427 | 2.0 | 3.0 | 1.3 | 3.4 | 2.8 | 12.5 |
| 41 | CYFIP1 | BC005097 | 2.2 | 2.1 | 2.6 | 1.3 | 4.0 | 12.2 |
| 42 | PLAGL2 | AK026951 | 1.2 | 2.7 | 2.3 | 2.4 | 3.3 | 11.9 |
| 43 | EHD4 | AW779971 | 2.7 | 2.3 | 2.3 | 1.9 | 2.6 | 11.9 |
| 44 | KIAA1666 | XM_300791 | 2.1 | 2.9 | 2.4 | 2.3 | 2.2 | 11.9 |
| 45 | RAP80 | BX537376 | 2.4 | 2.1 | 3.0 | 1.8 | 2.5 | 11.7 |
| 46 | LOC118812 | BG537484 | 0.0 | 2.3 | 2.3 | 3.2 | 3.7 | 11.5 |
| 47 | UTX | AF000993 | 1.0 | 2.2 | 2.8 | 3.2 | 2.2 | 11.4 |
| 48 | PCBP3 | AK094301 | 2.4 | 2.9 | 1.3 | 2.3 | 2.5 | 11.4 |
| 49 | AP3S2 | BC002785 | 2.4 | 2.3 | 1.2 | 2.8 | 2.3 | 11.0 |
| 50 | WINS1 | AA741459 | 1.4 | 3.0 | 2.2 | 2.1 | 2.2 | 10.9 |
| 51 | na[2] | AF504647 | 0.8 | 2.0 | 2.1 | 2.1 | 3.6 | 10.7 |
| 52 | LOC203859 | AL832374 | 2.0 | 2.6 | 2.5 | 3.4 | 0.0 | 10.5 |
| 53 | HNMT | NM_006895 | 2.3 | 2.0 | 1.9 | 2.1 | 2.2 | 10.5 |
| 54 | LOC282965 | XM_210833 | 1.1 | 2.8 | 2.0 | 2.2 | 2.0 | 10.1 |
| 55 | PDK2 | AK055119 | 1.0 | 2.4 | 2.2 | 2.4 | 2.0 | 10.0 |
| N/C[3] | ACTB | BC053988 | 0.0 | 0.0 | 0.0 | 0.0 | 0.0 | 0.0 |

[1]Probe sets are ranked by the sum(*) of the fold change value (IP-mRNA/input RNA) of all five cell lines.
[2]na: not annotated
[3]N/C: negative control Identification of the mRNA-Binding Region in KOC1

To determine the region of KOC1 that is required for binding to KOC1-associated mRNAs, we performed northwestern blot analysis using immunoprecipitated recombinant proteins of KOC1 deletion-mutants expressed in A549 cells (FIG. 4a) and DIG-labeled RAB35 mRNA, which is one of the KOC1 associated mRNAs. The KOC1DEL3, which lacked four KH domains, and KOC1DEL5, which lacked N-terminal two RRMs and C-terminal two KH domains, did not bind to the RAB35 mRNA. On the other hand, the KOC1DEL4, which is a construct with only the four KH domains and the KOC1DEL2, a construct without C-terminal two KH domains showed very weak binding affinities for mRNAs compared to the full-length KOC1 construct (FIG. 4b), suggesting the importance of two RRMs as well as of C-terminal two KH domains for binding to KOC1-associated mRNAs.

Figure 4:
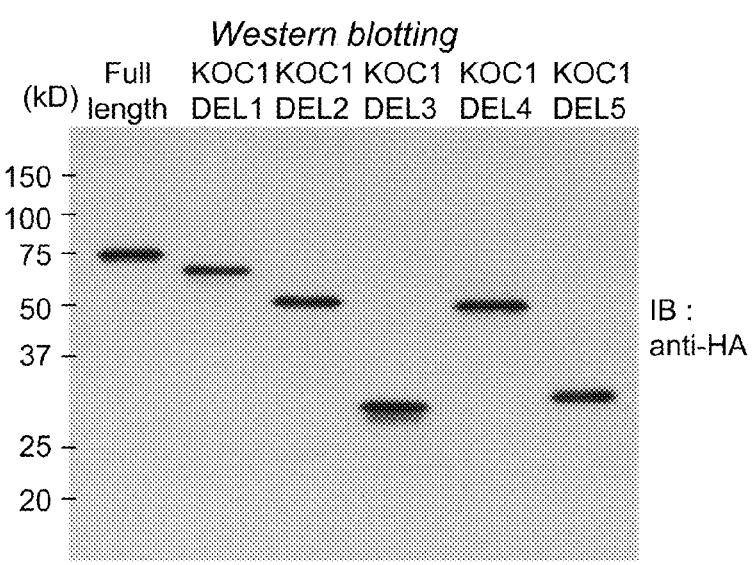
FIG. 4 shows photographs confirming the relationship between KOC1 and KOC1-associated mRNAs.
  (a) depicts the result of Western blotting with immunoprecipitated KOC1 deletion mutants and DIG-labeled RAB35 full length mRNA for identification of the mRNA-binding region in KOC1.
  (b) depicts the result of Northwestern with immunoprecipitated KOC1 deletion mutants and DIG-labeled RAB35 full length mRNA for identification of the mRNA-binding region in KOC1. The KOC1DEL3 and KOC1DEL5, did not bind to any of these mRNAs, and the KOC1DEL4, which is a construct with the four KH domains only, showed similar binding affinities for mRNAs to the KOC1DEL2, a construct without C-terminal two KH domains.
  (c) depicts the result of IP-RT-PCR for confirmation of IP-microarray and the ability of various KOC1 deletion mutants transfected into A549 cells to bind directly to representative eight endogenous mRNAs (CCT2, SBP2, SLC25A3, RAB35, PSMB7, GL, PKP4, and WINS1) among 55 candidate genes (see Table 2).
Figure 4:
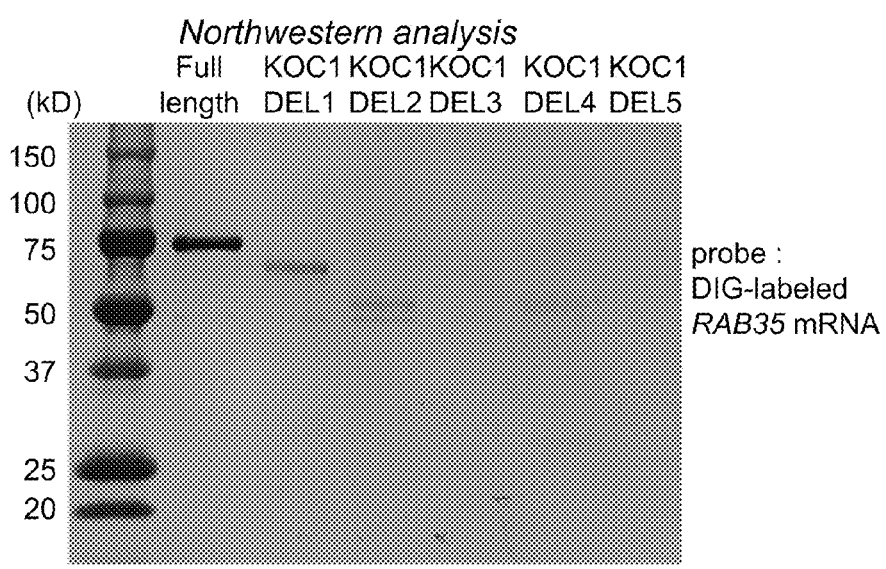
Figure 4:
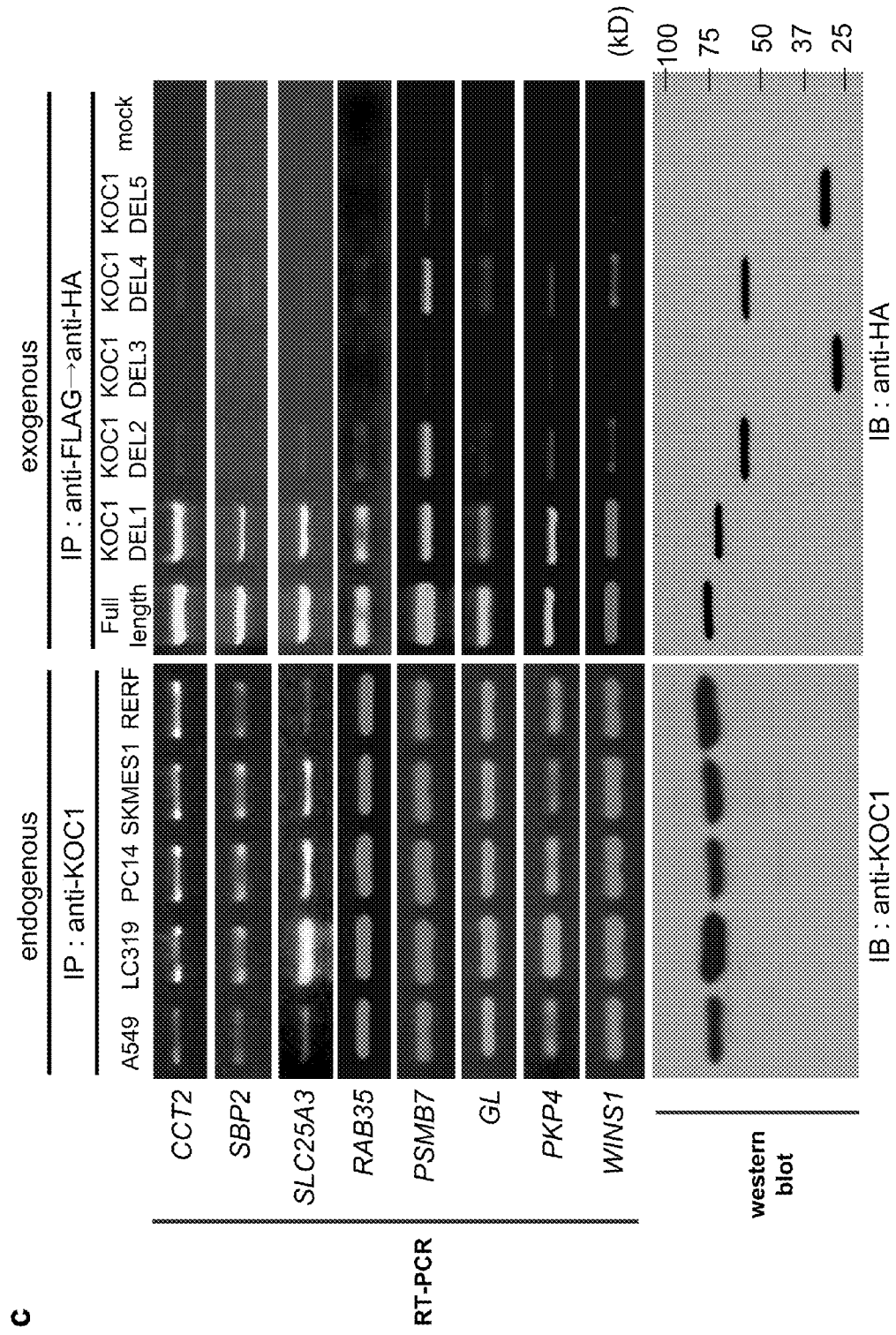

We further expressed five of the KOC1 deletion-mutants in A549 cells and performed immunoprecipitation experiments twice with the cell lysates, first with monoclonal anti-HA and then with monoclonal anti-FLAG M2 antibody. Using IP-mRNA, we examined the ability of each deleted-protein to bind to eight endogenous mRNAs (CCT2, SBP2, SLC25A3, RAB35, PSMB7, GL, PKP4, and WINS1) selected from the above list (see Table 2). The results were completely concordant to that of northwestern blot analysis, independently confirming that both C-terminal two KH domains and two RRMs in the N-terminal are indispensable for effective binding of KOC1 to mRNAs (FIG. 4c).

Figure 5:
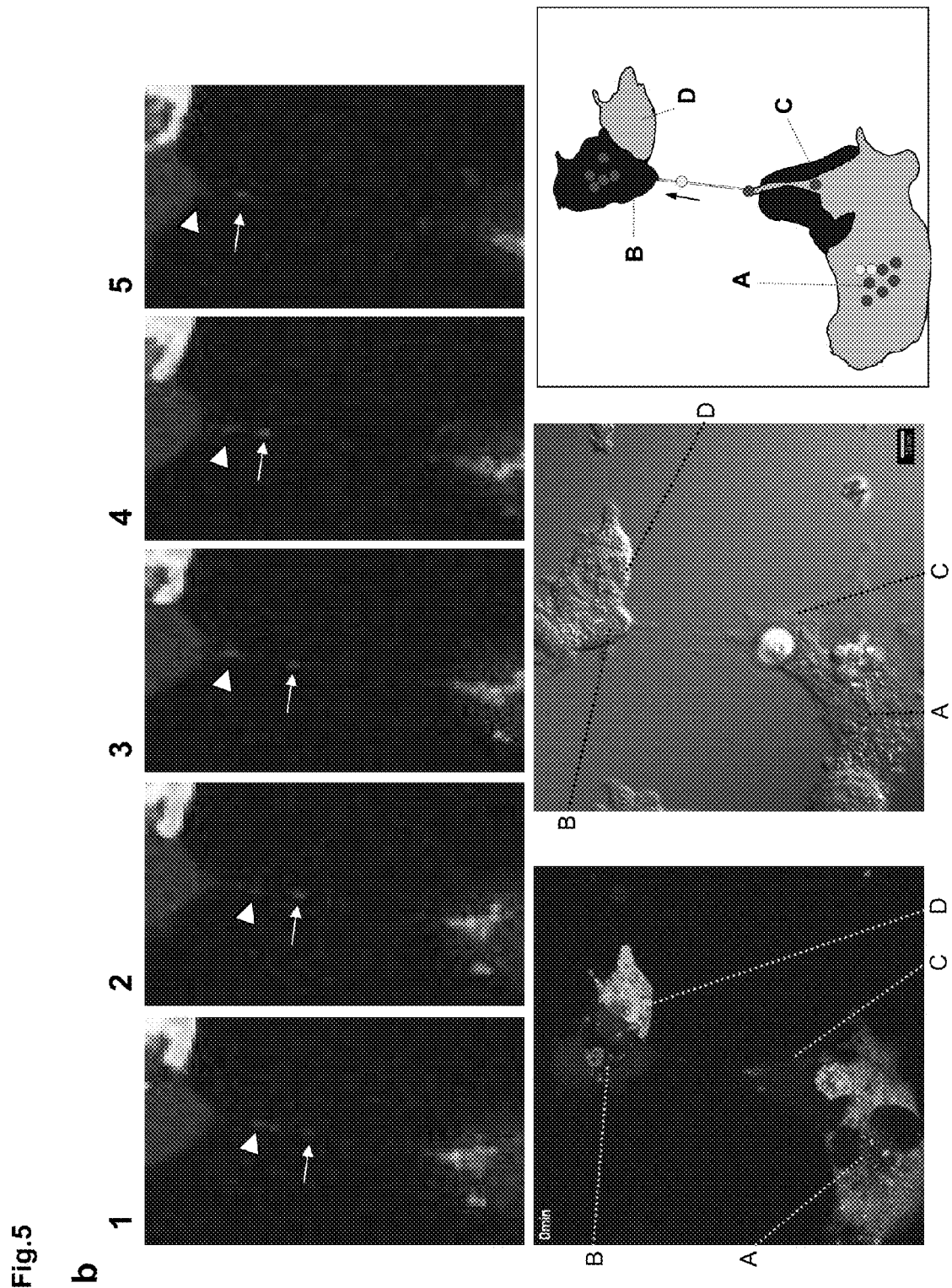
FIG. 5 shows photographs showing movement of KOC1-KIF11-mRNA ribonucleoprotein complexes in living cultured mammalian cells.
  (a) are photographs showing transport of the KOC1-KIF11 protein complex. Small particles that expressed fluorescent cyan (ECFP) KOC1 and yellow (EYFP) KIF11 proteins were co-localized, and transferred together between connected COS-7 cells through ultrafine intercellular structures (arrows).
  (b) are photographs showing transport of KOC1-RAB35 mRNA RNP complex from one COS-7 cell that contains a high level of KOC1-RNP complex (cell A) to another cell with a lower level of the complex (stained simply with CellTracker; cell B). Small particles of KOC1 RAB35 mRNA complex as well as KOC1 particles were transferred from cell A to cell B through ultrafine intercellular structures (arrows).

Microtubule Dependent Intra- and Inter-Cellular Transport of an KOC1-KIF11 Ribonucleoprotein Complex and KOC1-Associated mRNAs To further investigate the functional roles of KOC1 and KIF11, we prepared plasmids designed to express ECFP-KOC1 (cyan) and EYFP-KIF11 (yellow). We then transfected the two plasmids together into COS-7 cells, and examined their localization using immunofluorescence video-microscopy and real-time confocal microscopy. Cells expressing both KOC1 and KIF11 protruded into the processes, and then connected with adjacent cells (data not shown). Amore detailed observation of living cells found that the KOC1 had formed a complex with KIF11 (KOC1-KIF11 RNP complex; green particle) that was transported from one cell to another through an ultrafine structure connecting the two cells (FIG. 5a). Movement of the KOC1-KIF11 complex appeared to be unidirectional from one cell to another.

Furthermore, to examine whether KOC1-KIF11 complex could specifically transport KOC1-associated-mRNAs from one cell having a high level of KOC1-RNP complex to another having a lower level of the complex, we mixed and co-cultured two different cell populations; one is COS-7 cells that had been transfected with pEGFP-KOC1 (green) as well as Alexa Fluor 546-labeled full-length RAB35 mRNA (red), and the other is parental COS-7 cells simply labeled with CellTracker (blue). We observed that not only KOC1 particles (green), but also RNP particles of KOC1-RAB35 mRNA (yellow) were transferred through the ultrafine structure from the former cells to the latter ones (FIG. 5b). Using in situ hybridization on A549 cells in which both KOC1 and KIF11 were over-expressed, we further confirmed that the endogenous RAB35 mRNA (green) localized on the ultrafine intercellular structures as well as in the cytoplasm (data not shown).

Figure 6:
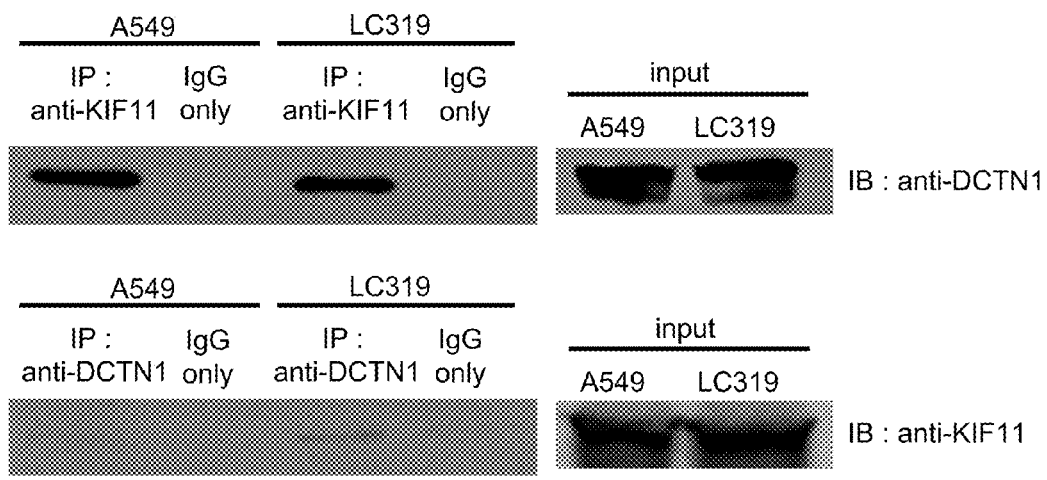
FIG. 6 shows photographs showing localization of KOC1-KIF11-mRNA ribonucleoprotein complexes.
  (a) depicts the result of immunoprecipitation of cell extracts from A549 and LC319 confirming of direct interaction between endogenous KIF11 and DCTN1 (upper and lower panels).

We also investigated the endogenous location of KOC1 and KIF11 particles on the ultrafine structure of microtubules bridging individual A549 cells by an immunocytochemical study, using affinity-purified anti-KOC1- or anti-KIF11 for primary antibody and Alexa594-labeled anti-rabbit IgG for secondary antibody (Molecular Probe) and anti-alpha-tubulin-FITC monoclonal antibody. A549 cells treated with 10 µM of the microtubule disrupting agent nocodazole (SIGMA) for four hours showed collapse and aggregation of endogenous KOC1 and KIF11, along with the depolymerization of microtubules in the cytoplasm. Moreover, no particle was found on the residual structure between the cells. The result suggested the possibility of a microtubule-dependent transporting mechanism involving the KOC1-KIF11 complex. To further clarify the detailed mechanism by which the KOC1-KIF11 complex transports mRNAs in NSCLC cells, we have searched for other component(s) that might be interacting with KIF11. Immunoprecipitation with anti-KIF11 polyclonal antibody using a lysate of LC319 cells identified a 150-kDa protein, which was later determined to be a dynactin 1 (DCTN1; p150, glued homolog, *Drosophila*) by MALDI-TOF mass-spectrometric analysis. DCTN1 is the largest subunit of DCTN, which binds to the cytoplasmic motor-protein dynein and activates vesicle transport along microtubules (Holzbaur, E. L. & Tokito, M. K. *Genomics* 31, 398-399 (1996); Tokito, M. K. et al., *Mol. Biol. Cell* 7, 1167-1180 (1996)), or binds to KIF11 to probably participate in centrosome separation (Blangy, A. et al., *J. Biol. Chem.* 272, 19418-19424 (1997)). We observed endogenous co-localization of KOC1/KIF11 and DCTN1 on the ultrafine structure between the individual A549 cells by immunocytochemistry, using the combination of affinity-purified anti-KOC1- or anti-KIF11-polyclonal antibodies for primary antibody and Alexa488-labeled anti-rabbit IgG for secondary antibody, and the combination of anti-DCTN1 monoclonal antibody (BD transduction Laboratories, #610473) for primary antibody and anti-Alexa594-labeled anti-rabbit IgG for secondary antibody. And we confirmed direct interaction between endogenous KIF11 and DCTN1 by immunoprecipitation experiments with extracts from A549 and LC319 cells, using anti-KIF11 polyclonal antibody and anti-DCTN1 monoclonal antibody (BD transduction Laboratories, #610473) (FIG. 6a).

To further demonstrate the KIF11-dependent intercellular transport of mRNA, we examined the effect of monastrol, the cell-permeable inhibitor that specifically inhibits the KIF11. Previous reports indicated that monastrol partially inhibits KIF11 ATPase activity through binding directly to the motor domain (DeBonis, S. et al., *Biochemistry* 42, 338-349 (2003); Kononen, J. et al., *Nat. Med.* 4, 844-847 (1998)). Treatment of A549 cells with 150 µM monastrol (SIGMA) for 24 hours induced the accumulation of endogenous KIF11 and exogenous EYFP-KIF11 at the center of monoaster along microtubules and the cell cycle arrest in mitosis with monopolar spindles, which is called "monoastral spindle". Treatment of A549 cells with 150 µM of monastrol for 24 hours induced cell cycle arrest for mitotic cells with monopolar spindles that is called "monoastral spindle" and also caused accumulation of endogenous KIF11 at the center of monoaster along microtubules. On the other hand, most non-mitotic cells lost protrusion into the processes and then lost connection to adjacent cells within 2-hour of the monastrol treatment. Further quantitative analysis by counting the number of intercellular ultrafine structures (n=252 structures) with time-lapse videomicroscopy demonstrated that more than a half of the cell-to-cell connections in non-mitotic cells tested disappeared by the one-hour monastrol treatment. However, six hours after the release of the cells from the monastrol exposure, the intercellular bridge formation was re-constituted and cells at normal mitosis process was observed, indicating that KIF11 was indispensable for the formation of ultrafine intercellular structures (data not shown).

Some cells lost protrusion into the processes and then did not connected with adjacent cells. A more detailed observation of living cells found that no KOC1-KIF11 RNP complex (green particle) was transported from one cell to another through an ultrafine structure connecting the two cells, which subsequently disappeared during observation.

In this study we demonstrated endogenous interaction of KOC1, KIF11 and DCTN1 in human lung cancers, and revealed a possible role of those complexes in transport of mRNAs from one cell to another. DCTN1, the largest subunit of DCTN, binds to the cytoplasmic motor protein dynein and activates vesicle transport along microtubules (Holzbaur, E. L. & Tokito, M. K. *Genomics* 31, 398-399 (1996)). Dynein-DCTN interaction is probably a key component of the mechanism of axonal transport of vesicles and organelles (Holzbaur, E. L. & Tokito, M. K. *Genomics* 31, 398-399 (1996); Tokito, M. K. et al., *Mol. Biol. Cell* 7, 1167-1180 (1996)). The binding of DCTN to dynein is reportedly critical for neuronal function, since antibodies that specifically disrupt this binding block vesicle motility along microtubules. In vitro interaction of DCTN1 and KIF11, and their co-localization during mitosis have been observed (Blangy, A. et al., *J. Biol. Chem.* 272, 19418-19424 (1997)), but no report has shown an intercellular transporting system involving this complex. Since in our experiments KIF11, a member of the kinesin family, was over-expressed in NSCLCs along with KOC1, we suggest that direct interaction of KOC1, KIF11, and DCTN1 could play a significant role in establishing specific alignment of microtubules between lung-cancer cells.

Protein Synthesis by Transported KOC1-Associated mRNAs in the Receiving Cells

Figure 7:
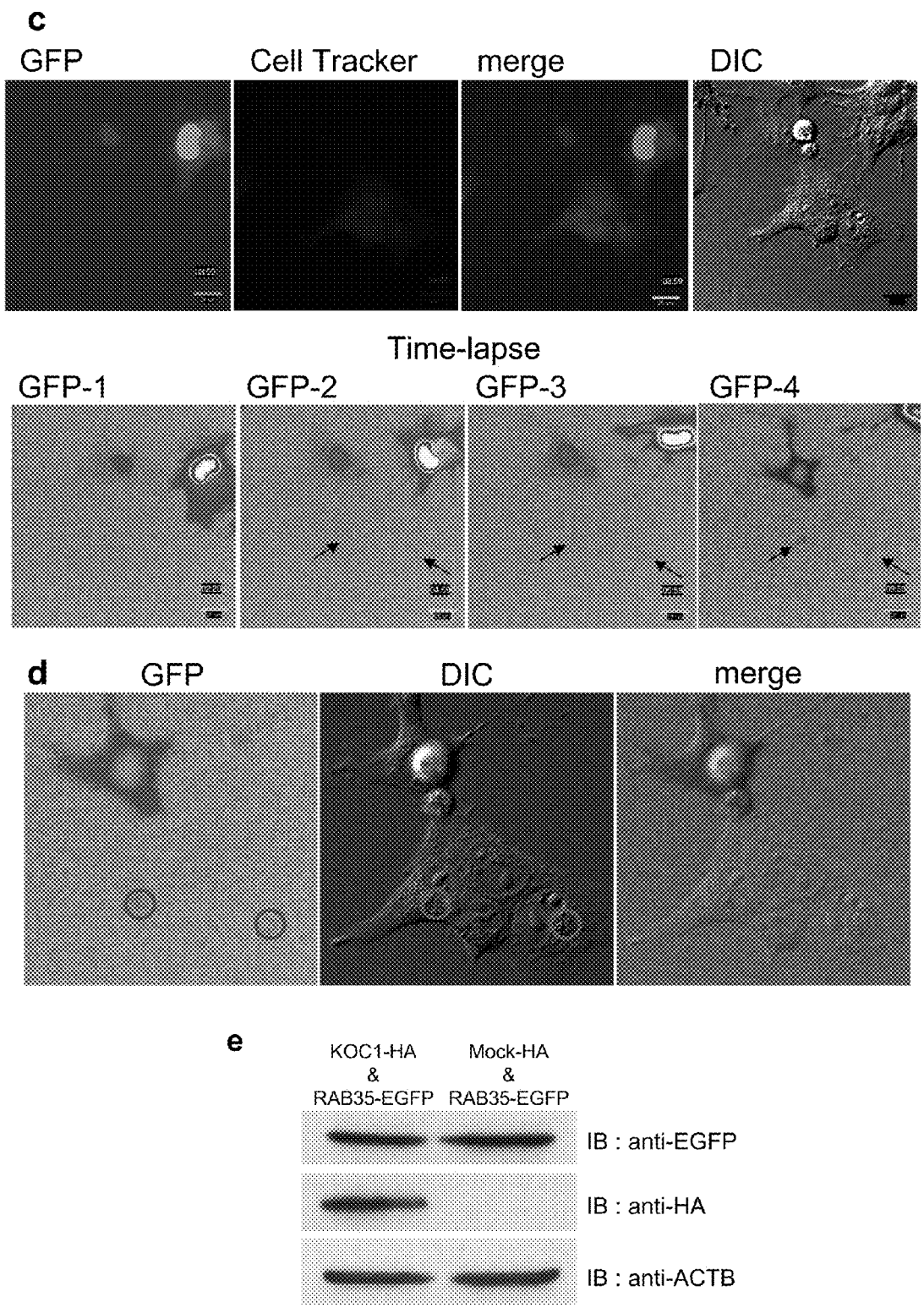
FIG. 7 shows photographs showing translation of KOC1-associated mRNAs transported into the recipient cells.
  (a) are photographs showing translation of mRNA transported into the recipient cells monitored by in situ hybridization.
  (b) are photographs showing protein synthesis based on transported mRNA in receiving cell. Constructs with full length RAB35 mRNA fused in frame to a myc tag sequence (upper panel). Co-localization of myc-tagged RAB35 proteins in the cytoplasm of CellTracker-stained receiving cells using immunocytochemistry (lower panels).
  (c) are photographs showing protein synthesis based on transported mRNA in receiving cell. Constructs with full length RAB35 mRNA fused in frame to a EGFP protein sequence.
  (d) are photographs showing protein synthesis based on transported mRNA in receiving cell. Expression of EGFP-fused RAB35 proteins in CellTracker-positive receiving cells using time-lapse video microscopy. EGFP and related-DIC image were shown.
  (e) are photographs showing that no significant difference in the protein level of RAB35-EGFP fused-protein was found between COS-7 cells that were co-transfected with RAB35-EGFP and HA-tagged-KOC1 vectors, and those with RAB35-EGFP and mock plasmid vectors. This indicates that KOC1 is not likely to interfere with translation of RAB35-EGFP mRNA.

To elucidate whether the mRNA transport by KOC1-KIF11 RNP complex is physiologically relevant (the recipient cell can synthesize the protein by translating the mRNAs transported), we constructed an expression vector of full length RAB35 mRNA, one of the binding targets of the KOC1/KIF11 complex, fused in frame to myc tagged and an EGFP protein sequences. We then investigated whether this chimeric mRNA could be transportable from one cell to another and subsequently translated into the protein production in the recipient cell. FLAG-tagged KOC1 and KIF11 expressing-COS7 cells were transfected with constructs with these RAB35 mRNA-expressing construct (cell A). Parental mRNA-recipient COS-7 cells were simply stained with Cell-Tracker (blue; cell B). These two cell populations were mixed together and co-cultured for 24 hours. We first confirmed the intercellular transportation of RAB35-EGFP mRNAs between cells A and B by in situ hybridization using antisense EGFP as a probe; after co-culture of the cells for 24 hours, weak-staining of RAB35-EGFP mRNAs were detected in the CellTracker-stained cell B as well as on the ultrafine structure between the two cell types (FIG. 7a). We then examined a presence of the EGFP-fused RAB35 proteins in the Cell-Tracker-stained B-type cells were found using immunocytochemistry and time-lapse video microscopy, respectively (FIGS. 7b and 7c). During these observations using time-lapse video microscopy, no visible EGFP-protein particle was transported from the type-A to type-B cells, but the EGFP protein gradually appeared in the apparatus of cytoplasm, which seemed to be endoplasmic reticulum (ER) of in the type-B cells (FIG. 7d). These results have indicated that KOC1 and KIF11 should functionally associate with a subset of mRNAs, which encode proteins possibly inducing cell proliferation and/or adhesion, and that the presence of KOC1 and KIF11 is indispensable to the cell-to-cell transportation. Although previous reports suggested that high KOC1 levels might interfere with translation of bound mRNAs such as IGF2 leader-3, our experiment of co-transfecting KOC1 and full-length RAB35-EGFP mRNA constructs together into COS-7 cells detected no decrease of RAB35-EGFP-fused protein levels (FIG. 7e).

Our experiments also revealed formation of protruding processes connecting adjacent cells, and showed predominant co-distribution of transfected RAB35 mRNAs and KOC1 protein on ultra-fine intercellular structures in two lung-cancer cell lines (A549 and LC319) that expressed high levels of endogenous KOC1 and KIF11. On the other hand, we did not find specific localization of transfected RAB35 mRNAs in NCI-H520 cells, which express KIF11 but not KOC1. That observation supported the importance of co-activation of KOC1 and KIF11 for communication among cancer cells. Among the known cell-to-cell communication systems in human cancers, formation of functional gap-junctions between malignant glioma cells and vascular endothelial cells appears to influence angiogenesis in the tumors (Zhang, W. et al., Cancer Res. 59, 1994-2003 (1999); Zhang, W. et al., J. Neurosurg. 98, 846-853 (2003)). However, to our knowledge ours is the first report to describe inter-cellular transport of mRNA by means of ribonucleoprotein particles combined with motor proteins in mammalian somatic cells and to assess its biological significance for formation of an inter-cellular network critical for growth and survival of cancer cells.

(5) Inhibition of Growth of NSCLC Cells by siRNA Against KIF11

Figure 8:
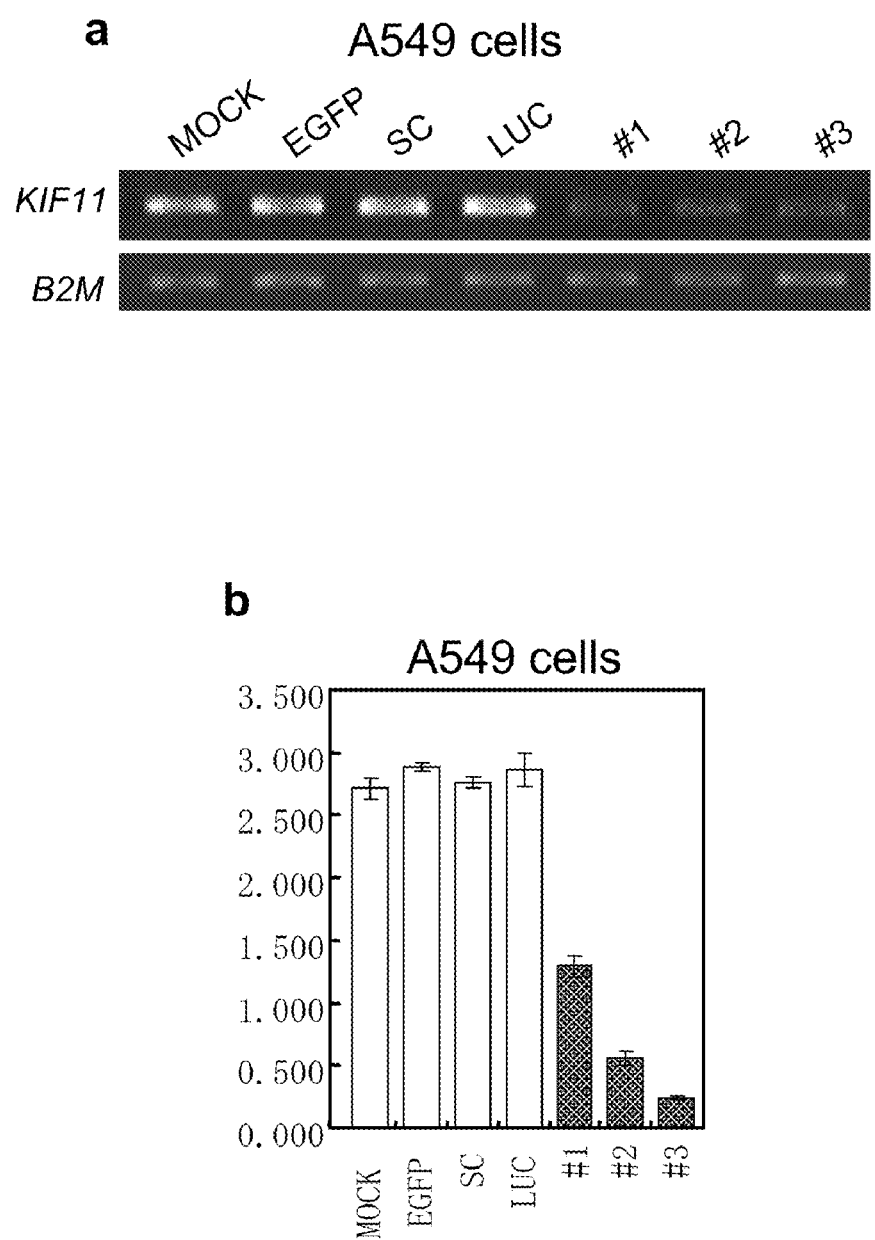
FIG. 8 shows the effect of KIF11 siRNAs on cells.
(a) depicts the inhibition on the growth of NSCLC cells by siRNAs against KIF11. The expression of KIF11 in response to specific siRNAs (si-KIF#1, #2, and #3) or control siRNAs (EGFP, LUC, SC) in A549 cells, was analyzed by semiquantitative RT-PCR.
(b) depicts the viability of A549 cells in response to si-KIF#1, #2, #3, EGFP, LUC, or SC, evaluated by triplicate MTT assays.

Transfection of either siRNA plasmids for KIF11 into A549 (FIG. 8a) or LC319 (data not shown) cells suppressed mRNA expression of the KIF11 in comparison to cells containing any of the three control siRNAs and mock transfection. In accordance with the reduced mRNA expression, A549 and LC319 cells showed significant decreases in cell viability and colony numbers measured by MTT (FIG. 8b) and colony-formation assays (data not shown). We also investigated the effect by siRNA against KIF11 on intercellular transport using time-lapse videoscopy. A similar phenomenon to monastrol treatment was observed; some cells reduced protrusion into the processes and the disappearance of the ultrafine structure connecting the two cells.

Figure 9:
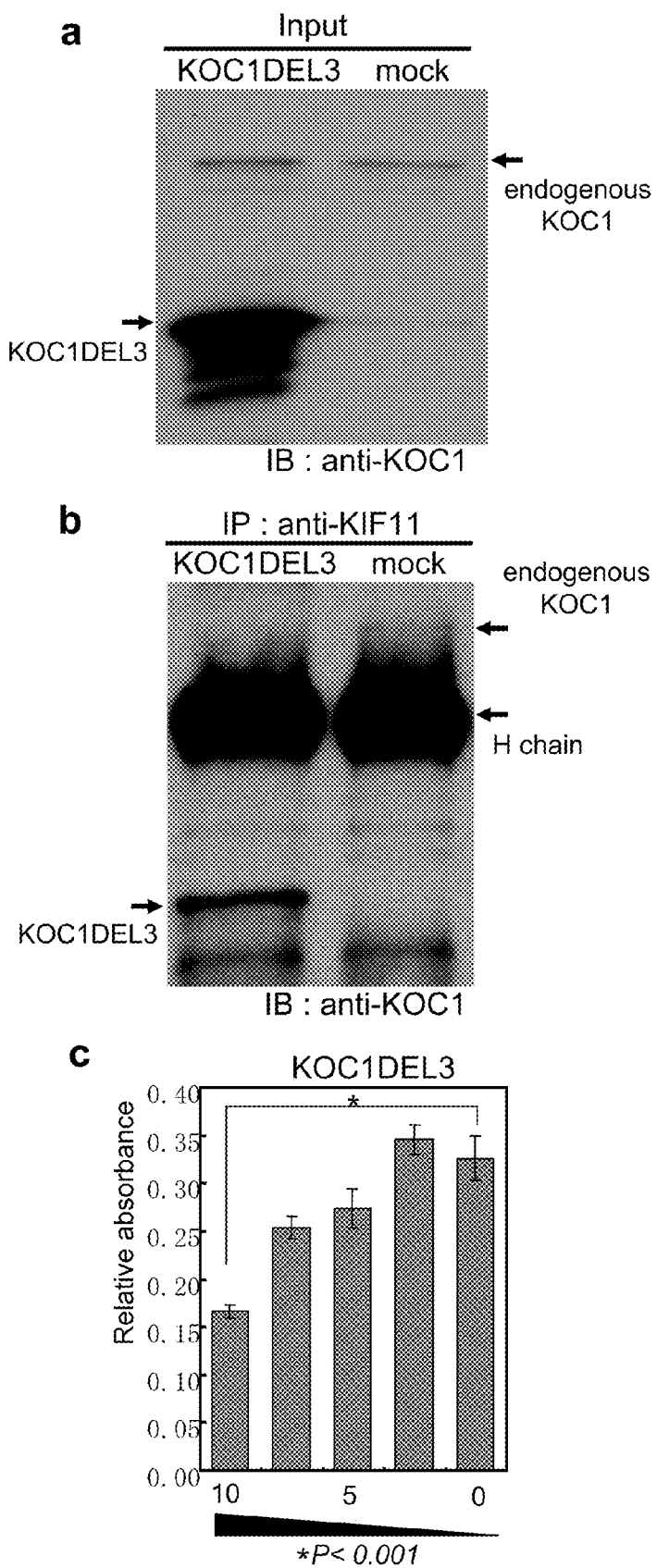
FIG. 9 shows the effect of KOC1 dominant-negative on cells.
(a) depicts the results of immunoprecipitation confirming interaction of KOC1 deletion-mutant KOC1DEL3 with endogenous KIF11 in LC319 cells.
(b) depicts the results of immunoprecipitation confirming reduction of the complex formation between endogenous KOC1 and KIF11 in LC319 cells over-expressing the RRM domains.
(c) depicts the viability of LC319 cells in response to dose-dependent dominant-negative effect of KOC1DEL3 evaluated by triplicate MTT assays. X-axis indicates dosage of KOC1DEL3 plasmid-DNA (μg) transfected into LC319 cells in individual assays.
(d) depicts the results of immunoprecipitation detecting reduction of the complex formation between endogenous KOC1 and KIF11 in A549 cells that were transfected with the KOC1DEL2 construct.
(e) depicts the results of immunoprecipitation detecting interaction of the KOC1DEL2 with endogenous KIF11 in A549 cells.
(f) depicts the viability of A549 cells in response to dose-dependent dominant-negative effect of KOC1DEL2 evaluated by triplicate MTT assays. X-axis indicates dosage of KOC1DEL2 plasmid-DNA (μg) transfected into A549 cells in individual assays.
Figure 9:
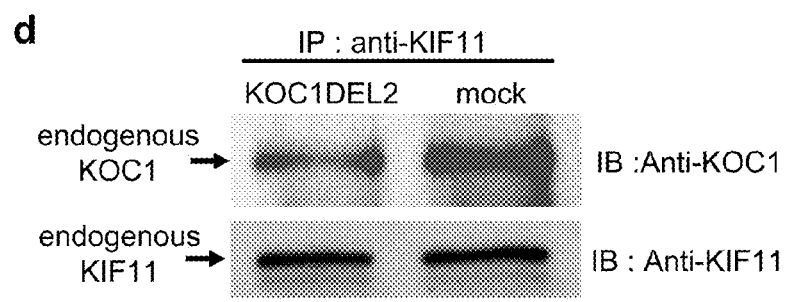
Figure 9:
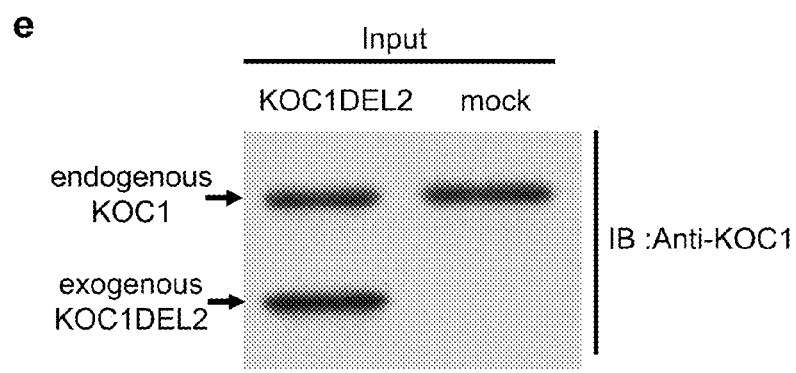
Figure 9:
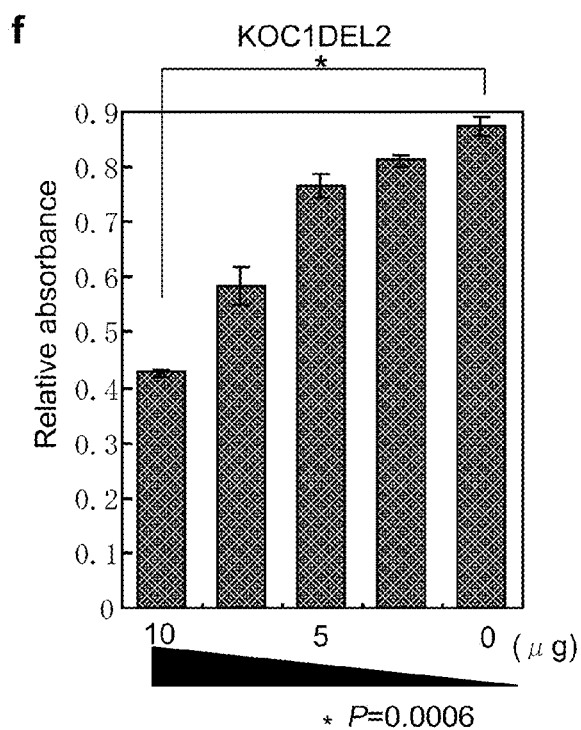

To investigate the functional significance of KOC1-KIF11 interaction for growth or survival of lung-cancer cells, a deletion fragment of KOC1 containing the two RRMs, which was able to interact with KIF11 (KOC1DEL3; FIG. 3a, b) was examined for a dominant-negative function of suppressing direct interaction between endogenous KOC1 and KIF11. We transfected KOC1DEL3 and mock plasmid (control) into LC319 cells and detected interaction of KOC1DEL3 with endogenous KIF11. We further verified that overexpression of the RRM domains reduce complex formation between KOC1 and KIF11 by immunoprecipitation (FIG. 9a,b). Expectedly, transfection of that fragment resulted in significant dose-dependent decreases in cell viability as measured by MTT assay (P<0.001, KOC1DEL3 vs mock; FIG. 9c). We also confirmed that transfection of construct containing only KH-domains control have no effect on proliferation.

Furthermore, to investigate the functional significance of KOC1-KIF11 interaction for growth or survival of lung-cancer cells, a deletion fragment of KOC1, which lacked the C-terminal two KH-domains indispensable for mRNA binding but was able to interact with KIF11 (KOC1DEL2; FIG. 3a, b), was examined for a dominant-negative function of suppressing direct interaction between endogenous KOC1 and KIF11. We transfected KOC1DEL2 and mock plasmid (control) into A549 cells and detected interaction of KOC1DEL2 with endogenous KIF11 (FIG. 9d). We further verified by immunoprecipitation that over-expression of the KOC1DEL2 reduced complex formation between endogenous KOC1 and KIF11 (FIG. 9e). Expectedly, transfection of the dominant-negative fragment resulted in significant dose-dependent decreases in cell viability as measured by MTT assay (P=0.0006, KOC1DEL2 vs mock; FIG. 9f).

Figure 10:
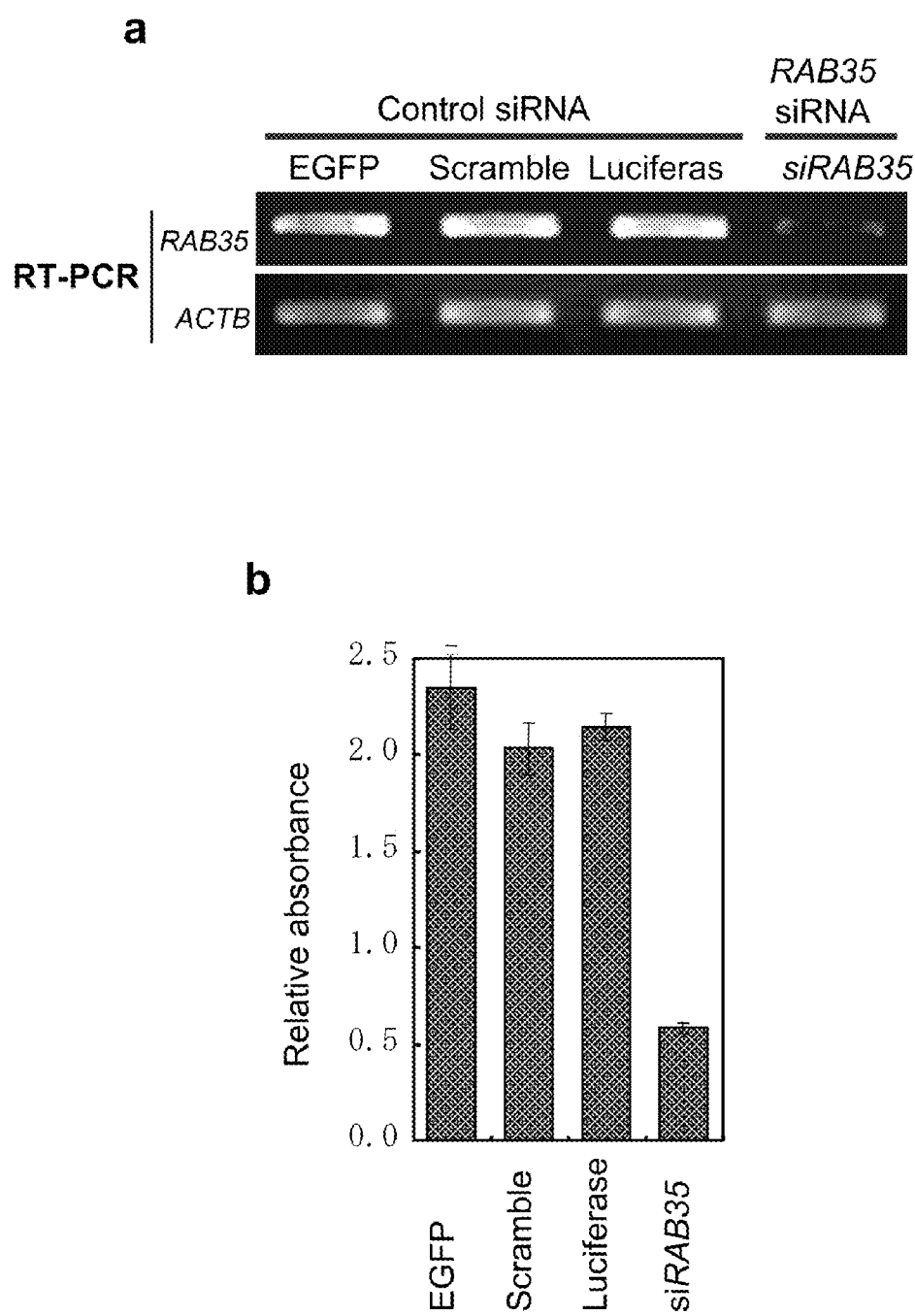
FIG. 10 shows the effect of RAB35 siRNAs on cells.
(a) depicts the result of semi-quantitative RT-PCR analyzing mRNA knock-down effect in response to si-RAB35 or control siRNAs in A549 cells.
(b) show results of MTT assays of A549 cells transfected with specific siRNA or control plasmids (EGFP, Scramble, or Luciferase). Error bars represent the standard deviation of triplicate assays.

We also examined some biological role(s) of these KIF11-transporting mRNAs in controlling the cell growth or survival of lung-cancer cells, we constructed plasmid to express siRNA against RAB35 (si-RAB35), which was identified as the KOC1-RNP complex-associated mRNAs. Transfection of the plasmids (si-RAB35) into A549 cells significantly suppressed expression of endogenous RAB35 in comparison with the controls, and resulted in significant decreases in cell viability and colony numbers measured by MTT and colony-formation assays (FIG. 10a,b).

Figure 11:
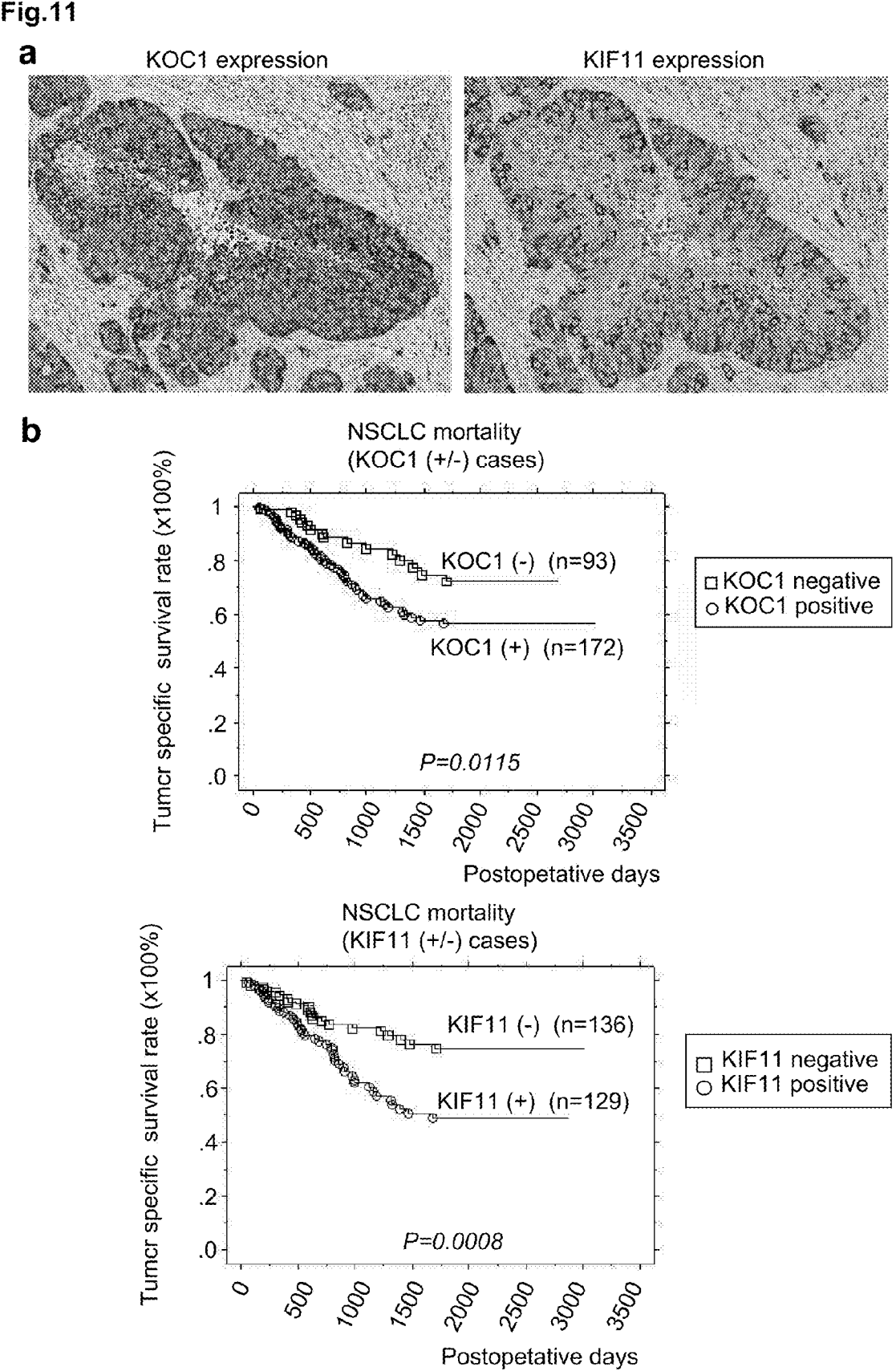
FIG. 11 shows association of KOC1 and KIF11 over-expression with worse outcomes in NSCLC.
(a) depicts the results of immunohistochemical evaluation of representative samples from surgically-resected SCC tissues, using anti-KOC1 (left) and anti-KIF11 (right) polyclonal antibodies on tissue microarrays (X200).
(b) depicts the results of Kaplan-Meier analysis of tumor-specific survival times according to KOC1 expression (left panel) and KIF11 expression (right panel) on tissue microarrays.

Association of KOC1 and KIF11 Over-Expression with Poor Prognosis of NSCLC Patients We performed immunohistochemical analysis with anti-KOC1 and anti-KIF11 polyclonal antibodies using tissue microarrays consisting of 265 NSCLC tissues (FIG. 1a). Of the 265 cases, KOC1 staining was positive for 172 (64.9%); 129 cases were positive for KIF11 (48.7%). The expression pattern of KOC1 was significantly concordant with KIF11 expression in these tumors ($X^2$=60.8, P<0.0001). We then asked whether KOC1 and/or KIF11 over-expression could be associated with clinical outcome. We found that expression of KOC1 in NSCLCs was significantly associated with pT factor status ($X^2$=23.1, P<0.0001) and with tumor-specific 5-year survival (P=0.0115 by the Log-rank test) (FIG. 11b, upper panel). Expression of KIF11 in NSCLCs was significantly associated with pT factor ($X^2$=15.0, P<0.0001), pN factor ($X^2$=4.4, P=0.0356), and 5 year-survival (P=0.0008 by the Log-rank test) (FIG. 11b, lower panel). By univariate analysis pT, pN, gender, and KOC1/KIF11 expression were each significantly related to a poor tumor-specific survival among NSCLC patients. Furthermore, KOC1 and KIF11 were determined to be independent prognostic factors by multivariate analysis using a Cox proportional-hazard model (P=0.0499 and P=0.0259, respectively).

(6) Screening of Candidate Receptors for NMU in NSCLC

Two known NMU receptors, NMU1R (FM3/GPR66) and NMU2R (FM4) play important roles in energy homeostasis (Fujii, R. et al., J. Biol. Chem. 275: 21068-21074 (2000); Howard, A. D. et al., Nature 406: 70-74 (2000); Funes, S. et al., Peptides 23: 1607-1615 (2002)). NMU1R is present in many peripheral human tissues (Fujii, R. et al., J. Biol. Chem. 275: 21068-21074 (2000); Howard, A. D. et al., Nature 406: 70-74 (2000); Funes, S. et al., Peptides 23:1607-1615 (2002)), but NMU2R is located only in brain. To investigate whether NMU1R and NMU2R genes were expressed in NSCLCs, expression of these NMU receptors were analyzed in normal human brain and lung, in NSCLC cell lines, and in clinical tissues by semiquantitative RT-PCR experiments. Neither NMU1R nor NMU2R expression was detected in any of the cell lines or clinical samples examined, although NMU1R was expressed in lung and NMU2R in brain (data now shown), suggesting that NMU could be mediating growth of lung-cancer cells through interaction with other receptor(s).

Figure 13:
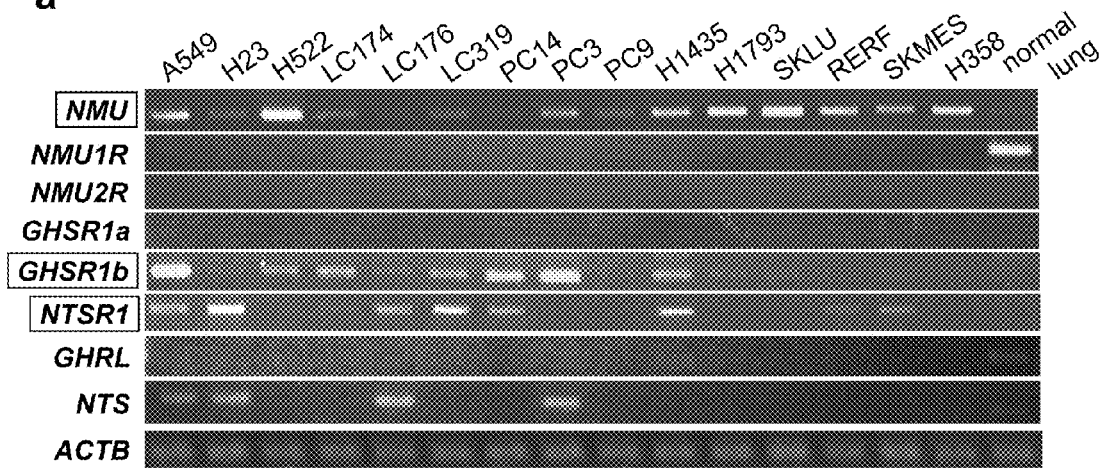
FIG. 13 (a) shows the result of semiquantitative RT-PCR analysis depicting the expression of NMU, candidate receptors, and their known ligands detected in NSCLC cell lines.
(b) shows GHSR1b expression in normal human tissues.
(c) depicts the result of immunocytochemical staining using FITC-labeled anti-FLAG antibody showing the co-localization of NMU and GHSR1b/NTSR1 on the cell surface of COS-7 cells that were transiently transfected with FLAG-tagged GHSR1b or NTSR1.
(d) depicts the interaction of NMU with GHSR1b/NTSR1. COS-7 cells were transiently transfected with the same vectors, and binding of rhodamine-labeled NMU-25 to the cell surface was detected by flow cytometry. As negative controls for these assays, three ligand/cell combinations were prepared: 1) non-transfected COS-7 cells; 2) NMU-25-rhodamine vs non-transfected COS-7 cells; and 3) COS-7 cells transfected only with GHSR1b or NTSR1.
(e) depicts the results of receptor-ligand binding assay using the LC319 and PC-14 cells treated with NMU-25.
(f) depicts cAMP production of NMU-treated NSCLC cells.
Figure 13:
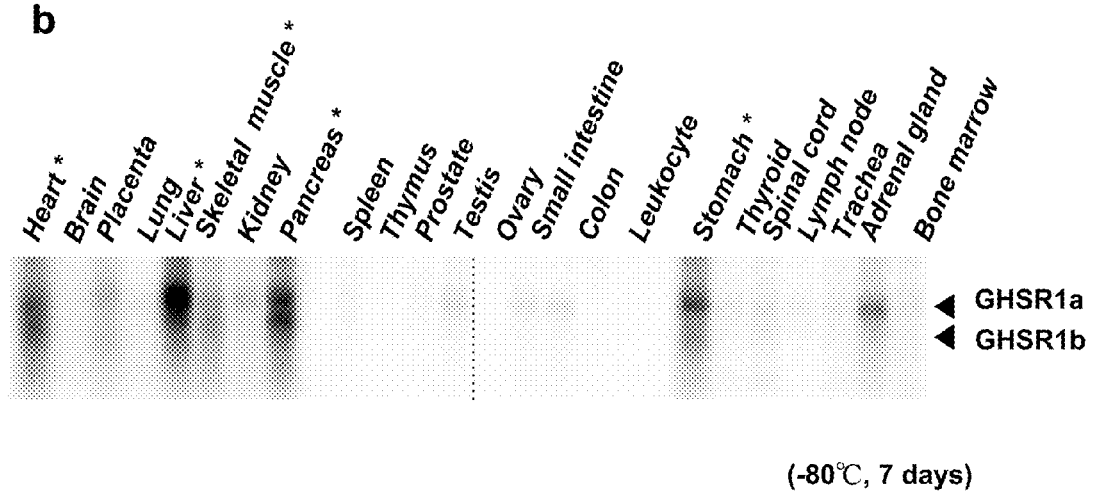
Figure 13:
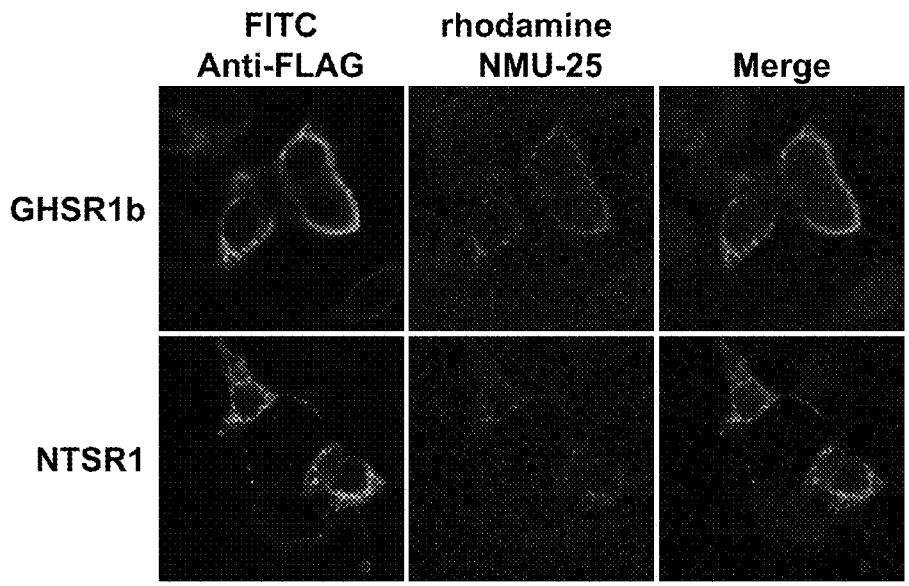
Figure 13:
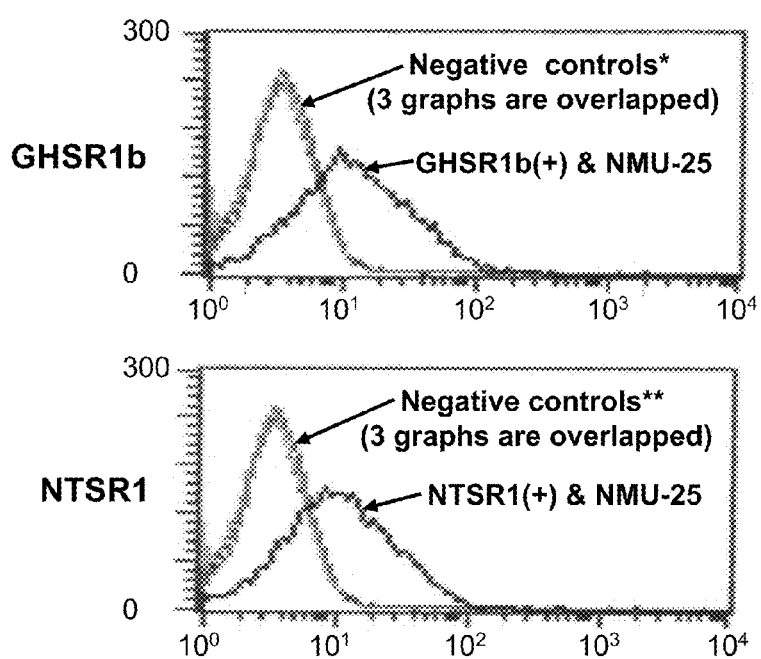
Figure 13:
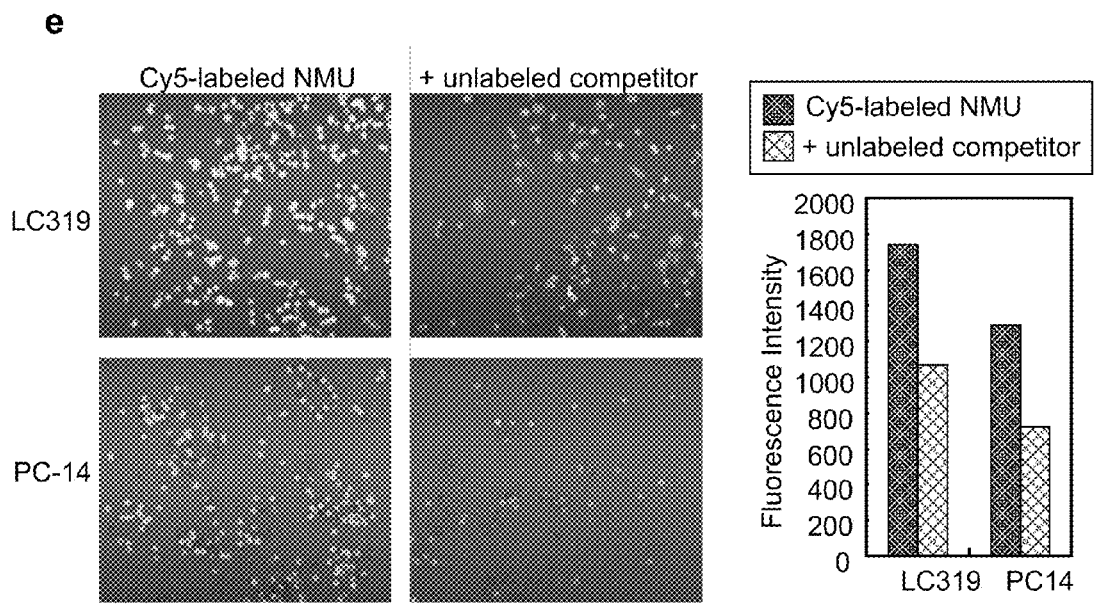
Figure 13:
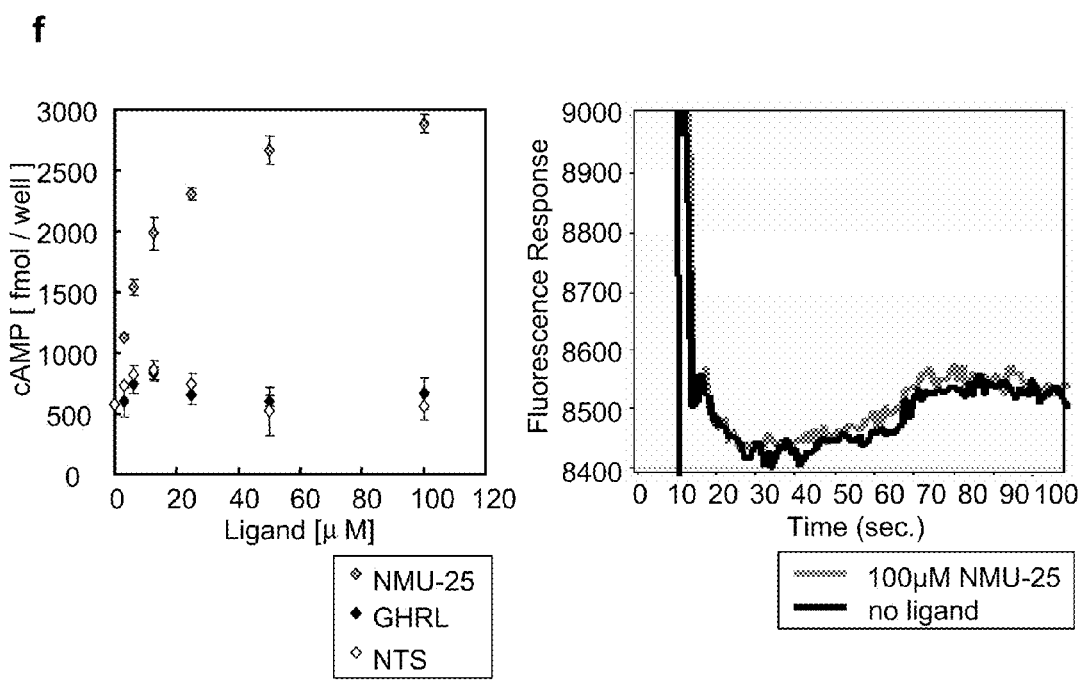

Since NMU2R and NMU1R were originally isolated as homologues of known neuropeptide GPCRs, unidentified NMU receptor(s) were speculated to be members of the same family that would show some degree of homology to NMU1R/NMU2R. Hence, candidate NMU receptors were searched using the BLAST program. The results and their high expression levels in NSCLCs in the expression profile data of the present inventors indicated GHSR1b (NM_004122; SEQ ID NOs: 3 and 4) and NTSR1 (NM_002531; SEQ ID NOs: 5 and 6) to be good candidates. GHSR has two transcripts, types 1a and 1b. The full-length human type 1a cDNA encodes a predicted polypeptide of 366 amino acids with seven transmembrane domains, a typical feature of G protein-coupled receptors. A single intron divides its open reading frame into two exons encoding transmembrane domains 1-5 and 6-7, thus placing the GHSR1a into the intron-containing class of GPCRs. Type 1b is a non-spliced mRNA variant transcribed from a single exon that encodes a polypeptide of 289 amino acids with five transmembrane domains. The semiquantitative RT-PCR analysis using specific primers for each variant indicated that GHSR1a was not expressed in NSCLCs. On the other hand, GHSR1b and NTSR1 were expressed at a relatively high level in some NSCLC cell lines, but not at all in normal lung (FIG. 13a). The GHSR1b product has 46% homology to NMU1R, and NTSR1 encodes 418 amino acids with 47% homology to NMU1R.

(7) Identification of Candidate Receptors for NMU in NSCLC

To confirm direct interaction between NMU and GHSR1b/NTSR1, COS-7 cells were transiently transfected with plasmids designed to express FLAG-tagged GHSR1b or NTSR1, and cultured in the presence of rhodamine-labeled NMU-25. Then the localization of FLAG-tagged GHSR1b/NTSR1 and NMU-25-rhodamine in the cells were examined using anti-FLAG antibodies conjugated to FITC, and found that NMU-25 and either of both receptors were located together on the cell membrane (FIG. 13c). Co-localization of NMU-25 with these receptors was not observed in control assays involving either of the following ligand/cell combinations: 1) NMU-25-rhodamine incubated with COS-7 cells that were not transfected with either of the receptor plasmids; 2) non-transfected COS-7 cells incubated without NMU-25-rhodamine; and 3) COS-7 cells transfected with either of the receptor plasmids, but incubated without NMU-25-rhodamine. The result was confirmed by flow cytometry, which revealed binding of rhodamine-labeled NMU-25 to the surface of COS-7 cells that expressed either of the two receptors (FIG. 13d) and binding of rhodamine-labeled NMU-25 to the surface of COS-7 cells in a dose dependent manner.

(8) GHSR1b Expression in Normal Human Tissues

As the expression of GHSR1b in normal human tissues was not precisely reported at the time, the distribution of GHSR1b was determined using human multiple tissue Northern-blot. Northern blotting with GHSR1b cDNA as a probe identified a 0.9-kb transcript as a very weak signal band in comparison with a 1.1-kb transcript GHSR1a, seen in the heart, liver, skeletal muscle, pancreas, and stomach, among the 23 normal human tissues examined (FIG. 13b). To further confirm binding of NMU-25 to the endogenous GHSR1b and NTSR1 on the NSCLC cells, we performed receptor-ligand binding assay using the LC319 and PC-14 cells treated with NMU-25. We detected binding of Cy5-labeled NMU-25 to the surface of these two cell lines that expressed both of the two receptors, but scarcely expressed NMU1R/NMU2R (FIG. 13e).

Biologically active ligands for GPCRs have been reported to bind specifically to their cognate receptors and cause an increase in second-messengers such as intracellular-$Ca^{2+}$ and cAMP levels. We therefore determined the ability of NMU to induce these second-messengers in LC319 cells through its interaction with GHSR1b/NTSR1. cAMP production, but not $Ca^{2+}$ flux in LC319 cells, which express both GHSR1b and NTSR1 was observed in a NMU-25 dose dependent manner, when the cells were cultured in the presence of NMU-25 at final concentrations of 3-100 µM in the culture media. The results demonstrate that NSCLC cells express functional GHSR1b/NTSR1 (FIG. 13f left panel). This effect was confirmed to be NMU-25 specific by adding other reported ligands for GHSR1b/NTSR1, GHRL or NTS (FIG. 13f right panel). In addition, GHRL and NTS caused the mobilization response of intracellular calcium in LC319 cells (data not shown), suggesting a variety of function for the poorly understood for GHSR1b and/or NTSR1.

(9) Inhibition of Growth of NSCLC Cells by siRNA Against GHSR/NTSR1

Furthermore, the biological significance of the NMU-receptor interaction in pulmonary carcinogenesis was examined using plasmids designed to express siRNA against GHSR or NTSR1 (si-GHSR-1, si-NTSR1-1, and si-NTSR1-2). Transfection of either of these plasmids into A549 or LC319 cells suppressed expression of the endogenous receptor in comparison to cells containing any of the three control siRNAs (FIG. 14a). In accordance with the reduced expression of the receptors, A549 and LC319 cells showed significant decreases in cell viability (FIG. 14b) and numbers of colonies (data not shown). These results strongly supported the possibility that NMU, by interaction with GHSR1b and NTSR1, might play a very significant role in development/progression of NSCLC.

Identification of Downstream Genes of NMU

To further elucidate the NMU-signaling pathway and identify downstream genes regulated by NMU, siRNA against NMU (si-NMU) or LUC (control siRNA) were transfected into LC319 cells which had overexpressed NMU and down-regulations in gene expression were monitored using a cDNA microarray that contained 32,256 genes. Among hundreds of genes detected by this method, we performed Self-organizing map (SOM) clustering analysis to further select candidate genes. SOM clustering is data mining and visualization method originally developed by Kohonen (Kohonen, T. (1990). The self-organizing map. IEEE 78, 1464-1480.) and applied to the analysis of gene expression data from microarrays. The clustering method is similar to k-means clustering (Kaech, S. M., et al., (2002). Cell 111, 837-851.) but differs in that genes are divided into groups based on expression patterns, and relationships between groups are illustrated by two-dimensional maps. The genes passing our variation filter were grouped by a 5×4 SOM.

Figure 15:
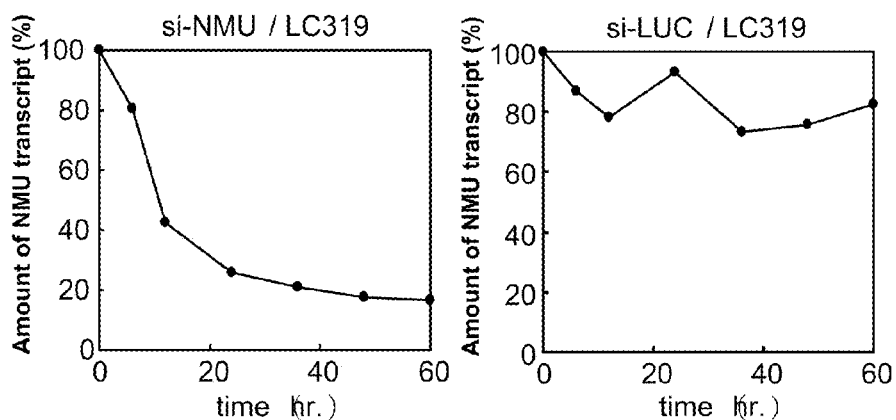
FIG. 15 shows validation of candidate downstream genes of NMU.
(a) depicts time-dependent reduction of NMU transcript by si-NMU.
(b) depicts the result of semiquantitative RT-PCR experiments of mRNAs from LC319 cells treated with si-NMU, with gene-specific primers confirming time-dependent reduction of candidate downstream target gene expression.
(c) depicts the result of semiquantitative RT-PCR using mRNAs from LC319 cells incubated with NMU-25 or BSA (control) (100 μM) detecting induction of FOXM1 as the candidate downstream target gene of NMU.
Figure 15:
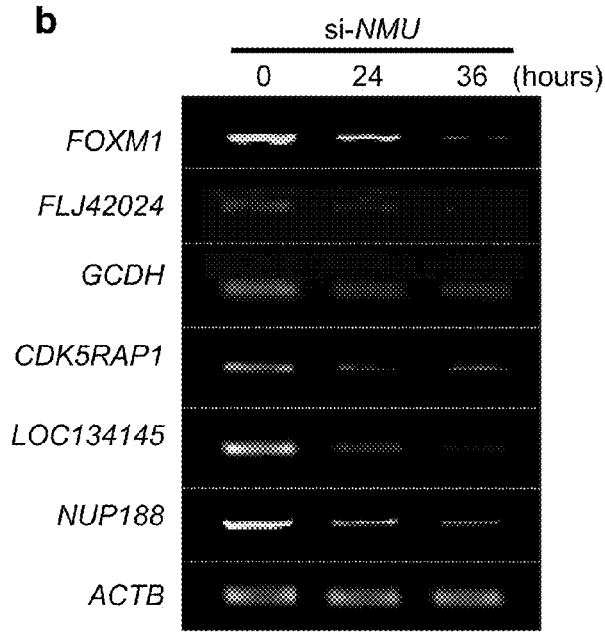
Figure 15:
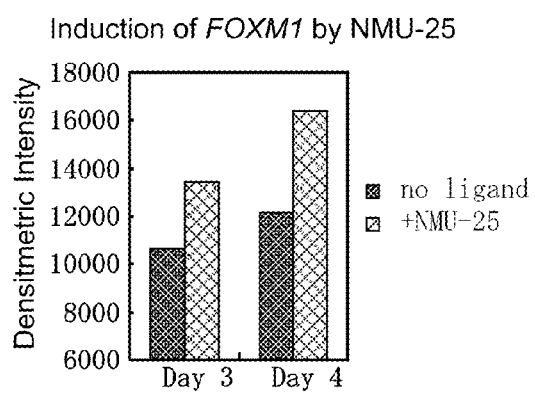
Figure 15:
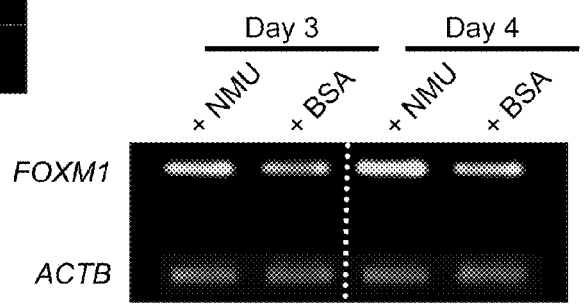

We initially selected 70 genes using SOM cluster analysis, whose intensity were significantly decreased in accordance with the reduction of NMU expression (FIG. 15a). Semi-quantitative RT-PCR analysis confirmed reduction of candidate transcripts in a time-dependent manner in LC319 cells transfected with si-NMU, but not with control siRNA for LUC (FIG. 15b). These transcripts were also confirmed to be up-regulated greater than 2-fold in LC319 cells expressing exogenous NMU, compared with that of normal lung tissues. Overexpression of these genes in accordance with NMU expression were evaluated as well in lung-cancer tissues and cell lines (data not shown). We finally identified 6 candidate NMU target genes, which satisfied the above selection criteria; FOXM1, FLJ42024, GCDH, CDK5RAP1, LOC134145, and NUP188 (FIG. 15b).

FOXM1 mRNA levels were significantly elevated in lung cancers compared with normal lung tissues and its expression showed good concordance with NMU and two receptors for NMU, GHSR1b and NTSR1, whereas the function of FOXM1 in lung carcinogenesis remains unclear. Therefore, we chose FOXM1 for further analysis. To determine specific induction of the FOXM1 by the NMU ligand-receptor signaling, LC319 cells expressing GHSR1b and NTSR1 were cultured in the presence of NMU-25 or BSA (control) at final concentrations of 100 µM in the culture media. NMU-25-treated cells showed higher expression of FOXM1 compared to the control cells (FIG. 15c). Furthermore, FOXM1 was also confirmed to be up-regulated in LC319 cells expressing exogenous NMU, compared with that of control cells transfected with mock vector (data not shown).

Figure 16:
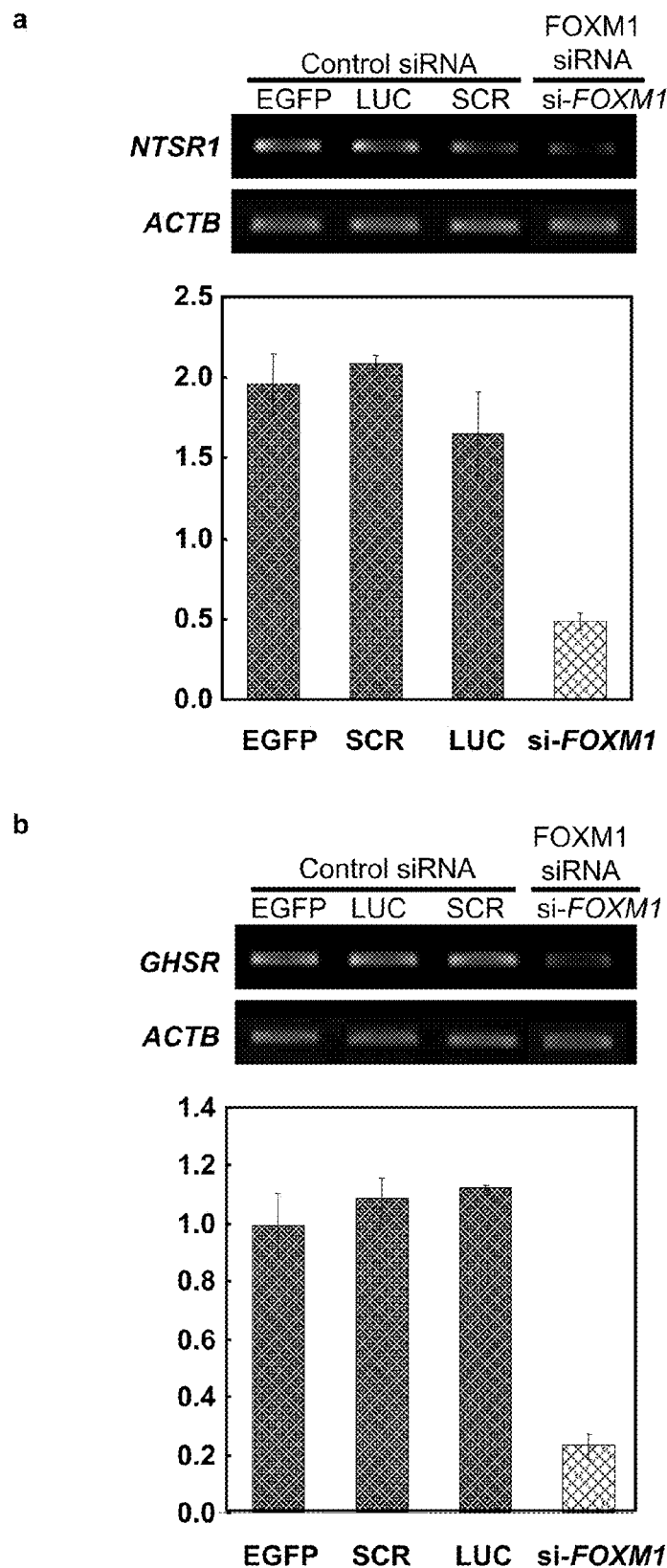
FIG. 16 shows the effect of FOXM1 siRNAs on cells.
(a) depicts inhibition of growth of NSCLC cells by siRNAs against FOXM1. Expression of FOXM1 in response to specific siRNAs (si-FOXM1) or control siRNAs (EGFP, LUC, SCR) in A549 cells, analyzed by semiquantitative RT-PCR (upper panel). Viability of A549 cells, evaluated by triplicate MTT assays, in response to si-FOXM1, EGFP, LUC, or SCR (lower panel).
(b) depicts inhibition of growth of NSCLC cells by siRNAs against FOXM1. Expression of FOXM1 in response to specific siRNAs (si-FOXM1) or control siRNAs (EGFP, LUC, SCR) in LC319 cells, analyzed by semiquantitative RT-PCR (upper panel). Viability of A549 cells, evaluated by triplicate MTT assays, in response to si-FOXM1, EGFP, LUC, or SCR (lower panel).
Figure 17:
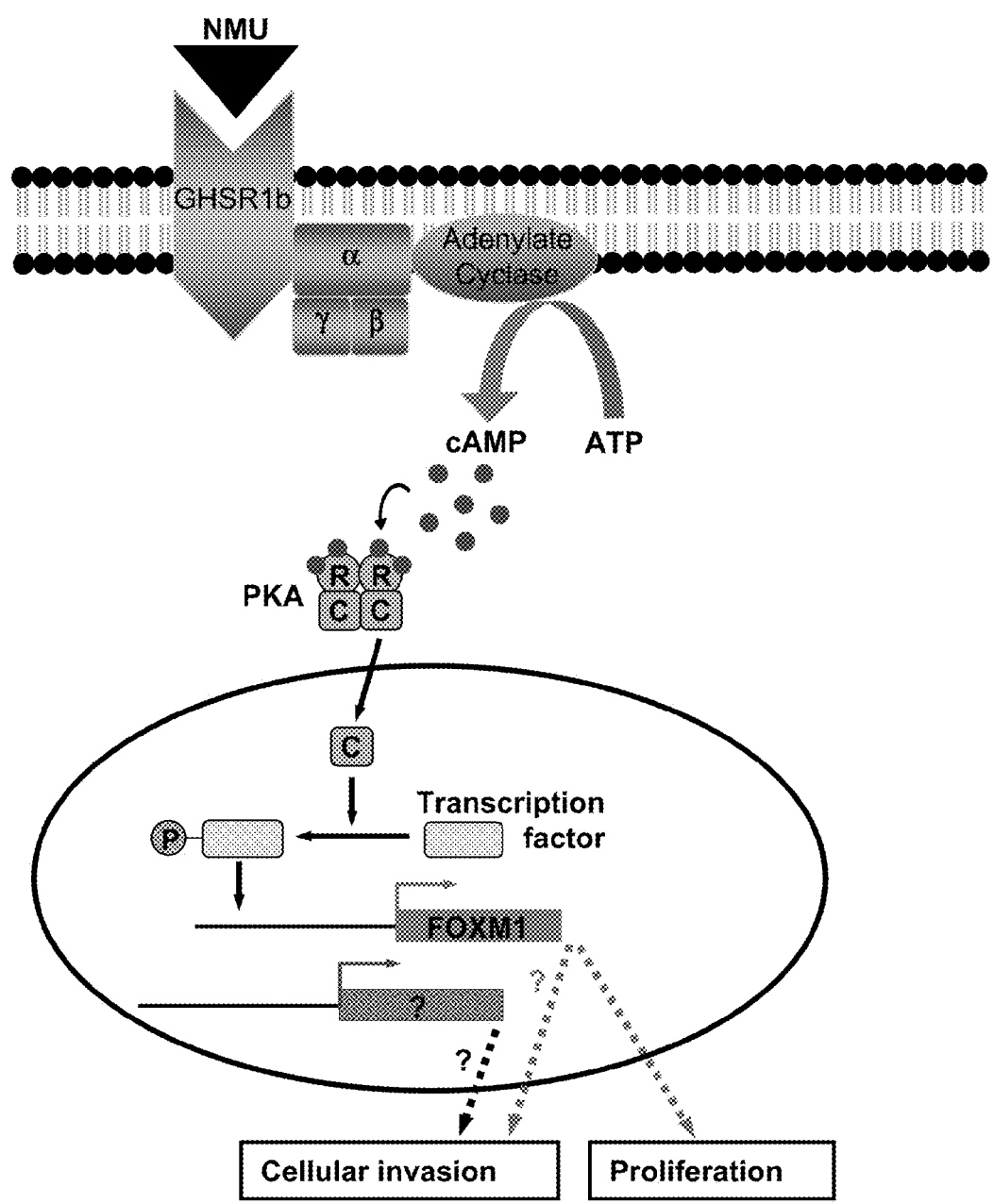
FIG. 17 is a schematic model for promotion of cancer cell growth and invasion through the NMU-receptor interaction in the autocrine NMU-GHSR1b oncogenic signaling pathway. Binding of NMU to GHSR1b and/or NTSR1 leads to the activation of adenylate cyclase, accumulation of intracellular cAMP and following activation of cAMP-dependent protein kinase (PKA). The release of catalytic subunits of PKA (C)

We then examined the biological significance of the FOXM1 activation by NMU signaling for growth or survival of lung-cancer cells, using plasmids designed to express siRNA against FOXM1 (si-FOXM1). Transfection of si-FOXM1 into A549 or LC319 cells suppressed expression of the endogenous FOXM1 in comparison to cells containing any of the three control siRNAs (FIGS. 16a and 16b). In accordance with the reduced expression of the FOXM1, A549 and LC319 cells showed significant decreases in cell viability and numbers of colonies (FIGS. 16a and b). These results strongly demonstrated that NMU, by the interaction with GHSR1b/NTSR1 and subsequent activation of its downstream targets, such as FOXM1, could significantly affect the growth of lung-cancer cells.

Microarray data of LC319 cells treated with siRNA for NMU presented herein proved that NMU signaling pathway could affect the growth promotion of lung-cancer cells by transactivating a set of downstream genes involving transcripts whose protein products can function as a transcription factor and are capable of controlling cell growth or participating in signal transduction. We provided evidence that the FOXM1 transcription factor is a downstream target of NMU signaling by additional biological assays. FOXM1 was known to be over-expressed in several types of human cancers (Teh, M. T. et al., *Cancer Res.* 62, 4773-4780; van den Boom, J. et al., (2003). *Am. J. Pathol.* 163, 1033-1043; Kalinichenko, V. V. et al., (2004). *Genes. Dev.* 18, 830-850). The "forkhead" gene family, originally identified in *Drosophila*, comprises transcription factors with a conserved 100-amino acid DNA-binding motif, and has been shown to play important roles in regulating the expression of genes involved in cell growth, proliferation, differentiation, longevity, and transformation. Cotransfection assays in the human hepatoma HepG2 cell line demonstrated that FOXM1 protein stimulated expression of both the cyclin B1 (CCNB1) and cyclin D1 (CCND1) (Wang, X. et al., (2002). *Proc. Nat. Acad. Sci.* 99, 16881-16886.), suggesting that these cyclin genes are direct FOXM1 transcription targets and that FOXM1 controls the transcription network of genes that are essential for cell division and exit from mitosis. It should be noted that we observed activation of CCNB1 in the majority of a series of NSCLC we examined and its good concordance of the expression to FOXM1 (data not shown). On the other hand, it was also demonstrated that p27 (Kip1) and p19 (Arf) (CDKN2A) interact with FOXM1 and inhibit FOXM1 transcriptional activity (Kalinichenko, V. V. et al., (2004). *Genes. Dev.* 18, 830-850). The promotion of cell growth in NSCLC cells by NMU might reflect transactivation of FOXM1, which would affect the function of those molecular pathways in consequence.

By immunohistochemical analysis on tissue microarray, we detected increased expression of NMU protein in the majority of NSCLC (SCC, ADC, LCC, and BAC) and SCLC samples, but not in normal lung tissues. Since NMU is a secreted protein and most of the clinical NSCLC samples used for our analysis were at an early and operable stage, NMU might serve as a biomarker for diagnosis of early-stage lung cancer, in combination with fiberscopic transbronchial biopsy (TBB) or blood tests.

In summary, we have shown that NMU and two newly revealed receptors for this molecule, GHSR1b and NTSR1, are likely to play an essential role for an autocrine growth-promoting pathway in NSCLCs by modulating transcription of down stream target genes. The data reported here strongly imply the possibility of designing new anti-cancer drugs, specific for lung cancer, that target the NMU-GHSR1b/NTSR1 pathway. They also suggest a potential for siRNAs themselves to interfere with this pathway, as a novel approach to treatment of chemotherapy-resistant, advanced lung cancers.

INDUSTRIAL APPLICABILITY

The expression of human genes KIF11, GHSR1b, NTSR1 and FOXM1 are markedly elevated in non-small cell lung cancer (NSCLC) as compared to normal lung tissues. Accordingly, these genes can be conveniently used as diagnostic markers of NSCLC and the proteins encoded thereby may be used in diagnostic assays of NSCLC.

The present inventors have also shown that the expression of KIF11, GHSR1b, NTSR1 or FOXM1 promotes cell growth whereas cell growth is suppressed by small interfering RNAs corresponding to KIF11, GHSR1b, NTSR1 or FOXM1 gene. These findings show that each of KIF11, KOC1, GHSR1b, NTSR1 and FOXM1 proteins stimulate oncogenic activity. Thus, each of these oncoproteins is a useful target for the development of anti-cancer pharmaceuticals. For example, agents that block the expression of KIF11, KOC1, GHSR1b, NTSR1 or FOXM1, or prevent its activity may find therapeutic utility as anti-cancer agents, particularly anti-cancer agents for the treatment of NSCLC. Examples of such agents include antisense oligonucleotides, small interfering RNAs, and ribozymes against the KIF11, KOC1, GHSR1b, NTSR1 or FOXM1 gene, and antibodies that recognize KIF11, KOC1, GHSR1b, NTSR1 or FOXM1 polypeptide.

While the invention has been described in detail and with reference to specific embodiments thereof, it will be apparent to one skilled in the art that various changes and modifications can be made therein without departing from the spirit and scope of the invention.

The invention claimed is:

1. A method of diagnosing non-small cell lung cancer (NSCLC) in a subject, comprising determining the expression level of KIF11 in a lung tissue sample derived from the subject, wherein an increase of said expression level compared to a normal control level of said gene indicates that said subject suffers from NSCLC.

2. The method of claim 1, wherein said increase is at least 10% greater than said normal control level.

3. The method of claim 1, wherein said expression level is determined by a method selected from the group consisting of:
   (1) detecting mRNA of KIF11;
   (2) detecting protein encoded by KIF11; and
   (3) detecting the biological activity of protein encoded by KIF11.

4. The method of claim 1, wherein said expression level is determined by detecting hybridization of a KIF11 probe to a gene transcript of said patient-derived lung tissue sample.

5. The method of claim 4, wherein said hybridization step is carried out on a DNA array.

6. A method of predicting an NSCLC prognosis, wherein the method comprises the steps of:
   (a) detecting the expression level of KIF11 in an NSCLC tissue collected from a subject diagnosed with NSCLC, and
   (b) indicating a poor prognosis when an elevation of the expression level of KIF11 is detected.

7. The method of claim 6, wherein the expression level is detected by any one of the method selected from the group consisting of:
   (a) detecting the mRNA encoding the amino acid sequence of SEQ ID NO: 2 (KIF11),
   (b) detecting the protein comprising the amino acid sequence of SEQ ID NO: 2 (KIF11), and
   (c) detecting the biological activity of the protein comprising the amino acid sequence of SEQ ID NO: 2 (KIF11).

* * * * *

UNITED STATES PATENT AND TRADEMARK OFFICE
CERTIFICATE OF CORRECTION

| | | |
|---|---|---|
| PATENT NO. | : 7,972,772 B2 | Page 1 of 1 |
| APPLICATION NO. | : 12/700669 | |
| DATED | : July 5, 2011 | |
| INVENTOR(S) | : Nakamura et al. | |

It is certified that error appears in the above-identified patent and that said Letters Patent is hereby corrected as shown below:

At column 163 Claim 4, line 30, please delete "patient-derived".

Signed and Sealed this
Twentieth Day of December, 2011

David J. Kappos
*Director of the United States Patent and Trademark Office*

SEQUENCE LISTING

<160> NUMBER OF SEQ ID NOS: 127

<210> SEQ ID NO 1
<211> LENGTH: 4908

```
<212> TYPE: DNA
<213> ORGANISM: Homo sapiens
<220> FEATURE:
<221> NAME/KEY: CDS
<222> LOCATION: (141)..(3311)

<400> SEQUENCE: 1
acctgcgtgc agtcggtcct ccaggccacg cagcgcccga gagtaccagg gagactccgg      60
cccctgtcgg cgccaagccc ctccgcccct cacagcgccc aggtccgcgg ccgggccttg     120 atttttggc ggggaccgtc atg gcg tcg cag cca aat tcg tct gcg aag aag     173
                        Met Ala Ser Gln Pro Asn Ser Ser Ala Lys Lys
                          1               5                  10 aaa gag gag aag ggg aag aac atc cag gtg gtg gtg aga tgc aga cca     221
Lys Glu Glu Lys Gly Lys Asn Ile Gln Val Val Val Arg Cys Arg Pro
             15                  20                  25 ttt aat ttg gca gag cgg aaa gct agc gcc cat tca ata gta gaa tgt     269
Phe Asn Leu Ala Glu Arg Lys Ala Ser Ala His Ser Ile Val Glu Cys
         30                  35                  40 gat cct gta cga aaa gaa gtt agt gta cga act gga gga ttg gct gac     317
Asp Pro Val Arg Lys Glu Val Ser Val Arg Thr Gly Gly Leu Ala Asp
     45                  50                  55 aag agc tca agg aaa aca tac act ttt gat atg gtg ttt gga gca tct     365
Lys Ser Ser Arg Lys Thr Tyr Thr Phe Asp Met Val Phe Gly Ala Ser
 60                  65                  70                  75 act aaa cag att gat gtt tac cga agt gtt gtt tgt cca att ctg gat     413
Thr Lys Gln Ile Asp Val Tyr Arg Ser Val Val Cys Pro Ile Leu Asp
                 80                  85                  90 gaa gtt att atg ggc tat aat tgc act atc ttt gcg tat ggc caa act     461
Glu Val Ile Met Gly Tyr Asn Cys Thr Ile Phe Ala Tyr Gly Gln Thr
             95                 100                 105 ggc act gga aaa act ttt aca atg gaa ggt gaa agg tca cct aat gaa     509
Gly Thr Gly Lys Thr Phe Thr Met Glu Gly Glu Arg Ser Pro Asn Glu
         110                 115                 120 gag tat acc tgg gaa gag gat ccc ttg gct ggt ata att cca cgt acc     557
Glu Tyr Thr Trp Glu Glu Asp Pro Leu Ala Gly Ile Ile Pro Arg Thr
     125                 130                 135 ctt cat caa att ttt gag aaa ctt act gat aat ggt act gaa ttt tca     605
Leu His Gln Ile Phe Glu Lys Leu Thr Asp Asn Gly Thr Glu Phe Ser
140                 145                 150                 155 gtc aaa gtg tct ctg ttg gag atc tat aat gaa gag ctt ttt gat ctt     653
Val Lys Val Ser Leu Leu Glu Ile Tyr Asn Glu Glu Leu Phe Asp Leu
                 160                 165                 170 ctt aat cca tca tct gat gtt tct gag aga cta cag atg ttt gat gat     701
Leu Asn Pro Ser Ser Asp Val Ser Glu Arg Leu Gln Met Phe Asp Asp
             175                 180                 185 ccc cgt aac aag aga gga gtg ata att aaa ggt tta gaa gaa att aca     749
Pro Arg Asn Lys Arg Gly Val Ile Ile Lys Gly Leu Glu Glu Ile Thr
         190                 195                 200 gta cac aac aag gat gaa gtc tat caa att tta gaa aag ggg gca gca     797
Val His Asn Lys Asp Glu Val Tyr Gln Ile Leu Glu Lys Gly Ala Ala
     205                 210                 215 aaa agg aca act gca gct act ctg atg aat gca tac tct agt cgt tcc     845
Lys Arg Thr Thr Ala Ala Thr Leu Met Asn Ala Tyr Ser Ser Arg Ser
220                 225                 230                 235 cac tca gtt ttc tct gtt aca ata cat atg aaa gaa act acg att gat     893
His Ser Val Phe Ser Val Thr Ile His Met Lys Glu Thr Thr Ile Asp
                 240                 245                 250 gga gaa gag ctt gtt aaa atc gga aag ttg aac ttg gtt gat ctt gca     941
Gly Glu Glu Leu Val Lys Ile Gly Lys Leu Asn Leu Val Asp Leu Ala
             255                 260                 265
```

```
gga agt gaa aac att ggc cgt tct gga gct gtt gat aag aga gct cgg      989
Gly Ser Glu Asn Ile Gly Arg Ser Gly Ala Val Asp Lys Arg Ala Arg
        270                 275                 280 gaa gct gga aat ata aat caa tcc ctg ttg act ttg gga agg gtc att     1037
Glu Ala Gly Asn Ile Asn Gln Ser Leu Leu Thr Leu Gly Arg Val Ile
285                 290                 295 act gcc ctt gta gaa aga aca cct cat gtt cct tat cga gaa tct aaa     1085
Thr Ala Leu Val Glu Arg Thr Pro His Val Pro Tyr Arg Glu Ser Lys
300                 305                 310                 315 cta act aga atc ctc cag gat tct ctt gga ggg cgt aca aga aca tct     1133
Leu Thr Arg Ile Leu Gln Asp Ser Leu Gly Gly Arg Thr Arg Thr Ser
                320                 325                 330 ata att gca aca att tct cct gca tct ctc aat ctt gag gaa act ctg     1181
Ile Ile Ala Thr Ile Ser Pro Ala Ser Leu Asn Leu Glu Glu Thr Leu
                335                 340                 345 agt aca ttg gaa tat gct cat aga gca aag aac ata ttg aat aag cct     1229
Ser Thr Leu Glu Tyr Ala His Arg Ala Lys Asn Ile Leu Asn Lys Pro
        350                 355                 360 gaa gtg aat cag aaa ctc acc aaa aaa gct ctt att aag gag tat acg     1277
Glu Val Asn Gln Lys Leu Thr Lys Lys Ala Leu Ile Lys Glu Tyr Thr
365                 370                 375 gag gag ata gaa cgt tta aaa cga gat ctt gct gca gcc cgt gag aaa     1325
Glu Glu Ile Glu Arg Leu Lys Arg Asp Leu Ala Ala Ala Arg Glu Lys
380                 385                 390                 395 aat gga gtg tat att tct gaa gaa aat ttt aga gtc atg agt gga aaa     1373
Asn Gly Val Tyr Ile Ser Glu Glu Asn Phe Arg Val Met Ser Gly Lys
                400                 405                 410 tta act gtt caa gaa gag cag att gta gaa ttg att gaa aaa att ggt     1421
Leu Thr Val Gln Glu Glu Gln Ile Val Glu Leu Ile Glu Lys Ile Gly
                415                 420                 425 gct gtt gag gag gag ctg aat agg gtt aca gag ttg ttt atg gat aat     1469
Ala Val Glu Glu Glu Leu Asn Arg Val Thr Glu Leu Phe Met Asp Asn
        430                 435                 440 aaa aat gaa ctt gac cag tgt aaa tct gac ctg caa aat aaa aca caa     1517
Lys Asn Glu Leu Asp Gln Cys Lys Ser Asp Leu Gln Asn Lys Thr Gln
445                 450                 455 gaa ctt gaa acc act caa aaa cat ttg caa gaa act aaa tta caa ctt     1565
Glu Leu Glu Thr Thr Gln Lys His Leu Gln Glu Thr Lys Leu Gln Leu
460                 465                 470                 475 gtt aaa gaa gaa tat atc aca tca gct ttg gaa agt act gag gag aaa     1613
Val Lys Glu Glu Tyr Ile Thr Ser Ala Leu Glu Ser Thr Glu Glu Lys
                480                 485                 490 ctt cat gat gct gcc agc aag ctg ctt aac aca gtt gaa gaa act aca     1661
Leu His Asp Ala Ala Ser Lys Leu Leu Asn Thr Val Glu Glu Thr Thr
                495                 500                 505 aaa gat gta tct ggt ctc cat tcc aaa ctg gat cgt aag aag gca gtt     1709
Lys Asp Val Ser Gly Leu His Ser Lys Leu Asp Arg Lys Lys Ala Val
        510                 515                 520 gac caa cac aat gca gaa gct cag gat att ttt ggc aaa aac ctg aat     1757
Asp Gln His Asn Ala Glu Ala Gln Asp Ile Phe Gly Lys Asn Leu Asn
525                 530                 535 agt ctg ttt aat aat atg gaa gaa tta att aag gat ggc agc tca aag     1805
Ser Leu Phe Asn Asn Met Glu Glu Leu Ile Lys Asp Gly Ser Ser Lys
540                 545                 550                 555 caa aag gcc atg cta gaa gta cat aag acc tta ttt ggt aat ctg ctg     1853
Gln Lys Ala Met Leu Glu Val His Lys Thr Leu Phe Gly Asn Leu Leu
                560                 565                 570 tct tcc agt gtc tct gca tta gat acc att act aca gta gca ctt gga     1901
Ser Ser Ser Val Ser Ala Leu Asp Thr Ile Thr Thr Val Ala Leu Gly
                575                 580                 585
```

```
tct ctc aca tct att cca gaa aat gtg tct act cat gtt tct cag att    1949
Ser Leu Thr Ser Ile Pro Glu Asn Val Ser Thr His Val Ser Gln Ile
        590             595             600 ttt aat atg ata cta aaa gaa caa tca tta gca gca gaa agt aaa act    1997
Phe Asn Met Ile Leu Lys Glu Gln Ser Leu Ala Ala Glu Ser Lys Thr
        605             610             615 gta cta cag gaa ttg att aat gta ctc aag act gat ctt cta agt tca    2045
Val Leu Gln Glu Leu Ile Asn Val Leu Lys Thr Asp Leu Leu Ser Ser
620             625             630             635 ctg gaa atg att tta tcc cca act gtg gtg tct ata ctg aaa atc aat    2093
Leu Glu Met Ile Leu Ser Pro Thr Val Val Ser Ile Leu Lys Ile Asn
            640             645             650 agt caa cta aag cat att ttc aag act tca ttg aca gtg gcc gat aag    2141
Ser Gln Leu Lys His Ile Phe Lys Thr Ser Leu Thr Val Ala Asp Lys
        655             660             665 ata gaa gat caa aaa aag gaa cta gat ggc ttt ctc agt ata ctg tgt    2189
Ile Glu Asp Gln Lys Lys Glu Leu Asp Gly Phe Leu Ser Ile Leu Cys
        670             675             680 aac aat cta cat gaa cta caa gaa aat acc att tgt tcc ttg gtt gag    2237
Asn Asn Leu His Glu Leu Gln Glu Asn Thr Ile Cys Ser Leu Val Glu
        685             690             695 tca caa aag caa tgt gga aac cta act gaa gac ctg aag aca ata aag    2285
Ser Gln Lys Gln Cys Gly Asn Leu Thr Glu Asp Leu Lys Thr Ile Lys
700             705             710             715 cag acc cat tcc cag gaa ctt tgc aag tta atg aat ctt tgg aca gag    2333
Gln Thr His Ser Gln Glu Leu Cys Lys Leu Met Asn Leu Trp Thr Glu
            720             725             730 aga ttc tgt gct ttg gag gaa aag tgt gaa aat ata cag aaa cca ctt    2381
Arg Phe Cys Ala Leu Glu Glu Lys Cys Glu Asn Ile Gln Lys Pro Leu
        735             740             745 agt agt gtc cag gaa aat ata cag cag aaa tct aag gat ata gtc aac    2429
Ser Ser Val Gln Glu Asn Ile Gln Gln Lys Ser Lys Asp Ile Val Asn
        750             755             760 aaa atg act ttt cac agt caa aaa ttt tgt gct gat tct gat ggc ttc    2477
Lys Met Thr Phe His Ser Gln Lys Phe Cys Ala Asp Ser Asp Gly Phe
765             770             775 tca cag gaa ctc aga aat ttt aac caa gaa ggt aca aaa ttg gtt gaa    2525
Ser Gln Glu Leu Arg Asn Phe Asn Gln Glu Gly Thr Lys Leu Val Glu
780             785             790             795 gaa tct gtg aaa cac tct gat aaa ctc aat ggc aac ctg gaa aaa ata    2573
Glu Ser Val Lys His Ser Asp Lys Leu Asn Gly Asn Leu Glu Lys Ile
            800             805             810 tct caa gag act gaa cag aga tgt gaa tct ctg aac aca aga aca gtt    2621
Ser Gln Glu Thr Glu Gln Arg Cys Glu Ser Leu Asn Thr Arg Thr Val
        815             820             825 tat ttt tct gaa cag tgg gta tct tcc tta aat gaa agg gaa cag gaa    2669
Tyr Phe Ser Glu Gln Trp Val Ser Ser Leu Asn Glu Arg Glu Gln Glu
        830             835             840 ctt cac aac tta ttg gag gtt gta agc caa tgt tgt gag gct tca agt    2717
Leu His Asn Leu Leu Glu Val Val Ser Gln Cys Cys Glu Ala Ser Ser
        845             850             855 tca gac atc act gag aaa tca gat gga cgt aag gca gct cat gag aaa    2765
Ser Asp Ile Thr Glu Lys Ser Asp Gly Arg Lys Ala Ala His Glu Lys
860             865             870             875 cag cat aac att ttt ctt gat cag atg act att gat gaa gat aaa ttg    2813
Gln His Asn Ile Phe Leu Asp Gln Met Thr Ile Asp Glu Asp Lys Leu
            880             885             890 ata gca caa aat cta gaa ctt aat gaa acc ata aaa att ggt ttg act    2861
Ile Ala Gln Asn Leu Glu Leu Asn Glu Thr Ile Lys Ile Gly Leu Thr
        895             900             905
```

-continued

| | | |
|---|---|---|
| aag ctt aat tgc ttt ctg gaa cag gat ctg aaa ctg gat atc cca aca<br>Lys Leu Asn Cys Phe Leu Glu Gln Asp Leu Lys Leu Asp Ile Pro Thr<br>910                       915                    920 | | 2909 |
| ggt acg aca cca cag agg aaa agt tat tta tac cca tca aca ctg gta<br>Gly Thr Thr Pro Gln Arg Lys Ser Tyr Leu Tyr Pro Ser Thr Leu Val<br>925                       930                    935 | | 2957 |
| aga act gaa cca cgt gaa cat ctc ctt gat cag ctg aaa agg aaa cag<br>Arg Thr Glu Pro Arg Glu His Leu Leu Asp Gln Leu Lys Arg Lys Gln<br>940                       945                  950               955 | | 3005 |
| cct gag ctg tta atg atg cta aac tgt tca gaa aac aac aaa gaa gag<br>Pro Glu Leu Leu Met Met Leu Asn Cys Ser Glu Asn Asn Lys Glu Glu<br>960                       965                    970 | | 3053 |
| aca att ccg gat gtg gat gta gaa gag gca gtt ctg ggg cag tat act<br>Thr Ile Pro Asp Val Asp Val Glu Glu Ala Val Leu Gly Gln Tyr Thr<br>975                       980                    985 | | 3101 |
| gaa gaa cct cta agt caa gag cca tct gta gat gct ggt gtg gat tgt<br>Glu Glu Pro Leu Ser Gln Glu Pro Ser Val Asp Ala Gly Val Asp Cys<br>990                       995                    1000 | | 3149 |
| tca tca att ggc ggg gtt cca ttt ttc cag cat aaa aaa tca cat<br>Ser Ser Ile Gly Gly Val Pro Phe Phe Gln His Lys Lys Ser His<br>         1005                     1010                 1015 | | 3194 |
| gga aaa gac aaa gaa aac aga ggc att aac aca ctg gag agg tct<br>Gly Lys Asp Lys Glu Asn Arg Gly Ile Asn Thr Leu Glu Arg Ser<br>1020                     1025                 1030 | | 3239 |
| aaa gtg gaa gaa act aca gag cac ttg gtt aca aag agc aga tta<br>Lys Val Glu Glu Thr Thr Glu His Leu Val Thr Lys Ser Arg Leu<br>1035                     1040                 1045 | | 3284 |
| cct ctg cga gcc cag atc aac ctt taa ttcacttggg ggttggcaat<br>Pro Leu Arg Ala Gln Ile Asn Leu<br>1050                     1055 | | 3331 |
| tttatttta aagaaaactt aaaaataaaa cctgaaaccc cagaacttga gccttgtgta | | 3391 |
| tagattttaa aagaatatat atatcagccg ggcgcggtgg ctcatgcctg taatcccagc | | 3451 |
| actttgggag gctgaggcgg gtggattgct tgagcccagg agtttgagac cagcctggcc | | 3511 |
| aacgtggcaa aacctcgtct ctgttaaaaa ttagccgggc gtggtggcac actcctgtaa | | 3571 |
| tcccagctac tggggaggct gaggcacgag aatcacttga acccaggaag cggggttgca | | 3631 |
| gtgagccaaa ggtacaccac tacactccag cctgggcaac agagcaagac tcggtctcaa | | 3691 |
| aaacaaaatt taaaaagat ataaggcagt actgtaaatt cagttgaatt ttgatatcta | | 3751 |
| cccatttttc tgtcatccct atagttcact ttgtattaaa ttgggtttca tttgggattt | | 3811 |
| gcaatgtaaa tacgtatttc tagttttcat ataaagtagt tctttttataa caaatgaaaa | | 3871 |
| gtattttct tgtatattat taagtaatga atatataaga actgtactct tctcagcttg | | 3931 |
| agcttaacat aggtaaatat caccaacatc tgtccttaga aaggaccatc tcatgttttt | | 3991 |
| tttcttgcta tgacttgtgt attttcttgc atcctcccta gacttcccta tttcgctttc | | 4051 |
| tcctcggctc actttctccc ttttttatttt tcaccaaacc atttgtagag ctacaaaacc | | 4111 |
| tatcctttct tattttcagt agtcagaatt ttatctagaa atcttttaac accttttag | | 4171 |
| tggttatttc taaaatcact gtcaacaata aatctaaccc tagttgtatc cctccttaa | | 4231 |
| gtatttaaaa cttgttgccc caaatgtgaa agcatttaat tcctttaaga ggcctaactc | | 4291 |
| attcaccctg acagagttca caaaaagccc actttagagt atacattgct attatgggag | | 4351 |
| accacccaga catctgacta atggctctgt gccacactcc aagacctgtg ccttttagag | | 4411 |
| aagctcacaa tgatttaagg actgtttgaa acttccaatt atgtctataa tttatattct | | 4471 |
| tttgtttaca tgatgaaact ttttgttgtt gcttgtttgt atataataca atgtgtacat | | 4531 |

-continued

```
gtatcttttt ctcgattcaa atcttaaccc ttaggactct ggtattttg atctggcaac    4591 catatttctg gaagttgaga tgtttcagct tgaagaacca aaacagaagg aatatgtaca    4651
aagaataaat tttctgctca cgatgagttt agtgtgtaaa gtttagagac atctgacttt    4711
gatagctaaa ttaaaccaaa ccctattgaa gaattgaata tatgctactt caagaaacta    4771
aattgatctc gtagaattat cttaataaaa taatggctat aatttctctg caaaatcaga    4831
tgtcagcata agcgatggat aataccaat aaactgccct cagtaaatcc atggttaata    4891
aatgtggttt ctacatt                                                    4908

<210> SEQ ID NO 2
<211> LENGTH: 1056
<212> TYPE: PRT
<213> ORGANISM: Homo sapiens

<400> SEQUENCE: 2

Met Ala Ser Gln Pro Asn Ser Ser Ala Lys Lys Lys Glu Glu Lys Gly
1               5                   10                  15

Lys Asn Ile Gln Val Val Arg Cys Arg Pro Phe Asn Leu Ala Glu
            20                  25                  30

Arg Lys Ala Ser Ala His Ser Ile Val Glu Cys Asp Pro Val Arg Lys
        35                  40                  45

Glu Val Ser Val Arg Thr Gly Gly Leu Ala Asp Lys Ser Ser Arg Lys
    50                  55                  60

Thr Tyr Thr Phe Asp Met Val Phe Gly Ala Ser Thr Lys Gln Ile Asp
65                  70                  75                  80

Val Tyr Arg Ser Val Val Cys Pro Ile Leu Asp Glu Val Ile Met Gly
                85                  90                  95

Tyr Asn Cys Thr Ile Phe Ala Tyr Gly Gln Thr Gly Thr Gly Lys Thr
            100                 105                 110

Phe Thr Met Glu Gly Glu Arg Ser Pro Asn Glu Glu Tyr Thr Trp Glu
        115                 120                 125

Glu Asp Pro Leu Ala Gly Ile Ile Pro Arg Thr Leu His Gln Ile Phe
    130                 135                 140

Glu Lys Leu Thr Asp Asn Gly Thr Glu Phe Ser Val Lys Val Ser Leu
145                 150                 155                 160

Leu Glu Ile Tyr Asn Glu Glu Leu Phe Asp Leu Leu Asn Pro Ser Ser
                165                 170                 175

Asp Val Ser Glu Arg Leu Gln Met Phe Asp Asp Pro Arg Asn Lys Arg
            180                 185                 190

Gly Val Ile Ile Lys Gly Leu Glu Glu Ile Thr Val His Asn Lys Asp
        195                 200                 205

Glu Val Tyr Gln Ile Leu Glu Lys Gly Ala Ala Lys Arg Thr Thr Ala
    210                 215                 220

Ala Thr Leu Met Asn Ala Tyr Ser Ser Arg Ser His Ser Val Phe Ser
225                 230                 235                 240

Val Thr Ile His Met Lys Glu Thr Thr Ile Asp Gly Glu Glu Leu Val
                245                 250                 255

Lys Ile Gly Lys Leu Asn Leu Val Asp Leu Ala Gly Ser Glu Asn Ile
            260                 265                 270

Gly Arg Ser Gly Ala Val Asp Lys Arg Ala Arg Glu Ala Gly Asn Ile
        275                 280                 285

Asn Gln Ser Leu Leu Thr Leu Gly Arg Val Ile Thr Ala Leu Val Glu
    290                 295                 300

Arg Thr Pro His Val Pro Tyr Arg Glu Ser Lys Leu Thr Arg Ile Leu
```

```
             305                 310                 315                 320
Gln Asp Ser Leu Gly Gly Arg Thr Arg Thr Ser Ile Ile Ala Thr Ile
                325                 330                 335

Ser Pro Ala Ser Leu Asn Leu Glu Glu Thr Leu Ser Thr Leu Glu Tyr
                340                 345                 350

Ala His Arg Ala Lys Asn Ile Leu Asn Lys Pro Glu Val Asn Gln Lys
                355                 360                 365

Leu Thr Lys Lys Ala Leu Ile Lys Glu Tyr Thr Glu Ile Glu Arg
370                 375                 380

Leu Lys Arg Asp Leu Ala Ala Arg Glu Lys Asn Gly Val Tyr Ile
385                 390                 395                 400

Ser Glu Glu Asn Phe Arg Val Met Ser Gly Lys Leu Thr Val Gln Glu
                405                 410                 415

Glu Gln Ile Val Glu Leu Ile Glu Lys Ile Gly Ala Val Glu Glu Glu
                420                 425                 430

Leu Asn Arg Val Thr Glu Leu Phe Met Asp Asn Lys Asn Glu Leu Asp
                435                 440                 445

Gln Cys Lys Ser Asp Leu Gln Asn Lys Thr Gln Glu Leu Glu Thr Thr
                450                 455                 460

Gln Lys His Leu Gln Glu Thr Lys Leu Gln Leu Val Lys Glu Glu Tyr
465                 470                 475                 480

Ile Thr Ser Ala Leu Glu Ser Thr Glu Glu Lys Leu His Asp Ala Ala
                485                 490                 495

Ser Lys Leu Leu Asn Thr Val Glu Glu Thr Thr Lys Asp Val Ser Gly
                500                 505                 510

Leu His Ser Lys Leu Asp Arg Lys Lys Ala Val Asp Gln His Asn Ala
                515                 520                 525

Glu Ala Gln Asp Ile Phe Gly Lys Asn Leu Asn Ser Leu Phe Asn Asn
                530                 535                 540

Met Glu Glu Leu Ile Lys Asp Gly Ser Ser Lys Gln Lys Ala Met Leu
545                 550                 555                 560

Glu Val His Lys Thr Leu Phe Gly Asn Leu Leu Ser Ser Ser Val Ser
                565                 570                 575

Ala Leu Asp Thr Ile Thr Thr Val Ala Leu Gly Ser Leu Thr Ser Ile
                580                 585                 590

Pro Glu Asn Val Ser Thr His Val Ser Gln Ile Phe Asn Met Ile Leu
                595                 600                 605

Lys Glu Gln Ser Leu Ala Ala Glu Ser Lys Thr Val Leu Gln Glu Leu
                610                 615                 620

Ile Asn Val Leu Lys Thr Asp Leu Leu Ser Ser Leu Glu Met Ile Leu
625                 630                 635                 640

Ser Pro Thr Val Val Ser Ile Leu Lys Ile Asn Ser Gln Leu Lys His
                645                 650                 655

Ile Phe Lys Thr Ser Leu Thr Val Ala Asp Lys Ile Glu Asp Gln Lys
                660                 665                 670

Lys Glu Leu Asp Gly Phe Leu Ser Ile Leu Cys Asn Asn Leu His Glu
                675                 680                 685

Leu Gln Glu Asn Thr Ile Cys Ser Leu Val Glu Ser Gln Lys Gln Cys
                690                 695                 700

Gly Asn Leu Thr Glu Asp Leu Lys Thr Ile Lys Gln Thr His Ser Gln
705                 710                 715                 720

Glu Leu Cys Lys Leu Met Asn Leu Trp Thr Glu Arg Phe Cys Ala Leu
                725                 730                 735
```

```
Glu Glu Lys Cys Glu Asn Ile Gln Lys Pro Leu Ser Ser Val Gln Glu
            740                 745                 750

Asn Ile Gln Gln Lys Ser Lys Asp Ile Val Asn Lys Met Thr Phe His
        755                 760                 765

Ser Gln Lys Phe Cys Ala Asp Ser Asp Gly Phe Ser Gln Glu Leu Arg
    770                 775                 780

Asn Phe Asn Gln Glu Gly Thr Lys Leu Val Glu Ser Val Lys His
785                 790                 795                 800

Ser Asp Lys Leu Asn Gly Asn Leu Glu Lys Ile Ser Gln Glu Thr Glu
            805                 810                 815

Gln Arg Cys Glu Ser Leu Asn Thr Arg Thr Val Tyr Phe Ser Glu Gln
        820                 825                 830

Trp Val Ser Ser Leu Asn Glu Arg Glu Gln Glu Leu His Asn Leu Leu
    835                 840                 845

Glu Val Val Ser Gln Cys Cys Glu Ala Ser Ser Asp Ile Thr Glu
            850                 855                 860

Lys Ser Asp Gly Arg Lys Ala Ala His Glu Lys Gln His Asn Ile Phe
865                 870                 875                 880

Leu Asp Gln Met Thr Ile Asp Glu Asp Lys Leu Ile Ala Gln Asn Leu
                885                 890                 895

Glu Leu Asn Glu Thr Ile Lys Ile Gly Leu Thr Lys Leu Asn Cys Phe
            900                 905                 910

Leu Glu Gln Asp Leu Lys Leu Asp Ile Pro Thr Gly Thr Thr Pro Gln
        915                 920                 925

Arg Lys Ser Tyr Leu Tyr Pro Ser Thr Leu Val Arg Thr Glu Pro Arg
    930                 935                 940

Glu His Leu Leu Asp Gln Leu Lys Arg Lys Gln Pro Glu Leu Leu Met
945                 950                 955                 960

Met Leu Asn Cys Ser Glu Asn Asn Lys Glu Glu Thr Ile Pro Asp Val
                965                 970                 975

Asp Val Glu Glu Ala Val Leu Gly Gln Tyr Thr Glu Pro Leu Ser
            980                 985                 990

Gln Glu Pro Ser Val Asp Ala Gly Val Asp Cys Ser Ser Ile Gly Gly
        995                 1000                1005

Val Pro Phe Phe Gln His Lys Lys Ser His Gly Lys Asp Lys Glu
    1010                1015                1020

Asn Arg Gly Ile Asn Thr Leu Glu Arg Ser Lys Val Glu Glu Thr
    1025                1030                1035

Thr Glu His Leu Val Thr Lys Ser Arg Leu Pro Leu Arg Ala Gln
    1040                1045                1050

Ile Asn Leu
    1055

<210> SEQ ID NO 3
<211> LENGTH: 870
<212> TYPE: DNA
<213> ORGANISM: Homo sapiens
<220> FEATURE:
<221> NAME/KEY: CDS
<222> LOCATION: (1)..(870)

<400> SEQUENCE: 3 atg tgg aac gcg acg ccc agc gaa gag ccg ggg ttc aac ctc aca ctg      48
Met Trp Asn Ala Thr Pro Ser Glu Glu Pro Gly Phe Asn Leu Thr Leu
1               5                   10                  15 gcc gac ctg gac tgg gat gct tcc ccc ggc aac gac tcg ctg ggc gac      96
Ala Asp Leu Asp Trp Asp Ala Ser Pro Gly Asn Asp Ser Leu Gly Asp
```

|  |  |  |  |  |  |  |  |  |  |  |  |  |  |  |  |
|---|---|---|---|---|---|---|---|---|---|---|---|---|---|---|---|
|  |  | 20 |  |  |  | 25 |  |  |  | 30 |  |  |  |  |  |
| gag | ctg | ctg | cag | ctc | ttc | ccc | gcg | ccg | ctg | ctg | gcg | ggc | gtc | aca | gcc |
| Glu | Leu | Leu | Gln | Leu | Phe | Pro | Ala | Pro | Leu | Leu | Ala | Gly | Val | Thr | Ala |
|  |  | 35 |  |  |  | 40 |  |  |  | 45 |  |  |  |  |  |

144 acc tgc gtg gca ctc ttc gtg gtg ggt atc gct ggc aac ctg ctc acc     192
Thr Cys Val Ala Leu Phe Val Val Gly Ile Ala Gly Asn Leu Leu Thr
         50                  55                  60 atg ctg gtg gtg tcg cgc ttc cgc gag ctg cgc acc acc acc aac ctc     240
Met Leu Val Val Ser Arg Phe Arg Glu Leu Arg Thr Thr Thr Asn Leu
 65                  70                  75                  80 tac ctg tcc agc atg gcc ttc tcc gat ctg ctc atc ttc ctc tgc atg     288
Tyr Leu Ser Ser Met Ala Phe Ser Asp Leu Leu Ile Phe Leu Cys Met
                 85                  90                  95 ccc ctg gac ctc gtt cgc ctc tgg cag tac cgg ccc tgg aac ttc ggc     336
Pro Leu Asp Leu Val Arg Leu Trp Gln Tyr Arg Pro Trp Asn Phe Gly
            100                 105                 110 gac ctc ctc tgc aaa ctc ttc caa ttc gtc agt gag agc tgc acc tac     384
Asp Leu Leu Cys Lys Leu Phe Gln Phe Val Ser Glu Ser Cys Thr Tyr
        115                 120                 125 gcc acg gtg ctc acc atc aca gcg ctg agc gtc gag cgc tac ttc gcc     432
Ala Thr Val Leu Thr Ile Thr Ala Leu Ser Val Glu Arg Tyr Phe Ala
    130                 135                 140 atc tgc ttc cca ctc cgg gcc aag gtg gtg gtc acc aag ggg cgg gtg     480
Ile Cys Phe Pro Leu Arg Ala Lys Val Val Val Thr Lys Gly Arg Val
145                 150                 155                 160 aag ctg gtc atc ttc gtc atc tgg gcc gtg gcc ttc tgc agc gcc ggg     528
Lys Leu Val Ile Phe Val Ile Trp Ala Val Ala Phe Cys Ser Ala Gly
                165                 170                 175 ccc atc ttc gtg cta gtc ggg gtg gag cac gag aac ggc acc gac cct     576
Pro Ile Phe Val Leu Val Gly Val Glu His Glu Asn Gly Thr Asp Pro
            180                 185                 190 tgg gac acc aac gag tgc cgc ccc acc gag ttt gcg gtg cgc tct gga     624
Trp Asp Thr Asn Glu Cys Arg Pro Thr Glu Phe Ala Val Arg Ser Gly
        195                 200                 205 ctg ctc acg gtc atg gtg tgg gtg tcc agc atc ttc ttc ctt cct         672
Leu Leu Thr Val Met Val Trp Val Ser Ser Ile Phe Phe Leu Pro
    210                 215                 220 gtc ttc tgt ctc acg gtc ctc tac agt ctc atc ggc agg aag ctg tgg     720
Val Phe Cys Leu Thr Val Leu Tyr Ser Leu Ile Gly Arg Lys Leu Trp
225                 230                 235                 240 cgg agg agg cgc ggc gat gct gtc gtg ggt gcc tcg ctc agg gac cag     768
Arg Arg Arg Arg Gly Asp Ala Val Val Gly Ala Ser Leu Arg Asp Gln
                245                 250                 255 aac cac aag caa acc gtg aaa atg ctg ggt ggg tct cag cgc gcg ctc     816
Asn His Lys Gln Thr Val Lys Met Leu Gly Gly Ser Gln Arg Ala Leu
            260                 265                 270 agg ctt tct ctc gcg ggt cct atc ctc tcc ctg tgc ctt ctc cct tct     864
Arg Leu Ser Leu Ala Gly Pro Ile Leu Ser Leu Cys Leu Leu Pro Ser
        275                 280                 285 ctc tga                                                              870
Leu

<210> SEQ ID NO 4
<211> LENGTH: 289
<212> TYPE: PRT
<213> ORGANISM: Homo sapiens

<400> SEQUENCE: 4

Met Trp Asn Ala Thr Pro Ser Glu Glu Pro Gly Phe Asn Leu Thr Leu
 1               5                  10                  15

```
Ala Asp Leu Asp Trp Asp Ala Ser Pro Gly Asn Asp Ser Leu Gly Asp
         20                  25                  30

Glu Leu Leu Gln Leu Phe Pro Ala Pro Leu Leu Ala Gly Val Thr Ala
         35                  40                  45

Thr Cys Val Ala Leu Phe Val Val Gly Ile Ala Gly Asn Leu Leu Thr
 50                  55                  60

Met Leu Val Val Ser Arg Phe Arg Glu Leu Arg Thr Thr Thr Asn Leu
 65                  70                  75                  80

Tyr Leu Ser Ser Met Ala Phe Ser Asp Leu Leu Ile Phe Leu Cys Met
                 85                  90                  95

Pro Leu Asp Leu Val Arg Leu Trp Gln Tyr Arg Pro Trp Asn Phe Gly
            100                 105                 110

Asp Leu Leu Cys Lys Leu Phe Gln Phe Val Ser Glu Ser Cys Thr Tyr
        115                 120                 125

Ala Thr Val Leu Thr Ile Thr Ala Leu Ser Val Glu Arg Tyr Phe Ala
    130                 135                 140

Ile Cys Phe Pro Leu Arg Ala Lys Val Val Val Thr Lys Gly Arg Val
145                 150                 155                 160

Lys Leu Val Ile Phe Val Ile Trp Ala Val Ala Phe Cys Ser Ala Gly
                165                 170                 175

Pro Ile Phe Val Leu Val Gly Val Glu His Glu Asn Gly Thr Asp Pro
            180                 185                 190

Trp Asp Thr Asn Glu Cys Arg Pro Thr Glu Phe Ala Val Arg Ser Gly
        195                 200                 205

Leu Leu Thr Val Met Val Trp Val Ser Ser Ile Phe Phe Phe Leu Pro
    210                 215                 220

Val Phe Cys Leu Thr Val Leu Tyr Ser Leu Ile Gly Arg Lys Leu Trp
225                 230                 235                 240

Arg Arg Arg Arg Gly Asp Ala Val Val Gly Ala Ser Leu Arg Asp Gln
                245                 250                 255

Asn His Lys Gln Thr Val Lys Met Leu Gly Gly Ser Gln Arg Ala Leu
            260                 265                 270

Arg Leu Ser Leu Ala Gly Pro Ile Leu Ser Leu Cys Leu Leu Pro Ser
        275                 280                 285

Leu

<210> SEQ ID NO 5
<211> LENGTH: 4131
<212> TYPE: DNA
<213> ORGANISM: Homo sapiens
<220> FEATURE:
<221> NAME/KEY: CDS
<222> LOCATION: (373)..(1629)

<400> SEQUENCE: 5
tcaagctcgc cccgcgcagc ccgagccggg ctgggcgctg tcctcggggg cctggggaac      60
cgcgcggttt ggagatcgga ggcacctgga acccgtggca agcgccgagc cgggagacag     120
cccgaggaac cacgggttct ggagctagga gccggaagct gggagtccgg aggagagcgg     180
agcccggagc ccggagcccg gggcggcgcg tctgggtctg gcgcttcccg actggacggc     240
gcgcccgctg gtcttcgcca cgcgccctcc cctgggctcg cgttcatcgg tccccgcctg     300
agacgcgccc actcctgccc ggacttccag ccccggaggc gccggacaga gccgcggact     360
ccagcgccca cc atg cgc ctc aac agc tcc gcg ccg gga acc ccg ggc acg     411
              Met Arg Leu Asn Ser Ser Ala Pro Gly Thr Pro Gly Thr
               1               5                  10
```

| | | | | | | | | | | | | | | | | |
|---|---|---|---|---|---|---|---|---|---|---|---|---|---|---|---|---|
| ccg | gcc | gcc | gac | ccc | ttc | cag | cgg | gcg | cag | gcc | gga | ctg | gag | gag | gcg | 459 |
| Pro | Ala | Ala | Asp | Pro | Phe | Gln | Arg | Ala | Gln | Ala | Gly | Leu | Glu | Glu | Ala | |
| | 15 | | | | 20 | | | | 25 | | | | | | | |
| ctg | ctg | gcc | ccg | ggc | ttc | ggc | aac | gct | tcg | ggc | aac | gcg | tcg | gag | cgc | 507 |
| Leu | Leu | Ala | Pro | Gly | Phe | Gly | Asn | Ala | Ser | Gly | Asn | Ala | Ser | Glu | Arg | |
| 30 | | | | | 35 | | | | | 40 | | | | | 45 | |
| gtc | ctg | gcg | gca | ccc | agc | agc | gag | ctg | gac | gtg | aac | acc | gac | atc | tac | 555 |
| Val | Leu | Ala | Ala | Pro | Ser | Ser | Glu | Leu | Asp | Val | Asn | Thr | Asp | Ile | Tyr | |
| | | | | 50 | | | | | 55 | | | | | 60 | | |
| tcc | aaa | gtg | ctg | gtg | acc | gcc | gtg | tac | ctg | gcg | ctc | ttc | gtg | gtg | ggc | 603 |
| Ser | Lys | Val | Leu | Val | Thr | Ala | Val | Tyr | Leu | Ala | Leu | Phe | Val | Val | Gly | |
| | | 65 | | | | | 70 | | | | | 75 | | | | |
| acg | gtg | ggc | aac | acg | gtg | acg | gcg | ttc | acg | ctg | gcg | cgg | aag | aag | tcg | 651 |
| Thr | Val | Gly | Asn | Thr | Val | Thr | Ala | Phe | Thr | Leu | Ala | Arg | Lys | Lys | Ser | |
| | | 80 | | | | | 85 | | | | | 90 | | | | |
| ctg | cag | agc | ctg | cag | agc | acg | gtg | cat | tac | cac | ctg | ggc | agc | ctg | gcg | 699 |
| Leu | Gln | Ser | Leu | Gln | Ser | Thr | Val | His | Tyr | His | Leu | Gly | Ser | Leu | Ala | |
| | 95 | | | | 100 | | | | | 105 | | | | | | |
| ctg | tcc | gac | ctg | ctc | acc | ctg | ctg | ctg | gcc | atg | ccc | gtg | gag | ctg | tac | 747 |
| Leu | Ser | Asp | Leu | Leu | Thr | Leu | Leu | Leu | Ala | Met | Pro | Val | Glu | Leu | Tyr | |
| 110 | | | | | 115 | | | | | 120 | | | | | 125 | |
| aac | ttc | atc | tgg | gtg | cac | cac | ccc | tgg | gcc | ttc | ggc | gac | gcc | ggc | tgc | 795 |
| Asn | Phe | Ile | Trp | Val | His | His | Pro | Trp | Ala | Phe | Gly | Asp | Ala | Gly | Cys | |
| | | | | 130 | | | | | 135 | | | | | 140 | | |
| cgc | ggc | tac | tac | ttc | ctg | cgc | gac | gcc | tgc | acc | tac | gcc | acg | gcc | ctc | 843 |
| Arg | Gly | Tyr | Tyr | Phe | Leu | Arg | Asp | Ala | Cys | Thr | Tyr | Ala | Thr | Ala | Leu | |
| | | | | 145 | | | | | 150 | | | | | 155 | | |
| aac | gtg | gcc | agc | ctg | agt | gtg | gag | cgc | tac | ctg | gcc | atc | tgc | cac | ccc | 891 |
| Asn | Val | Ala | Ser | Leu | Ser | Val | Glu | Arg | Tyr | Leu | Ala | Ile | Cys | His | Pro | |
| | | | 160 | | | | | 165 | | | | | 170 | | | |
| ttc | aag | gcc | aag | acc | ctc | atg | tcc | cga | agc | cgc | acc | aag | aag | ttc | atc | 939 |
| Phe | Lys | Ala | Lys | Thr | Leu | Met | Ser | Arg | Ser | Arg | Thr | Lys | Lys | Phe | Ile | |
| | 175 | | | | | 180 | | | | | 185 | | | | | |
| agc | gcc | atc | tgg | ctc | gcc | tcg | gcc | ctg | ctg | acg | gtg | cct | atg | ctg | ttc | 987 |
| Ser | Ala | Ile | Trp | Leu | Ala | Ser | Ala | Leu | Leu | Thr | Val | Pro | Met | Leu | Phe | |
| 190 | | | | | 195 | | | | | 200 | | | | | 205 | |
| acc | atg | ggc | gag | cag | aac | cgc | agc | gcc | gac | ggc | cag | cac | gcc | ggc | ggc | 1035 |
| Thr | Met | Gly | Glu | Gln | Asn | Arg | Ser | Ala | Asp | Gly | Gln | His | Ala | Gly | Gly | |
| | | | | 210 | | | | | 215 | | | | | 220 | | |
| ctg | gtg | tgc | acc | ccc | acc | atc | cac | act | gcc | acc | gtc | aag | gtc | gtc | ata | 1083 |
| Leu | Val | Cys | Thr | Pro | Thr | Ile | His | Thr | Ala | Thr | Val | Lys | Val | Val | Ile | |
| | | | 225 | | | | | 230 | | | | | 235 | | | |
| cag | gtc | aac | acc | ttc | atg | tcc | ttc | ata | ttc | ccc | atg | gtg | gtc | atc | tcg | 1131 |
| Gln | Val | Asn | Thr | Phe | Met | Ser | Phe | Ile | Phe | Pro | Met | Val | Val | Ile | Ser | |
| | | | 240 | | | | | 245 | | | | | 250 | | | |
| gtc | ctg | aac | acc | atc | atc | gcc | aac | aag | ctg | acc | gtc | atg | gta | cgc | cag | 1179 |
| Val | Leu | Asn | Thr | Ile | Ile | Ala | Asn | Lys | Leu | Thr | Val | Met | Val | Arg | Gln | |
| | 255 | | | | | 260 | | | | | 265 | | | | | |
| gcg | gcc | gag | cag | ggc | caa | gtg | tgc | acg | gtc | ggg | ggc | gag | cac | agc | aca | 1227 |
| Ala | Ala | Glu | Gln | Gly | Gln | Val | Cys | Thr | Val | Gly | Gly | Glu | His | Ser | Thr | |
| 270 | | | | | 275 | | | | | 280 | | | | | 285 | |
| ttc | agc | atg | gcc | atc | gag | cct | ggc | agg | gtc | cag | gcc | ctg | cgg | cac | ggc | 1275 |
| Phe | Ser | Met | Ala | Ile | Glu | Pro | Gly | Arg | Val | Gln | Ala | Leu | Arg | His | Gly | |
| | | | | 290 | | | | | 295 | | | | | 300 | | |
| gtg | cgc | gtc | cta | cgt | gca | gtg | gtc | atc | gcc | ttt | gtg | gtc | tgc | tgg | ctg | 1323 |
| Val | Arg | Val | Leu | Arg | Ala | Val | Val | Ile | Ala | Phe | Val | Val | Cys | Trp | Leu | |
| | | | 305 | | | | | 310 | | | | | 315 | | | |
| ccc | tac | cac | gtg | cgg | cgc | ctc | atg | ttc | tgc | tac | atc | tcg | gat | gag | cag | 1371 |
| Pro | Tyr | His | Val | Arg | Arg | Leu | Met | Phe | Cys | Tyr | Ile | Ser | Asp | Glu | Gln | |
| | | 320 | | | | | 325 | | | | | 330 | | | | |

| | |
|---|---|
| tgg act ccg ttc ctc tat gac ttc tac cac tac ttc tac atg gtg acc<br>Trp Thr Pro Phe Leu Tyr Asp Phe Tyr His Tyr Phe Tyr Met Val Thr<br>  335                             340                    345 | 1419 |
| aac gca ctc ttc tac gtc agc tcc acc atc aac ccc atc ctg tac aac<br>Asn Ala Leu Phe Tyr Val Ser Ser Thr Ile Asn Pro Ile Leu Tyr Asn<br>350                       355                       360                    365 | 1467 |
| ctc gtc tct gcc aac ttc cgc cac atc ttc ctg gcc aca ctg gcc tgc<br>Leu Val Ser Ala Asn Phe Arg His Ile Phe Leu Ala Thr Leu Ala Cys<br>                    370                       375                   380 | 1515 |
| ctc tgc ccg gtg tgg cgg cgc agg agg aag agg cca gcc ttc tcg agg<br>Leu Cys Pro Val Trp Arg Arg Arg Lys Arg Pro Ala Phe Ser Arg<br>              385                       390                       395 | 1563 |
| aag gcc gac agc gtg tcc agc aac cac acc ctc tcc agc aat gcc acc<br>Lys Ala Asp Ser Val Ser Ser Asn His Thr Leu Ser Ser Asn Ala Thr<br>                400                       405                    410 | 1611 |
| cgc gag acg ctg tac tag gctgtgcgcc ccggaacgtg tccaggagga<br>Arg Glu Thr Leu Tyr<br>               415 | 1659 |
| gcctggccat gggtccttgc ccccgacaga cagagcagcc cccacccggg agccttgatg | 1719 |
| ggggtcaggc agaggccagc ctgcactgga gtctgaggcc tgggaccccc ccctcccacc | 1779 |
| ccctaaccca tgtttctcat tagtgtctcc cgggcctgtc cccaactcct ccccaccct | 1839 |
| cccccatctc ctctttgaaa gccagaacaa gagagcgctc ctctcccaga taggaaaagg | 1899 |
| gcctctaaca aggagaaatt agtgtgcggc aaaaggcagt tttctttgtt ctcagactaa | 1959 |
| tggatggttc cagagaagga aatgaaatgt gctgggtggg gccgggcctc cggcggcccg | 2019 |
| gctgctgttc ccatgtccac atctctgagg cctgcacccc ctctgtctag ctcggggagt | 2079 |
| ccagccccag tcccgcaggc tccgtggctt tgggcctcac gtgcagaccc tgccatgcag | 2139 |
| acccatgccc cctcccca ggcagctcca agaaagctcc ctgactcgcc ccttcaggcc | 2199 |
| tgcaagctg ggggcccatc gccgtgggga gtccctccca ccaccctcgc cgcaggcagc | 2259 |
| tgcagccccc agagggggacc acaagcccaa aaaggacaaa atgggctgg cctggaatgg | 2319 |
| cccagacccc agcctcccct cctccctccc atcctcaccc aggccaaggc ccaggggctc | 2379 |
| tgccaggaca ccacatggga gggggctcag gcctcagcct caagatcttc agctgtggcc | 2439 |
| tctcgggctc ggcagaaggg acgccggatc aggggcctgg tctccagcac ctgcccgagt | 2499 |
| ggccgtggcc aggatggggt gcgcattccg tgtgctttgc ttgtagctgt gcaggctgag | 2559 |
| gtctggagcc aggcccagag ctggcttcag ggtggggcct tgagaagggg aatgtgggac | 2619 |
| aggggcgatg tgcctggtc tctgagtaag atgccaggtc ccaggaactc aggcttcagg | 2679 |
| tgagaaggag cggtgtgtcc aggcaccgct ggccggcagc cctgggctga ggcacagact | 2739 |
| catttgtcac cttctggcgg cggcagccct ggccccggcc tccaagcagt tgaaaaagct | 2799 |
| ggcgcctcct tggtctctag gatccaggct ccacagagca catgactagc caggcccctg | 2859 |
| gcttaagaag gtcgcctaag cctaagagaa gacagtccca ggagaagctg gccgggacca | 2919 |
| gccaggagct gggagccaca ggaagcaaaa gtcagccttt tcttcaaggg atttccctgt | 2979 |
| ctcagagcag cctttgcccc agggaaatgg gctctgggct ggctgcctgc accggccatg | 3039 |
| tcgacccagg acccggacac ctggtcttgg gctgtgttca gccactttgc cttctctgga | 3099 |
| ctcagtttcc ccgtctgaga aatgagagtc gaatgctaca gtatctgcag tcgcttggat | 3159 |
| ctggctgttg agttgacggg ttccttgaac cccacaaaat ccctctccaa ccacaggacc | 3219 |
| cttcggctca ccaagaacgg ggcccagggg agtcaggcct attcgctgca cttcctgcca | 3279 |
| aactttgccc ccacaagcct ggtcatcagc caggcagccc tcccagtgcc caagggccac | 3339 |

```
caaccccagg gaaacagggc cagcacagag gggccttcct cccccacaga gctcccatga    3399
catagtctgc tctgggcgga agagctttgc tgccagccag ggatgtccag aggtcggtgc    3459
agcccctatc cctgctcagg agtgggctca gagtctagca aatgctaagg cccctcaggc    3519
tgggctctga acgaggacct ggactcgag  ccagacaggg cagcctcaga cccttctctg    3579
gggctcctgg accttgggcc ataatttctg agcctcggtt tccccatcta aggaacagat    3639
gtggtcgttc cgccctctca gctggatgag actgtcctgg aggatccacc ccggaacaga    3699
cagaacggtg tctctcagga tggtgctctg agagagggca gagtggatgc cccactgccc    3759
tagaccctcg gtagacgtgg ggtctctggg gcggggtctg tggctgtgac tgaagtcggc    3819
tttcccgttg atgtcttgat gctcctatct gtgcacttac cgtaggtagg gacacgtgtc    3879
catgcaccac agacacaccc acgacacctg atctcgtatc actagcttgc ggccaggtca    3939
tgatgtggcc ccggaagctg gccctgcgtg ccatgagtgc gtcggtcatg gagtccggag    3999
cccctgagcc ggcccctggt gacggcacag ccctcacagc tcaaacgccc accccactc    4059 ccaccatctg caggtggtga aaacaaaccc cgtgtatctc tcaataaagg tggccgaagg    4119
gcctcgatgt gg                                                        4131

<210> SEQ ID NO 6
<211> LENGTH: 418
<212> TYPE: PRT
<213> ORGANISM: Homo sapiens

<400> SEQUENCE: 6

Met Arg Leu Asn Ser Ser Ala Pro Gly Thr Pro Gly Thr Pro Ala Ala
  1               5                  10                  15

Asp Pro Phe Gln Arg Ala Gln Ala Gly Leu Glu Glu Ala Leu Leu Ala
             20                  25                  30

Pro Gly Phe Gly Asn Ala Ser Gly Asn Ala Ser Glu Arg Val Leu Ala
         35                  40                  45

Ala Pro Ser Ser Glu Leu Asp Val Asn Thr Asp Ile Tyr Ser Lys Val
     50                  55                  60

Leu Val Thr Ala Val Tyr Leu Ala Leu Phe Val Val Gly Thr Val Gly
 65                  70                  75                  80

Asn Thr Val Thr Ala Phe Thr Leu Ala Arg Lys Lys Ser Leu Gln Ser
                 85                  90                  95

Leu Gln Ser Thr Val His Tyr His Leu Gly Ser Leu Ala Leu Ser Asp
            100                 105                 110

Leu Leu Thr Leu Leu Leu Ala Met Pro Val Glu Leu Tyr Asn Phe Ile
        115                 120                 125

Trp Val His His Pro Trp Ala Phe Gly Asp Ala Gly Cys Arg Gly Tyr
    130                 135                 140

Tyr Phe Leu Arg Asp Ala Cys Thr Tyr Ala Thr Ala Leu Asn Val Ala
145                 150                 155                 160

Ser Leu Ser Val Glu Arg Tyr Leu Ala Ile Cys His Pro Phe Lys Ala
                165                 170                 175

Lys Thr Leu Met Ser Arg Ser Arg Thr Lys Lys Phe Ile Ser Ala Ile
            180                 185                 190

Trp Leu Ala Ser Ala Leu Leu Thr Val Pro Met Leu Phe Thr Met Gly
        195                 200                 205

Glu Gln Asn Arg Ser Ala Asp Gly Gln His Ala Gly Gly Leu Val Cys
    210                 215                 220

Thr Pro Thr Ile His Thr Ala Thr Val Lys Val Val Ile Gln Val Asn
225                 230                 235                 240
```

Thr Phe Met Ser Phe Ile Phe Pro Met Val Val Ile Ser Val Leu Asn
            245                 250                 255

Thr Ile Ile Ala Asn Lys Leu Thr Val Met Val Arg Gln Ala Ala Glu
        260                 265                 270

Gln Gly Gln Val Cys Thr Val Gly Gly Glu His Ser Thr Phe Ser Met
    275                 280                 285

Ala Ile Glu Pro Gly Arg Val Gln Ala Leu Arg His Gly Val Arg Val
290                 295                 300

Leu Arg Ala Val Val Ile Ala Phe Val Val Cys Trp Leu Pro Tyr His
305                 310                 315                 320

Val Arg Arg Leu Met Phe Cys Tyr Ile Ser Asp Glu Gln Trp Thr Pro
                325                 330                 335

Phe Leu Tyr Asp Phe Tyr His Tyr Phe Tyr Met Val Thr Asn Ala Leu
            340                 345                 350

Phe Tyr Val Ser Ser Thr Ile Asn Pro Ile Leu Tyr Asn Leu Val Ser
        355                 360                 365

Ala Asn Phe Arg His Ile Phe Leu Ala Thr Leu Ala Cys Leu Cys Pro
    370                 375                 380

Val Trp Arg Arg Arg Lys Arg Pro Ala Phe Ser Arg Lys Ala Asp
385                 390                 395                 400

Ser Val Ser Ser Asn His Thr Leu Ser Ser Asn Ala Thr Arg Glu Thr
                405                 410                 415

Leu Tyr

<210> SEQ ID NO 7
<211> LENGTH: 23
<212> TYPE: DNA
<213> ORGANISM: Artificial
<220> FEATURE:
<223> OTHER INFORMATION: An artificially synthesized primer sequence for
      RT-PCR

<400> SEQUENCE: 7
taaatggctt caggagactt cag                                           23

<210> SEQ ID NO 8
<211> LENGTH: 24
<212> TYPE: DNA
<213> ORGANISM: Artificial
<220> FEATURE:
<223> OTHER INFORMATION: An artificially synthesized primer sequence for
      RT-PCR

<400> SEQUENCE: 8
ggttttaaat gcagctccta tgtg                                          24

<210> SEQ ID NO 9
<211> LENGTH: 23
<212> TYPE: DNA
<213> ORGANISM: Artificial
<220> FEATURE:
<223> OTHER INFORMATION: An artificially synthesized primer sequence for
      RT-PCR

<400> SEQUENCE: 9
ctgaacagtg ggtatcttcc tta                                           23

<210> SEQ ID NO 10
<211> LENGTH: 23
<212> TYPE: DNA
<213> ORGANISM: Artificial

```
<220> FEATURE:
<223> OTHER INFORMATION: An artificially synthesized primer sequence for
      RT-PCR

<400> SEQUENCE: 10
gatggctctt gacttagagg ttc                                          23

<210> SEQ ID NO 11
<211> LENGTH: 22
<212> TYPE: DNA
<213> ORGANISM: Artificial
<220> FEATURE:
<223> OTHER INFORMATION: An artificially synthesized primer sequence for
      RT-PCR

<400> SEQUENCE: 11
tgaagagatt cagagtggac ga                                           22

<210> SEQ ID NO 12
<211> LENGTH: 23
<212> TYPE: DNA
<213> ORGANISM: Artificial
<220> FEATURE:
<223> OTHER INFORMATION: An artificially synthesized primer sequence for
      RT-PCR

<400> SEQUENCE: 12
actgagaaca ttgacaacac agg                                          23

<210> SEQ ID NO 13
<211> LENGTH: 22
<212> TYPE: DNA
<213> ORGANISM: Artificial
<220> FEATURE:
<223> OTHER INFORMATION: An artificially synthesized primer sequence for
      RT-PCR

<400> SEQUENCE: 13
aagagggaca gggacaagta gt                                           22

<210> SEQ ID NO 14
<211> LENGTH: 21
<212> TYPE: DNA
<213> ORGANISM: Artificial
<220> FEATURE:
<223> OTHER INFORMATION: An artificially synthesized primer sequence for
      RT-PCR

<400> SEQUENCE: 14
atgccactgt tactgcttca g                                            21

<210> SEQ ID NO 15
<211> LENGTH: 23
<212> TYPE: DNA
<213> ORGANISM: Artificial
<220> FEATURE:
<223> OTHER INFORMATION: An artificially synthesized primer sequence for
      RT-PCR

<400> SEQUENCE: 15
ggctcttaca actcatgtac cca                                          23

<210> SEQ ID NO 16
<211> LENGTH: 24
<212> TYPE: DNA
<213> ORGANISM: Artificial
<220> FEATURE:
<223> OTHER INFORMATION: An artificially synthesized primer sequence for
```

|   |   |
|---|---|
| RT-PCR | |
| <400> SEQUENCE: 16 | |
| tgatacagag acatgaagtg agca | 24 |
| <210> SEQ ID NO 17<br><211> LENGTH: 19<br><212> TYPE: DNA<br><213> ORGANISM: Artificial<br><220> FEATURE:<br><223> OTHER INFORMATION: An artificially synthesized primer sequence for RT-PCR | |
| <400> SEQUENCE: 17 | |
| tggtgtttgc cttcatcct | 19 |
| <210> SEQ ID NO 18<br><211> LENGTH: 20<br><212> TYPE: DNA<br><213> ORGANISM: Artificial<br><220> FEATURE:<br><223> OTHER INFORMATION: An artificially synthesized primer sequence for RT-PCR | |
| <400> SEQUENCE: 18 | |
| gaatcccaga agtctgaaca | 20 |
| <210> SEQ ID NO 19<br><211> LENGTH: 19<br><212> TYPE: DNA<br><213> ORGANISM: Artificial<br><220> FEATURE:<br><223> OTHER INFORMATION: An artificially synthesized primer sequence for RT-PCR | |
| <400> SEQUENCE: 19 | |
| acggtcctct acagtctca | 19 |
| <210> SEQ ID NO 20<br><211> LENGTH: 18<br><212> TYPE: DNA<br><213> ORGANISM: Artificial<br><220> FEATURE:<br><223> OTHER INFORMATION: An artificially synthesized primer sequence for RT-PCR | |
| <400> SEQUENCE: 20 | |
| cacagggaga ggatagga | 18 |
| <210> SEQ ID NO 21<br><211> LENGTH: 23<br><212> TYPE: DNA<br><213> ORGANISM: Artificial<br><220> FEATURE:<br><223> OTHER INFORMATION: An artificially synthesized primer sequence for RT-PCR | |
| <400> SEQUENCE: 21 | |
| agtgggctca gagtctagca aat | 23 |
| <210> SEQ ID NO 22<br><211> LENGTH: 23<br><212> TYPE: DNA<br><213> ORGANISM: Artificial<br><220> FEATURE:<br><223> OTHER INFORMATION: An artificially synthesized primer sequence for RT-PCR | |

```
<400> SEQUENCE: 22
tattgagaga tacacggggt ttg                                         23

<210> SEQ ID NO 23
<211> LENGTH: 21
<212> TYPE: DNA
<213> ORGANISM: Artificial
<220> FEATURE:
<223> OTHER INFORMATION: An artificially synthesized primer sequence for
      RT-PCR

<400> SEQUENCE: 23
tgagccctga acaccagaga g                                           21

<210> SEQ ID NO 24
<211> LENGTH: 21
<212> TYPE: DNA
<213> ORGANISM: Artificial
<220> FEATURE:
<223> OTHER INFORMATION: An artificially synthesized primer sequence for
      RT-PCR

<400> SEQUENCE: 24
aaagccagat gagcgcttct a                                           21

<210> SEQ ID NO 25
<211> LENGTH: 22
<212> TYPE: DNA
<213> ORGANISM: Artificial
<220> FEATURE:
<223> OTHER INFORMATION: An artificially synthesized primer sequence for
      RT-PCR

<400> SEQUENCE: 25
tcttcagcat gatgtgttgt gt                                          22

<210> SEQ ID NO 26
<211> LENGTH: 24
<212> TYPE: DNA
<213> ORGANISM: Artificial
<220> FEATURE:
<223> OTHER INFORMATION: An artificially synthesized primer sequence for
      RT-PCR

<400> SEQUENCE: 26
tgagagattc atgaggaagt cttg                                        24

<210> SEQ ID NO 27
<211> LENGTH: 21
<212> TYPE: DNA
<213> ORGANISM: Artificial
<220> FEATURE:
<223> OTHER INFORMATION: An artificially synthesized primer sequence for
      RT-PCR

<400> SEQUENCE: 27
gaggtgatag cattgctttc g                                           21

<210> SEQ ID NO 28
<211> LENGTH: 21
<212> TYPE: DNA
<213> ORGANISM: Artificial
<220> FEATURE:
<223> OTHER INFORMATION: An artificially synthesized primer sequence for
      RT-PCR

<400> SEQUENCE: 28
```

```
caagtcagtg tacaggtaag c                                              21

<210> SEQ ID NO 29
<211> LENGTH: 19
<212> TYPE: DNA
<213> ORGANISM: Artificial
<220> FEATURE:
<223> OTHER INFORMATION: A target sequence for siRNA

<400> SEQUENCE: 29
gaagcagcac gacttcttc                                                 19

<210> SEQ ID NO 30
<211> LENGTH: 19
<212> TYPE: DNA
<213> ORGANISM: Artificial
<220> FEATURE:
<223> OTHER INFORMATION: A target sequence for siRNA

<400> SEQUENCE: 30
cgtacgcgga atacttcga                                                 19

<210> SEQ ID NO 31
<211> LENGTH: 19
<212> TYPE: DNA
<213> ORGANISM: Artificial
<220> FEATURE:
<223> OTHER INFORMATION: A target sequence for siRNA

<400> SEQUENCE: 31
gcgcgctttg taggattcg                                                 19

<210> SEQ ID NO 32
<211> LENGTH: 19
<212> TYPE: DNA
<213> ORGANISM: Artificial
<220> FEATURE:
<223> OTHER INFORMATION: A target sequence for siRNA

<400> SEQUENCE: 32
gttagtgtac gaactggag                                                 19

<210> SEQ ID NO 33
<211> LENGTH: 19
<212> TYPE: DNA
<213> ORGANISM: Artificial
<220> FEATURE:
<223> OTHER INFORMATION: A target sequence for siRNA

<400> SEQUENCE: 33
gtgtctctgt tggagatct                                                 19

<210> SEQ ID NO 34
<211> LENGTH: 19
<212> TYPE: DNA
<213> ORGANISM: Artificial
<220> FEATURE:
<223> OTHER INFORMATION: A target sequence for siRNA

<400> SEQUENCE: 34
gaaggcagtt gaccaacac                                                 19

<210> SEQ ID NO 35
<211> LENGTH: 19
<212> TYPE: DNA
<213> ORGANISM: Artificial
<220> FEATURE:
```

<223> OTHER INFORMATION: A target sequence for siRNA

<400> SEQUENCE: 35
cctctacctg tccagcatg    19

<210> SEQ ID NO 36
<211> LENGTH: 19
<212> TYPE: DNA
<213> ORGANISM: Artificial
<220> FEATURE:
<223> OTHER INFORMATION: A target sequence for siRNA

<400> SEQUENCE: 36
gttcatcagc gccatctgg    19

<210> SEQ ID NO 37
<211> LENGTH: 19
<212> TYPE: DNA
<213> ORGANISM: Artificial
<220> FEATURE:
<223> OTHER INFORMATION: A target sequence for siRNA

<400> SEQUENCE: 37
ggtcgtcata caggtcaac    19

<210> SEQ ID NO 38
<211> LENGTH: 32
<212> TYPE: DNA
<213> ORGANISM: Artificial
<220> FEATURE:
<223> OTHER INFORMATION: An artificially synthesized primer sequence for
      RT-PCR

<400> SEQUENCE: 38
ggaattccat gtggaacgcg acgcccagcg aa    32

<210> SEQ ID NO 39
<211> LENGTH: 40
<212> TYPE: DNA
<213> ORGANISM: Artificial
<220> FEATURE:
<223> OTHER INFORMATION: An artificially synthesized primer sequence for
      RT-PCR

<400> SEQUENCE: 39
cgcggatccg cgtgtattaa tactagattc tgtccaggcc    40

<210> SEQ ID NO 40
<211> LENGTH: 32
<212> TYPE: DNA
<213> ORGANISM: Artificial
<220> FEATURE:
<223> OTHER INFORMATION: An artificially synthesized primer sequence for
      RT-PCR

<400> SEQUENCE: 40
ggaattccat gtggaacgcg acgcccagcg aa    32

<210> SEQ ID NO 41
<211> LENGTH: 36
<212> TYPE: DNA
<213> ORGANISM: Artificial
<220> FEATURE:
<223> OTHER INFORMATION: An artificially synthesized primer sequence for
      RT-PCR

<400> SEQUENCE: 41

```
cgcggatccg cggagagaag ggagaaggca caggga                              36
```

<210> SEQ ID NO 42
<211> LENGTH: 36
<212> TYPE: DNA
<213> ORGANISM: Artificial
<220> FEATURE:
<223> OTHER INFORMATION: An artificially synthesized primer sequence for
      RT-PCR

<400> SEQUENCE: 42

```
ggaattccat gcgcctcaac agctccgcgc cgggaa                              36
```

<210> SEQ ID NO 43
<211> LENGTH: 39
<212> TYPE: DNA
<213> ORGANISM: Artificial
<220> FEATURE:
<223> OTHER INFORMATION: An artificially synthesized primer sequence for
      RT-PCR

<400> SEQUENCE: 43

```
cgcggatccg cggtacagcg tctcgcgggt ggcattgct                           39
```

<210> SEQ ID NO 44
<211> LENGTH: 22
<212> TYPE: DNA
<213> ORGANISM: Artificial
<220> FEATURE:
<223> OTHER INFORMATION: An artificially synthesized primer sequence for
      PCR of H1RNA gene promoter region

<400> SEQUENCE: 44

```
tggtagccaa gtgcaggtta ta                                             22
```

<210> SEQ ID NO 45
<211> LENGTH: 22
<212> TYPE: DNA
<213> ORGANISM: Artificial
<220> FEATURE:
<223> OTHER INFORMATION: An artificially synthesized primer sequence for
      PCR of H1RNA gene promoter region

<400> SEQUENCE: 45

```
ccaaagggtt tctgcagttt ca                                             22
```

<210> SEQ ID NO 46
<211> LENGTH: 30
<212> TYPE: DNA
<213> ORGANISM: Artificial
<220> FEATURE:
<223> OTHER INFORMATION: An artificially synthesized primer sequence for
      PCR of pcDNA3.1 H1RNA gene fragment

<400> SEQUENCE: 46

```
tgcggatcca gagcagattg tactgagagt                                     30
```

<210> SEQ ID NO 47
<211> LENGTH: 29
<212> TYPE: DNA
<213> ORGANISM: Artificial
<220> FEATURE:
<223> OTHER INFORMATION: An artificially synthesized primer sequence for
      PCR of pcDNA3.1 H1RNA gene fragment

<400> SEQUENCE: 47

```
ctctatctcg agtgaggcgg aaagaacca                                      29
```

<210> SEQ ID NO 48
<211> LENGTH: 47
<212> TYPE: DNA
<213> ORGANISM: Artificial
<220> FEATURE:
<223> OTHER INFORMATION: An artificially synthesized primer sequence for
      PCR of the ligated DNA

<400> SEQUENCE: 48
tttaagcttg aagaccattt ttggaaaaaa aaaaaaaaa aaaaaac                    47

<210> SEQ ID NO 49
<211> LENGTH: 34
<212> TYPE: DNA
<213> ORGANISM: Artificial
<220> FEATURE:
<223> OTHER INFORMATION: An artificially synthesized primer sequence for
      PCR of the ligated DNA

<400> SEQUENCE: 49
tttaagcttg aagacatggg aaagagtggt ctca                                  34

<210> SEQ ID NO 50
<211> LENGTH: 5085
<212> TYPE: DNA
<213> ORGANISM: Artificial
<220> FEATURE:
<223> OTHER INFORMATION: An artificially synthesized vector sequence

<400> SEQUENCE: 50
gacggatcgg gagatctccc gatcccctat ggtgcactct cagtacaatc tgctctggat     60
ccactagtaa cggccgccag tgtgctggaa ttcggcttgg tagccaagtg caggttatag    120
ggagctgaag gaaggggggt cacagtaggt ggcatcgttc ctttctgact gcccgccccc    180
cgcatgccgt cccgcgatat tgagctccga acctctcgcc ctgccgccgc cggtgctccg    240
tcgccgccgc gccgccatgg aattcgaacg ctgacgtcat caacccgctc caaggaatcg    300
cgggcccagt gtcactaggc gggaacaccc agcgcgcgtg cgccctggca ggaagatggc    360
tgtgagggac aggggagtgg cgccctgcaa tatttgcatg tcgctatgtg ttctgggaaa    420
tcaccataaa cgtgaaatgt ctttggattt gggaatctta aagttctgt atgagaccac      480 tctttccctt tttgggaaaa aaaaaaaaaa aaaaaaacg aaaccgggcc gggcgcggtg     540
gttcacgcct ataatcccag cactttggga ggccgaggcg ggcggatcac aaggtcagga    600
ggtcgagacc atccaggcta acacggtgaa acccccccc atctctacta aaaaaaaaaa      660
atacaaaaaa ttagccatta gccgggcgtg gtggcgggcg cctataatcc cagctacttg    720
ggaggctgaa gcagaatggc gtgaacccgg gaggcggacg ttgcagtgag ccagagatcgc    780 gccgactgca ttccagcctg ggcgacagag cgagtctcaa aaaaaaaacc gagtggaatg    840
tgaaaagctc cgtgaaactg cagaaaccca agccgaattc tgcagatatc catcacactg    900
gcggccgctc gagtgaggcg gaaagaacca gctgggctc taggggtat ccccacgcgc      960 cctgtagcgg cgcattaagc gcggcgggtg tggtggttac gcgcagcgtg accgctacac    1020
ttgccagcgc cctagcgccc gctccttttcg ctttcttccc ttcctttctc gccacgttcg   1080
ccggctttcc ccgtcaagct ctaaatcggg ggctcccttt agggttccga tttagtgctt    1140
tacggcacct cgaccccaaa aaacttgatt agggtgatgg ttcacgtagt gggccatcgc    1200
cctgatagac ggttttttcgc cctttgacgt tggagtccac gttctttaat agtggactct   1260
tgttccaaac tggaacaaca ctcaaccta tctcggtcta ttcttttgat ttataaggga    1320

-continued

| | |
|---|---|
| ttttgccgat ttcggcctat tggttaaaaa atgagctgat ttaacaaaaa tttaacgcga | 1380 |
| attaattctg tggaatgtgt gtcagttagg gtgtggaaag tccccaggct ccccagcagg | 1440 |
| cagaagtatg caaagcatgc atctcaatta gtcagcaacc aggtgtggaa agtccccagg | 1500 |
| ctccccagca ggcagaagta tgcaaagcat gcatctcaat tagtcagcaa ccatagtccc | 1560 |
| gcccctaact ccgcccatcc cgcccctaac tccgcccagt tccgcccatt ctccgcccca | 1620 |
| tggctgacta attttttta tttatgcaga ggccgaggcc gcctctgcct ctgagctatt | 1680 |
| ccagaagtag tgaggaggct ttttggagg cctaggcttt tgcaaaaagc tcccgggagc | 1740 |
| ttgtatatcc attttcggat ctgatcaaga dacaggatga ggatcgtttc gcatgattga | 1800 |
| acaagatgga ttgcacgcag gttctccggc cgcttgggtg gagaggctat tcggctatga | 1860 |
| ctgggcacaa cagacaatcg gctgctctga tgccgccgtg ttccggctgt cagcgcaggg | 1920 |
| gcgcccggtt ctttttgtca agaccgacct gtccggtgcc ctgaatgaac tgcaggacga | 1980 |
| ggcagcgcgg ctatcgtggc tggccacgac gggcgttcct tgcgcagctg tgctcgacgt | 2040 |
| tgtcactgaa gcgggaaggg actggctgct attgggcgaa gtgccggggc aggatctcct | 2100 |
| gtcatctcac cttgctcctg ccgagaaagt atccatcatg gctgatgcaa tgcggcggct | 2160 |
| gcatacgctt gatccggcta cctgcccatt cgaccaccaa gcgaaacatc gcatcgagcg | 2220 |
| agcacgtact cggatggaag ccggtcttgt cgatcaggat gatctggacg aagagcatca | 2280 |
| ggggctcgcg ccagccgaac tgttcgccag gctcaaggcg cgcatgcccg acggcgagga | 2340 |
| tctcgtcgtg acccatggcg atgcctgctt gccgaatatc atggtggaaa atggccgctt | 2400 |
| ttctggattc atcgactgtg gccggctggg tgtggcggac cgctatcagg acatagcgtt | 2460 |
| ggctacccgt gatattgctg aagagcttgg cggcgaatgg gctgaccgct tcctcgtgct | 2520 |
| ttacggtatc gccgctcccg attcgcagcg catcgccttc tatcgccttc ttgacgagtt | 2580 |
| cttctgagcg ggactctggg gttcgaaatg accgaccaag cgacgcccaa cctgccatca | 2640 |
| cgagatttcg attccaccgc cgccttctat gaaaggttgg gcttcggaat cgttttccgg | 2700 |
| gacgccggct ggatgatcct ccagcgcggg gatctcatgc tggagttctt cgcccacccc | 2760 |
| aacttgttta ttgcagctta taatggttac aaataaagca atagcatcac aaatttcaca | 2820 |
| aataaagcat ttttttcact gcattctagt tgtggtttgt ccaaactcat caatgtatct | 2880 |
| tatcatgtct gtataccgtc gacctctagc tagagcttgg cgtaatcatg gtcatagctg | 2940 |
| tttcctgtgt gaaattgtta tccgctcaca attccacaca acatacgagc cggaagcata | 3000 |
| aagtgtaaag cctggggtgc ctaatgagtg agctaactca cattaattgc gttgcgctca | 3060 |
| ctgcccgctt tccagtcggg aaacctgtcg tgccagctgc attaatgaat cggccaacgc | 3120 |
| gcggggagag gcggtttgcg tattgggcgc tcttccgctt cctcgctcac tgactcgctg | 3180 |
| cgctcggtcg ttcggctgcg gcgagcggta tcagctcact caaaggcggt aatacggtta | 3240 |
| tccacagaat caggggataa cgcaggaaag aacatgtgag caaaaggcca gcaaaaggcc | 3300 |
| aggaaccgta aaaaggccgc gttgctggcg ttttccata ggctccgccc cctgacgag | 3360 |
| catcacaaaa atcgacgctc aagtcagagg tggcgaaacc cgacaggact ataaagatac | 3420 |
| caggcgtttc cccctggaag ctccctcgtg cgctctcctg ttccgaccct gccgcttacc | 3480 |
| ggatacctgt ccgcctttct cccttcggga agcgtggcgc tttctcatag ctcacgctgt | 3540 |
| aggtatctca gttcggtgta ggtcgttcgc tccaagctgg gctgtgtgca cgaaccccc | 3600 |
| gttcagcccg accgctgcgc cttatccggt aactatcgtc ttgagtccaa cccgtaaga | 3660 |
| cacgacttat cgccactggc agcagccact ggtaacagga ttagcagagc gaggtatgta | 3720 |

-continued

```
ggcggtgcta cagagttctt gaagtggtgg cctaactacg gctacactag aagaacagta    3780
tttggtatct gcgctctgct gaagccagtt accttcggaa aaagagttgg tagctcttga    3840
tccggcaaac aaaccaccgc tggtagcggt ttttttgttt gcaagcagca gattacgcgc    3900
agaaaaaaag gatctcaaga agatcctttg atcttttcta cggggtctga cgctcagtgg    3960
aacgaaaact cacgttaagg gattttggtc atgagattat caaaaaggat cttcacctag    4020
atccttttaa attaaaaatg aagttttaaa tcaatctaaa gtatatatga gtaaacttgg    4080
tctgacagtt accaatgctt aatcagtgag gcacctatct cagcgatctg tctatttcgt    4140
tcatccatag ttgcctgact ccccgtcgtg tagataacta cgatacggga gggcttacca    4200
tctggcccca gtgctgcaat gataccgcga gacccacgct caccggctcc agatttatca    4260
gcaataaacc agccagccgg aagggccgag cgcagaagtg gtcctgcaac tttatccgcc    4320
tccatccagt ctattaattg ttgccgggaa gctagagtaa gtagttcgcc agttaatagt    4380
ttgcgcaacg ttgttgccat tgctacaggc atcgtggtgt cacgctcgtc gtttggtatg    4440
gcttcattca gctccggttc ccaacgatca aggcgagtta catgatcccc catgttgtgc    4500
aaaaaagcgg ttagctcctt cggtcctccg atcgttgtca gaagtaagtt ggccgcagtg    4560
ttatcactca tggttatggc agcactgcat aattctctta ctgtcatgcc atccgtaaga    4620
tgcttttctg tgactggtga gtactcaacc aagtcattct gagaatagtg tatgcggcga    4680
ccgagttgct cttgcccggc gtcaatacgg gataataccg cgccacatag cagaacttta    4740
aaagtgctca tcattggaaa acgttcttcg gggcgaaaac tctcaaggat cttaccgctg    4800
ttgagatcca gttcgatgta acccactcgt gcacccaact gatcttcagc atcttttact    4860
ttcaccagcg tttctgggtg agcaaaaaca ggaaggcaaa atgccgcaaa aaagggaata    4920
agggcgacac ggaaatgttg aatactcata ctcttccttt ttcaatatta ttgaagcatt    4980
tatcagggtt attgtctcat gagcggatac atatttgaat gtatttagaa aaataaacaa    5040
ataggggttc cgcgcacatt tccccgaaaa gtgccacctg acgtc                    5085
```

<210> SEQ ID NO 51
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 51
tcccgttagt gtacgaactg gagttcaaga gactccagtt cgtacactaa c            51

<210> SEQ ID NO 52
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 52
aaaagttagt gtacgaactg gagtctcttg aactccagtt cgtacactaa c            51

<210> SEQ ID NO 53
<211> LENGTH: 47
<212> TYPE: DNA
<213> ORGANISM: Artificial
<220> FEATURE:
<223> OTHER INFORMATION: An artificially synthesized oligonucleotide
      sequence for hairpin siRNA

<400> SEQUENCE: 53
gttagtgtac gaactggagt tcaagagact ccagttcgta cactaac         47

<210> SEQ ID NO 54
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 54
tcccgtgtct ctgttggaga tctttcaaga gaagatctcc aacagagaca c    51

<210> SEQ ID NO 55
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 55
aaaagtgtct ctgttggaga tcttctcttg aaagatctcc aacagagaca c    51

<210> SEQ ID NO 56
<211> LENGTH: 47
<212> TYPE: DNA
<213> ORGANISM: Artificial
<220> FEATURE:
<223> OTHER INFORMATION: An artificially synthesized oligonucleotide
      sequence for hairpin siRNA

<400> SEQUENCE: 56
gtgtctctgt tggagatctt tcaagagaag atctccaaca gagacac         47

<210> SEQ ID NO 57
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 57
tcccgaaggc agttgaccaa cacttcaaga gagtgttggt caactgcctt c    51

<210> SEQ ID NO 58
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 58
aaaagaaggc agttgaccaa cactctcttg aagtgttggt caactgcctt c    51

<210> SEQ ID NO 59
<211> LENGTH: 47
<212> TYPE: DNA
<213> ORGANISM: Artificial
<220> FEATURE:
<223> OTHER INFORMATION: An artificially synthesized oligonucleotide
      sequence for hairpin siRNA

<400> SEQUENCE: 59

```
gaaggcagtt gaccaacact tcaagagagt gttggtcaac tgccttc       47
```

<210> SEQ ID NO 60
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 60

```
tcccctcta cctgtccagc atgttcaaga gacatgctgg acaggtagag g     51
```

<210> SEQ ID NO 61
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 61

```
aaaacctcta cctgtccagc atgtctcttg aacatgctgg acaggtagag g     51
```

<210> SEQ ID NO 62
<211> LENGTH: 47
<212> TYPE: DNA
<213> ORGANISM: Artificial
<220> FEATURE:
<223> OTHER INFORMATION: An artificially synthesized oligonucleotide
      sequence for hairpin siRNA

<400> SEQUENCE: 62

```
cctctacctg tccagcatgt tcaagagaca tgctggacag gtagagg        47
```

<210> SEQ ID NO 63
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 63

```
tcccgttcat cagcgccatc tggttcaaga gaccagatgg cgctgatgaa c     51
```

<210> SEQ ID NO 64
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 64

```
aaaagttcat cagcgccatc tggtctcttg aaccagatgg cgctgatgaa c     51
```

<210> SEQ ID NO 65
<211> LENGTH: 47
<212> TYPE: DNA
<213> ORGANISM: Artificial
<220> FEATURE:
<223> OTHER INFORMATION: An artificially synthesized oligonucleotide
      sequence for hairpin siRNA

<400> SEQUENCE: 65

```
gttcatcagc gccatctggt tcaagagacc agatggcgct gatgaac        47
```

<210> SEQ ID NO 66
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 66
tcccggtcgt catacaggtc aacttcaaga gagttgacct gtatgacgac c         51

<210> SEQ ID NO 67
<211> LENGTH: 51
<212> TYPE: DNA
<213> ORGANISM: Artificial
<220> FEATURE:
<223> OTHER INFORMATION: An artificially synthesized oligonucleotide
      sequence for construction of siRNA expression vector

<400> SEQUENCE: 67
aaaaggtcgt catacaggtc aactctcttg aagttgacct gtatgacgac c         51

<210> SEQ ID NO 68
<211> LENGTH: 47
<212> TYPE: DNA
<213> ORGANISM: Artificial
<220> FEATURE:
<223> OTHER INFORMATION: An artificially synthesized oligonucleotide
      sequence for hairpin siRNA

<400> SEQUENCE: 68
ggtcgtcata caggtcaact tcaagagagt tgacctgtat gacgacc              47

<210> SEQ ID NO 69
<211> LENGTH: 20
<212> TYPE: DNA
<213> ORGANISM: Artificial
<220> FEATURE:
<223> OTHER INFORMATION: An artificially synthesized primer sequence for
      construction of IMP-3 deletion mutant

<400> SEQUENCE: 69
atgaacaaac tgtatatcgg                                            20

<210> SEQ ID NO 70
<211> LENGTH: 18
<212> TYPE: DNA
<213> ORGANISM: Artificial
<220> FEATURE:
<223> OTHER INFORMATION: An artificially synthesized primer sequence for
      construction of IMP-3 deletion mutant

<400> SEQUENCE: 70
cttccgtctt gactgagg                                              18

<210> SEQ ID NO 71
<211> LENGTH: 20
<212> TYPE: DNA
<213> ORGANISM: Artificial
<220> FEATURE:
<223> OTHER INFORMATION: An artificially synthesized primer sequence for
      construction of IMP-3 deletion mutant

<400> SEQUENCE: 71
atgaacaaac tgtatatcgg                                            20

```
<210> SEQ ID NO 72
<211> LENGTH: 19
<212> TYPE: DNA
<213> ORGANISM: Artificial
<220> FEATURE:
<223> OTHER INFORMATION: An artificially synthesized primer sequence for
      construction of IMP-3 deletion mutant

<400> SEQUENCE: 72
atgagcttca agtttcacc                                                  19

<210> SEQ ID NO 73
<211> LENGTH: 20
<212> TYPE: DNA
<213> ORGANISM: Artificial
<220> FEATURE:
<223> OTHER INFORMATION: An artificially synthesized primer sequence for
      construction of IMP-3 deletion mutant

<400> SEQUENCE: 73
atgaacaaac tgtatatcgg                                                 20

<210> SEQ ID NO 74
<211> LENGTH: 18
<212> TYPE: DNA
<213> ORGANISM: Artificial
<220> FEATURE:
<223> OTHER INFORMATION: An artificially synthesized primer sequence for
      construction of IMP-3 deletion mutant

<400> SEQUENCE: 74
ctccgtttct gattgctc                                                   18

<210> SEQ ID NO 75
<211> LENGTH: 20
<212> TYPE: DNA
<213> ORGANISM: Artificial
<220> FEATURE:
<223> OTHER INFORMATION: An artificially synthesized primer sequence for
      construction of IMP-3 deletion mutant

<400> SEQUENCE: 75
atgaacaaac tgtatatcgg                                                 20

<210> SEQ ID NO 76
<211> LENGTH: 21
<212> TYPE: DNA
<213> ORGANISM: Artificial
<220> FEATURE:
<223> OTHER INFORMATION: An artificially synthesized primer sequence for
      construction of IMP-3 deletion mutant

<400> SEQUENCE: 76
aggcaaatca catggtttct g                                               21

<210> SEQ ID NO 77
<211> LENGTH: 18
<212> TYPE: DNA
<213> ORGANISM: Artificial
<220> FEATURE:
<223> OTHER INFORMATION: An artificially synthesized primer sequence for
      construction of IMP-3 deletion mutant

<400> SEQUENCE: 77
ttgcctctgc gcctgctg                                                   18

<210> SEQ ID NO 78
<211> LENGTH: 18
```

```
<212> TYPE: DNA
<213> ORGANISM: Artificial
<220> FEATURE:
<223> OTHER INFORMATION: An artificially synthesized primer sequence for
      construction of IMP-3 deletion mutant

<400> SEQUENCE: 78
cttccgtctt gactgagg                                                    18

<210> SEQ ID NO 79
<211> LENGTH: 18
<212> TYPE: DNA
<213> ORGANISM: Artificial
<220> FEATURE:
<223> OTHER INFORMATION: An artificially synthesized primer sequence for
      construction of IMP-3 deletion mutant

<400> SEQUENCE: 79
ttgcctctgc gcctgctg                                                    18

<210> SEQ ID NO 80
<211> LENGTH: 18
<212> TYPE: DNA
<213> ORGANISM: Artificial
<220> FEATURE:
<223> OTHER INFORMATION: An artificially synthesized primer sequence for
      construction of IMP-3 deletion mutant

<400> SEQUENCE: 80
ctccgttctt gattgctc                                                    18

<210> SEQ ID NO 81
<211> LENGTH: 23
<212> TYPE: DNA
<213> ORGANISM: Artificial
<220> FEATURE:
<223> OTHER INFORMATION: An artificially synthesized primer sequence for
      IP-RT-PCR

<400> SEQUENCE: 81
ttatcctgaa cagctctttg gtg                                              23

<210> SEQ ID NO 82
<211> LENGTH: 23
<212> TYPE: DNA
<213> ORGANISM: Artificial
<220> FEATURE:
<223> OTHER INFORMATION: An artificially synthesized primer sequence for
      IP-RT-PCR

<400> SEQUENCE: 82
aagcgaaggt cagctaaata tcc                                              23

<210> SEQ ID NO 83
<211> LENGTH: 23
<212> TYPE: DNA
<213> ORGANISM: Artificial
<220> FEATURE:
<223> OTHER INFORMATION: An artificially synthesized primer sequence for
      IP-RT-PCR

<400> SEQUENCE: 83
ctttctgagc acactacgga tct                                              23

<210> SEQ ID NO 84
<211> LENGTH: 23
<212> TYPE: DNA
<213> ORGANISM: Artificial
```

```
-continued

<220> FEATURE:
<223> OTHER INFORMATION: An artificially synthesized primer sequence for
      IP-RT-PCR

<400> SEQUENCE: 84
aagccctctt acttacaggg aaa                                              23

<210> SEQ ID NO 85
<211> LENGTH: 21
<212> TYPE: DNA
<213> ORGANISM: Artificial
<220> FEATURE:
<223> OTHER INFORMATION: An artificially synthesized primer sequence for
      IP-RT-PCR

<400> SEQUENCE: 85
ggttcccctg gatttagtga a                                                21

<210> SEQ ID NO 86
<211> LENGTH: 25
<212> TYPE: DNA
<213> ORGANISM: Artificial
<220> FEATURE:
<223> OTHER INFORMATION: An artificially synthesized primer sequence for
      IP-RT-PCR

<400> SEQUENCE: 86
caacagtaaa tctgaaactc ttgcc                                            25

<210> SEQ ID NO 87
<211> LENGTH: 23
<212> TYPE: DNA
<213> ORGANISM: Artificial
<220> FEATURE:
<223> OTHER INFORMATION: An artificially synthesized primer sequence for
      IP-RT-PCR

<400> SEQUENCE: 87
gacaaaggta gcaagaggat ttc                                              23

<210> SEQ ID NO 88
<211> LENGTH: 22
<212> TYPE: DNA
<213> ORGANISM: Artificial
<220> FEATURE:
<223> OTHER INFORMATION: An artificially synthesized primer sequence for
      IP-RT-PCR

<400> SEQUENCE: 88
ctggtgttaa actcggttct tc                                               22

<210> SEQ ID NO 89
<211> LENGTH: 23
<212> TYPE: DNA
<213> ORGANISM: Artificial
<220> FEATURE:
<223> OTHER INFORMATION: An artificially synthesized primer sequence for
      IP-RT-PCR

<400> SEQUENCE: 89
ctagtgagtg aggctattgc agc                                              23

<210> SEQ ID NO 90
<211> LENGTH: 24
<212> TYPE: DNA
<213> ORGANISM: Artificial
<220> FEATURE:
<223> OTHER INFORMATION: An artificially synthesized primer sequence for
```

IP-RT-PCR

<400> SEQUENCE: 90
gtctcttcta gcacctcaat ctcc                                    24

<210> SEQ ID NO 91
<211> LENGTH: 23
<212> TYPE: DNA
<213> ORGANISM: Artificial
<220> FEATURE:
<223> OTHER INFORMATION: An artificially synthesized primer sequence for
      IP-RT-PCR

<400> SEQUENCE: 91
atctgacttt ctgtccactg cat                                     23

<210> SEQ ID NO 92
<211> LENGTH: 22
<212> TYPE: DNA
<213> ORGANISM: Artificial
<220> FEATURE:
<223> OTHER INFORMATION: An artificially synthesized primer sequence for
      IP-RT-PCR

<400> SEQUENCE: 92
taattcagca taagccaaag cc                                      22

<210> SEQ ID NO 93
<211> LENGTH: 23
<212> TYPE: DNA
<213> ORGANISM: Artificial
<220> FEATURE:
<223> OTHER INFORMATION: An artificially synthesized primer sequence for
      IP-RT-PCR

<400> SEQUENCE: 93
acacagtatg gactgaaatc gac                                     23

<210> SEQ ID NO 94
<211> LENGTH: 23
<212> TYPE: DNA
<213> ORGANISM: Artificial
<220> FEATURE:
<223> OTHER INFORMATION: An artificially synthesized primer sequence for
      IP-RT-PCR

<400> SEQUENCE: 94
cacctcaatc tgaacaaggt tag                                     23

<210> SEQ ID NO 95
<211> LENGTH: 23
<212> TYPE: DNA
<213> ORGANISM: Artificial
<220> FEATURE:
<223> OTHER INFORMATION: An artificially synthesized primer sequence for
      IP-RT-PCR

<400> SEQUENCE: 95
ggcctctcaa agtctggtag att                                     23

<210> SEQ ID NO 96
<211> LENGTH: 23
<212> TYPE: DNA
<213> ORGANISM: Artificial
<220> FEATURE:
<223> OTHER INFORMATION: An artificially synthesized primer sequence for
      IP-RT-PCR

<400> SEQUENCE: 96
atattcccac ttcagagacg aca                                         23

<210> SEQ ID NO 97
<211> LENGTH: 197
<212> TYPE: PRT
<213> ORGANISM: Artificial
<220> FEATURE:
<223> OTHER INFORMATION: An artificially synthesized sequence of IMP-3
      deletion mutant

<400> SEQUENCE: 97

```
Met Asn Lys Leu Tyr Ile Gly Asn Leu Ser Glu Asn Ala Ala Pro Ser
1               5                   10                  15

Asp Leu Glu Ser Ile Phe Lys Asp Ala Lys Ile Pro Val Ser Gly Pro
            20                  25                  30

Phe Leu Val Lys Thr Gly Tyr Ala Phe Val Asp Cys Pro Asp Glu Ser
        35                  40                  45

Trp Ala Leu Lys Ala Ile Glu Ala Leu Ser Gly Lys Ile Glu Leu His
    50                  55                  60

Gly Lys Pro Ile Glu Val Glu His Ser Val Pro Lys Arg Gln Arg Ile
65                  70                  75                  80

Arg Lys Leu Gln Ile Arg Asn Ile Pro Pro His Leu Gln Trp Glu Val
                85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
    130                 135                 140

Glu Asn Phe Thr Leu Lys Val Ala Tyr Ile Pro Asp Glu Met Ala Ala
145                 150                 155                 160

Gln Gln Asn Pro Leu Gln Gln Pro Arg Gly Arg Arg Gly Leu Gly Gln
                165                 170                 175

Arg Gly Ser Ser Arg Gln Gly Ser Pro Gly Ser Val Ser Lys Gln Lys
            180                 185                 190

Pro Cys Asp Leu Pro
        195
```

<210> SEQ ID NO 98
<211> LENGTH: 23
<212> TYPE: DNA
<213> ORGANISM: Artificial
<220> FEATURE:
<223> OTHER INFORMATION: An artificially synthesized primer sequence for
      Quantitative RT-PCR

<400> SEQUENCE: 98
acgaactcat ttgctcactc ctt                                         23

<210> SEQ ID NO 99
<211> LENGTH: 21
<212> TYPE: DNA
<213> ORGANISM: Artificial
<220> FEATURE:
<223> OTHER INFORMATION: An artificially synthesized primer sequence for
      Quantitative RT-PCR

<400> SEQUENCE: 99
acccacaccc aacacaattg t                                           21

```
<210> SEQ ID NO 100
<211> LENGTH: 12
<212> TYPE: DNA
<213> ORGANISM: Artificial
<220> FEATURE:
<223> OTHER INFORMATION: An artificially synthesized primer sequence for
      Quantitative RT-PCR

<400> SEQUENCE: 100
acagcaaagc cc                                                         12

<210> SEQ ID NO 101
<211> LENGTH: 23
<212> TYPE: DNA
<213> ORGANISM: Artificial
<220> FEATURE:
<223> OTHER INFORMATION: An artificially synthesized primer sequence for
      Quantitative RT-PCR

<400> SEQUENCE: 101
ttcaccctga cagagttcac aaa                                             23

<210> SEQ ID NO 102
<211> LENGTH: 22
<212> TYPE: DNA
<213> ORGANISM: Artificial
<220> FEATURE:
<223> OTHER INFORMATION: An artificially synthesized primer sequence for
      Quantitative RT-PCR

<400> SEQUENCE: 102
gggtggtctc ccataatagc aa                                              22

<210> SEQ ID NO 103
<211> LENGTH: 19
<212> TYPE: DNA
<213> ORGANISM: Artificial
<220> FEATURE:
<223> OTHER INFORMATION: An artificially synthesized primer sequence for
      Quantitative RT-PCR

<400> SEQUENCE: 103
agcccacttt agagtatac                                                  19

<210> SEQ ID NO 104
<211> LENGTH: 4168
<212> TYPE: DNA
<213> ORGANISM: Homo sapiens

<400> SEQUENCE: 104
aagacttagg aagactggtg gatgcgtttg ggttgtagct aggcttttc tttttctttct     60 cttttaaaac acatctagac aaggaaaaaa caagcctcgg atctgatttt tcactcctcg    120
ttcttgtgct tggttcttac tgtgtttgtg tattttaaag gcgagaagac gaggggaaca    180
aaaccagctg gatccatcca tcaccgtggg tggttttaat ttttcgtttt ttctcgttat    240
ttttttttaa acaaccactc ttcacaatga acaaactgta tatcggaaac ctcagcgaga    300
acgccgcccc ctcggaccta gaaagtatct tcaaggacgc caagatcccg gtgtcgggac    360
ccttcctggt gaagactggc tacgcgttcg tggactgccc ggacgagagc tgggcctca    420 aggccatcga ggcgctttca ggtaaaatag aactgcacgg gaaacccata gaagttgagc    480
actcggtccc aaaaaggcaa aggattcgga aacttcagat acgaaatatc ccgcctcatt    540
tacagtggga ggtgctggat agtttactag tccagtatgg agtggtggag agctgtgagc    600
```

```
aagtgaacac tgactcggaa actgcagttg taaatgtaac ctattccagt aaggaccaag    660
ctagacaagc actagacaaa ctgaatggat ttcagttaga gaatttcacc ttgaaagtag    720
cctatatccc tgatgaaatg gccgcccagc aaaacccctt gcagcagccc cgaggtcgcc    780
gggggcttgg gcagagggc tcctcaaggc aggggtctcc aggatccgta tccaagcaga     840
aaccatgtga tttgcctctg cgcctgctgg ttcccaccca atttgttgga gccatcatag    900
gaaaagaagg tgccaccatt cggaacatca ccaaacagac ccagtctaaa atcgatgtcc    960
accgtaaaga aaatgcgggg gctgctgaga agtcgattac tatcctctct actcctgaag   1020
gcacctctgc ggcttgtaag tctattctgg agattatgca taaggaagct caagatataa   1080
aattcacaga agagatcccc ttgaagattt tagctcataa taactttgtt ggacgtctta   1140
ttggtaaaga aggaagaaat cttaaaaaaa ttgagcaaga cacagacact aaaatcacga   1200
tatctccatt gcaggaattg acgctgtata atccagaacg cactattaca gttaaaggca   1260
atgttgagac atgtgccaaa gctgaggagg agatcatgaa gaaaatcagg gagtcttatg   1320
aaaatgatat tgcttctatg aatcttcaag cacatttaat tcctggatta aatctgaacg   1380
ccttgggtct gttcccaccc acttcaggga tgccacctcc cacctcaggg cccccttcag   1440
ccatgactcc tccctacccg cagtttgagc aatcagaaac ggagactgtt catctgttta   1500
tcccagctct atcagtcggt gccatcatcg gcaagcaggg ccagcacatc aagcagcttt   1560
ctcgctttgc tggagcttca attaagattg ctccagcgga agcaccagat gctaaagtga   1620
ggatggtgat tatcactgga ccaccagagg ctcagttcaa ggctcaggga agaatttatg   1680
gaaaaattaa agaagaaaac tttgttagtc ctaaagaaga ggtgaaactt gaagctcata   1740
tcagagtgcc atcctttgct gctggcagag ttattggaaa aggaggcaaa acggtgaatg   1800
aacttcagaa tttgtcaagt gcagaagttg ttgtccctcg tgaccagaca cctgatgaga   1860
atgaccaagt ggttgtcaaa ataactggtc acttctatgc ttgccaggtt gcccagagaa   1920
aaattcagga aattctgact caggtaaagc agcaccaaca acagaaggct ctgcaaagtg   1980
gaccacctca gtcaagacgg aagtaaaggc tcaggaaaca gcccaccaca gaggcagatg   2040
ccaaaccaaa gacagattgc ttaaccaaca gatgggcgct gacccctat ccagaatcac    2100 atgcacaagt ttttacctag ccagttgttt ctgaggacca ggcaacttttt gaactcctgt   2160 ctctgtgaga atgtatactt tatgctctct gaaatgtatg acacccagct ttaaaacaaa   2220
caaacaaaca aacaaaaaaa gggtggggga gggagggaaa gagaagagct ctgcacttcc   2280
ctttgttgta gtctcacagt ataacagata ttctaattct tcttaatatt cccccataat   2340
gccagaaatt ggcttaatga tgctttcact aaattcatca aatagattgc tcctaaatcc   2400
aattgttaaa attggatcag aataattatc acaggaactt aaatgttaag ccattagcat   2460
agaaaaactg ttctcagttt tattttacc taacactaac atgagtaacc taagggaagt    2520
gctgaatggt gttggcaggg gtattaaacg tgcatttta ctcaactacc tcaggtattc    2580
agtaatacaa tgaaaagcaa aattgttcct ttttttgaa aatttatat actttataat    2640 gatagaagtc caaccgtttt ttaaaaata aatttaaaat ttaacagcaa tcagctaaca    2700
ggcaaattaa gattttact tctggctggt gacagtaaag ctggaaaatt aatttcaggg    2760 tttttttgagg ctttttgacac agttattagt taaatcaaat gttcaaaaat acggagcagt  2820
gcctagtatc tggagagcag cactaccatt tattctttca tttatagttg ggaaagtttt   2880
tgacggtact aacaaagtgg tcgcaggaga ttttggaacg gctggtttaa atggcttcag   2940
gagacttcag ttttttgttt agctacatga ttgaatgcat aataaatgct ttgtgcttct   3000
```

-continued

```
gactatcaat acctaaagaa agtgcatcag tgaagagatg caagactttc aactgactgg    3060
caaaaagcaa gctttagctt gtcttatagg atgcttagtt tgccactaca cttcagacca    3120
atgggacagt catagatggt gtgacagtgt ttaaacgcaa caaaaggcta catttccatg    3180
gggccagcac tgtcatgagc ctcactaagc tattttgaag attttttaagc actgataaat    3240 taaaaaaaaa aaattagact ccaccttaag tagtaaagta taacaggatt tctgtatact    3300
gtgcaatcag ttctttgaaa aaaaagtcaa aagatagaga atacaagaaa agttttttggg   3360 atataatttg aatgactgtg aaaacatatg acctttgata acgaactcat ttgctcactc    3420
cttgacagca aagcccagta cgtacaattg tgttgggtgt gggtggtctc caaggccacg    3480
ctgctctctg aattgatttt ttgagttttg tttgtaagat gatcacagtc atgttacact    3540
gatctaaagg acatatatat aacccttaa aaaaaaaatc actgcctcat tcttatttca     3600
agatgaattt ctatacagac tagatgtttt tctgaagatc aattagacat tttgaaaatg    3660
atttaaagtg ttttccttaa tgttctctga aaacaagttt cttttgtagt tttaaccaaa    3720
aaagtgccct ttttgtcact ggattctcct agcattcatg atttttttt catacaatga     3780 attaaaattg ctaaaatcat ggactggctt tctggttgga tttcaggtaa gatgtgttta    3840
aggccagagc ttttctcagt atttgatttt tttccccaat atttgatttt ttaaaaatat    3900
acacataggg gctgcattta tatctgctgg tttaaattct gtcatatttc acttctagcc    3960
ttttagtatg gcaaatcata ttttacttt acttaagcat ttgtaatttg gagtatctgg     4020
tactagctaa gaaataattc tataattgag ttttgtactc accatatatg gatcattcct    4080
catgtataat gtgccccaaa tgcagcttca ttttccagat accttgacgc agaataaatt    4140
ttttcatcat ttaggtgcaa aaaaaaaa                                       4168
```

<210> SEQ ID NO 105
<211> LENGTH: 579
<212> TYPE: PRT
<213> ORGANISM: Homo sapiens

<400> SEQUENCE: 105

```
Met Asn Lys Leu Tyr Ile Gly Asn Leu Ser Glu Asn Ala Ala Pro Ser
1               5                   10                  15

Asp Leu Glu Ser Ile Phe Lys Asp Ala Lys Ile Pro Val Ser Gly Pro
            20                  25                  30

Phe Leu Val Lys Thr Gly Tyr Ala Phe Val Asp Cys Pro Asp Glu Ser
        35                  40                  45

Trp Ala Leu Lys Ala Ile Glu Ala Leu Ser Gly Lys Ile Glu Leu His
    50                  55                  60

Gly Lys Pro Ile Glu Val Glu His Ser Val Pro Lys Arg Gln Arg Ile
65                  70                  75                  80

Arg Lys Leu Gln Ile Arg Asn Ile Pro Pro His Leu Gln Trp Glu Val
                85                  90                  95

Leu Asp Ser Leu Leu Val Gln Tyr Gly Val Val Glu Ser Cys Glu Gln
            100                 105                 110

Val Asn Thr Asp Ser Glu Thr Ala Val Val Asn Val Thr Tyr Ser Ser
        115                 120                 125

Lys Asp Gln Ala Arg Gln Ala Leu Asp Lys Leu Asn Gly Phe Gln Leu
    130                 135                 140

Glu Asn Phe Thr Leu Lys Val Ala Tyr Ile Pro Asp Glu Met Ala Ala
145                 150                 155                 160

Gln Gln Asn Pro Leu Gln Gln Pro Arg Gly Arg Arg Gly Leu Gly Gln
                165                 170                 175
```

```
Arg Gly Ser Ser Arg Gln Gly Ser Pro Gly Ser Val Ser Lys Gln Lys
            180                 185                 190

Pro Cys Asp Leu Pro Leu Arg Leu Leu Val Pro Thr Gln Phe Val Gly
            195                 200                 205

Ala Ile Ile Gly Lys Glu Gly Ala Thr Ile Arg Asn Ile Thr Lys Gln
210                 215                 220

Thr Gln Ser Lys Ile Asp Val His Arg Lys Glu Asn Ala Gly Ala Ala
225                 230                 235                 240

Glu Lys Ser Ile Thr Ile Leu Ser Thr Pro Glu Gly Thr Ser Ala Ala
            245                 250                 255

Cys Lys Ser Ile Leu Glu Ile Met His Lys Glu Ala Gln Asp Ile Lys
            260                 265                 270

Phe Thr Glu Glu Ile Pro Leu Lys Ile Leu Ala His Asn Asn Phe Val
            275                 280                 285

Gly Arg Leu Ile Gly Lys Glu Gly Arg Asn Leu Lys Lys Ile Glu Gln
            290                 295                 300

Asp Thr Asp Thr Lys Ile Thr Ile Ser Pro Leu Gln Glu Leu Thr Leu
305                 310                 315                 320

Tyr Asn Pro Glu Arg Thr Ile Thr Val Lys Gly Asn Val Glu Thr Cys
            325                 330                 335

Ala Lys Ala Glu Glu Glu Ile Met Lys Lys Ile Arg Glu Ser Tyr Glu
            340                 345                 350

Asn Asp Ile Ala Ser Met Asn Leu Gln Ala His Leu Ile Pro Gly Leu
            355                 360                 365

Asn Leu Asn Ala Leu Gly Leu Phe Pro Pro Thr Ser Gly Met Pro Pro
            370                 375                 380

Pro Thr Ser Gly Pro Pro Ser Ala Met Thr Pro Pro Tyr Pro Gln Phe
385                 390                 395                 400

Glu Gln Ser Glu Thr Glu Thr Val His Leu Phe Ile Pro Ala Leu Ser
            405                 410                 415

Val Gly Ala Ile Ile Gly Lys Gln Gly Gln His Ile Lys Gln Leu Ser
            420                 425                 430

Arg Phe Ala Gly Ala Ser Ile Lys Ile Ala Pro Ala Glu Ala Pro Asp
            435                 440                 445

Ala Lys Val Arg Met Val Ile Ile Thr Gly Pro Pro Glu Ala Gln Phe
450                 455                 460

Lys Ala Gln Gly Arg Ile Tyr Gly Lys Ile Lys Glu Glu Asn Phe Val
465                 470                 475                 480

Ser Pro Lys Glu Glu Val Lys Leu Glu Ala His Ile Arg Val Pro Ser
            485                 490                 495

Phe Ala Ala Gly Arg Val Ile Gly Lys Gly Gly Lys Thr Val Asn Glu
            500                 505                 510

Leu Gln Asn Leu Ser Ser Ala Glu Val Val Val Pro Arg Asp Gln Thr
            515                 520                 525

Pro Asp Glu Asn Asp Gln Val Val Lys Ile Thr Gly His Phe Tyr
530                 535                 540

Ala Cys Gln Val Ala Gln Arg Lys Ile Gln Glu Ile Leu Thr Gln Val
545                 550                 555                 560

Lys Gln His Gln Gln Lys Ala Leu Gln Ser Gly Pro Pro Gln Ser
            565                 570                 575

Arg Arg Lys

<210> SEQ ID NO 106
```

```
<211> LENGTH: 3487
<212> TYPE: DNA
<213> ORGANISM: Homo sapiens
<220> FEATURE:
<221> NAME/KEY: CDS
<222> LOCATION: (266)..(2512)

<400> SEQUENCE: 106
```

| | | | | | | | | | | |
|---|---|---|---|---|---|---|---|---|---|---|
| actgaaagct | ccggtgccag | accccacccc | cggccccggc | ccgggacccc | ctccctccc | | | | | 60 |
| gggatccccc | ggggttccca | ccccgcccgc | accgccgggg | accggccgg | tccggcgcga | | | | | 120 |
| gccccgtcc | ggggccctgg | ctcggccccc | aggttggagg | agcccggagc | ccgccttcgg | | | | | 180 |
| agctacggcc | taacggcggc | ggcgactgca | gtctggaggg | tccacacttg | tgattctcaa | | | | | 240 |

| tggagagtga | aaacgcagat | tcata | atg | aaa | act | agc | ccc | cgt | cgg | cca | ctg | | 292 |
|---|---|---|---|---|---|---|---|---|---|---|---|---|---|
| | | | Met | Lys | Thr | Ser | Pro | Arg | Arg | Pro | Leu | | |
| | | | 1 | | | | 5 | | | | | | |

| att | ctc | aaa | aga | cgg | agg | ctg | ccc | ctt | cct | gtt | caa | aat | gcc | cca | agt | 340 |
|---|---|---|---|---|---|---|---|---|---|---|---|---|---|---|---|---|
| Ile | Leu | Lys | Arg | Arg | Arg | Leu | Pro | Leu | Pro | Val | Gln | Asn | Ala | Pro | Ser | |
| 10 | | | | 15 | | | | | 20 | | | | | 25 | | |

| gaa | aca | tca | gag | gag | gaa | cct | aag | aga | tcc | cct | gcc | caa | cag | gag | tct | 388 |
|---|---|---|---|---|---|---|---|---|---|---|---|---|---|---|---|---|
| Glu | Thr | Ser | Glu | Glu | Glu | Pro | Lys | Arg | Ser | Pro | Ala | Gln | Gln | Glu | Ser | |
| | | | 30 | | | | | 35 | | | | | 40 | | | |

| aat | caa | gca | gag | gcc | tcc | aag | gaa | gtg | gca | gag | tcc | aac | tct | tgc | aag | 436 |
|---|---|---|---|---|---|---|---|---|---|---|---|---|---|---|---|---|
| Asn | Gln | Ala | Glu | Ala | Ser | Lys | Glu | Val | Ala | Glu | Ser | Asn | Ser | Cys | Lys | |
| | 45 | | | | | 50 | | | | | 55 | | | | | |

| ttt | cca | gct | ggg | atc | aag | att | att | aac | cac | ccc | acc | atg | ccc | aac | acg | 484 |
|---|---|---|---|---|---|---|---|---|---|---|---|---|---|---|---|---|
| Phe | Pro | Ala | Gly | Ile | Lys | Ile | Ile | Asn | His | Pro | Thr | Met | Pro | Asn | Thr | |
| | 60 | | | | 65 | | | | | 70 | | | | | | |

| caa | gta | gtg | gcc | atc | ccc | aac | aat | gct | aat | att | cac | agc | atc | atc | aca | 532 |
|---|---|---|---|---|---|---|---|---|---|---|---|---|---|---|---|---|
| Gln | Val | Val | Ala | Ile | Pro | Asn | Asn | Ala | Asn | Ile | His | Ser | Ile | Ile | Thr | |
| 75 | | | | | 80 | | | | | 85 | | | | | | |

| gca | ctg | act | gcc | aag | gga | aaa | gag | agt | ggc | agt | agt | ggg | ccc | aac | aaa | 580 |
|---|---|---|---|---|---|---|---|---|---|---|---|---|---|---|---|---|
| Ala | Leu | Thr | Ala | Lys | Gly | Lys | Glu | Ser | Gly | Ser | Ser | Gly | Pro | Asn | Lys | |
| 90 | | | | 95 | | | | | 100 | | | | | 105 | | |

| ttc | atc | ctc | atc | agc | tgt | ggg | gga | gcc | cca | act | cag | cct | cca | gga | ctc | 628 |
|---|---|---|---|---|---|---|---|---|---|---|---|---|---|---|---|---|
| Phe | Ile | Leu | Ile | Ser | Cys | Gly | Gly | Ala | Pro | Thr | Gln | Pro | Pro | Gly | Leu | |
| | | | 110 | | | | | 115 | | | | | 120 | | | |

| cgg | cct | caa | acc | caa | acc | agc | tat | gat | gcc | aaa | agg | aca | gaa | gtg | acc | 676 |
|---|---|---|---|---|---|---|---|---|---|---|---|---|---|---|---|---|
| Arg | Pro | Gln | Thr | Gln | Thr | Ser | Tyr | Asp | Ala | Lys | Arg | Thr | Glu | Val | Thr | |
| | | 125 | | | | | 130 | | | | | 135 | | | | |

| ctg | gag | acc | ttg | gga | cca | aaa | cct | gca | gct | agg | gat | gtg | aat | ctt | cct | 724 |
|---|---|---|---|---|---|---|---|---|---|---|---|---|---|---|---|---|
| Leu | Glu | Thr | Leu | Gly | Pro | Lys | Pro | Ala | Ala | Arg | Asp | Val | Asn | Leu | Pro | |
| | 140 | | | | | 145 | | | | | 150 | | | | | |

| aga | cca | cct | gga | gcc | ctt | tgc | gag | cag | aaa | cgg | gag | acc | tgt | gca | gat | 772 |
|---|---|---|---|---|---|---|---|---|---|---|---|---|---|---|---|---|
| Arg | Pro | Pro | Gly | Ala | Leu | Cys | Glu | Gln | Lys | Arg | Glu | Thr | Cys | Ala | Asp | |
| 155 | | | | | 160 | | | | | 165 | | | | | | |

| ggt | gag | gca | gca | ggc | tgc | act | atc | aac | aat | agc | cta | tcc | aac | atc | cag | 820 |
|---|---|---|---|---|---|---|---|---|---|---|---|---|---|---|---|---|
| Gly | Glu | Ala | Ala | Gly | Cys | Thr | Ile | Asn | Asn | Ser | Leu | Ser | Asn | Ile | Gln | |
| 170 | | | | 175 | | | | | 180 | | | | | 185 | | |

| tgg | ctt | cga | aag | atg | agt | tct | gat | gga | ctg | ggc | tcc | cgc | agc | atc | aag | 868 |
|---|---|---|---|---|---|---|---|---|---|---|---|---|---|---|---|---|
| Trp | Leu | Arg | Lys | Met | Ser | Ser | Asp | Gly | Leu | Gly | Ser | Arg | Ser | Ile | Lys | |
| | | | | 190 | | | | | 195 | | | | | 200 | | |

| caa | gag | atg | gag | gaa | aag | gag | aat | tgt | cac | ctg | gag | cag | cga | cag | gtt | 916 |
|---|---|---|---|---|---|---|---|---|---|---|---|---|---|---|---|---|
| Gln | Glu | Met | Glu | Glu | Lys | Glu | Asn | Cys | His | Leu | Glu | Gln | Arg | Gln | Val | |
| | | | 205 | | | | | 210 | | | | | 215 | | | |

| aag | gtt | gag | gag | cct | tcg | aga | cca | tca | gcg | tcc | tgg | cag | aac | tct | gtg | 964 |
|---|---|---|---|---|---|---|---|---|---|---|---|---|---|---|---|---|
| Lys | Val | Glu | Glu | Pro | Ser | Arg | Pro | Ser | Ala | Ser | Trp | Gln | Asn | Ser | Val | |
| | 220 | | | | | 225 | | | | | 230 | | | | | |

| tct | gag | cgg | cca | ccc | tac | tct | tac | atg | gcc | atg | ata | caa | ttc | gcc | atc | 1012 |
|---|---|---|---|---|---|---|---|---|---|---|---|---|---|---|---|---|
| Ser | Glu | Arg | Pro | Pro | Tyr | Ser | Tyr | Met | Ala | Met | Ile | Gln | Phe | Ala | Ile | |
| 235 | | | | | 240 | | | | | 245 | | | | | | |

|     |     |
| --- | --- |
| aac agc act gag agg aag cgc atg act ttg aaa gac atc tat acg tgg<br>Asn Ser Thr Glu Arg Lys Arg Met Thr Leu Lys Asp Ile Tyr Thr Trp<br>250                        255                        260                      265 | 1060 |
| att gag gac cac ttt ccc tac ttt aag cac att gcc aag cca ggc tgg<br>Ile Glu Asp His Phe Pro Tyr Phe Lys His Ile Ala Lys Pro Gly Trp<br>                        270                        275                        280 | 1108 |
| aag aac tcc atc cgc cac aac ctt tcc ctg cac gac atg ttt gtc cgg<br>Lys Asn Ser Ile Arg His Asn Leu Ser Leu His Asp Met Phe Val Arg<br>                285                        290                        295 | 1156 |
| gag acg tct gcc aat ggc aag gtc tcc ttc tgg acc att cac ccc agt<br>Glu Thr Ser Ala Asn Gly Lys Val Ser Phe Trp Thr Ile His Pro Ser<br>            300                        305                        310 | 1204 |
| gcc aac cgc tac ttg aca ttg gac cag gtg ttt aag cag cag aaa cga<br>Ala Asn Arg Tyr Leu Thr Leu Asp Gln Val Phe Lys Gln Gln Lys Arg<br>315                        320                        325 | 1252 |
| ccg aat cca gag ctc cgc cgg aac atg acc atc aaa acc gaa ctc ccc<br>Pro Asn Pro Glu Leu Arg Arg Asn Met Thr Ile Lys Thr Glu Leu Pro<br>330                        335                        340                        345 | 1300 |
| ctg ggc gca cgg cgg aag atg aag cca ctg cta cca cgg gtc agc tca<br>Leu Gly Ala Arg Arg Lys Met Lys Pro Leu Leu Pro Arg Val Ser Ser<br>                        350                        355                        360 | 1348 |
| tac ctg gta cct atc cag ttc ccg gtg aac cag tca ctg gtg ttg cag<br>Tyr Leu Val Pro Ile Gln Phe Pro Val Asn Gln Ser Leu Val Leu Gln<br>                365                        370                        375 | 1396 |
| ccc tcg gtg aag gtg cca ttg ccc ctg gcg gct tcc ctc atg agc tca<br>Pro Ser Val Lys Val Pro Leu Pro Leu Ala Ala Ser Leu Met Ser Ser<br>            380                        385                        390 | 1444 |
| gag ctt gcc cgc cat agc aag cga gtc cgc att gcc ccc aag gtg ctg<br>Glu Leu Ala Arg His Ser Lys Arg Val Arg Ile Ala Pro Lys Val Leu<br>395                        400                        405 | 1492 |
| cta gct gag gag ggg ata gct cct ctt tct tct gca gga cca ggg aaa<br>Leu Ala Glu Glu Gly Ile Ala Pro Leu Ser Ser Ala Gly Pro Gly Lys<br>410                        415                        420                        425 | 1540 |
| gag gag aaa ctc ctg ttt gga gaa ggg ttt tct cct ttg ctt cca gtt<br>Glu Glu Lys Leu Leu Phe Gly Glu Gly Phe Ser Pro Leu Leu Pro Val<br>                        430                        435                        440 | 1588 |
| cag act atc aag gag gaa gaa atc cag cct ggg gag gaa atg cca cac<br>Gln Thr Ile Lys Glu Glu Glu Ile Gln Pro Gly Glu Glu Met Pro His<br>                445                        450                        455 | 1636 |
| tta gcg aga ccc atc aaa gtg gag agc cct ccc ttg gaa gag tgg ccc<br>Leu Ala Arg Pro Ile Lys Val Glu Ser Pro Pro Leu Glu Glu Trp Pro<br>            460                        465                        470 | 1684 |
| tcc ccg gcc cca tct ttc aaa gag gaa tca tct cac tcc tgg gag gat<br>Ser Pro Ala Pro Ser Phe Lys Glu Glu Ser Ser His Ser Trp Glu Asp<br>475                        480                        485 | 1732 |
| tcg tcc caa tct ccc acc cca aga ccc aag aag tcc tac agt ggg ctt<br>Ser Ser Gln Ser Pro Thr Pro Arg Pro Lys Lys Ser Tyr Ser Gly Leu<br>490                        495                        500                        505 | 1780 |
| agg tcc cca acc cgg tgt gtc tcg gaa atg ctt gtg att caa cac agg<br>Arg Ser Pro Thr Arg Cys Val Ser Glu Met Leu Val Ile Gln His Arg<br>                        510                        515                        520 | 1828 |
| gag agg agg gag agg agc cgg tct cgg agg aaa cag cat cta ctg cct<br>Glu Arg Arg Glu Arg Ser Arg Ser Arg Arg Lys Gln His Leu Leu Pro<br>            525                        530                        535 | 1876 |
| ccc tgt gtg gat gag ccg gag ctg ctc ttc tca gag ggg ccc agt act<br>Pro Cys Val Asp Glu Pro Glu Leu Leu Phe Ser Glu Gly Pro Ser Thr<br>540                        545                        550 | 1924 |
| tcc cgc tgg gcc gca gag ctc ccg ttc cca gca gac tcc tct gac cct<br>Ser Arg Trp Ala Ala Glu Leu Pro Phe Pro Ala Asp Ser Ser Asp Pro<br>555                        560                        565 | 1972 |

```
gcc tcc cag ctc agc tac tcc cag gaa gtg gga gga cct ttt aag aca    2020
Ala Ser Gln Leu Ser Tyr Ser Gln Glu Val Gly Gly Pro Phe Lys Thr
570                 575                 580                 585 ccc att aag gaa acg ctg ccc atc tcc tcc acc ccg agc aaa tct gtc    2068
Pro Ile Lys Glu Thr Leu Pro Ile Ser Ser Thr Pro Ser Lys Ser Val
                590                 595                 600 ctc ccc aga acc cct gaa tcc tgg agg ctc acg ccc cca gcc aaa gta    2116
Leu Pro Arg Thr Pro Glu Ser Trp Arg Leu Thr Pro Pro Ala Lys Val
            605                 610                 615 ggg gga ctg gat ttc agc cca gta caa acc tcc cag ggt gcc tct gac    2164
Gly Gly Leu Asp Phe Ser Pro Val Gln Thr Ser Gln Gly Ala Ser Asp
        620                 625                 630 ccc ttg cct gac ccc ctg ggg ctg atg gat ctc agc acc act ccc ttg    2212
Pro Leu Pro Asp Pro Leu Gly Leu Met Asp Leu Ser Thr Thr Pro Leu
    635                 640                 645 caa agt gct ccc ccc ctt gaa tca ccg caa agg ctc ctc agt tca gaa    2260
Gln Ser Ala Pro Pro Leu Glu Ser Pro Gln Arg Leu Leu Ser Ser Glu
650                 655                 660                 665 ccc tta gac ctc atc tcc gtc ccc ttt ggc aac tct tct ccc tca gat    2308
Pro Leu Asp Leu Ile Ser Val Pro Phe Gly Asn Ser Ser Pro Ser Asp
                670                 675                 680 ata gac gtc ccc aag cca ggc tcc ccg gag cca cag gtt tct ggc ctt    2356
Ile Asp Val Pro Lys Pro Gly Ser Pro Glu Pro Gln Val Ser Gly Leu
            685                 690                 695 gca gcc aat cgt tct ctg aca gaa ggc ctg gtc ctg gac aca atg aat    2404
Ala Ala Asn Arg Ser Leu Thr Glu Gly Leu Val Leu Asp Thr Met Asn
        700                 705                 710 gac agc ctc agc aag atc ctg ctg gac atc agc ttt cct ggc ctg gac    2452
Asp Ser Leu Ser Lys Ile Leu Leu Asp Ile Ser Phe Pro Gly Leu Asp
    715                 720                 725 gag gac cca ctg ggc cct gac aac atc aac tgg tcc cag ttt att cct    2500
Glu Asp Pro Leu Gly Pro Asp Asn Ile Asn Trp Ser Gln Phe Ile Pro
730                 735                 740                 745 gag cta cag tag agccctgccc ttgccctgt gctcaagctg tccaccatcc         2552
Glu Leu Gln cgggcactcc aaggctcagt gcaccccaag cctctgagtg aggacagcag gcagggactg  2612
ttctgctcct catagctccc tgctgcctga ttatgcaaaa gtagcagtca caccctagcc  2672
actgctggga ccttgtgttc cccaagagta tctgattcct ctgctgtccc tgccaggagc  2732
tgaagggtgg gaacaacaaa ggcaatggtg aaaagagatt aggaaccccc cagcctgttt  2792
ccattctctg cccagcagtc tcttaccttc cctgatcttt gcagggtggt ccgtgtaaat  2852
agtataaatt ctccaaatta tcctctaatt ataaatgtaa gcttatttcc ttagatcatt  2912
atccagagac tgccagaagg tgggtaggat gacctggggt ttcaattgac ttctgttcct  2972
tgcttttagt tttgatagaa gggaagacct gcagtgcacg gtttcttcca ggctgaggta  3032
cctggatctt gggttcttca ctgcaggggac ccagacaagt ggatctgctt gccagagtcc  3092
tttttgcccc tccctgccac ctccccgtgt ttccaagtca gctttcctgc aagaagaaat  3152
cctggttaaa aaagtctttt gtattgggtc aggagttgaa tttggggtgg gaggatggat  3212
gcaactgaag cagagtgtgg gtgcccagat gtgcgctatt agatgtttct ctgataatgt  3272
ccccaatcat accagggaga ctggcattga cgagaactca ggtggaggct tgagaaggcc  3332
gaaagggccc ctgacctgcc tggcttcctt agcttgcccc tcagctttgc aaagagccac  3392
cctaggcccc agctgaccgc atgggtgtga gccagcttga gaacactaac tactcaataa  3452
aagcgaaggt ggacaaaaaa aaaaaaaaaa aaaaa                             3487
```

```
<210> SEQ ID NO 107
<211> LENGTH: 748
<212> TYPE: PRT
<213> ORGANISM: Homo sapiens

<400> SEQUENCE: 107

Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125

Tyr Asp Ala Lys Arg Thr Glu Val Thr Leu Glu Thr Leu Gly Pro Lys
130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
        195                 200                 205

Asn Cys His Leu Glu Gln Arg Gln Val Lys Val Glu Glu Pro Ser Arg
210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
        275                 280                 285

Leu Ser Leu His Asp Met Phe Val Arg Glu Thr Ser Ala Asn Gly Lys
290                 295                 300

Val Ser Phe Trp Thr Ile His Pro Ser Ala Asn Arg Tyr Leu Thr Leu
305                 310                 315                 320

Asp Gln Val Phe Lys Gln Gln Lys Arg Pro Asn Pro Glu Leu Arg Arg
                325                 330                 335

Asn Met Thr Ile Lys Thr Glu Leu Pro Leu Gly Ala Arg Arg Lys Met
            340                 345                 350

Lys Pro Leu Leu Pro Arg Val Ser Ser Tyr Leu Val Pro Ile Gln Phe
        355                 360                 365

Pro Val Asn Gln Ser Leu Val Leu Gln Pro Ser Val Lys Val Pro Leu
370                 375                 380
```

```
Pro Leu Ala Ala Ser Leu Met Ser Glu Leu Ala Arg His Ser Lys
385                 390                 395                 400

Arg Val Arg Ile Ala Pro Lys Val Leu Leu Ala Glu Glu Gly Ile Ala
            405                 410                 415

Pro Leu Ser Ser Ala Gly Pro Gly Lys Glu Lys Leu Leu Phe Gly
        420                 425                 430

Glu Gly Phe Ser Pro Leu Leu Pro Val Gln Thr Ile Lys Glu Glu
        435                 440                 445

Ile Gln Pro Gly Glu Glu Met Pro His Leu Ala Arg Pro Ile Lys Val
450                 455                 460

Glu Ser Pro Pro Leu Glu Glu Trp Pro Ser Pro Ala Pro Ser Phe Lys
465                 470                 475                 480

Glu Glu Ser Ser His Ser Trp Glu Asp Ser Ser Gln Ser Pro Thr Pro
                485                 490                 495

Arg Pro Lys Lys Ser Tyr Ser Gly Leu Arg Ser Pro Thr Arg Cys Val
            500                 505                 510

Ser Glu Met Leu Val Ile Gln His Arg Glu Arg Arg Glu Arg Ser Arg
        515                 520                 525

Ser Arg Arg Lys Gln His Leu Leu Pro Pro Cys Val Asp Glu Pro Glu
530                 535                 540

Leu Leu Phe Ser Glu Gly Pro Ser Thr Ser Arg Trp Ala Ala Glu Leu
545                 550                 555                 560

Pro Phe Pro Ala Asp Ser Ser Asp Pro Ala Ser Gln Leu Ser Tyr Ser
                565                 570                 575

Gln Glu Val Gly Gly Pro Phe Lys Thr Pro Ile Lys Glu Thr Leu Pro
            580                 585                 590

Ile Ser Ser Thr Pro Ser Lys Ser Val Leu Pro Arg Thr Pro Glu Ser
        595                 600                 605

Trp Arg Leu Thr Pro Pro Ala Lys Val Gly Gly Leu Asp Phe Ser Pro
610                 615                 620

Val Gln Thr Ser Gln Gly Ala Ser Asp Pro Leu Pro Asp Pro Leu Gly
625                 630                 635                 640

Leu Met Asp Leu Ser Thr Thr Pro Leu Gln Ser Ala Pro Pro Leu Glu
                645                 650                 655

Ser Pro Gln Arg Leu Leu Ser Ser Glu Pro Leu Asp Leu Ile Ser Val
            660                 665                 670

Pro Phe Gly Asn Ser Ser Pro Ser Asp Ile Asp Val Pro Lys Pro Gly
        675                 680                 685

Ser Pro Glu Pro Gln Val Ser Gly Leu Ala Ala Asn Arg Ser Leu Thr
690                 695                 700

Glu Gly Leu Val Leu Asp Thr Met Asn Asp Ser Leu Ser Lys Ile Leu
705                 710                 715                 720

Leu Asp Ile Ser Phe Pro Gly Leu Asp Glu Asp Pro Leu Gly Pro Asp
                725                 730                 735

Asn Ile Asn Trp Ser Gln Phe Ile Pro Glu Leu Gln
            740                 745

<210> SEQ ID NO 108
<211> LENGTH: 19
<212> TYPE: DNA
<213> ORGANISM: Artificial
<220> FEATURE:
<223> OTHER INFORMATION: A target sequence for siRNA.

<400> SEQUENCE: 108
gcagcagaaa cgaccgaat                                            19
```

```
<210> SEQ ID NO 109
<211> LENGTH: 51
<212> TYPE: DNA
<213> ORGANISM: Artificial
<220> FEATURE:
<223> OTHER INFORMATION: An artificially synthesized oligonucleotide
      sequence for siRNA.

<400> SEQUENCE: 109
tcccgcagca gaaacgaccg aatttcaaga gaattcggtc gtttctgctg c         51

<210> SEQ ID NO 110
<211> LENGTH: 51
<212> TYPE: DNA
<213> ORGANISM: Artificial
<220> FEATURE:
<223> OTHER INFORMATION: An artificially synthesized oligonucleotide
      sequence for siRNA.

<400> SEQUENCE: 110
aaaagcagca gaaacgaccg aattctcttg aaattcggtc gtttctgctg c         51

<210> SEQ ID NO 111
<211> LENGTH: 47
<212> TYPE: DNA
<213> ORGANISM: Artificial
<220> FEATURE:
<223> OTHER INFORMATION: An artificially synthesized hairpin siRNA
      sequence.

<400> SEQUENCE: 111
gcagcagaaa cgaccgaatt tcaagagaat tcggtcgttt ctgctgc               47

<210> SEQ ID NO 112
<211> LENGTH: 2931
<212> TYPE: DNA
<213> ORGANISM: Homo sapiens
<220> FEATURE:
<221> NAME/KEY: CDS
<222> LOCATION: (146)..(751)

<400> SEQUENCE: 112
agggggagcg gagggaggtg tttctgtcag ttccggctgt tgttcgggga agtggatccg    60
ccgctgccgg agcagcccga agggagctgc ggatcgcgag gccagtaccg accccgcccg   120
cccgcgcgca ccgcccccgc cgcc atg gcc cgg gac tac gac cac ctc ttc      172
                          Met Ala Arg Asp Tyr Asp His Leu Phe
                            1               5 aag ctg ctc atc atc ggc gac agc ggt gtg ggc aag agc agt tta ctg     220
Lys Leu Leu Ile Ile Gly Asp Ser Gly Val Gly Lys Ser Ser Leu Leu
 10              15                  20                  25 ttg cgt ttt gca gac aac act ttc tca ggc agc tac atc acc acg atc     268
Leu Arg Phe Ala Asp Asn Thr Phe Ser Gly Ser Tyr Ile Thr Thr Ile
             30                  35                  40 gga gtg gat ttc aag atc cgg acc gtg gag atc aac ggg gag aag gtg     316
Gly Val Asp Phe Lys Ile Arg Thr Val Glu Ile Asn Gly Glu Lys Val
         45                  50                  55 aag ctg cag atc tgg gac aca gcg ggg cag gag cgc ttc cgc acc atc     364
Lys Leu Gln Ile Trp Asp Thr Ala Gly Gln Glu Arg Phe Arg Thr Ile
     60                  65                  70 acc tcc acg tat tat cgg ggg acc cac ggg gtc att gtg gtt tac gac     412
Thr Ser Thr Tyr Tyr Arg Gly Thr His Gly Val Ile Val Val Tyr Asp
 75                  80                  85 gtc acc agt gcc gag tcc ttt gtc aac gtc aag cgg tgg ctt cac gaa     460
```

```
                Val Thr Ser Ala Glu Ser Phe Val Asn Val Lys Arg Trp Leu His Glu
                 90              95                 100                 105
atc aac cag aac tgt gat gat gtg tgc cga ata tta gtg ggt aat aag                 508
Ile Asn Gln Asn Cys Asp Asp Val Cys Arg Ile Leu Val Gly Asn Lys
                110                 115                 120 aat gac gac cct gag cgg aag gtg gtg gag acg gaa gat gcc tac aaa                 556
Asn Asp Asp Pro Glu Arg Lys Val Val Glu Thr Glu Asp Ala Tyr Lys
                125                 130                 135 ttc gcc ggg cag atg ggc atc cag ttg ttc gag acc agc gcc aag gag                 604
Phe Ala Gly Gln Met Gly Ile Gln Leu Phe Glu Thr Ser Ala Lys Glu
            140                 145                 150 aat gtc aac gtg gaa gag atg ttc aac tgc atc acg gag ctg gtc ctc                 652
Asn Val Asn Val Glu Glu Met Phe Asn Cys Ile Thr Glu Leu Val Leu
        155                 160                 165 cga gca aag aaa gac aac ctg gca aaa cag cag cag caa caa cag aac                 700
Arg Ala Lys Lys Asp Asn Leu Ala Lys Gln Gln Gln Gln Gln Gln Asn
170                 175                 180                 185 gat gtg gtg aag ctc acg aag aac agt aaa cga aag aaa cgc tgc tgc                 748
Asp Val Val Lys Leu Thr Lys Asn Ser Lys Arg Lys Lys Arg Cys Cys
                190                 195                 200 taa tggcacccag tccactgcag agactgcact gcggtccctc ccccagcccg                      801
aggcccacgg aggttcctcg ggggacagtc tcagtttcgt gccgttattt aaagaattct               861
ctccatgttt ttgtatcggg aggtgccatc ggcacttcct cccccgccct cctcgagtgc               921
caagaaggtg ttggaccagc ccgcccttcc ctactggtgc ccctcctcc  ccggccaagg               981 cgcctggacc tggcgaggac gctgcccgcc gagcggactg attcgcagag tctgtacata              1041
gtgtatattg ctctacccgg ccgcacacca cgtcctgctc tggcttttgc cttcttgatg              1101
ccagcctgct gcaacagacc ctccccgcgc ccctccccag cccatcttac tgcaagcagc              1161
gtcctgagga cacagcggca cgttctagct gcgtctgcgg ccagcccgtg ccagtggagt              1221
gggctccgcg ttgctcattc tctccgacag gttgtcagcc tctgtccccg ctgcacaggg              1281
tcttgcccct tctccggggc ctgtgccagc tcccttccct ccccgttgtc ctgtccccac              1341
agccattctg ggagctgggg aacctggtct caaggcaggc cctgcagttc acagaggtg               1401 gcaggtcttg ccctttggcc aacagatttc ttgtcctgcc ttctagatgc ctctgagctc              1461
caaacccagg gcagccatgg cttctcattt acaccaacag gtttcagttc aacagaaag               1521 gtcggggtag gttcgtgcag agatggggct ggcagggggg ctatgggagg attattttaa              1581
cagatcaaga aaatgaagcc aaatcaagtg aattaaattc ctcacaatta ttttctttcc              1641
ctgaggtttg attggcacag cagcaaaagt tgaggccacc ccacttgtgt ccactgtttt              1701
tagaaaaaaa tgaatggctt cctgccattg tggggctgga ctcttgggct ttcttggtgg              1761
gagcggagaa ggggcctccc acccttgtcc gagttgcctc ccactggagg tcaggagtct              1821
acactgcagc ctcgggcact gtggggagtg catgcctggg gcctctggtt ggggaccatg              1881
gacaggccct ggtcactgtc ctaacctttg tcaggacaaa ggtagcaaga ggatttcctg              1941
gcgggtggga aggaatggct ggggcggcca gttttgacac gccccagtgc cctggagaac              2001
aaccagggtc atctgcactt gatgactgct ccccgacccc cagcccggac acctcattcc              2061
cctcccacta cagggatcaa gtgacctggg aagaaccgag tttaacacca ggatgtgttt              2121
ccttagattt cctttcctag gcgatttcca gggagagccc tgattggaca atcacatcac              2181
agatcacact gcagtttcca tgttagcact gtggatgggt ttttaatcaa taaaaactgg              2241
gggtttcttc tcaccgactc tccacttgcc caaactgcca aaagctggtg attctgggac              2301
aggccttcac tttggagcca cgggatgggg tgggggagcc ccatgggcct gggaaggagg              2361
```

```
gtgctgtgga gggggctgca gggctgacca gcaggcagcc tcatctggtc gggggcgggg    2421
gcggcaggag cagaagcggg gtctccgtcc ttgggactgt cctggttggc cacgggccct    2481
gaggatgcac ggtgcctggg gctcctgtgc cggtgggcgg ggggcatgct ggcctctgag    2541
cgatcaggcg aggccagcga gggtgtgctt gcaaattcaa gcaataagag gggggttcct    2601
gggggcttcc agcccaggct agaagccccc atggcttctg gcagctggac atcagcccca    2661
ggtattgggg tgattttggt catgacagtg tgcctgtccc actgttacac gcatgaatgg    2721
gggttatggg gtggggtgg ggactcaggg ctggaccgac gtcctagtgg acctgatgtg    2781
aaattcctgt caaacaaaca ccacttttca atggtttgct aggagtattt ctgtattgaa    2841
agtttctaat tatgcttttt aaaaaaatac taaaaataaa ggttcaagct gccaaaaaaa    2901
aaaaaaaaaa aaaaaaaaa aaaaaaaaaa                                      2931
```

<210> SEQ ID NO 113
<211> LENGTH: 201
<212> TYPE: PRT
<213> ORGANISM: Homo sapiens

<400> SEQUENCE: 113

```
Met Ala Arg Asp Tyr Asp His Leu Phe Lys Leu Leu Ile Ile Gly Asp
1               5                   10                  15

Ser Gly Val Gly Lys Ser Ser Leu Leu Leu Arg Phe Ala Asp Asn Thr
            20                  25                  30

Phe Ser Gly Ser Tyr Ile Thr Thr Ile Gly Val Asp Phe Lys Ile Arg
        35                  40                  45

Thr Val Glu Ile Asn Gly Glu Lys Val Lys Leu Gln Ile Trp Asp Thr
    50                  55                  60

Ala Gly Gln Glu Arg Phe Arg Thr Ile Thr Ser Thr Tyr Tyr Arg Gly
65                  70                  75                  80

Thr His Gly Val Ile Val Val Tyr Asp Val Thr Ser Ala Glu Ser Phe
                85                  90                  95

Val Asn Val Lys Arg Trp Leu His Glu Ile Asn Gln Asn Cys Asp Asp
            100                 105                 110

Val Cys Arg Ile Leu Val Gly Asn Lys Asn Asp Asp Pro Glu Arg Lys
        115                 120                 125

Val Val Glu Thr Glu Asp Ala Tyr Lys Phe Ala Gly Gln Met Gly Ile
    130                 135                 140

Gln Leu Phe Glu Thr Ser Ala Lys Glu Asn Val Asn Val Glu Glu Met
145                 150                 155                 160

Phe Asn Cys Ile Thr Glu Leu Val Leu Arg Ala Lys Lys Asp Asn Leu
                165                 170                 175

Ala Lys Gln Gln Gln Gln Gln Asn Asp Val Val Lys Leu Thr Lys
            180                 185                 190

Asn Ser Lys Arg Lys Lys Arg Cys Cys
        195                 200
```

<210> SEQ ID NO 114
<211> LENGTH: 19
<212> TYPE: DNA
<213> ORGANISM: Artificial
<220> FEATURE:
<223> OTHER INFORMATION: A target sequence for siRNA.

<400> SEQUENCE: 114
gagatgttca actgcatca                                                    19

<210> SEQ ID NO 115
<211> LENGTH: 51
<212> TYPE: DNA
<213> ORGANISM: Artificial
<220> FEATURE:
<223> OTHER INFORMATION: An artificially synthesized oligonucleotide
      sequence for siRNA.

<400> SEQUENCE: 115
tcccgagatg ttcaactgca tcattcaaga gatgatgcag ttgaacatct c        51

<210> SEQ ID NO 116
<211> LENGTH: 51
<212> TYPE: DNA
<213> ORGANISM: Artificial
<220> FEATURE:
<223> OTHER INFORMATION: An artificially synthesized oligonucleotide
      sequence for siRNA.

<400> SEQUENCE: 116
aaaagagatg ttcaactgca tcatctcttg aatgatgcag ttgaacatct c        51

<210> SEQ ID NO 117
<211> LENGTH: 47
<212> TYPE: DNA
<213> ORGANISM: Artificial
<220> FEATURE:
<223> OTHER INFORMATION: An artificially synthesized hairpin siRNA
      sequence.

<400> SEQUENCE: 117
gagatgttca actgcatcat tcaagagatg atgcagttga acatctc        47

<210> SEQ ID NO 118
<211> LENGTH: 22
<212> TYPE: DNA
<213> ORGANISM: Artificial
<220> FEATURE:
<223> OTHER INFORMATION: An artificially synthesized primer sequence for
      RT-PCR.

<400> SEQUENCE: 118
aaaaagggga tgcctagaac tc        22

<210> SEQ ID NO 119
<211> LENGTH: 21
<212> TYPE: DNA
<213> ORGANISM: Artificial
<220> FEATURE:
<223> OTHER INFORMATION: An artificially synthesized primer sequence for
      RT-PCR.

<400> SEQUENCE: 119
ctttcagcac gtcaaggaca t        21

<210> SEQ ID NO 120
<211> LENGTH: 23
<212> TYPE: DNA
<213> ORGANISM: Artificial
<220> FEATURE:
<223> OTHER INFORMATION: An artificially synthesized primer sequence for
      RT-PCR.

<400> SEQUENCE: 120
acacctacga aggtacacat gac        23

<210> SEQ ID NO 121

```
<211> LENGTH: 23
<212> TYPE: DNA
<213> ORGANISM: Artificial
<220> FEATURE:
<223> OTHER INFORMATION: An artificially synthesized primer sequence for
      RT-PCR.

<400> SEQUENCE: 121
gctatttcag ggtaaatgga gtc                                               23

<210> SEQ ID NO 122
<211> LENGTH: 23
<212> TYPE: DNA
<213> ORGANISM: Artificial
<220> FEATURE:
<223> OTHER INFORMATION: An artificially synthesized primer sequence for
      RT-PCR.

<400> SEQUENCE: 122
cagagatgga ggatgtcaat aac                                               23

<210> SEQ ID NO 123
<211> LENGTH: 23
<212> TYPE: DNA
<213> ORGANISM: Artificial
<220> FEATURE:
<223> OTHER INFORMATION: An artificially synthesized primer sequence for
      RT-PCR.

<400> SEQUENCE: 123
catagcagct ttaaagagac acg                                               23

<210> SEQ ID NO 124
<211> LENGTH: 21
<212> TYPE: DNA
<213> ORGANISM: Artificial
<220> FEATURE:
<223> OTHER INFORMATION: An artificially synthesized primer sequence for
      RT-PCR.

<400> SEQUENCE: 124
ccaccataac agtggagtgg g                                                 21

<210> SEQ ID NO 125
<211> LENGTH: 24
<212> TYPE: DNA
<213> ORGANISM: Artificial
<220> FEATURE:
<223> OTHER INFORMATION: An artificially synthesized primer sequence for
      RT-PCR.

<400> SEQUENCE: 125
cagttacagg tgtatgactg ggag                                              24

<210> SEQ ID NO 126
<211> LENGTH: 23
<212> TYPE: DNA
<213> ORGANISM: Artificial
<220> FEATURE:
<223> OTHER INFORMATION: An artificially synthesized primer sequence for
      RT-PCR.

<400> SEQUENCE: 126
ctgaatacaa cttcctgttt gcc                                               23

<210> SEQ ID NO 127
<211> LENGTH: 23
<212> TYPE: DNA
```

-continued

```
<213> ORGANISM: Artificial
<220> FEATURE:
<223> OTHER INFORMATION: An artificially synthesized primer sequence for
      RT-PCR.

<400> SEQUENCE: 127
gaccacagaa ttaccaaaac tgc                                              23
```